(12) United States Patent
Hoenke et al.

(10) Patent No.: US 7,511,045 B2
(45) Date of Patent: Mar. 31, 2009

(54) COMPOUNDS FOR THE TREATMENT OF INFLAMMATORY DISEASES

(75) Inventors: Christoph Hoenke, Ingelheim (DE); Birgit Jung, Laupheim (DE); Domnic Martyres, Biberach (DE); Peter Nickolaus, Warthausen (DE); Pascale Pouzet, Biberach (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 0 days.

(21) Appl. No.: 11/408,122

(22) Filed: Apr. 20, 2006

(65) Prior Publication Data

US 2007/0259846 A1    Nov. 8, 2007

(30) Foreign Application Priority Data

Apr. 21, 2005 (DE) .................. 10 2005 019 201

(51) Int. Cl.
C07D 413/02 (2006.01)
C07D 417/04 (2006.01)
A61K 31/4365 (2006.01)
A61K 31/4355 (2006.01)

(52) U.S. Cl. .................. 514/252.16; 544/278
(58) Field of Classification Search .......... 544/278; 514/252.16
See application file for complete search history.

(56) References Cited

U.S. PATENT DOCUMENTS 3,318,881 A * 5/1967 Eberhard et al. ............... 544/80
4,256,737 A   3/1981 Nestor et al.
5,187,168 A   2/1993 Primeau et al.

FOREIGN PATENT DOCUMENTS

| DE | 1 940 572 | 2/1971 |
|---|---|---|
| DE | 2112950 | 10/1971 |
| DE | 2 032 687 | 1/1972 |
| EP | 0899263 A2 | 3/1999 |
| FR | 1 603 313 | 5/1971 |
| WO | WO03/055890 A1 | 7/2003 |
| WO | WO 03/059913 | 7/2003 |
| WO | WO2005/049033 A1 | 6/2005 |
| WO | WO2005/082865 | 9/2005 |

OTHER PUBLICATIONS

Asit K. Chakraborti, et al; 3D-QSAR Studies on Thieno[3,2-d]pyrimidines as Phosphodiesterase IV Inhibitors; Bioorganic & Medicinal Chemistry Letters (2003) vol. 13 pp. 1403-1408.

* cited by examiner

Primary Examiner—Bruck Kifle
(74) Attorney, Agent, or Firm—Michael P. Morris; Mary-Ellen M. Devlin; Timothy X. Witkowski

(57) ABSTRACT

Dihydrothienopyrimidines of formula 1

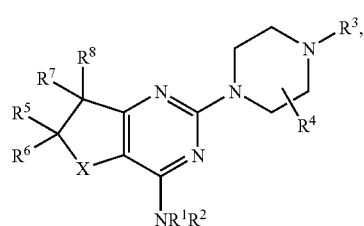

and the pharmacologically acceptable salts, enantiomers, racemates, hydrates, or solvates thereof, which are suitable for the treatment of respiratory or gastrointestinal complaints or diseases, inflammatory diseases of the joints, skin, or eyes, diseases of the peripheral or central nervous system or cancers, as well as pharmaceutical compositions which contain these compounds.

19 Claims, No Drawings

COMPOUNDS FOR THE TREATMENT OF INFLAMMATORY DISEASES

RELATED APPLICATIONS

This application claims priority to German Application No. DE 10 2005 019 201.7, filed Apr. 21, 2005, which is hereby incorporated by reference in its entirety.

FIELD OF THE INVENTION

The invention relates to new dihydrothienopyrimidines of formula 1, and the pharmacologically acceptable salts, pharmacologically acceptable salts, diastereomers, enantiomers, racemates, hydrates, or solvates thereof,

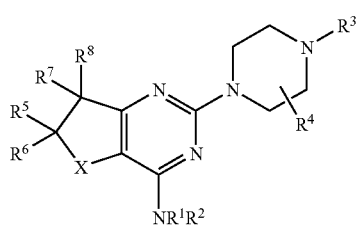

which are suitable for the treatment of respiratory or gastrointestinal complaints or diseases, inflammatory diseases of the joints, skin, or eyes, diseases of the peripheral or central nervous system or cancers, as well as pharmaceutical compositions which contain these compounds.

BACKGROUND OF THE INVENTION

U.S. Pat. No. 3,318,881 and BE 663693 disclose the preparation of dihydrothieno[3,2-d]pyrimidines which have cardiovascular and sedative properties.

SUMMARY OF THE INVENTION

Surprisingly it has now been found that dihydrothienopyrimidines of formula 1 are suitable for the treatment of inflammatory diseases. The present invention therefore relates to compounds of formula 1

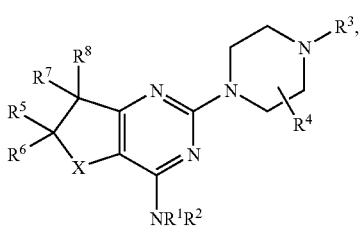

wherein:

X denotes O, S, SO, or $SO_2$;

$R^1$ denotes H, $C_{1-6}$-alkyl, $C_{2-6}$-alkenyl, $C_{2-6}$-alkynyl, $C_{6-10}$-aryl, $C_{6-10}$-aryl-$C_{1-6}$-alkylene, or $C_{5-10}$-heteroaryl-$C_{1-6}$-alkylene;

$R^2$ denotes H or an optionally mono- or polysubstituted group selected from among $C_{1-6}$-alkyl, $C_{2-6}$-alkenyl, $C_{2-6}$-alkynyl, an optionally mono- or poly-bridged mono- or bicyclic $C_{3-10}$-cycloalkyl, $C_{6-10}$-aryl, an aromatic or non-aromatic, heterocyclic $C_{3-10}$ ring, a bicyclic ring, and a $C_{6-10}$-aryl fused to a $C_{3-10}$ heterocycle; or $NR^1R^2$ together denote a heterocyclic ring which is optionally substituted by one or more groups selected from $C_{1-4}$-alkyl, $C_{2-6}$-alkenyl, $C_{2-6}$-alkynyl, straight-chain or branched $C_{1-6}$-alkanol, and oxo;

$R^3$ denotes a mono- or polysubstituted group selected from among a heterocyclic $C_{6-10}$ ring, $C_{3-7}$-cycloalkyl, $C_{6-10}$-aryl-$C_{1-6}$-alkylene, $C_{5-10}$-heteroaryl-$C_{1-6}$-alkylene, a fused, bicyclic ring which may optionally contain 1-4 heteroatoms selected independently of one another from N, O, or S, or $R^3$ denotes optionally substituted phenyl, or $R^3$ denotes a group $COR^{3.7}$, $COCH_2R^{3.8}$, $CONHR^{3.8}$, or $SO_2R^{3.8}$, wherein:

$R^{3.7}$ denotes H, $C_{1-6}$-alkyl, $C_{2-6}$-alkenyl, $C_{2-6}$-alkynyl, or $C_{6-10}$-aryl;

$R^{3.8}$ denotes $C_{1-6}$-alkyl, $C_{2-6}$-alkenyl, $C_{2-6}$-alkynyl, $C_{3-7}$-cycloalkyl, or a group selected from among $C_{6-10}$-aryl, a heterocyclic $C_{3-10}$ ring, and a bicyclic ring, which is optionally substituted by one or more groups selected from among $C_{1-6}$-alkyl, $C_{2-6}$-alkenyl, $C_{2-6}$-alkynyl, halogen, $NR^{3.8.1}R^{3.8.2}$, $C_{6-10}$-aryl, and a heterocyclic $C_{3-10}$ ring, wherein:

$R^{3.8.1}$ denotes H, $C_{1-6}$-alkyl, $C_{2-6}$-alkenyl, or $C_{2-6}$-alkynyl, and $R^{3.8.2}$ denotes H, $C_{1-6}$-alkyl, $C_{2-6}$-alkenyl, or $C_{2-6}$-alkynyl;

$R^4$ denotes H, $C_{1-4}$-alkyl, $C_{2-4}$-alkenyl, $C_{2-4}$-alkynyl, or oxo;

$R^5$ denotes H, $C_{1-4}$-alkyl, $C_{2-4}$-alkenyl, or $C_{2-4}$-alkynyl;

$R^6$ denotes H, $C_{1-4}$-alkyl, $C_{2-4}$-alkenyl, or $C_{2-4}$-alkynyl;

$R^7$ denotes H, $C_{1-4}$-alkyl, $C_{2-4}$-alkenyl, $C_{2-4}$-alkynyl, $C_{6-10}$-aryl, or OH;

$R^8$ denotes H, $C_{1-4}$-alkyl, $C_{2-4}$-alkenyl, $C_{2-4}$-alkynyl, $C_{6-10}$-aryl, or OH; or $R^7$ and $R^8$ together form oxo;

and the pharmacologically acceptable salts, diastereomers, enantiomers, racemates, hydrates, or solvates thereof.

Preferred compounds of formula 1 above are those wherein:

X denotes O, S, SO, or $SO_2$;

$R^1$ denotes H, $C_{1-6}$-alkyl, $C_{6-10}$-aryl, $C_{6-10}$-aryl-$C_{1-6}$-alkylene, or $C_{5-10}$-heteroaryl-$C_{1-6}$-alkylene, $R^2$ denotes H or $C_{1-6}$-alkyl, which may optionally be substituted by one or more groups selected from among $C_{1-6}$-haloalkyl, CN, $OR^{2.1}$, $NR^{2.1}R^{2.2}$, $COOR^{2.1}$, $CONR^{2.1}R^{2.2}$, $C_{3-7}$-cycloalkyl optionally substituted by $C_{1-4}$-alkyl or oxo, an aromatic or non-aromatic heterocycle optionally substituted by $C_{1-4}$-alkyl, oxo, OH, or halogen, $C_{6-10}$-aryl optionally substituted by $C_{1-4}$-alkyl or oxo and $C_{6-10}$-aryl fused to a $C_{5-6}$ heterocycle, while this fused ring system may optionally be substituted by $C_{1-4}$-alkyl or oxo, wherein:

$R^{2.1}$ denotes H or $C_{1-6}$-alkyl which is optionally substituted by a $C_{3-7}$-cycloalkyl, $C_{3-10}$ heterocycle, or $C_{6-10}$-aryl, each of which is optionally substituted, and $R^{2.2}$ denotes H or $C_{1-6}$-alkyl; or $R^2$ denotes a group selected from optionally mono- or polybridged $C_{3-10}$-cycloalkyl or a $C_{3-10}$-cycloalkyl, which may optionally be fused to a $C_{6-10}$-aryl ring which is optionally substituted by one or more groups selected from among $C_{1-6}$-alkyl, OH, $CH_2OR^{2.3}$, $COOR^{2.3}$, $COR^{2.3}$, $CONR^{2.3}R^{2.4}$, O—$C_{1-6}$-alkyl, O—$C_{7-11}$-aralkyl, $NR^{2.3}R^{2.4}$, and $NHCOR^{2.5}$, wherein:

$R^{2.3}$ is H or a heterocycle or a $C_{1-6}$-alkyl, which may optionally be substituted by a group selected from $C_{3-7}$-cycloalkyl, $C_{3-10}$ heterocycle, and $C_{6-10}$-aryl, while this group may optionally be substituted in each case by one or more groups selected from among $C_{1-6}$-alkyl, halogen, OH, and O—$C_{1-6}$-alkyl, wherein $R^{2.4}$ denotes H or $C_{1-6}$-alkyl, and $R^{2.5}$ denotes a group selected from among $C_{3-7}$-cycloalkyl, a heterocyclic $C_{3-10}$ ring, and $C_{1-6}$-alkyl, which may optionally be substituted by OH; or $R^2$ denotes a group of formula 1a

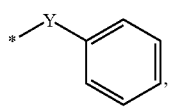, wherein:

Y denotes $C_{1-6}$-alkylene, optionally substituted by one or two $R^{2.7}$, wherein $R^{2.7}$ are in each case selected independently of one another from $C_{1-6}$-alkyl, COOH, CONH$_2$, OR$^{2.1}$, and COOR$^{2.1}$; or $R^{2.7}$ together with one or two carbon atoms of Y forms a carbocyclic ring with 3 carbon atoms, or $R^2$ denotes $C_{6-10}$-aryl, which may optionally be substituted by one or more groups selected independently of one another from among $C_{1-6}$-alkyl, $C_{1-6}$-haloalkyl, $C_{2-6}$-alkenyl, $C_{2-6}$-alkynyl, CN, halogen, OR$^{2.8}$, COOR$^{2.8}$, COR$^{2.10}$, NHCOMe, CONR$^{2.3}$R$^{2.4}$, a $C_{1-4}$ alkylene group substituted by NR$^{2.1}$R$^{2.2}$, or NR$^{2.1}$R$^{2.2}$, or $R^2$ denotes $C_{6-10}$-aryl, which may optionally be substituted by one or more groups selected independently of one another from among $C_{6-10}$-aryl-$C_{1-6}$-alkylene, $C_{5-10}$-heteroaryl-$C_{1-6}$-alkylene, $C_{3-7}$-cycloalkyl, a $C_{3-7}$-cycloalkyl-$C_{1-4}$-alkylene, $C_{6-10}$-aryl, and a heterocyclic $C_{3-10}$ ring, while these groups may each optionally be substituted by one or more groups selected from $C_{1-6}$-alkyl, $C_{1-6}$-haloalkyl, COOR$^{2.8}$, CN, halogen, OR$^{2.8}$, NHCOR$^{2.8}$, oxo, a $C_{3-10}$ heterocycle, a $C_{3-7}$-cycloalkyl-$C_{1-4}$ alkylene, a $C_{5-10}$ heterocycle-$C_{1-4}$-alkylene, and a NR$^{2.1}$R$^{2.2}$—$C_{1-4}$ alkylene, wherein:

$R^{2.8}$ denotes H, $C_{1-6}$-alkyl, $C_{6-10}$-aryl, a NR$^{2.1}$R$^{2.2}$—$C_{1-4}$ alkylene group, and $R^{2.10}$ denotes NHR$^{2.10.1}$ or a heterocyclic $C_{3-10}$ ring which may optionally be substituted by $C_{1-4}$-alkyl, and $R^{2.10.1}$ denotes H, $C_{3-7}$-cycloalkyl, $C_{2-6}$-alkenyl, $C_{2-6}$-alkynyl, $C_{1-6}$-alkyl, or $C_{1-6}$-alkyl-O—$C_{1-4}$-alkyl, or $R^2$ denotes $C_{6-10}$-aryl, to which an aromatic or non-aromatic $C_{3-10}$ heterocycle is fused; or $R^2$ denotes an aromatic or non-aromatic heterocyclic $C_{3-10}$ ring which may optionally be substituted by one or more groups selected from among halogen, OH, oxo, CN, $C_{1-6}$-alkyl, $C_{1-6}$-alkanol, $C_{6-10}$-aryl-$C_{1-6}$-alkylene, $C_{5-10}$-heteroaryl-$C_{1-6}$-alkylene, COR$^{2.11}$, $C_{3-7}$-cycloalkyl-$C_{1-4}$-alkylene, and $C_{3-10}$ heterocycle-$C_{1-4}$-alkylene, wherein:

$R^{2.11}$ denotes a group selected from among $C_{3-10}$ heterocycle-$C_{1-4}$-alkylene, $C_{3-7}$-cycloalkyl, and a heterocyclic aromatic or non-aromatic $C_{3-10}$ ring, which may optionally be substituted by $C_{1-6}$-alkyl, which may in turn optionally be substituted by OH, CH$_2$OH, OMe, NH$_2$, a $C_{3-10}$ heterocycle, or NHCOO-$^t$Bu; or $R^2$ denotes a group selected from among $C_{2-6}$-alkenyl or a bicyclic ring, which may optionally be substituted by methyl; or NR$^1$R$^2$ denotes a heterocyclic ring which may optionally be substituted by one or more groups selected from among $C_{1-4}$-alkyl, OH, and $C_{1-4}$-alkanol;

$R^3$ denotes a group selected from among a heterocyclic $C_{3-10}$ ring, a $C_{3-7}$-cycloalkyl, a bicyclic, fused aromatic or non-aromatic ring system, which optionally contains 1 to 4 heteroatoms selected from S, N, or O, or it denotes $C_{6-10}$-aryl-$C_{1-6}$-alkylene, $C_{5-10}$-heteroaryl-$C_{1-6}$-alkylene, and CH$_2$-benzo[1,3]dioxolyl, which may optionally be substituted by one or more groups selected from OH, halogen, $C_{1-6}$-alkyl, O—$C_{1-6}$-alkyl, $C_{1-6}$-haloalkyl, and CO—R$^{3.1}$, or $R^3$ denotes phenyl, which may optionally be substituted by one or more groups selected from among $C_{1-6}$-alkyl, $C_{2-6}$-alkenyl, $C_{2-6}$-alkynyl, $C_{1-4}$-haloalkyl, $C_{1-6}$-alkylene-NR$^{3.1}$R$^{3.2}$, CN, COOR$^{3.1}$, CONR$^{3.1}$R$^{3.2}$, NR$^{3.1}$R$^{3.2}$, NHCOR$^{3.1}$, CF$_3$, OR$^{3.1}$, halogen, NHCOR$^{3.1}$, NO$_2$, SO$_2$NR$^{3.1}$R$^{3.2}$, and $C_{1-6}$-alkylene-NHCOR$^{3.1}$, wherein:

$R^{3.1}$ denotes H, $C_{1-6}$-alkyl, $C_{2-6}$-alkenyl, or $C_{2-6}$-alkynyl, optionally bridged, mono- or bicyclic $C_{3-10}$ heterocycle, or $C_{3-10}$ heterocycle-$C_{1-4}$-alkylene group;

$R^{3.2}$ denotes H, $C_{1-6}$-alkyl, $C_{2-6}$-alkenyl, or $C_{2-6}$-alkynyl; or $R^3$ denotes a group of formula 1b

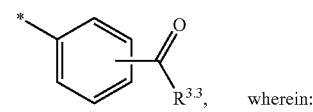, wherein:

$R^{3.3}$ denotes a group selected from among a heterocyclic $C_{3-10}$ ring which may optionally be substituted by one or more groups selected from among $C_{1-6}$-alkyl, oxo, COR$^{3.3.1}$, COR$^{3.3.2}$, $C_{1-6}$-alkylene-R$^{3.3.2}$, CH$_2$COpyrrolidine, and a heterocyclic $C_{3-10}$ ring, wherein a sulfur atom optionally contained in the heterocyclic ring, may optionally be in the form of the oxide or dioxide, wherein:

$R^{3.3.1}$ denotes $C_{1-6}$-alkyl;

$R^{3.3.2}$ denotes NH$_2$, NH($C_{1-6}$-alkyl), N($C_{1-6}$-alkyl)$_2$; or $R^{3.3}$ denotes a bicyclic ring or heterocyclic spiro ring; or $R^3$ denotes a group of formula 1c

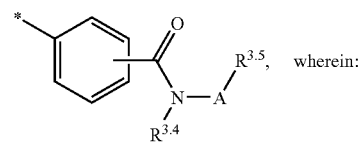, wherein:

A may be a bond or $C_{1-6}$-alkyl, which may optionally be substituted by oxo or NMe$_2$;

$R^{3.4}$ denotes H or $C_{1-6}$-alkyl;

$R^{3.5}$ denotes a group selected from among
$C_{1-6}$-alkyl, which may optionally be substituted by one or more groups selected from $C_{3-7}$-cycloalkyl, $C_{6-10}$-aryl, and a $C_{3-10}$ heterocycle, while this group may also optionally be substituted in each case by a group selected from among OH, oxo, $C_{1-6}$-alkyl, O—$C_{1-6}$-alkyl, and $C_{1-6}$-haloalkyl, or a group selected from a heterocyclic $C_{3-10}$ ring and a bicyclic ring, which is optionally substituted by one or more groups selected independently of one another from among oxo, $C_{1-6}$-alkyl, OH, $C_{6-10}$-aryl, a heterocyclic $C_{3-10}$ ring, $C_{1-6}$-alkylene-$R^{3.5.1}$, O—$C_{1-6}$-alkylene-$R^{3.5.1}$, and NH—$C_{1-6}$-alkylene-$R^{3.5.1}$, wherein $R^{3.5.1}$ denotes a group selected from among $C_{6-10}$-aryl and a heterocyclic $C_{3-10}$ ring which may optionally be substituted by $C_{1-6}$-alkyl; or $R^3$ denotes a group of formula 1d

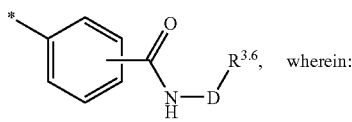

wherein:

D denotes $C_{2-4}$-alkynyl; an optionally bridged, bicyclic $C_{3-10}$-cycloalkyl group, which may optionally be substituted by one or more groups selected from $C_{1-6}$-alkyl, halogen, OH, $C_{1-6}$-haloalkyl, and O—$C_{1-6}$-alkyl, and $R^{3.6}$ denotes pyridinyl; or $R^3$ denotes a group selected from among $COR^{3.7}$, $COCH_2R^{3.8}$, $CONHR^{3.8}$, $SO_2R^{3.8}$, and a heterocyclic group fused to a $C_{6-10}$-aryl group, which may optionally be substituted by methyl, or $R^3$ denotes a group of formula 1e

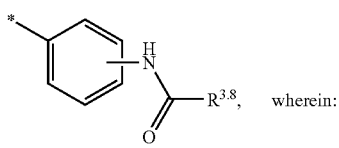

wherein:

$R^{3.7}$ denotes H, $C_{1-6}$-alkyl, $C_{6-10}$-aryl;

$R^{3.8}$ denotes a group selected from among $C_{1-6}$-alkyl, $C_{3-7}$-cycloalkyl, or a group selected from among $C_{6-10}$-aryl, a heterocyclic $C_{3-10}$ ring, and a bicyclic ring, which may optionally be substituted by one or more groups selected from among $C_{1-6}$-alkyl, halogen, $NR^{3.8.1}R^{3.8.2}$, $C_{6-10}$-aryl, and a heterocyclic $C_{3-10}$ ring;

$R^{3.8.1}$ denotes H or $C_{1-6}$-alkyl;

$R^{3.8.2}$ denotes H or $C_{1-6}$-alkyl;

$R^4$ denotes H, $C_{1-4}$-alkyl, or oxo;

$R^5$ denotes H or $C_{1-4}$-alkyl;

$R^6$ denotes H or $C_{1-4}$-alkyl;

$R^7$ denotes H, $C_{1-4}$-alkyl, $C_{6-10}$-aryl, or OH;

$R^8$ denotes H, $C_{1-4}$-alkyl, $C_{6-10}$-aryl, or OH; or $R^7$ and $R^8$ together form oxo;

and the pharmacologically acceptable salts, diastereomers, enantiomers, racemates, hydrates, or solvates thereof.

Preferred compounds of formula 1 above are those wherein

X denotes O, S, SO, or $SO_2$; preferably S, SO, or $SO_2$;

$R^1$ denotes H, $C_{1-4}$-alkyl;

$R^2$ denotes H or $C_{1-6}$-alkyl, optionally substituted by a group selected from among $C_{1-4}$-haloalkyl, CN, $OR^{2.1}$, $NR^{2.1}R^{2.2}$, $COOR^{2.1}$, and $CONR^{2.1}R^{2.2}$ or optionally substituted by a group selected from among $C_{3-7}$-cycloalkyl, $C_{6-10}$-aryl, and a heterocyclic, aromatic $C_{5-10}$ ring, optionally substituted by methyl or oxo;

$R^{2.1}$ denotes H or $C_{1-4}$-alkyl;

$R^{2.2}$ denotes H or $C_{1-4}$-alkyl; or $R^2$ denotes $C_{3-7}$-cycloalkyl, optionally substituted by a group selected from among $C_{1-4}$-alkyl, $CH_2OR^{2.3}$, $COOR^{2.3}$, $CONR^{2.3}R^{2.4}$, O-benzyl, $NR^{2.3}R^{2.4}$, or $NHCOR^{2.5}$, $R^{2.3}$ denotes H or $C_{2-4}$-alkyl, $R^{2.4}$ denotes H or $C_{1-4}$-alkyl, and $R^{2.5}$ denotes $C_{3-7}$-cycloalkyl, a heterocyclic, aromatic $C_{5-10}$ ring, or $C_{1-6}$-alkyl, optionally substituted by OH; or $R^2$ denotes a group of formula 1a

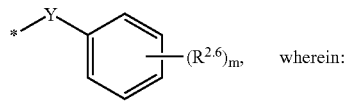

wherein:

Y denotes $C_{1-4}$-alkylene, optionally substituted by one or two $R^{2.7}$ m denotes 0, 1, 2;

$R^{2.7}$ each independently of one another denote $C_{1-4}$-alkyl, COOH, $CONH_2$; or together with one or two carbon atoms of Y forms a carbocyclic ring with 3 carbon atoms, or $R^2$ denotes $C_{6-10}$-aryl, optionally substituted by one or more groups selected from among $C_{1-4}$-alkyl, CN, halogen, $OR^{2.8}$, $COOR^{2.8}$, $COR^{2.10}$, and NHCOMe, $R^{2.8}$ denotes $C_{1-4}$-alkyl or $C_{6-10}$-aryl;

$R^{2.10}$ denotes $NHR^{2.10.1}$ or a heterocyclic non-aromatic $C_{3-10}$ ring, optionally substituted by $C_{1-4}$-alkyl; preferably a heterocyclic, non-aromatic $C_{3-10}$ ring which may contain one, two, or three heteroatoms, selected from among oxygen and nitrogen, wherein $R^{2.10.1}$ denotes H, cyclopropyl, or $C_{1-6}$-alkyl, optionally substituted by O—$C_{1-4}$-alkyl; or $R^2$ denotes $C_{6-10}$-aryl, optionally substituted by a group selected from among phenyl and a heterocyclic $C_{3-10}$ ring, optionally substituted by $C_{1-4}$-alkyl, $COOR^{2.8}$, CN, halogen, $OR^{2.8}$, NHCOMe, or oxo; or $R^2$ denotes a heterocyclic, non-aromatic $C_{5-10}$ ring, optionally substituted by a group selected from among benzyl or $COR^{2.11}$;

$R^{2.11}$ denotes a group selected from among $C_{3-7}$-cycloalkyl and a heterocyclic aromatic or non-aromatic $C_{5-10}$ ring, optionally substituted by one or more $C_{1-4}$-alkyl, optionally substituted by OH, OMe, $NH_2$, or NHCOO-$^t$Bu; or $R^2$ denotes a group selected from among $C_{2-6}$-alkenyl, indanyl, 1,2,3,4-tetrahydronaphthalyl, or 8-methyl-8-azabicyclo[3.2.1]octane; or $NR^1R^2$ together denotes a heterocyclic, non-aromatic $C_{3-10}$ ring which is optionally substituted by methyl;

$R^3$ denotes a group selected from among a heterocyclic, aromatic $C_{5-10}$ ring, $C_{6-10}$-aryl-$C_{1-6}$-alkylene, $C_{5-10}$-heteroaryl-$C_{1-6}$-alkylene, and $CH_2$-benzo[1,3]dioxolyl; or $R^3$ denotes phenyl, optionally substituted by one or more groups selected from among $C_{1-4}$-alkyl, $C_{1-4}$-alkylene-$NR^{3.1}R^{3.2}$, CN, $COOR^{3.1}$, $CONR^{3.1}R^{3.2}$, $CF_3$, $OR^{3.1}$, halogen, $NHCOR^{3.1}$, $NO_2$, $SO_2NR^{3.1}R^{3.2}$, $C_{1-4}$-alkylene-NH-$COR^{3.1}$;

$R^{3.1}$ denotes H or $C_{1-4}$-alkyl;

$R^{3.2}$ denotes H or $C_{1-4}$-alkyl; or $R^3$ denotes a group of formula 1b

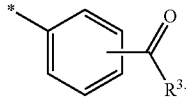

wherein:

- $R^{3.3}$ denotes a group selected from among a heterocyclic, non-aromatic $C_{3-10}$ ring, optionally substituted by one or more groups selected from among $C_{1-4}$-alkyl, oxo, $COR^{3.3.1}$, $COR^{3.3.2}$, $C_{1-4}$-alkylene-$R^{3.3.2}$, $CH_2CO$pyrrolidine, heterocyclic $C_{3-10}$ ring, wherein a sulfur atom optionally contained in the heterocyclic $C_{3-10}$ ring may optionally be in the form of the oxide or dioxide;
- $R^{3.3.1}$ denotes $C_{1-4}$-alkyl;
- $R^{3.3.2}$ denotes $NH_2$, $NH(C_{1-4}$-alkyl$)$, or $N(C_{1-4}$-alkyl$)_2$; or
- $R^{3.3}$ denotes a fused, bicyclic heteroring or heterocyclic spiroring; or $R^3$ denotes a group of formula 1c

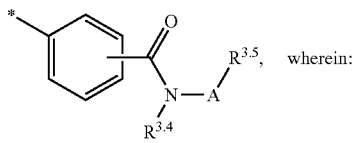

wherein:

- A denotes a bond or $C_{1-4}$-alkyl, optionally substituted by oxo or $NMe_2$;
- $R^{3.4}$ denotes H or $C_{1-4}$-alkyl;
- $R^{3.5}$ denotes a group selected from among a heterocyclic $C_{3-10}$ ring or a bicyclic ring, optionally substituted by one or more groups selected independently of one another from among oxo, $C_{1-4}$-alkyl, OH, $C_{6-10}$-aryl, heterocyclic, aromatic $C_{5-10}$ ring, $C_{1-4}$-alkylene-$R^{3.5.1}$, O—$C_{1-4}$-alkylene-$R^{3.5.1}$, NH—$C_{1-4}$-alkylene-$R^{3.5.1}$;
- $R^{3.5.1}$ denotes a group selected from among $C_{6-10}$-aryl, heterocyclic $C_{3-10}$ ring, optionally substituted by $C_{1-4}$-alkyl; or $R^3$ denotes a group of formula 1d

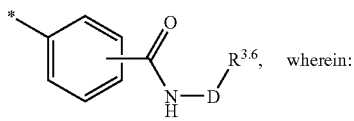

wherein:

- D denotes $C_{2-4}$-alkynyl;
- $R^{3.6}$ denotes pyridinyl; or
- $R^3$ denotes a group $COR^{3.7}$, $COCH_2R^{3.8}$, $CONHR^{3.8}$, $SO_2R^{3.8}$, or a group of formula 1e

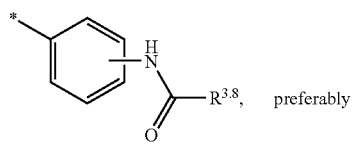

preferably

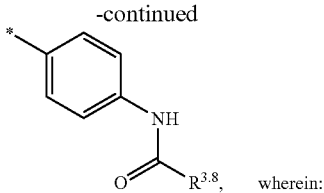

wherein:

- $R^{3.7}$ denotes H, $C_{1-4}$-alkyl, or $C_{6-10}$-aryl;
- $R^{3.8}$ denotes $C_{1-4}$-alkyl, $C_{3-7}$-cycloalkyl, or a group selected from among $C_{6-10}$-aryl, heterocyclic $C_{5-10}$ ring, and a bicyclic ring, optionally substituted by one or more groups selected from among $C_{1-4}$-alkyl, halogen, $NR^{3.8.1}R^{3.8.2}$, $C_{6-10}$-aryl, and heterocyclic, non-aromatic $C_{3-10}$ ring, wherein
  - $R^{3.8.1}$ denotes H or $C_{1-4}$-alkyl; and
  - $R^{3.8.2}$ denotes H or $C_{1-4}$-alkyl;
- $R^4$ denotes H, methyl, or oxo;
- $R^5$ denotes H or methyl;
- $R^6$ denotes H or methyl;
- $R^7$ denotes H, methyl, phenyl, or OH;
- $R^8$ denotes H, methyl, phenyl, or OH; or
- $R^7$ and $R^8$ together form oxo;

and the pharmacologically acceptable salts, diastereomers, enantiomers, racemates, hydrates, or solvates thereof.

Preferred compounds of formula 1 above are those wherein

X denotes O, S, SO, or $SO_2$; preferably S, SO, or $SO_2$;

$R^1$ denotes H, methyl, ethyl, or propyl; preferably H and propyl $R^2$ denotes H or $C_{1-6}$-alkyl, which may optionally be substituted by one or more groups selected from among $CF_3$, CN, OH, $NMe_2$, OMe, COOH, and $CONMe_2$, or $R^2$ denotes $C_{1-6}$-alkyl, which may optionally be substituted by one or more groups selected from cyclopropyl, cyclopentyl, cyclohexyl, phenyl, pyrrolidinyl, imidazolidinyl, pyrazolyl, imidazolyl, and pyridinyl, which may optionally be substituted by methyl or oxo; or $R^2$ denotes $C_{3-7}$-cycloalkyl, which may optionally be substituted by a group selected from among methyl, $OR^{2.3}$, $CH_2OR^{2.3}$, COOH, $CONR^{2.3}R^{2.4}$, CONH-$^tBu$, O-benzyl, $NR^{2.3}R^{2.4}$, and $NHCOR^{2.5}$, wherein

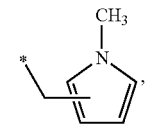

- $R^{2.3}$ denotes H, methyl, or
- $R^{2.4}$ denotes H or methyl;
- $R^{2.5}$ denotes $CH_2C(CH_3)_3$, $CH_2C(CH_3)_2(CH_2OH)$, cyclopentyl, tetrahydrofuranyl, pyrrolyl, pyrazolyl, imidazolyl, or isoxazolyl, or
- $R^2$ denotes a group of formula 1a

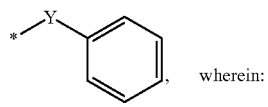

wherein:

Y denotes $C_{1-4}$-alkylene, optionally substituted by one or two $R^{2.7}$ $R^{2.7}$ each independently of one another denote $C_{1-4}$-alkyl, COOH, $CONH_2$; or $R^{2.7}$ together with one or two carbon atoms of Y forms a carbocyclic ring with 3 carbon atoms, or $R^2$ denotes $C_{6-10}$-aryl, which may optionally be substituted by one or more groups selected independently of one another from among methyl, tert-butyl, CN, F, Cl, Br, OH, OMe, OEt, O-phenyl, COOH, COOMe, $COR^{2.10}$, NHCOMe, and morpholinyl-$C_{1-4}$-alkylene, wherein $R^{2.10}$ denotes $NH_2$, NHMe, NH-$^i$Pr, NH-cyclopropyl, $NHCH_2CH_2OMe$, or a heterocyclic, non-aromatic $C_{3-10}$ ring, which may contain one, two, or three heteroatoms selected from among oxygen and nitrogen; preferably NH2, NHMe, NH-$^i$Pr, NH-cyclopropyl, $NHCH_2CH_2OMe$, morpholinyl, or methylpiperazinyl; or $R^2$ denotes $C_{6-10}$-aryl, which may optionally be substituted by a group selected from among phenyl and a heterocyclic $C_{3-10}$ ring, which may optionally be substituted by one or more groups selected from among methyl, tert-butyl, COOH, COOMe, CN, F, Cl, Br, OH, OMe, OEt, and NHCOMe, oxo; preferably phenyl, imidazolidinyl, optionally substituted by methyl or oxo; or $R^2$ denotes a heterocyclic non-aromatic $C_{3-10}$ ring which may optionally be substituted by a group selected from among benzyl and $COR^{2.11}$, wherein $R^{2.11}$ denotes a group selected from among cyclopentyl, tetrahydrofuranyl, furan, pyridyl, pyrrolyl, pyrazolyl, imidazolyl, which may optionally be substituted by one or two methyl groups, or by one or more groups selected from among $CH_2C(CH_3)_3$, $C(CH_3)_2(CH_2OH)$, $CH_2OMe$, $C(CH_3)_2NH_2$, and $C(CH_3)_2NHCOO$-$^t$Bu; or $R^2$ denotes a group selected from among $C_{2-6}$-alkenyl, indanyl, 1,2,3,4-tetrahydronaphthalyl, and 8-methyl-8-azabicyclo[3.2.1]octane; or $NR^1R^2$ denotes a group selected from among pyrrolidinyl, piperidinyl, piperazinyl, and morpholinyl, which may optionally be substituted by methyl;

$R^3$ denotes H or a group selected from among pyridinyl, pyrimidinyl, benzyl, and $CH_2$-benzo[1,3]dioxolyl; or $R^3$ denotes phenyl, which may optionally be substituted by one, two, or three groups selected from among methyl, $CH_2NH_2$, CN, COOH, $CONH_2$, $CF_3$, OH, F, Cl, Br, OMe, NHCOMe, $NR^{3.1}COR^{3.2}$, $CONR^{3.1}R^{3.2}$, $NO_2$, $SONMe_2$, and $CH_2NHCOMe$; wherein $R^{3.1}$ denotes H, $C_{1-6}$-alkyl, or an optionally bridged, mono- or bicyclic $C_{3-10}$ heterocycle; and $R^{3.2}$ denotes H or $C_{1-6}$-alkyl; or $R^3$ denotes a group of formula 1b

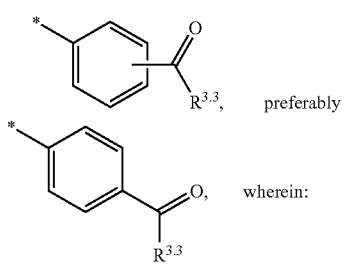

1b $R^{3.3}$ denotes a group selected from among piperidinyl, piperazinyl, azepanyl, which may optionally be substituted by one or more groups selected independently of one another from among methyl, oxo, $COCH_3$, $CONH_2$, $CH_2NEt_2$, $CH_2CH_2NMe_2$, $CH_2CO$pyrrolidine, pyridinyl, isothiazolidinyl-1,1-dioxide, and thiazolidinyl-1,1-dioxide, or $R^{3.3}$ denotes a group of formula

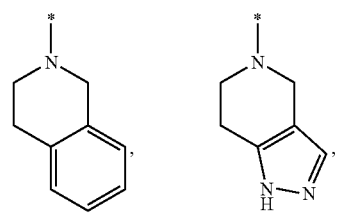

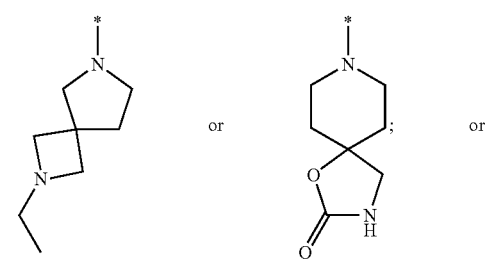

$R^3$ denotes a group of formula 1c

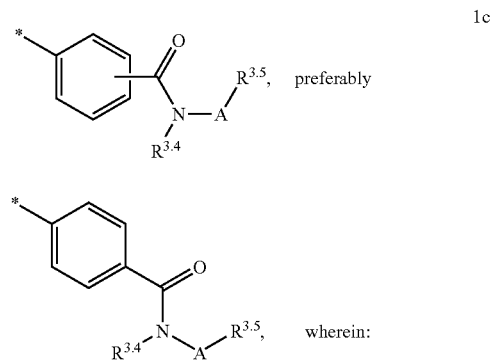

1c

A denotes a bond or $C_{1-4}$-alkyl, which may optionally be substituted by oxo or $NMe_2$, $R^{3.4}$ denotes H or methyl;

$R^{3.5}$ denotes a group selected from among pyrrolidinyl, piperidinyl, piperazinyl, morpholinyl, cyclohexyl, imidazolyl, pyrazolyl, phenyl, pyridinyl, benzimidazolyl, imidazolidin-2-one, pyrrolidin-2-one, pyrrolidin-3-one, tetrahydrothiophene-1,1-dioxide, and 1-azabicyclo[2.2.2]octane, which may optionally be substituted by one or more groups selected independently of one another from among methyl, ethyl, OH, phenyl, pyridinyl, pyrazolyl, pyrrolidinyl, $(CH_2)_o$—$R^{3.5.1}$, O—$(CH_2)_o$—$R^{3.5.1}$, and NH—$(CH_2)_o$—$R^{3.5.1}$, wherein: o denotes 0, 1, or 2, and $R^{3.5.1}$ denotes a group selected from among phenyl, pyrrolidinyl, piperidinyl, and imidazolidin-2-one, which may optionally be substituted by methyl; or $R^3$ denotes a group of formula 1d

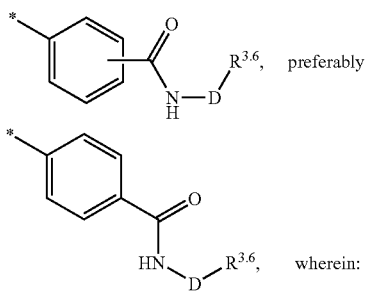

denotes $C_{2-4}$-alkynyl;
$R^{3.6}$ denotes pyridinyl; or
$R^3$ denotes a group $COR^{3.7}$, $COCH_2R^{3.8}$, $CONHR^{3.8}$, $SO_2R^{3.8}$, or a group of formula 1e

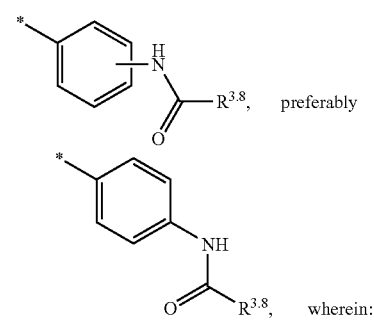

$R^{3.7}$ denotes H, methyl, or phenyl;
$R^{3.8}$ denotes a group selected from among isopropyl, cyclopropyl, cyclopentyl, cyclohexyl, pyrrolidinyl, pyrrolidin-2-one, furanyl, and azabicyclo[2.2.2]octanyl or a group selected from among piperidinyl, pyrazolyl, imidazolyl, isoxazolyl, pyridinyl, phenyl, benzyl, which may optionally be substituted by one or more groups selected from among methyl, chlorine, $NH_2$, $NMe_2$, phenyl, and morpholinyl;
$R^4$ denotes H, methyl, or oxo;
$R^5$ denotes H or methyl;
$R^6$ denotes H or methyl;
$R^7$ denotes H, methyl, or OH; preferably H or methyl;
$R^8$ denotes H, methyl, or OH; preferably H or methyl; or
$R^7$ and $R^8$ together form oxo;

and the pharmacologically acceptable salts, diastereomers, enantiomers, racemates, hydrates, or solvates thereof.

Preferred compounds of formula 1 above are those wherein:
X denotes S, SO, or $SO_2$;
$R^1$ denotes H, methyl, or ethyl;
$R^2$ denotes a group selected from H, ethyl, n-propyl, isopropyl, n-butyl, n-pentyl, n-hexyl,

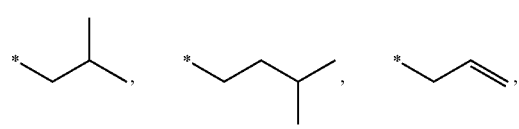

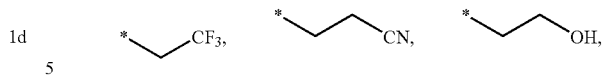

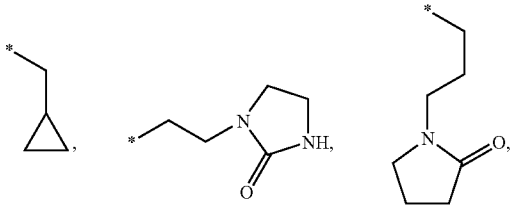

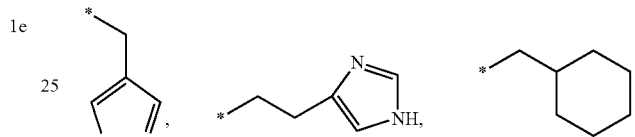

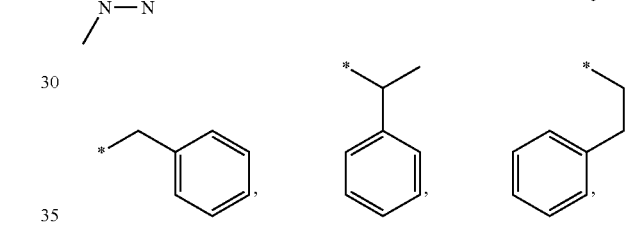

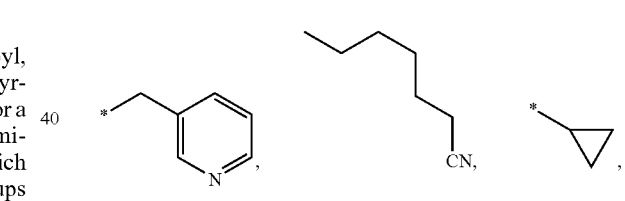

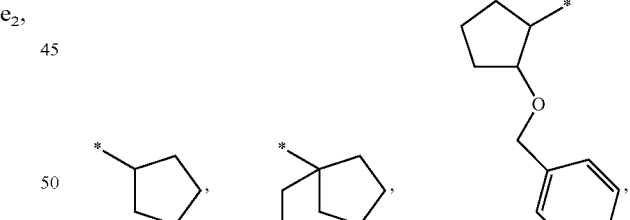

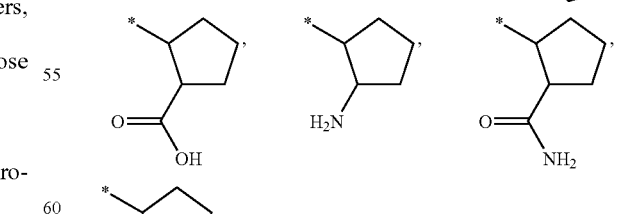

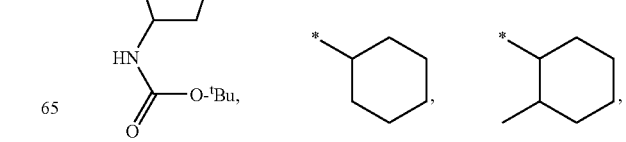

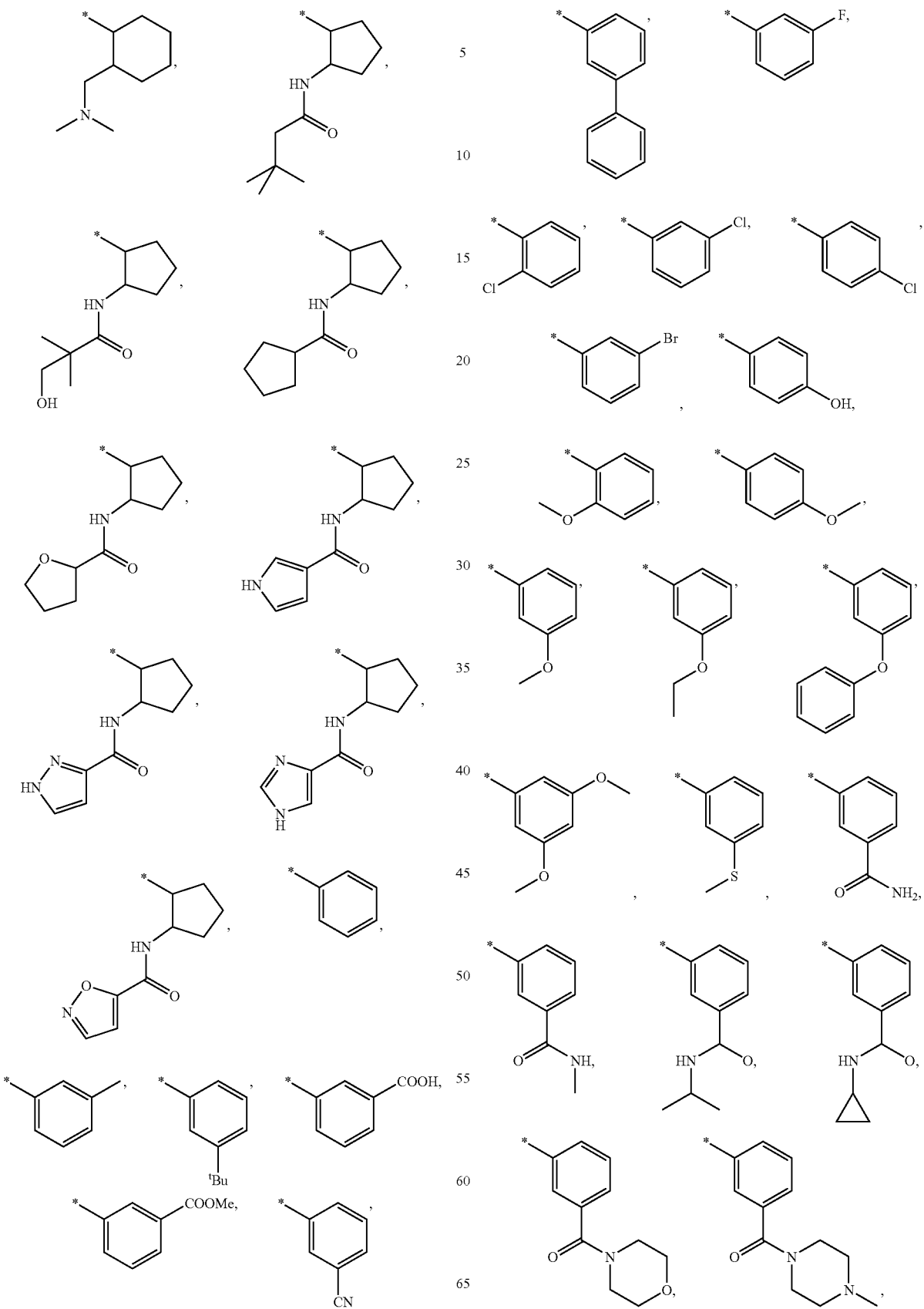

-continued
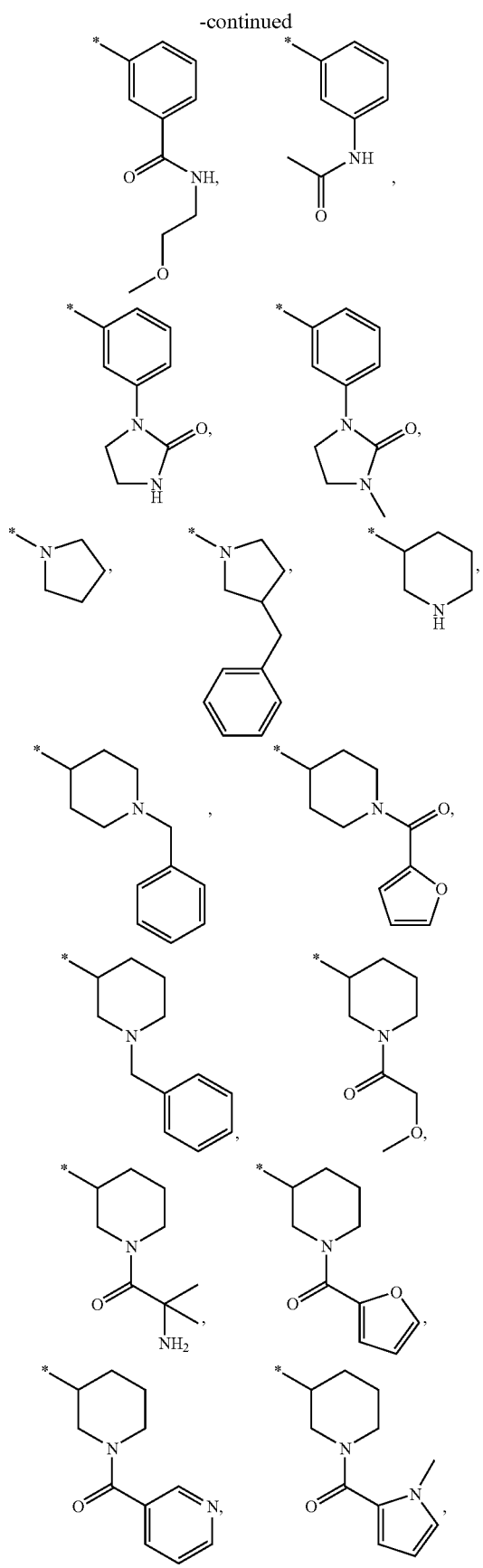
-continued
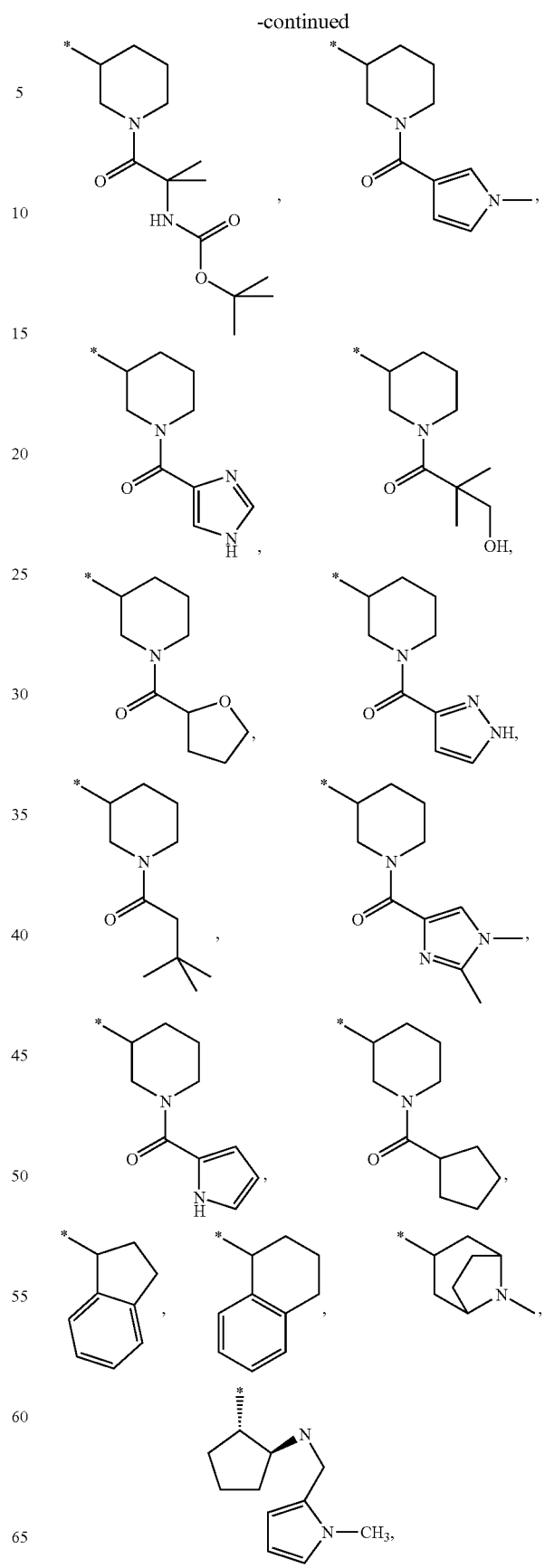

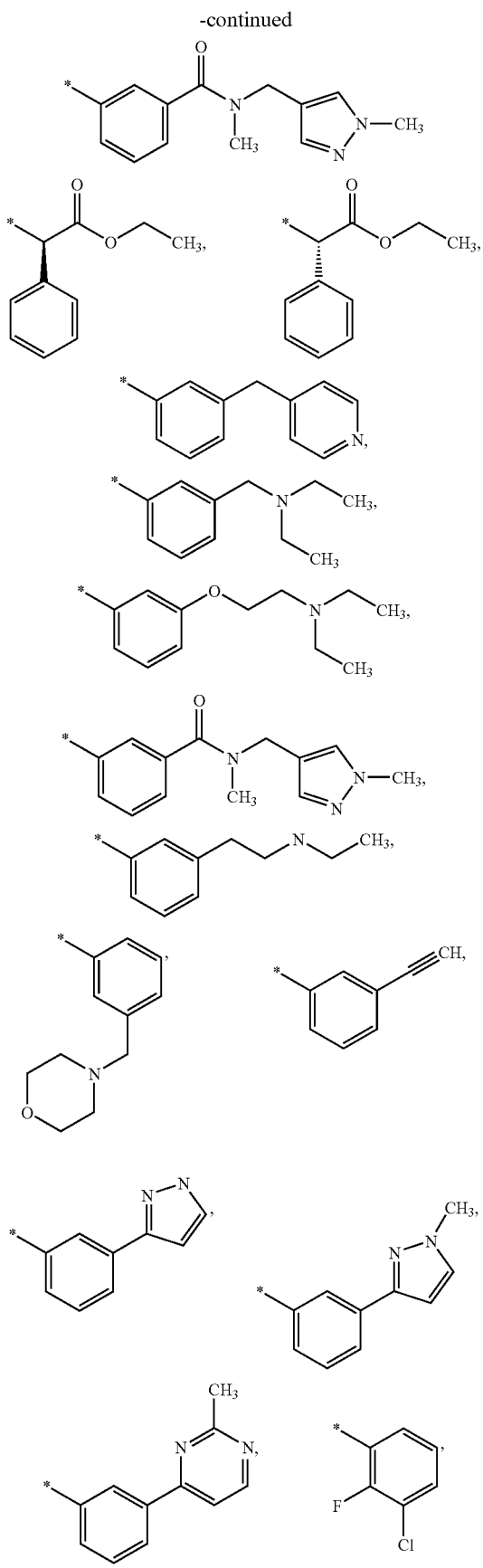
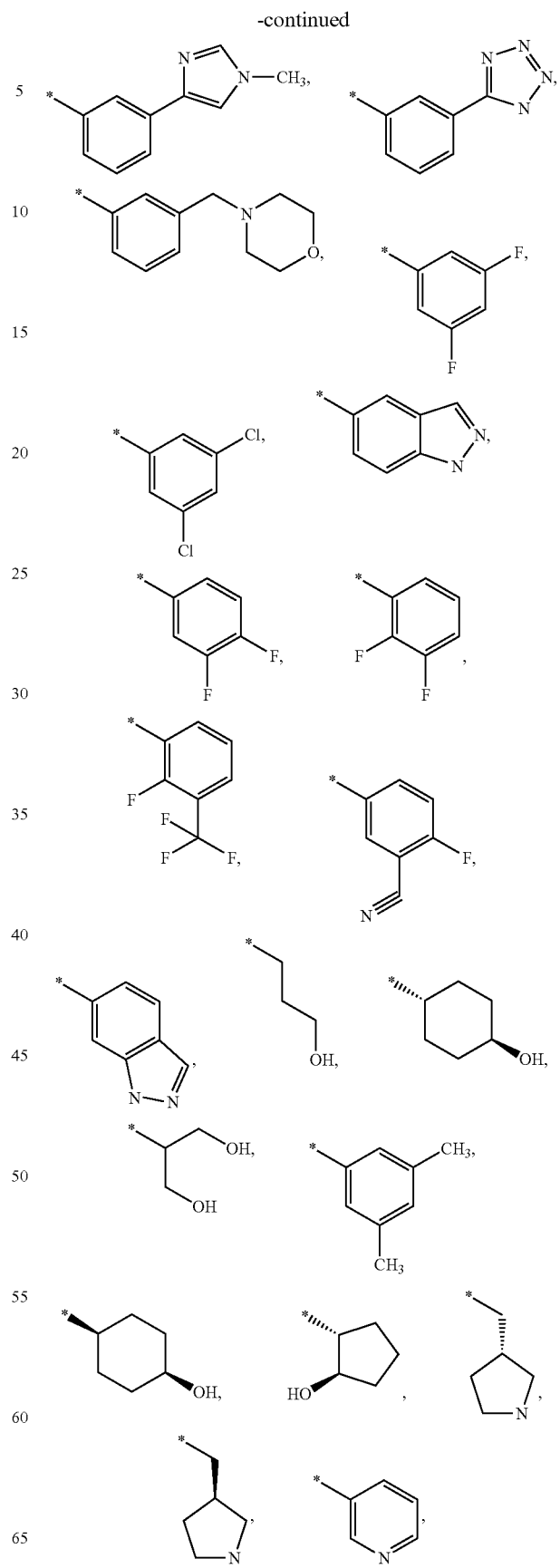

-continued
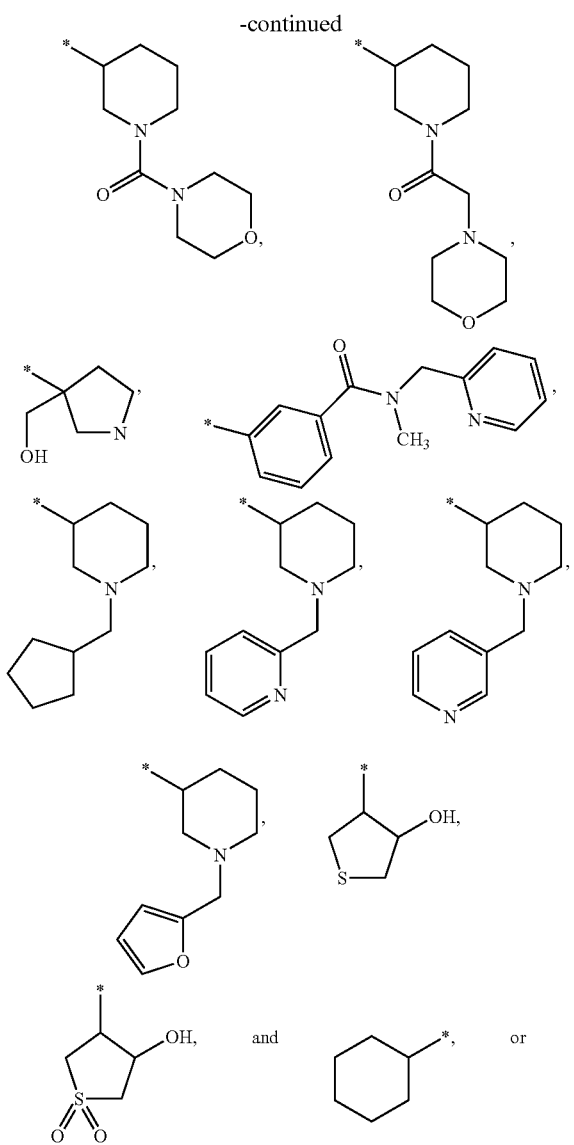
NR¹R² denotes a group selected from among
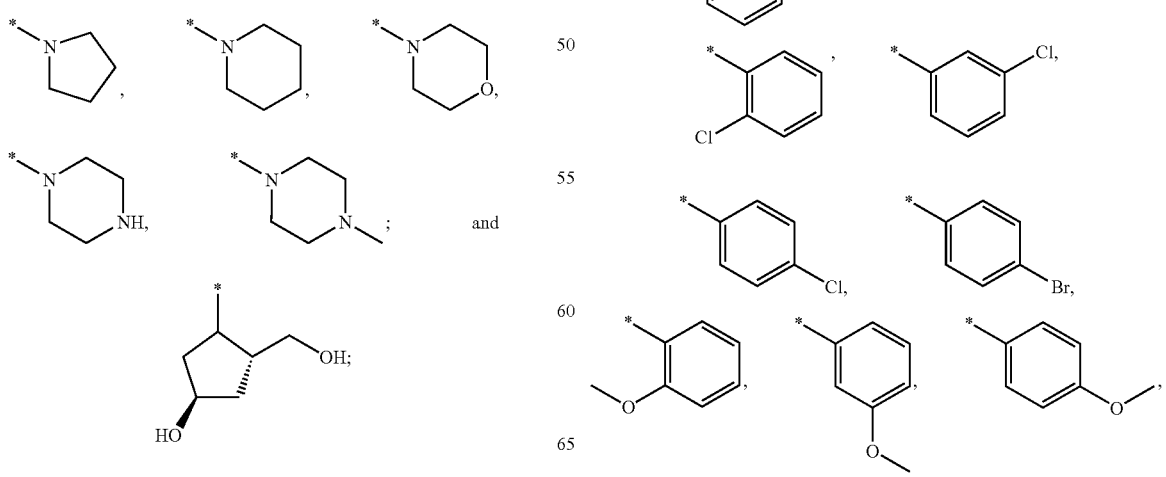
R³ denotes a group selected from among
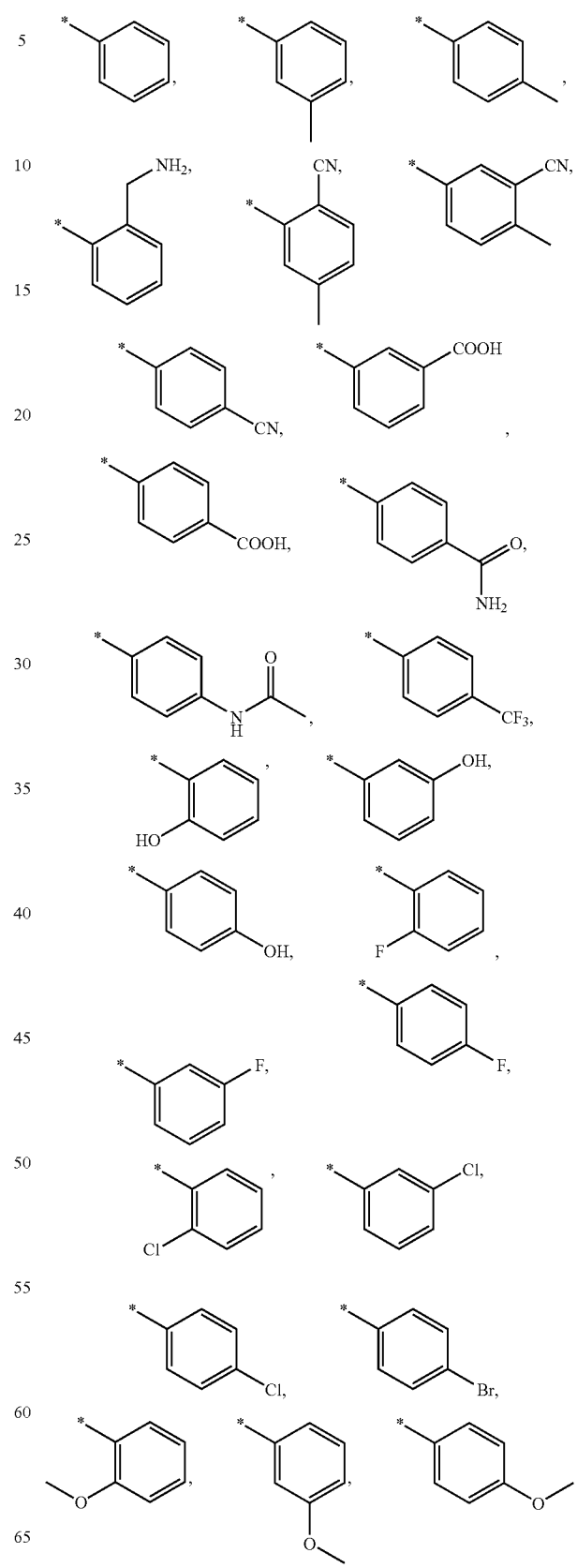

-continued
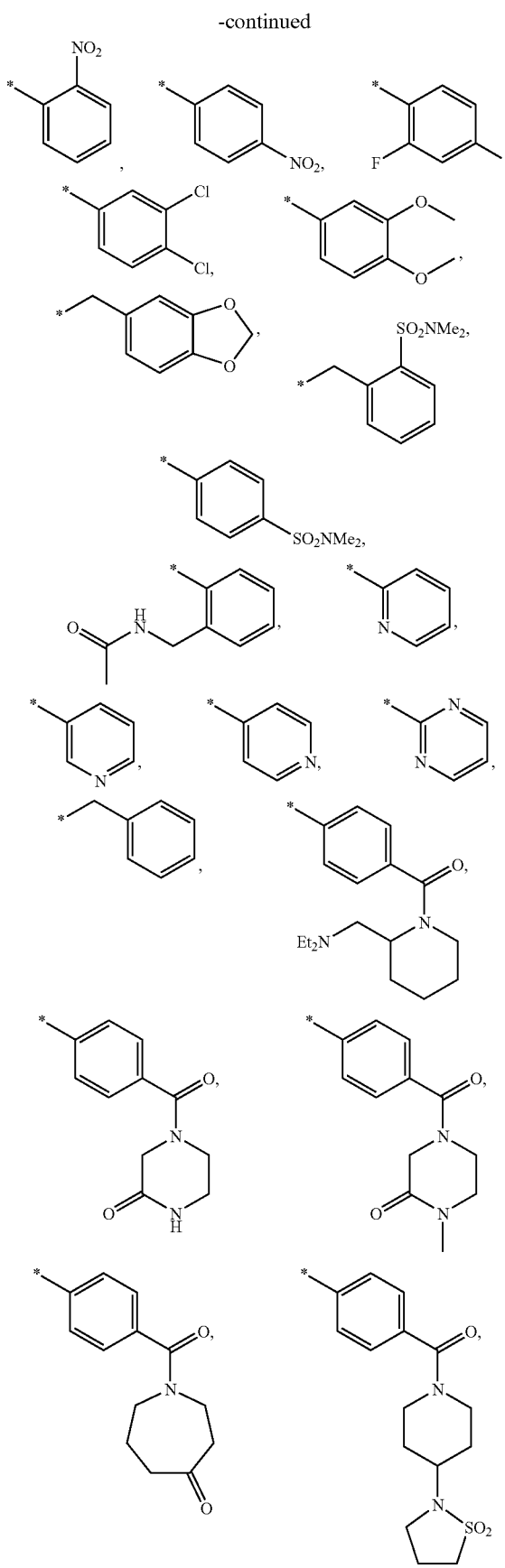
-continued
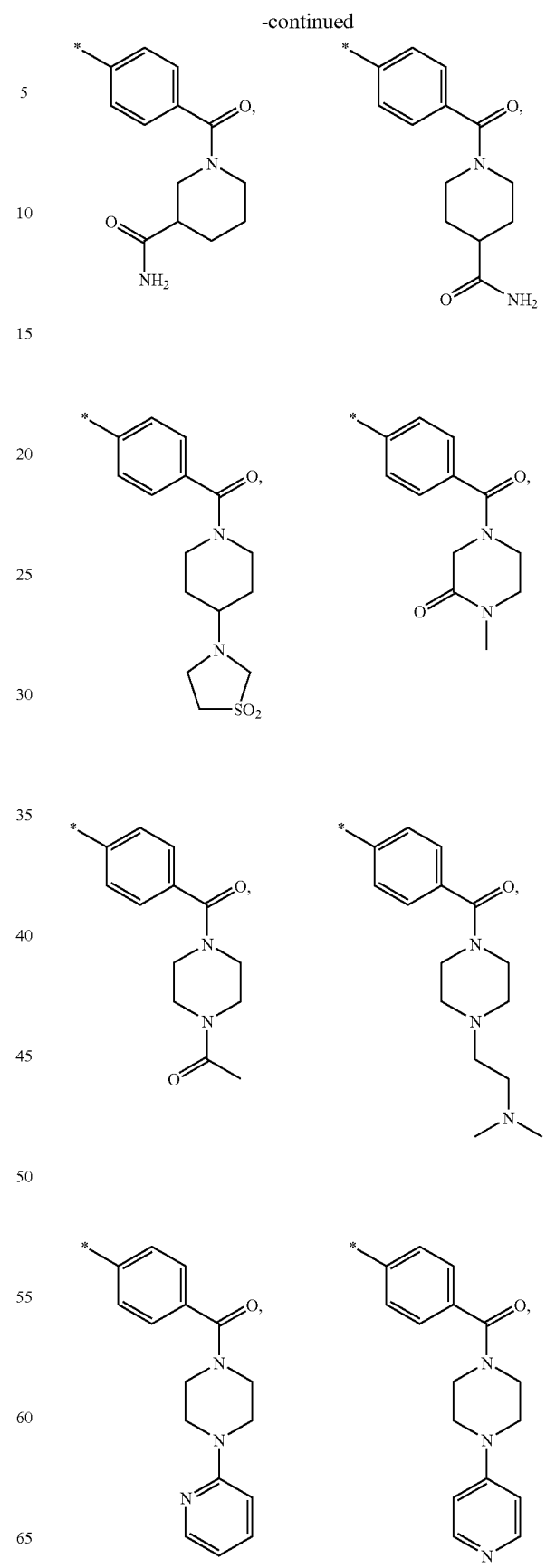

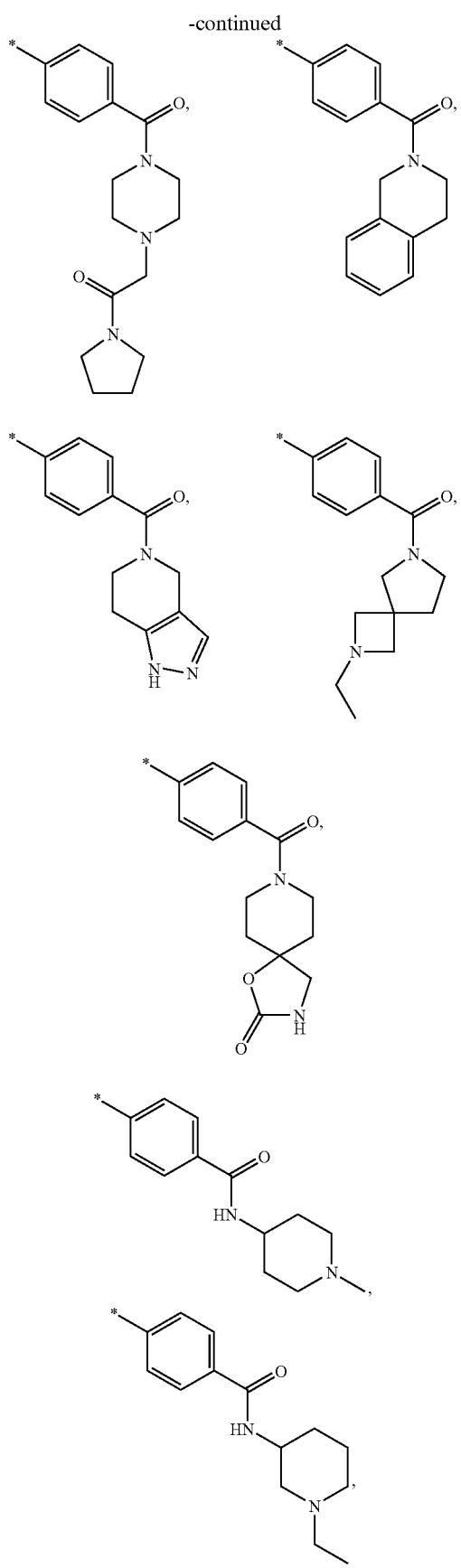

-continued
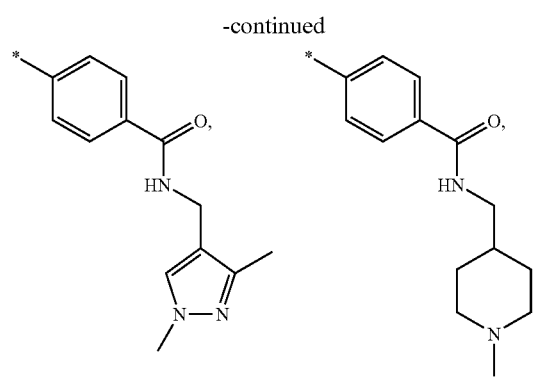
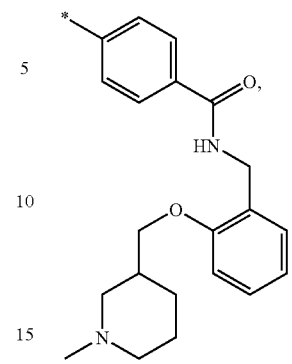
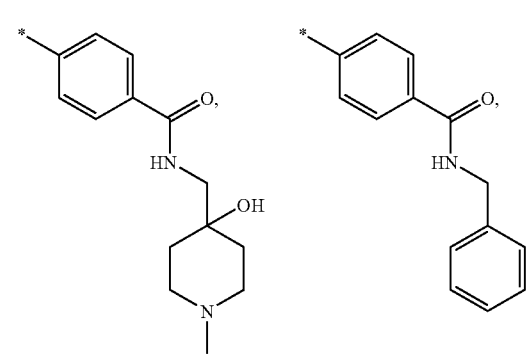
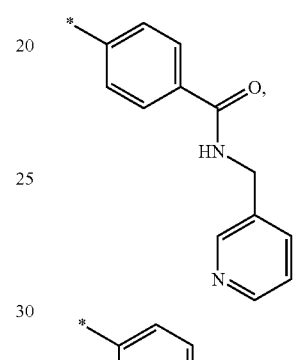
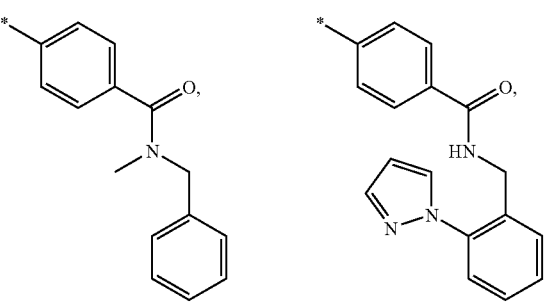
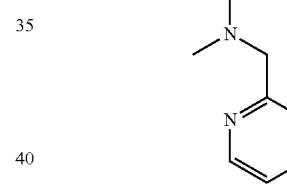
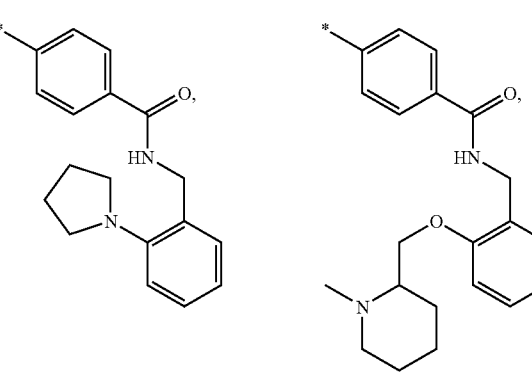
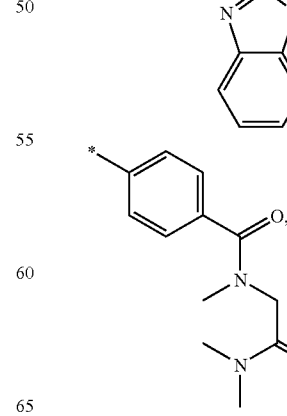
-continued
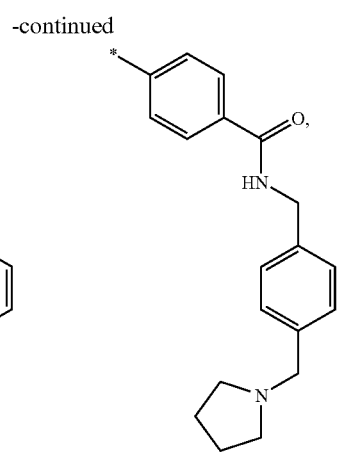
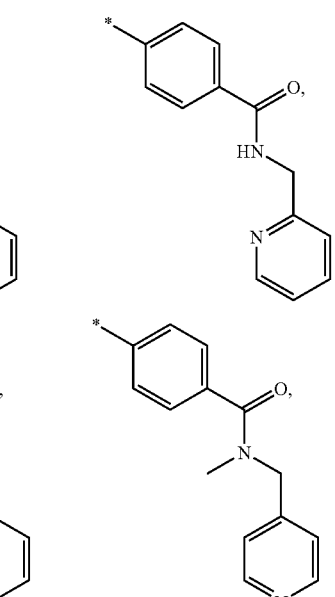
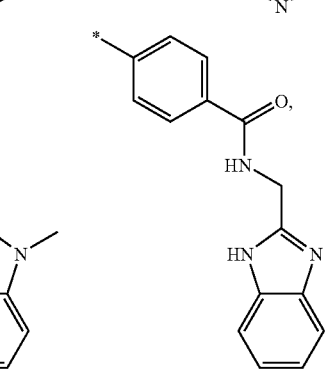
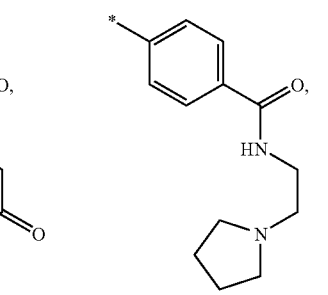

-continued
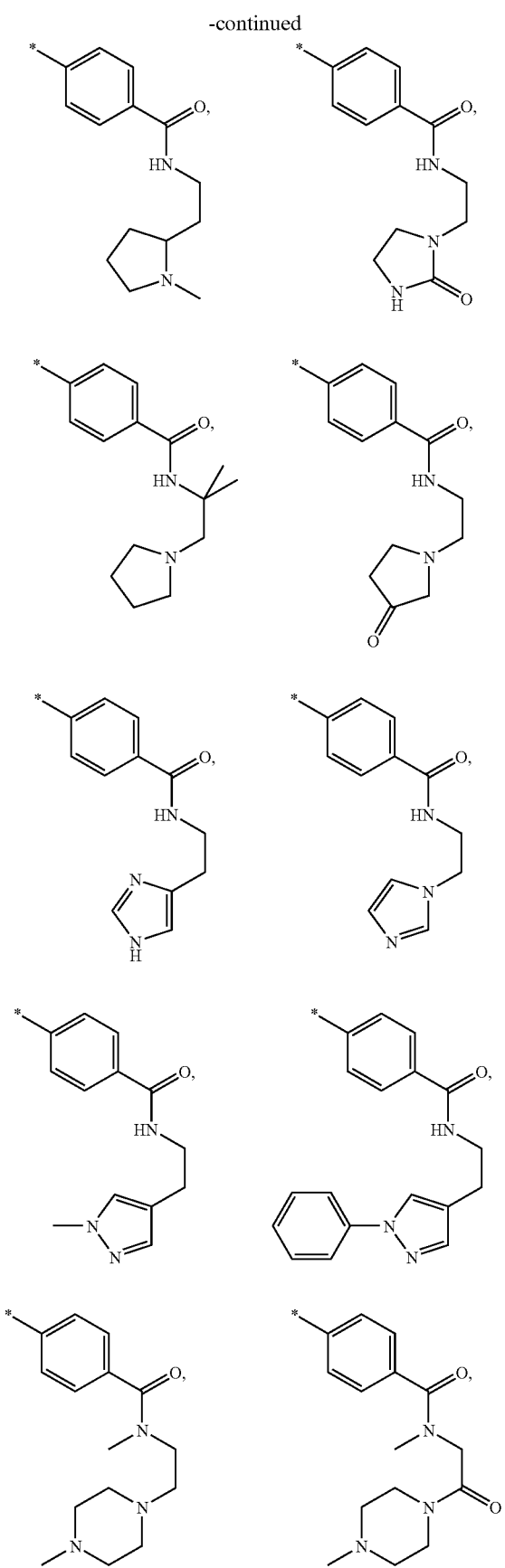 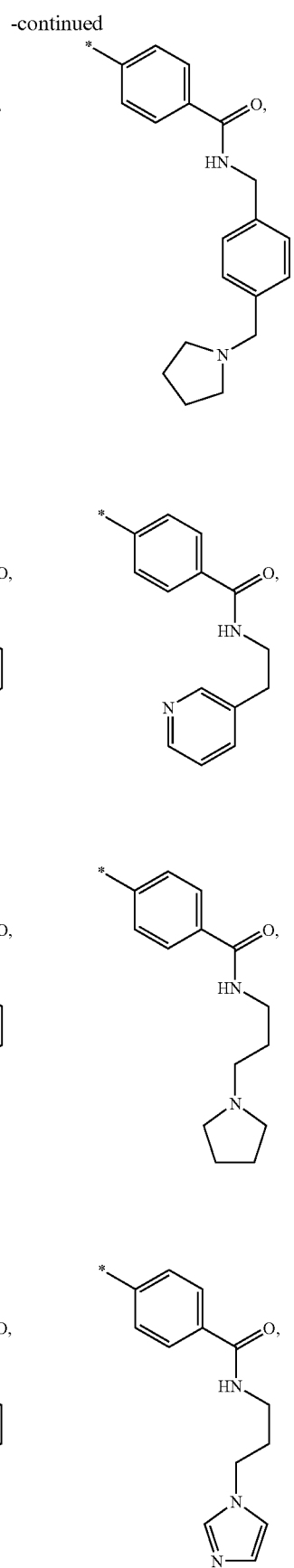

-continued
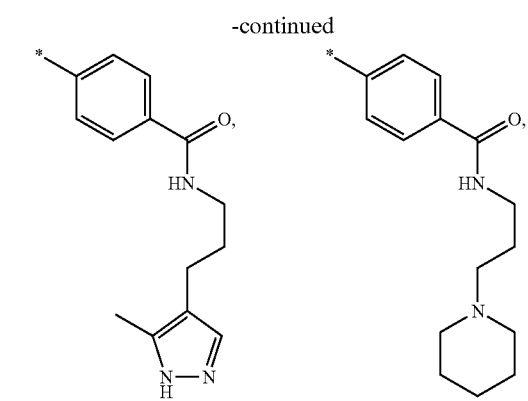
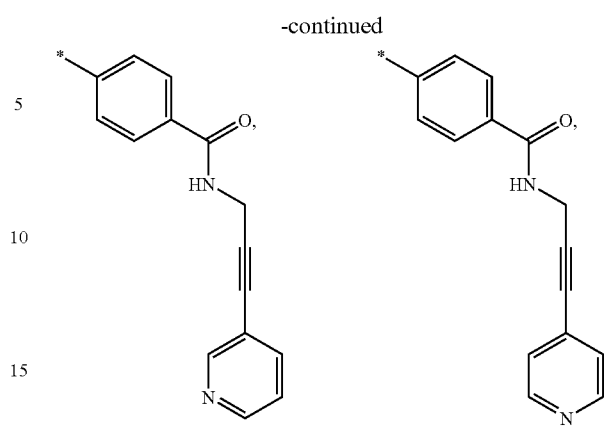
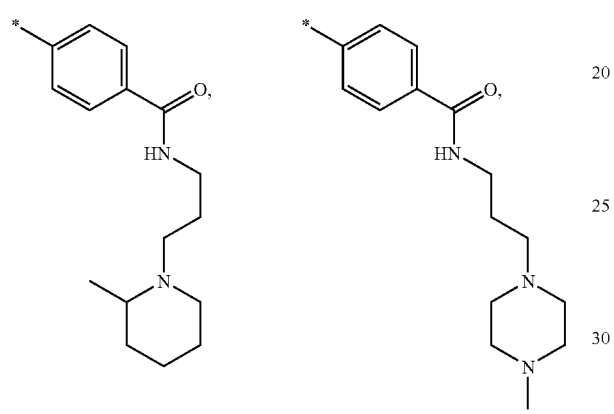
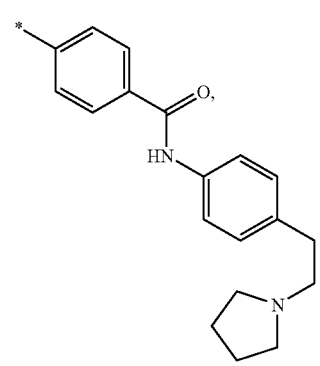
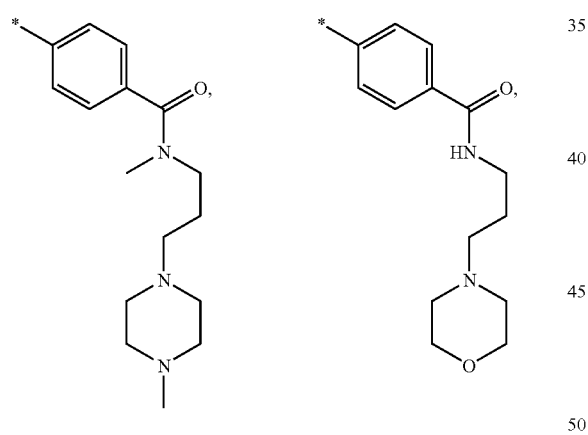
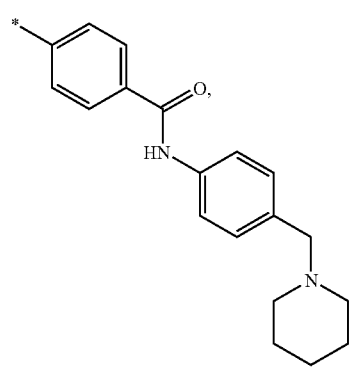
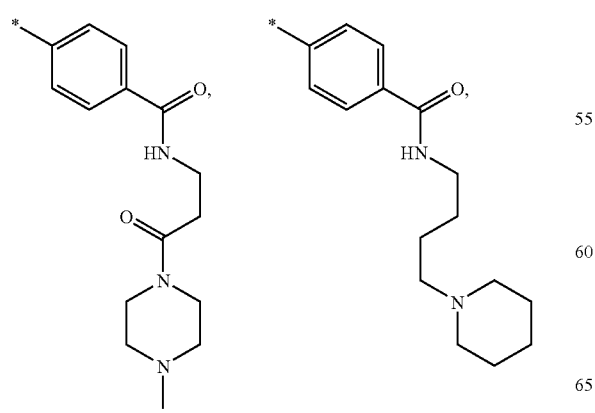
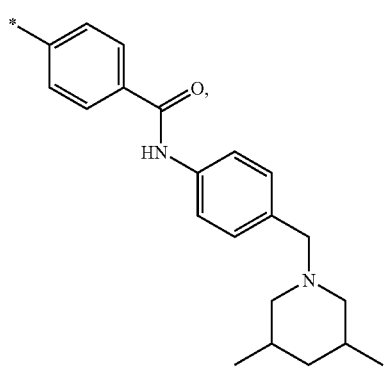

-continued
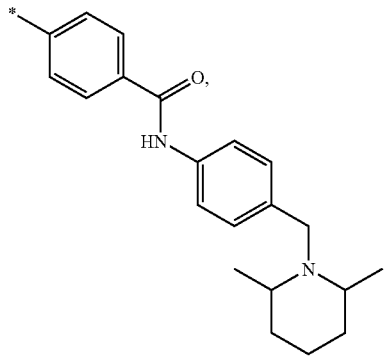
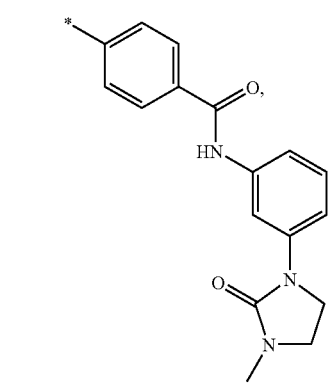
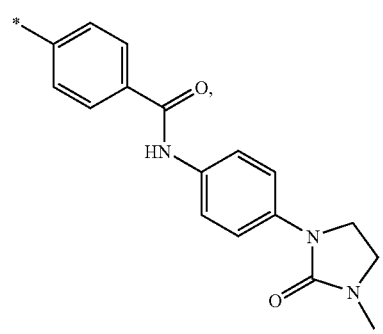
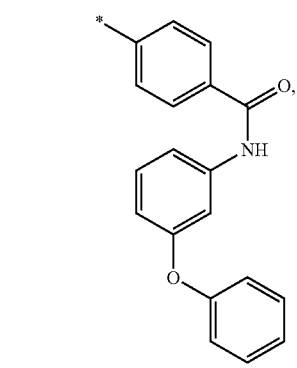
-continued
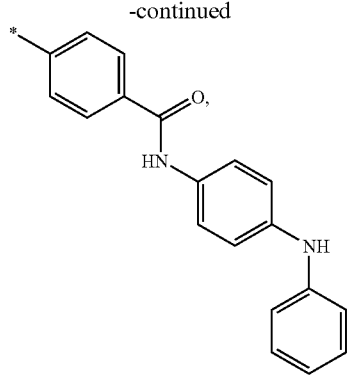
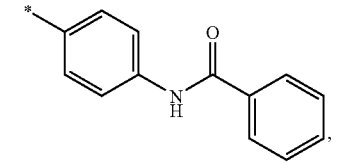
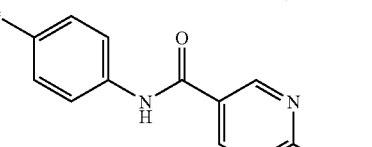
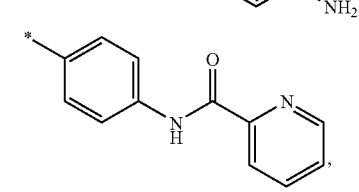
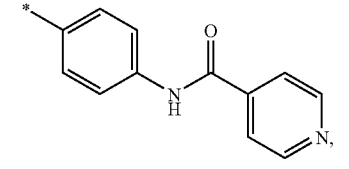
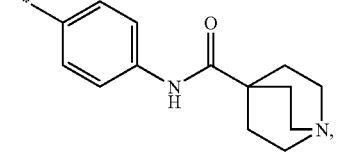
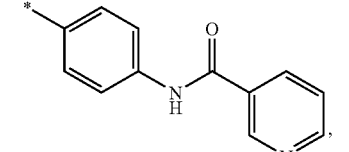
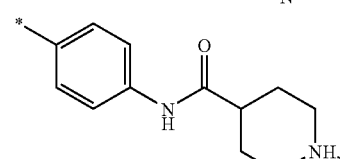
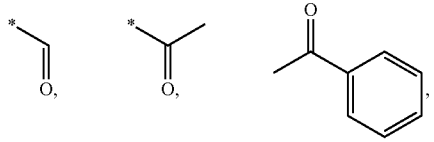

-continued
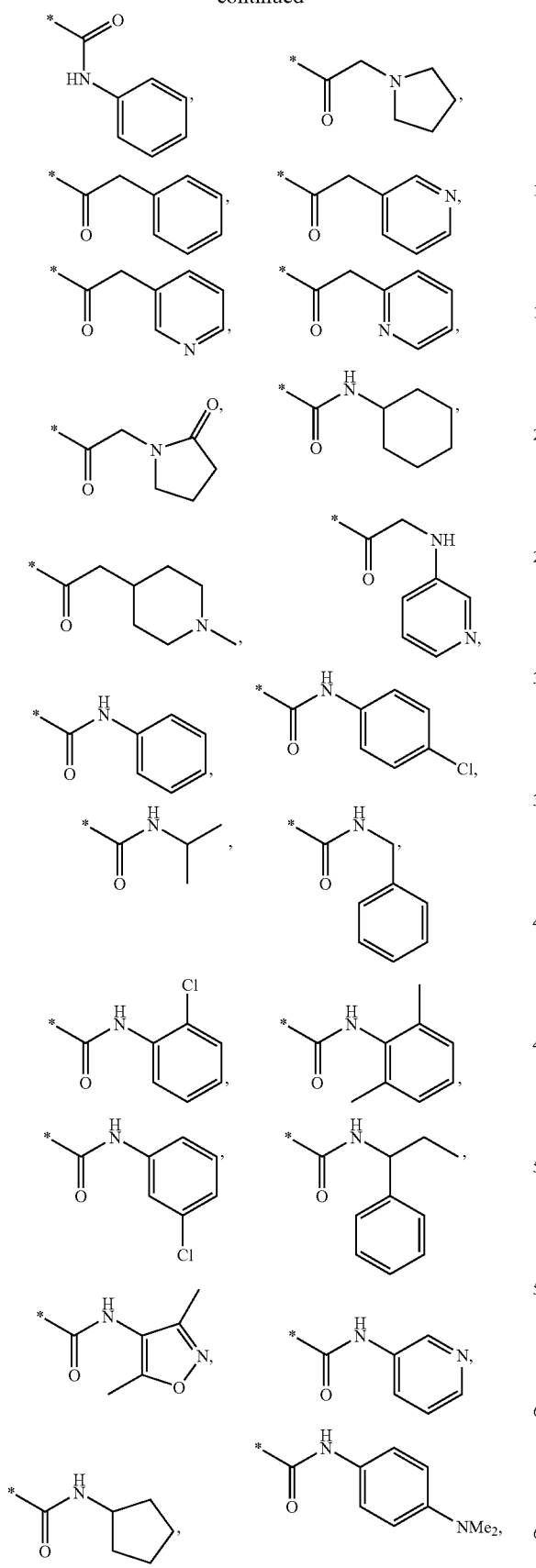
-continued
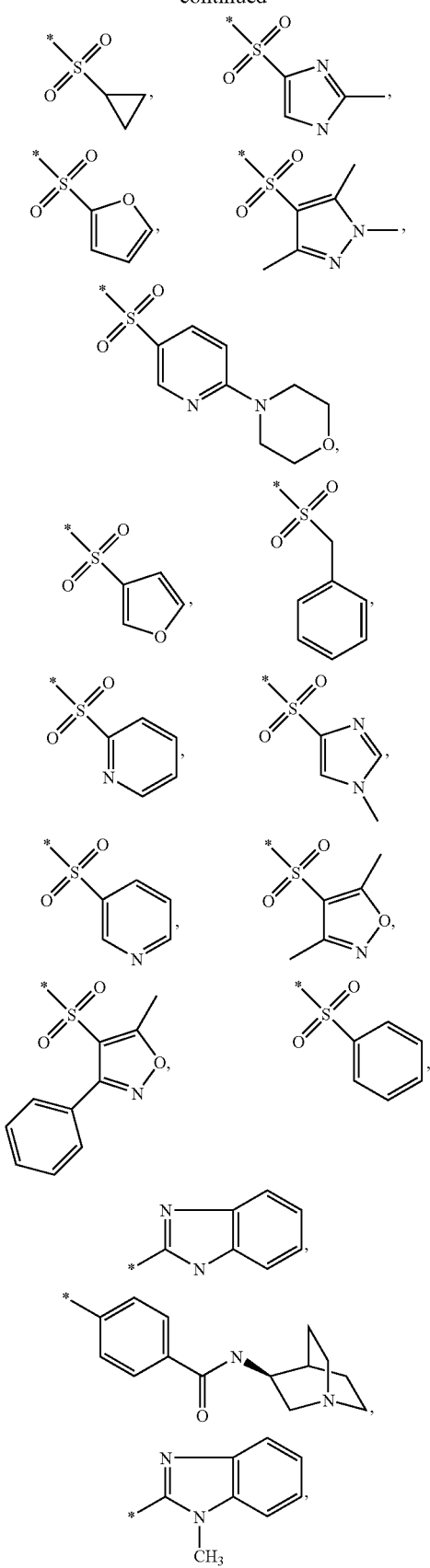

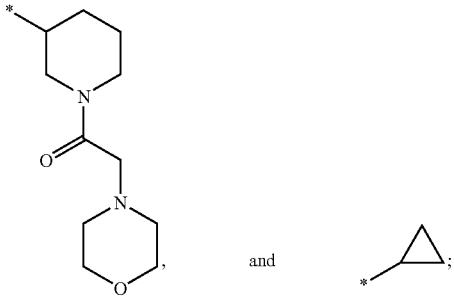

$R^4$ denotes H, methyl, or oxo;
$R^5$ denotes H or methyl;
$R^6$ denotes H or methyl;
$R^7$ denotes H or methyl; and
$R^8$ denotes H or methyl;

and the pharmacologically acceptable salts, diastereomers, enantiomers, racemates, hydrates, or solvates thereof.

Particularly preferred are the above compounds of formula 1, wherein X, $R^2$, $R^3$, $R^4$, $R^5$, $R^6$, $R^7$, and $R^8$ are as hereinbefore defined and $R^1$ denotes H; and the pharmacologically acceptable salts, diastereomers, enantiomers, racemates, hydrates, or solvates thereof.

Particularly preferred are the above compounds of formula 1, wherein $R^1$, $R^2$, $R^3$, $R^4$, $R^5$, $R^6$, $R^7$, and $R^8$ are as hereinbefore defined and X denotes SO; and the pharmacologically acceptable salts, diastereomers, enantiomers, racemates, hydrates, or solvates thereof.

Particularly preferred are the above compounds of formula 1, wherein $R^1$, $R^3$, $R^4$, and X are as hereinbefore defined and $R^5$, $R^6$, $R^7$, and $R^8$ denote H; and the pharmacologically acceptable salts, diastereomers, enantiomers, racemates, hydrates, or solvates thereof.

Particularly preferred are the above compounds of formula 1, wherein $R^1$, $R^2$, $R^3$, $R^5$, $R^6$, $R^7$, $R^8$, and X are as hereinbefore defined and $R^4$ denotes H; and the pharmacologically acceptable salts, diastereomers, enantiomers, racemates, hydrates, or solvates thereof.

Particularly preferred are the above compounds of formula 1, wherein $R^1$, $R^3$, $R^4$, $R^5$, $R^7$, $R^8$, and X are as hereinbefore defined and wherein $R^2$ denotes $C_{6-10}$-aryl, which may optionally be substituted by one or more groups selected independently of one another from among $C_{1-6}$-alkyl, $C_{1-4}$-haloalkyl, $C_{2-6}$-alkenyl, $C_{2-6}$-alkynyl, CN, halogen, $OR^{2.8}$, $COOR^{2.8}$, $COR^{2.10}$, $NR^{2.8}R^{2.9}$, $NHCOR^{2.8}$, $SR^{2.8}$, $SOR^{2.8}$, $SO_2R^{2.8}$, and $SO_2NR^{2.8}R^{2.9}$, or $R^2$ denotes $C_{6-10}$-aryl, which may optionally be substituted by one or more groups selected from among $C_{6-10}$-aryl-$C_{1-6}$-alkylene, $C_{5-10}$-heteroaryl-$C_{1-6}$-alkylene, $C_{6-10}$-aryl, and a heterocyclic $C_{3-10}$ ring, which may optionally be substituted by a group selected from among $C_{1-6}$-alkyl, $C_{1-6}$-haloalkyl, $COOR^{2.8}$, CN, halogen, $OR^{2.8}$, $NHCOR^{2.8}$, oxo, a $C_{3-7}$-cycloalkyl-$C_{1-4}$ alkylene, a heterocycle-$C_{1-4}$ alkylene, and a $NR^{2.1}R^{2.2}$—$C_{1-4}$-alkylene, wherein:

$R^{2.8}$ denotes H, $C_{1-6}$-alkyl, $C_{2-6}$-alkenyl, $C_{2-6}$-alkynyl, a $NR^{2.1}R^{2.2}$—$C_{1-4}$-alkylene, or $C_{6-10}$-aryl;
$R^{2.9}$ denotes H, $C_{1-6}$-alkyl, $C_{2-6}$-alkenyl, or $C_{2-6}$-alkynyl;
$R^{2.10}$ denotes $NHR^{2.10.1}$, $C_{1-6}$-alkylene-O—$C_{1-4}$-alkyl, or a heterocyclic $C_{3-10}$ ring which may optionally be substituted by $C_{1-4}$-alkyl, wherein $R^{2.10.1}$ denotes H, $C_{1-6}$-alkyl, $C_{2-6}$-alkenyl, $C_{2-6}$-alkynyl, or $C_{3-7}$-cycloalkyl; or $R^2$ denotes $C_{6-10}$-aryl, to which an aromatic or non-aromatic $C_{3-10}$ heterocycle is fused; or
$R^2$ denotes $C_{6-10}$-aryl, which may optionally be substituted by a group selected from among $C_{6-10}$-aryl and a heterocyclic $C_{3-10}$ ring, which is optionally substituted by one or more groups selected from among $C_{1-6}$-alkyl, $C_{2-6}$-alkenyl, $C_{2-6}$-alkynyl, $C_{1-4}$-haloalkyl, CN, halogen, $OR^{2.8}$, $COOR^{2.8}$, $COR^{2.10}NR^{2.8}R^{2.9}$, $NHCOR^{2.8}$, $SR^{2.8}$, $SOR^{2.8}$, $SO_2R^{2.8}$, $SO_2NR^{2.8}R^{2.9}$, and oxo;

and the pharmacologically acceptable salts, diastereomers, enantiomers, racemates, hydrates, or solvates thereof.

Particularly preferred are the above compounds of formula 1, wherein X, $R^1$, $R^3$, $R^4$, $R^5$, $R^6$, $R^7$, and $R^8$ are as hereinbefore defined, and $R^2$ denotes $C_{6-10}$-aryl, optionally substituted by one or more groups selected independently of one another from among $C_{1-6}$-alkyl, $C_{2-6}$-alkenyl, $C_{2-6}$-alkynyl, $C_{1-4}$-haloalkyl, CN, halogen, $OR^{2.8}$, $COOR^{2.8}$, $COR^{2.10}$, $NR^{2.8}R^{2.9}$, $NHCOR^{2.8}$, $SR^{2.8}$, $SOR^{2.8}$, $SO_2R^{2.8}$, and $SO_2NR^{2.8}R^{2.9}$, wherein:

$R^{2.8}$ denotes H, $C_{1-6}$-alkyl, $C_{2-6}$-alkenyl, $C_{2-6}$-alkynyl, or $C_{6-10}$-aryl;
$R^{2.9}$ denotes H, $C_{1-6}$-alkyl, $C_{2-6}$-alkenyl, or $C_{2-6}$-alkynyl;
$R^{2.10}$ denotes $NHR^{2.10.1}$ $C_{1-6}$-alkylene-O—$C_{1-4}$-alkyl, or a heterocyclic $C_{3-10}$ ring, optionally substituted by $C_{1-4}$-alkyl, wherein $R^{2.10.1}$ denotes H, $C_{1-6}$-alkyl, $C_{2-6}$-alkenyl, $C_{2-6}$-alkynyl, or $C_{3-7}$-cycloalkyl; or $R^2$ denotes $C_{6-10}$-aryl, optionally substituted by a group selected from among $C_{6-10}$-aryl and a heterocyclic $C_{3-10}$ ring, optionally substituted by $C_{1-6}$-alkyl, $C_{2-6}$-alkenyl, $C_{2-6}$-alkynyl, $C_{1-4}$-haloalkyl, CN, halogen, $OR^{2.8}$, $COOR^{2.8}$, $COR^{2.10}NR^{2.8}R^{2.9}$, $NHCOR^{2.8}$, $SR^{2.8}$, $SOR^{2.8}$, $SO_2R^{2.8}$, $SO_2NR^{2.8}$ $R^{2.9}$, and oxo;

and the pharmacologically acceptable salts, diastereomers, enantiomers, racemates, hydrates, or solvates thereof.

Particularly preferred are the above compounds of formula 1, wherein X, $R^1$, $R^3$, $R^4$, $R^5$, $R^6$, $R^7$, and $R^8$ are as hereinbefore defined, and $R^2$ denotes $C_{6-10}$-aryl, which may optionally be substituted by one or more groups selected from among $C_{1-4}$-alkyl, CN, halogen, $OR^{2.8}$, $COOR^{2.8}$, $COR^{2.10}$, and NHCOMe, wherein:

$R^{2.8}$ denotes $C_{1-4}$-alkyl or $C_{6-10}$-aryl;
$R^{2.10}$ denotes $NHR^{2.10.1}$, morpholinyl, or methylpiperazinyl, and $R^{2.10.1}$ denotes H, cyclopropyl, or $C_{1-4}$-alkyl, which may optionally be substituted by one or more groups selected from O—$C_{1-4}$-alkyl, OH, or $C_{6-10}$-aryl; or $R^2$ denotes $C_{6-10}$-aryl, which may optionally be substituted by a group selected from among phenyl and a heterocyclic $C_{3-10}$ ring, which may optionally be substituted by $C_{1-4}$-alkyl, $COOR^{2.8}$, CN, halogen, $OR^{2.8}$, NHCOMe, and oxo;

and the pharmacologically acceptable salts, diastereomers, enantiomers, racemates, hydrates, or solvates thereof.

Particularly preferred are the above compounds of formula 1, wherein X, $R^1$, $R^3$, $R^4$, $R^5$, $R^6$, $R^7$, and $R^8$ are as hereinbefore defined, and wherein:

$R^2$ denotes $C_{6-10}$-aryl, optionally substituted by one or more groups selected independently of one another from among methyl, tert-butyl, CN, F, Cl, Br, OH, OMe, OEt, O-phenyl, COOH, COOMe, $COR^{2.10}$, and NHCOMe and the pharmacologically acceptable salts, diastereomers, enantiomers, racemates, hydrates, or solvates thereof.

Particularly preferred are the above compounds of formula 1, wherein X, $R^1$, $R^3$, $R^4$, $R^5$, $R^6$, $R^7$, and $R^8$ are as hereinbefore defined and $R^2$ denotes

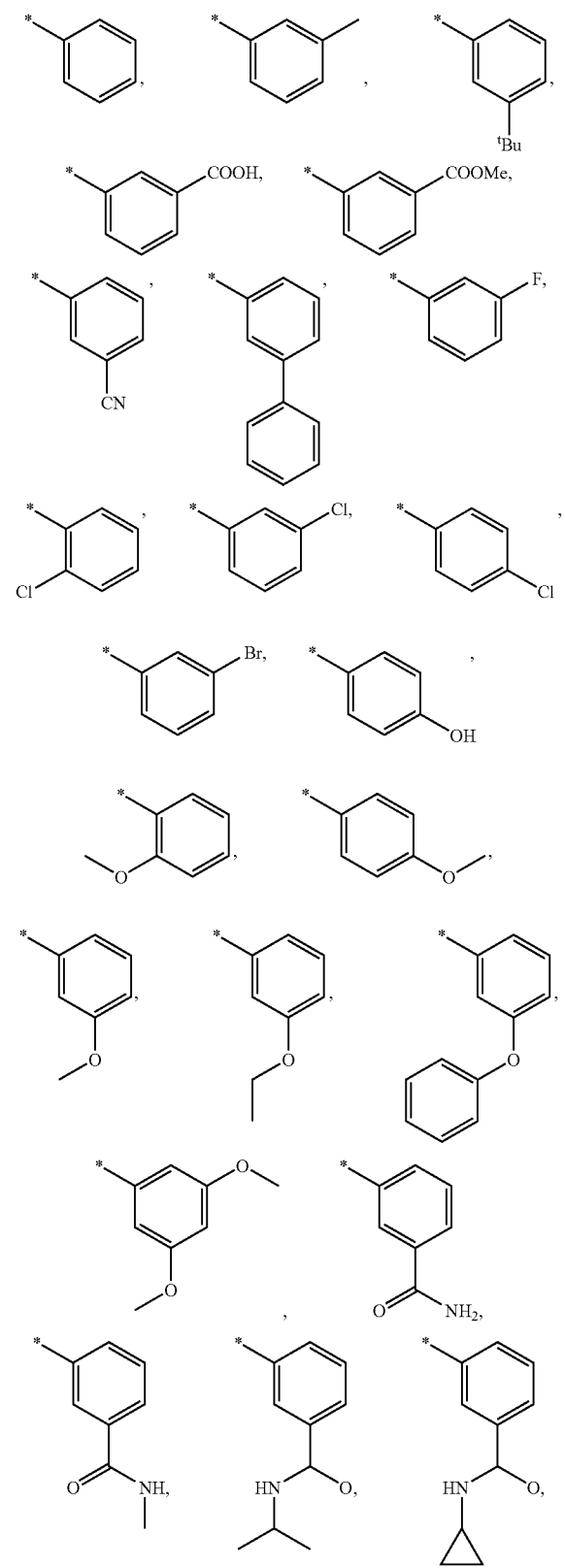

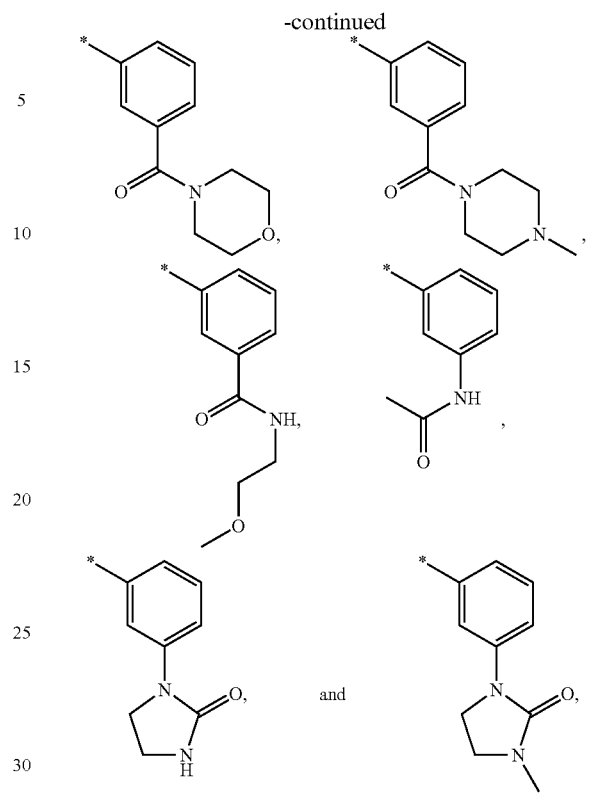

and the pharmacologically acceptable salts, diastereomers, enantiomers, racemates, hydrates, or solvates thereof.

Particularly preferred are the above compounds of formula 1, wherein X, $R^1$, $R^3$, $R^4$, $R^5$, $R^6$, $R^7$, and $R^8$ are as hereinbefore defined and $R^2$ denotes H; and the pharmacologically acceptable salts, diastereomers, enantiomers, racemates, hydrates, or solvates thereof.

Particularly preferred are the above compounds of formula 1, wherein X, $R^1$, $R^3$, $R^4$, $R^5$, $R^6$, $R^7$, and $R^8$ are as hereinbefore defined, and wherein:

$R^2$ denotes a group selected from among $C_{1-6}$-alkyl, $C_{2-6}$-alkenyl, and $C_{2-6}$-alkynyl; preferably $C_{1-6}$-alkyl; particularly preferably propyl, which may optionally be substituted by a group selected from among $C_{1-6}$-haloalkyl, CN, $OR^{2.1}$, $NR^{2.1}R^{2.2}$, $COOR^{2.1}$, $NHCOR^{2.1}$, $SR^{2.1}$, $SOR^{2.1}$, $SO_2R^{2.1}$, and $CONR^{2.1}R^{2.2}$, preferably by a group selected from among $C_{1-4}$-haloalkyl, CN, $OR^{2.1}$, $NR^{2.1}R^{2.2}$, $COOR^2$, and $CONR^{2.1}R^{2.2}$ or which may optionally be substituted by a group selected from among $C_{3-7}$-cycloalkyl, $C_{6-10}$-aryl, and a heterocyclic, aromatic $C_{3-10}$ ring, which may in turn optionally be substituted by $C_{1-6}$-alkyl, $C_{2-6}$-alkenyl, $C_{2-6}$-alkynyl, or oxo; preferably by methyl or oxo, wherein:

$R^{2.1}$ denotes H or is selected from among $C_{1-4}$-alkyl, $C_{2-6}$-alkenyl, or $C_{2-6}$-alkynyl, preferably H or $C_{1-4}$-alkyl; and $R^{2.2}$ denotes H or is selected from among $C_{1-4}$-alkyl, $C_{2-6}$-alkenyl, or $C_{2-6}$-alkynyl, preferably H or $C_{1-4}$-alkyl;

and the pharmacologically acceptable salts, diastereomers, enantiomers, racemates, hydrates, or solvates thereof.

Particularly preferred are the above compounds of formula 1, wherein X, $R^1$, $R^3$, $R^4$, $R^5$, $R^6$, $R^7$, and $R^8$ are as hereinbefore defined, and $R^2$ denotes a group selected from among $C_{1-6}$-alkyl, $C_{2-6}$-alkenyl, and $C_{2-6}$-alkynyl; preferably $C_{1-6}$-alkyl; particularly preferably propyl, optionally substituted by a group selected from among $C_{1-6}$-haloalkyl, CN, $OR^{2.1}$, $NR^{2.1}R^{2.2}$, $NHCOR^{2.1}$, $SR^{2.1}$, $SOR^{2.1}$, $SO^{2.1}$, $SO_2NR^{2.1}R^{2.2}$, $COOR^{2.1}$, and $CONR^{2.1}R^{2.2}$ or optionally substituted by a group selected from among $C_{3-7}$-cycloalkyl, $C_{6-10}$-aryl, and a heterocyclic $C_{3-10}$ ring, optionally substituted by $C_{1-6}$-alkyl, $C_{2-6}$-alkenyl, $C_{2-6}$-alkynyl, or oxo, wherein:

$R^{2.1}$ denotes H, $C_{1-6}$-alkyl, $C_{2-6}$-alkenyl, or $C_{2-6}$-alkynyl; and $R^{2.2}$ denotes H, $C_{1-6}$-alkyl, $C_{2-6}$-alkenyl, or $C_{2-6}$-alkynyl;

and the pharmacologically acceptable salts, diastereomers, enantiomers, racemates, hydrates, or solvates thereof.

Particularly preferred are the above compounds of formula 1, wherein X, $R^1$, $R^3$, $R^4$, $R^5$, $R^6$, $R^7$, and $R^8$ are as hereinbefore defined, and $R^2$ denotes $C_{1-6}$-alkyl, which may optionally be substituted by a group selected from among $C_{1-4}$-haloalkyl, CN, $OR^{2.1}$, $NR^{2.1}R^{2.2}$, $COOR^{2.1}$, and $CONR^{2.1}R^{2.2}$ or which may optionally be substituted by a group selected from among $C_{3-7}$-cycloalkyl, $C_{6-10}$-aryl, and a heterocyclic, aromatic $C_{3-10}$ ring, which may in turn optionally be substituted by methyl or oxo, wherein:

$R^{2.1}$ denotes H or $C_{1-4}$-alkyl; and $R^{2.2}$ denotes H or $C_{1-4}$-alkyl;

and the pharmacologically acceptable salts, diastereomers, enantiomers, racemates, hydrates, or solvates thereof.

Particularly preferred are the above compounds of formula 1, wherein X, $R^1$, $R^3$, $R^4$, $R^5$, $R^6$, $R^7$, and $R^8$ are as hereinbefore defined, and $R^2$ denotes $C_{1-6}$-alkyl; preferably propyl; particularly preferably n-propyl, optionally substituted by a group selected from among $CF_3$, CN, OH, $NMe_2$, OMe, COOH, and $CONMe_2$ or optionally substituted by a group selected from among cyclopropyl, cyclopentyl, cyclohexyl, phenyl, pyrrolidinyl, imidazolidinyl, pyrazolyl, imidazolyl, and pyridinyl, optionally substituted by methyl or oxo;

and the pharmacologically acceptable salts, diastereomers, enantiomers, racemates, hydrates, or solvates thereof.

Particularly preferred are the above compounds of formula 1, wherein X, $R^1$, $R^3$, $R^4$, $R^5$, $R^6$, $R^7$, and $R^8$ are as hereinbefore defined, and wherein $R^2$ denotes a group selected from among ethyl, n-propyl, isopropyl, n-butyl, n-pentyl, n-hexyl,

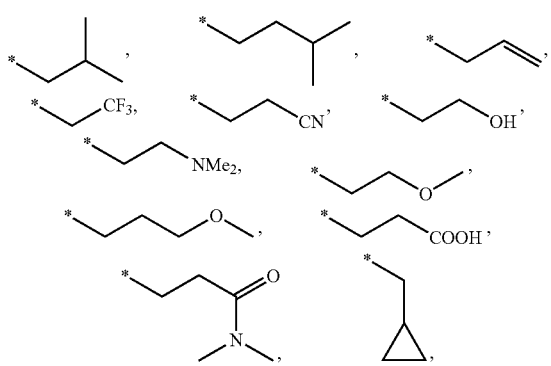

-continued

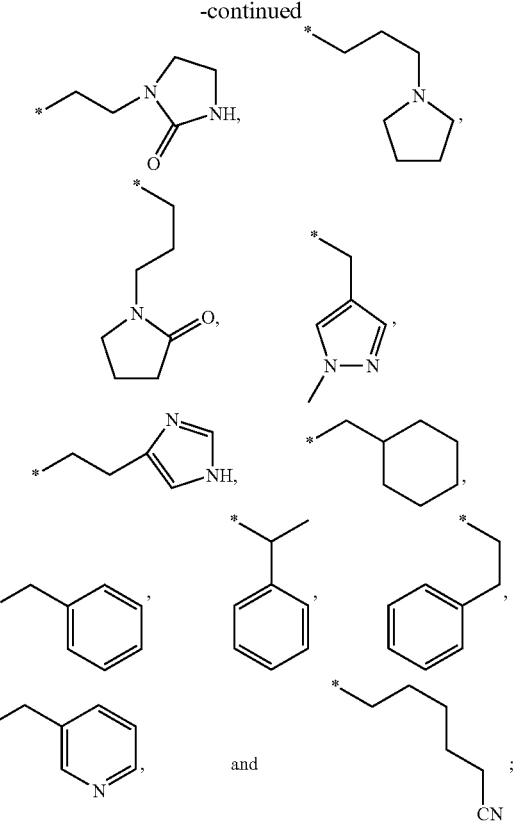

and the pharmacologically acceptable salts, diastereomers, enantiomers, racemates, hydrates, or solvates thereof.

Particularly preferred are the above compounds of formula 1, wherein X, $R^1$, $R^3$, $R^4$, $R^5$, $R^6$, $R^7$, and $R^8$ are as hereinbefore defined, and wherein $R^2$ denotes $C_{6-10}$-aryl, which may optionally be substituted in the meta position by one or more groups selected independently of one another from among $C_{1-4}$-alkyl, CN, halogen, $OR^{2.8}$, $COOR^{2.8}$, $COR^{2.10}$, and NHCOMe, wherein:

$R^{2.8}$ denotes $C_{1-4}$-alkyl or $C_{6-10}$-aryl; and $R^{2.10}$ denotes $NHR^{2.10.1}$, morpholinyl, or methylpiperazinyl, and $R^{2.10.1}$ denotes H, cyclopropyl, or $C_{1-4}$-alkyl, wherein the $C_{1-4}$-alkyl may optionally be substituted by one or more groups selected from among $C_{1-4}$-alkyl, OH, and $C_{6-10}$-aryl; or $R^2$ denotes $NH(R^{2.10.1})$ or cyclohexyl, or $NR^1R^2$ denotes a heterocyclic $C_{5-6}$ ring selected from among pyrrolidine and piperazine, which may optionally be substituted by one or more groups selected from among $C_{1-4}$-alkyl, OH, and $C_{1-4}$-alkanol, and the pharmacologically acceptable salts, diastereomers, enantiomers, racemates, hydrates, or solvates thereof.

Particularly preferred are the above compounds of formula 1, wherein X, $R^1$, $R^2$, $R^4$, $R^5$, $R^6$, $R^7$, and $R^8$ are as hereinbefore defined, and wherein $R^3$ denotes phenyl, which may optionally be substituted by one or more groups selected from among $C_{1-6}$-alkyl, $C_{2-6}$-alkenyl, $C_{2-6}$-alkynyl, $C_{1-4}$-haloalkyl, $C_{1-6}$-alkylene-$NR^{3.1}R^{3.2}$, CN, halogen, $OR^{3.1}$, $COOR^{3.1}$, $CONR^{3.1}R^{3.2}$, $NR^{3.1}R^{3.2}$, $NHCOR^{3.1}$, $NO_2$, $SR^{3.1}$, $SOR^{3.1}$, $SO_2R^{3.1}$, $SO_2NR^{3.1}R^{3.2}$, and $C_{1-6}$-alkylene-$NHCOR^{3.1}$, wherein:

$R^{3.1}$ denotes H, $C_{1-6}$-alkyl, $C_{2-6}$-alkenyl, or $C_{2-6}$-alkynyl; and $R^{3.2}$ denotes H, $C_{1-6}$-alkyl, $C_{2-6}$-alkenyl, or $C_{2-6}$-alkynyl;

and the pharmacologically acceptable salts, diastereomers, enantiomers, racemates, hydrates, or solvates thereof.

Particularly preferred are the above compounds of formula 1, wherein X, $R^1$, $R^2$, $R^4$, $R^5$, $R^6$, $R^7$, and $R^8$ are as hereinbefore defined, and wherein:

$R^3$ denotes phenyl, which may optionally be substituted in the para position by a group selected from among $C_{1-6}$-alkyl, $C_{2-6}$-alkenyl, $C_{2-6}$-alkynyl, $C_{1-4}$-haloalkyl, $C_{1-6}$-alkylene-$NR^{3.1}R^{3.2}$, CN, halogen, $OR^{3.1}$, $COOR^{3.1}$, $CONR^{3.1}R^{3.2}$, $NR^{3.1}R^{3.2}$, $NHCOR^{3.1}$, $NO_2$, $SR^{3.1}$, $SOR^{3.1}$, $SO_2R^{3.1}$, $SO_2NR^{3.1}R^{3.2}$, and $C_{1-6}$-alkylene-$NHCOR^{3.1}$, wherein:

$R^{3.1}$ denotes H, $C_{1-6}$-alkyl, $C_{2-6}$-alkenyl, or $C_{2-6}$-alkynyl;

$R^{3.2}$ denotes H, $C_{1-6}$-alkyl, $C_{2-6}$-alkenyl, or $C_{2-6}$-alkynyl;

and the pharmacologically acceptable salts, diastereomers, enantiomers, racemates, hydrates, or solvates thereof.

Particularly preferred are the above compounds of formula 1, wherein X, $R^1$, $R^2$, $R^4$, $R^5$, $R^6$, $R^7$, and $R^8$ are as hereinbefore defined, and $R^3$ denotes phenyl, which may optionally be substituted by one or more groups selected from among $C_{1-4}$-alkyl, $C_{1-4}$-alkylene-$NR^{3.1}R^{3.2}$, CN, $COOR^{3.1}$, $CONR^{3.1}R^{3.2}$, $CF_3$, $OR^{3.1}$, halogen, $NHCOR^{3.1}$, $NO_2$, $SO_2NR^{3.1}R^{3.2}$, and $C_{1-4}$-alkylene-$NHCOR^{3.1}$, wherein:

$R^{3.1}$ denotes H or $C_{1-4}$-alkyl; and $R^{3.2}$ denotes H or $C_{1-4}$-alkyl;

and the pharmacologically acceptable salts, diastereomers, enantiomers, racemates, hydrates, or solvates thereof.

Particularly preferred are the above compounds of formula 1, wherein X, $R^1$, $R^2$, $R^4$, $R^5$, $R^6$, $R^7$, and $R^8$ are as hereinbefore defined, and $R^3$ denotes phenyl, which may optionally be substituted by one, two, or three groups selected from among methyl, $CH_2NH_2$, CN, COOH, $CONH_2$, $CF_3$, OH, F, Cl, Br, OMe, NHCOMe, $NO_2$, $SONMe_2$, and $CH_2NHCOMe$;

and the pharmacologically acceptable salts, diastereomers, enantiomers, racemates, hydrates, or solvates thereof.

Particularly preferred are the above compounds of formula 1, wherein X, $R^1$, $R^2$, $R^4$, $R^5$, $R^6$, $R^7$, and $R^8$ are as hereinbefore defined, and $R^3$ denotes a group of formula 1b

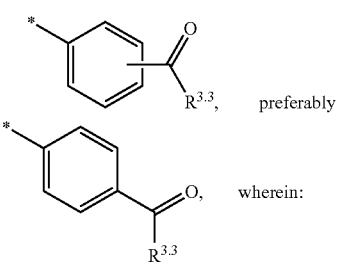

1b $R^{3.3}$ denotes a heterocyclic $C_{3-10}$ ring which may optionally be substituted by one or more groups selected from among $C_{1-6}$-alkyl, oxo, $COR^{3.3.1}$, $COR^{3.3.2}$, $C_{1-6}$-alkylene-$R^{3.3.2}$, $CH_2COpyrrolidine$, and a heterocyclic $C_{3-10}$ ring, wherein a sulfur atom optionally contained in the heterocyclic $C_{3-10}$ ring may optionally also be present as the oxide or dioxide, wherein:

$R^{3.3.1}$ denotes $C_{1-6}$-alkyl; and $R^{3.3.2}$ denotes $NH_2$, $NH(C_{1-6}$-alkyl), or $N(C_{1-6}$-alkyl)$_2$; or $R^{3.3}$ denotes a bicyclic ring or a heterocyclic spiro ring;

and the pharmacologically acceptable salts, diastereomers, enantiomers, racemates, hydrates, or solvates thereof.

Particularly preferred are the above compounds of formula 1, wherein X, $R^1$, $R^2$, $R^4$, $R^5$, $R^6$, $R^7$, and $R^8$ are as hereinbefore defined, and wherein $R^3$ denotes a group of formula 1b

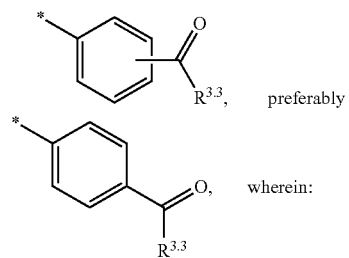

1b $R^{3.3}$ denotes a group selected from among piperidinyl, piperazinyl, and azepanyl, which may optionally be substituted by one or more groups selected from among methyl, oxo, $COCH_3$, $CONH_2$, $CH_2NEt_2$, $CH_2CH_2NMe_2$, $CH_2COpyrrolidine$, pyridinyl, isothiazolidinyl-1,1-dioxide, and thiazolidinyl-1,1-dioxide;

and the pharmacologically acceptable salts, diastereomers, enantiomers, racemates, hydrates, or solvates thereof.

Particularly preferred are the above compounds of formula 1, wherein X, $R^1$, $R^2$, $R^4$, $R^5$, $R^6$, $R^7$, and $R^8$ are as hereinbefore defined, and wherein $R^3$ denotes a group of formula 1c

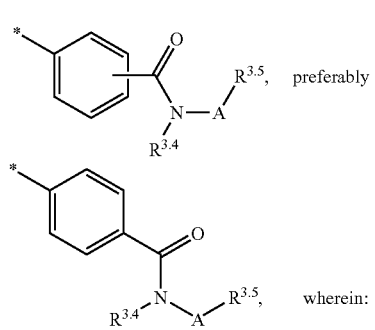

1c

A denotes a bond or $C_{1-6}$-alkyl, which may optionally be substituted by oxo or $NMe_2$;

$R^{3.4}$ denotes H or $C_{1-6}$-alkyl;

$R^{3.5}$ denotes a group selected from among $C_{1-6}$-alkyl, which may optionally be substituted by a group selected from among $C_{3-7}$-cycloalkyl, $C_{6-10}$-aryl, and a $C_{5-10}$ heterocycle, which may also optionally be substituted in each case by one or more groups selected from among halogen, OH, oxo, $C_{1-6}$-alkyl, O—$C_{1-6}$-alkyl, $C_{1-6}$-haloalkyl, a heterocyclic $C_{3-10}$ ring, and a bicyclic ring, while these groups may each optionally be substituted by one or more groups selected from among oxo, $C_{1-6}$-alkyl, OH, $C_{6-10}$-aryl, a heterocyclic ring, $C_{1-6}$-alkylene-$R^{3.5}$, O—$C_{1-6}$-alkylene-$R^{3.5}$, and NH—$C_{1-6}$-alkylene-$R^{3.5.1}$, or $R^{3.5}$ denotes a group selected from among heterocyclic or bicyclic ring, optionally substituted by one or more groups selected independently of one another from among oxo, $C_{1-6}$-alkyl, OH, aryl, a heterocyclic ring, $C_{1-6}$-alkylene-$R^{3.5.1}$, O—$C_{1-6}$-alkylene-$R^{3.5.1}$, NH—$C_{1-6}$-alkylene-$R^{3.5.1}$, wherein $R^{3.5.1}$ denotes a group selected from among $C_{6-10}$-aryl, and heterocyclic $C_{3-10}$ ring which may optionally be substituted by $C_{1-6}$-alkyl;

and the pharmacologically acceptable salts, diastereomers, enantiomers, racemates, hydrates, or solvates thereof.

Particularly preferred are the above compounds of formula 1, wherein X, $R^1$, $R^2$, $R^4$, $R^5$, $R^6$, $R^7$, and $R^8$ are as hereinbefore defined, and wherein $R^3$ denotes a group of formula 1c

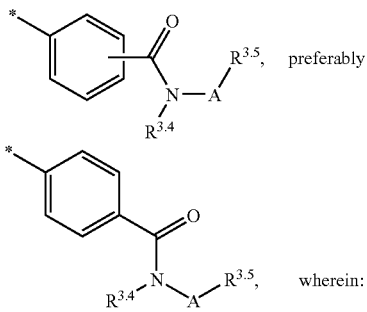

1c

A denotes a bond or $C_{1-4}$-alkyl, optionally substituted by oxo or $NMe_2$;

$R^{3.4}$ denotes H or methyl;

$R^{3.5}$ denotes a group selected from among pyrrolidinyl, piperidinyl, piperazinyl, morpholinyl, cyclohexyl, imidazolyl, pyrazolyl, phenyl, pyridinyl, benzimidazolyl, imidazolidin-2-one, pyrrolidin-2-one, pyrrolidin-3-one, 1-azabicyclo[2.2.2]octane, optionally substituted by one or more groups selected independently of one another from among methyl, ethyl, OH, phenyl, pyridinyl, pyrazolyl, pyrrolidinyl, $(CH_2)_o$—$R^{3.5.1}$, O—$(CH_2)_o$—$R^{3.5.1}$, NH—$(CH_2)_o$—$R^{3.5.1}$, wherein: o denotes 0, 1, or 2, and $R^{3.5.1}$ denotes a group selected from among phenyl, pyrrolidinyl, piperidinyl, and imidazolidin-2-one, optionally substituted by methyl, and the pharmacologically acceptable salts, diastereomers, enantiomers, racemates, hydrates, or solvates thereof.

Particularly preferred are the above compounds of formula 1, wherein X, $R^1$, $R^2$, $R^4$, $R^5$, $R^6$, $R^7$, and $R^8$ are as hereinbefore defined, and wherein $R^3$ denotes a group of formula 1d

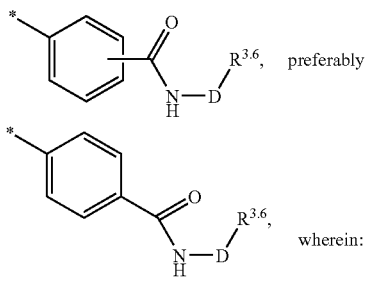

1d is D denotes $C_{2-4}$-alkynyl;

$R^{3.6}$ denotes pyridinyl;

and the pharmacologically acceptable salts, diastereomers, enantiomers, racemates, hydrates, or solvates thereof.

Particularly preferred are the above compounds of formula 1, wherein X, $R^1$, $R^2$, $R^4$, $R^6$, $R^7$, and $R^8$ are as hereinbefore defined, and wherein $R^3$ denotes a group of formula 1e

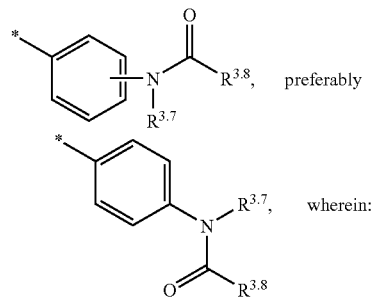

1e $R^{3.7}$ denotes H, $C_{1-6}$-alkyl, $C_{2-6}$-alkenyl, $C_{2-6}$-alkynyl, or $C_{1-6}$-haloalkyl;

$R^{3.8}$ denotes H or a group selected from among $C_{1-6}$-alkyl, $C_{2-6}$-alkenyl; $C_{2-6}$-alkynyl, $C_{1-6}$-haloalkyl, O—$C_{1-6}$-alkyl, $C_{6-10}$-aryl, a heterocyclic $C_{3-10}$ ring, and a bicyclic ring which is optionally substituted by one or more groups selected from among halogen, $C_{1-6}$-alkyl, OH, $C_{1-6}$-haloalkyl, and O—$C_{1-6}$-alkyl, and the pharmacologically acceptable salts, diastereomers, enantiomers, racemates, hydrates, or solvates thereof.

The present invention also relates to the following intermediate products for synthesizing the compounds according to the invention:

compounds according to formula VIII according to preparation method B in Scheme 1,
compounds according to formula IV and V according to preparation method A in Scheme 1,
compounds according to formula I in Scheme 1,
compounds according to formula IV, VI, VII, and VIII in Scheme 2,
compounds according to formula V, VII, and VIII in Scheme 3,
compounds according to formula V, VII, and IX in Scheme 4,
compounds according to formula V, VI, VII, VIII, and IX in Scheme 5,
compounds according to formula V, VII, VIII, and IX in Scheme 6,
compounds according to formula V, VII, VIII, XI, and XII in Scheme 7,
compounds according to formula I and II in Scheme 8,
compounds according to formula II and III in Scheme 9,
compounds according to formula V, VI, VIII, and X in Scheme 10,
compounds according to formula III and V in Scheme 11,
compounds according to formula III and V in Scheme 12,
compounds according to formula II, III, IV, and V in Scheme 13, and
compounds according to formula IV, V, VII, VIII, IX, and X in Scheme 14, wherein $R^1$, $R^2$, $R^3$, $R^4$, $R^5$, $R^6$, $R^7$, $R^8$, and X have the meanings defined hereinbefore and wherein $R^9$, $R^{10}$, $R^{11}$, $R^{12}$ in each case independently of one another denote a group selected from among H, halogen, $C_{1-6}$-alkyl, $C_{1-6}$-haloalkyl, $C_{6-10}$-aryl, $C_{3-7}$-cycloalkyl, aromatic or non-aromatic $C_{3-10}$ heterocycle, $C_{6-10}$-aryl-$C_{1-6}$-alkylene, $C_{3-7}$-cycloalkyl-$C_{1-6}$-alkylene, and $C_{3-10}$ heterocycle-$C_{1-6}$-alkylene, which may optionally be substituted by one or more groups selected from among OH, oxo, $C_{1-6}$-alkyl, phenyl $C_{3-7}$-cycloalkyl, $C_{3-7}$-heterocycle, and halogen, and wherein $R^{13}$ is selected from among OH, halogen, O—$C_{1-6}$-alkyl, $C_{1-6}$-alkyl, phenyl, $C_{3-7}$-cycloalkyl, and $C_{3-7}$ heterocycle.

Preferred objects of the present invention are the following intermediate products for synthesizing the compounds according to the invention:

compounds according to formula I in Scheme 1,
compounds according to formula VI, VII, and VIII in Scheme 2,
compounds according to formula VII and VIII in Scheme 3,
compounds according to formula VII and IX in Scheme 4,
compounds according to formula VI, VII, VIII, and IX in Scheme 5,
compounds according to formula VII, VIII, and IX in Scheme 6,
compounds according to formula VII, VIII, XI, and XII in Scheme 7,
compounds according to formula I and II in Scheme 8,
compounds according to formula II and III in Scheme 9,
compounds according to formula X in Scheme 10,
compounds according to formula III and V in Scheme 11,
compounds according to formula III and V in Scheme 12,
compounds according to formula II, III, IV, and V in Scheme 13, and
compounds according to formula VII, VIII, IX, and X in Scheme 14.

TERMS AND DEFINITIONS USED

Unless otherwise stated, all the substituents are independent of one another. If, for example, there are a plurality of $C_{1-6}$-alkyl groups as substituents in one group, in the case of three substituents $C_{1-6}$-alkyl, one may represent methyl, one n-propyl, and one tert-butyl.

Within the scope of this application, in the definition of possible substituents, these may also be represented in the form of a structural formula. An asterisk (*) in the structural formula of the substituent is to be understood as being the linking point to the rest of the molecule. Moreover, the atom of the substituent which follows the linking point is referred to as the atom in position number 1. Thus, for example, the groups N-piperidinyl (I), 4-piperidinyl (II), 2-tolyl (III), 3-tolyl (IV), and 4-tolyl (V) are shown as follows:

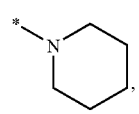

I

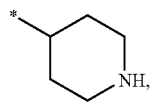

II

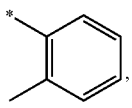

III

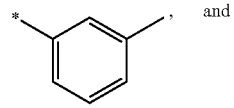

IV
and

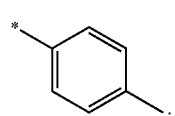

V

If there is no asterisk (*) in the structural formula of the substituent, each hydrogen atom may be removed from the substituent and the valency thus freed may act as a binding site to the rest of a molecule. Thus, for example, VI may represent 2-tolyl, 3-tolyl, 4-tolyl, and benzyl

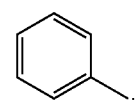

VI

By the term "$C_{1-6}$-alkyl" (including those which are part of other groups) are meant branched and unbranched alkyl groups with 1 to 6 carbon atoms and by the term "$C_{1-4}$-alkyl" are meant branched and unbranched alkyl groups with 1 to 4 carbon atoms. Alkyl groups with 1 to 4 carbon atoms are preferred. Examples include: methyl, ethyl, n-propyl, isopropyl, n-butyl, isobutyl, sec-butyl, tert-butyl, n-pentyl, isopentyl, neopentyl, or hexyl. The following abbreviations may optionally also be used for the abovementioned groups: Me, Et, n-Pr, i-Pr, n-Bu, i-Bu, t-Bu, etc. Unless stated otherwise, the definitions propyl, butyl, pentyl, and hexyl include all the possible isomeric forms of the groups in question. Thus, for example, propyl includes n-propyl and isopropyl, butyl includes isobutyl, sec-butyl and tert-butyl etc.

By the term "$C_{1-6}$-alkylene" (including those which are part of other groups) are meant branched and unbranched alkylene groups with 1 to 6 carbon atoms and by the term "$C_{1-4}$-alkylene" are meant branched and unbranched alkylene groups with 1 to 4 carbon atoms. Preferred are alkylene groups with 1 to 4 carbon atoms. Examples include: methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene, or hexylene. Unless stated otherwise, the definitions propylene, butylene, pentylene, and hexylene include all the possible isomeric forms of the groups in question with the same number of carbons. Thus, for example, propyl also includes 1-methylethylene and butylene includes 1-methylpropylene, 1,1-dimethylethylene, 1,2-dimethylethylene.

If the carbon chain is substituted by a group which together with one or two carbon atoms of the alkylene chain forms a carbocyclic ring with 3, 5, or 6 carbon atoms, the following examples of rings are also included:

 ;  ; 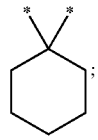 ;

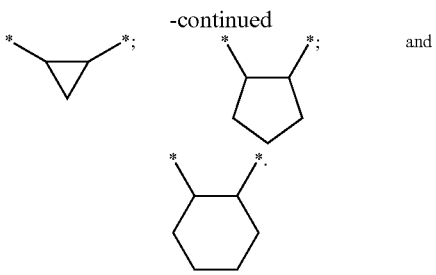

By the term "$C_{2-6}$-alkenyl" (including those which are part of other groups) are meant branched and unbranched alkenyl groups with 2 to 6 carbon atoms and by the term "$C_{2-4}$-alkenyl" are meant branched and unbranched alkenyl groups with 2 to 4 carbon atoms, provided that they have at least one double bond. Alkenyl groups with 2 to 4 carbon atoms are preferred. Examples include: ethenyl or vinyl, propenyl, butenyl, pentenyl, or hexenyl. Unless stated otherwise, the definitions propenyl, butenyl, pentenyl, and hexenyl include all the possible isomeric forms of the groups in question. Thus, for example, propenyl includes 1-propenyl and 2-propenyl, butenyl includes 1-, 2-, and 3-butenyl, 1-methyl-1-propenyl, 1-methyl-2-propenyl, etc.

By the term "$C_{2-6}$-alkenylene" (including those which are part of other groups) are meant branched and unbranched alkenylene groups with 2 to 6 carbon atoms and by the term "$C_{2-4}$-alkenylene" are meant branched and unbranched alkylene groups with 2 to 4 carbon atoms. Preferred are alkenylene groups with 2 to 4 carbon atoms. Examples include: ethenylene, propenylene, 1-methylethenylene, butenylene, 1-methylpropenylene, 1,1-dimethylethenylene, 1,2-dimethylethenylene, pentenylene, 1,1-dimethylpropenylene, 2,2-dimethylpropenylene, 1,2-dimethylpropenylene, 1,3-dimethylpropenylene, or hexenylene. Unless stated otherwise, the definitions propenylene, butenylene, pentenylene, and hexenylene include all the possible isomeric forms of the groups in question with the same number of carbons. Thus, for example, propenyl also includes 1-methylethenylene and butenylene includes 1-methylpropenylene, 1,1-dimethylethenylene, and 1,2-dimethylethenylene.

By the term "$C_{2-6}$-alkynyl" (including those which are part of other groups) are meant branched and unbranched alkynyl groups with 2 to 6 carbon atoms and by the term "$C_{2-4}$-alkynyl" are meant branched and unbranched alkynyl groups with 2 to 4 carbon atoms, provided that they have at least one triple bond. Alkynyl groups with 2 to 4 carbon atoms are preferred. Examples include: ethynyl, propynyl, butynyl, pentynyl, or hexynyl. Unless stated otherwise, the definitions propynyl, butynyl, pentynyl, and hexynyl include all the possible isomeric forms of the groups in question. Thus, for example, propynyl includes 1-propynyl and 2-propynyl, butynyl includes 1-, 2-, and 3-butynyl, 1-methyl-1-propynyl, 1-methyl-2-propynyl etc.

By the term "$C_{2-6}$-alkynylene" (including those which are part of other groups) are meant branched and unbranched alkynylene groups with 2 to 6 carbon atoms and by the term "$C_{2-4}$-alkynylene" are meant branched and unbranched alkylene groups with 2 to 4 carbon atoms. Preferred are alkynylene groups with 2 to 4 carbon atoms. Examples include: ethynylene, propynylene, 1-methylethynylene, butynylene, 1-methylpropynylene, 1,1-dimethylethynylene, 1,2-dimethylethynylene, pentynylene, 1,1-dimethylpropynylene, 2,2-dimethylpropynylene, 1,2-dimethylpropynylene, 1,3-dimethylpropynylene, or hexynylene. Unless stated otherwise, the definitions propynylene, butynylene, pentynylene, and hexynylene include all the possible isomeric forms of the groups in question with the same number of carbons. Thus, for example, propynyl also includes 1-methylethynylene and butynylene includes 1-methylpropynylene, 1,1-dimethylethynylene, 1,2-dimethylethynylene.

By the term "aryl" (including those which are part of other groups) are meant aromatic ring systems with 6 or 10 carbon atoms. Examples include: phenyl or naphthyl, the preferred aryl group being phenyl. Unless otherwise stated, the aromatic groups may be substituted by one or more groups selected from among methyl, ethyl, isopropyl, tert-butyl, hydroxy, fluorine, chlorine, bromine, and iodine.

By the term "aryl-$C_{1-6}$-alkylene" (including those which are part of other groups) are meant branched and unbranched alkylene groups with 1 to 6 carbon atoms, which are substituted by an aromatic ring system with 6 or 10 carbon atoms. Examples include: benzyl, 1- or 2-phenylethyl, or 1- or 2-naphthylethyl. Unless otherwise stated, the aromatic groups may be substituted by one or more groups selected from among methyl, ethyl, isopropyl, tert-butyl, hydroxy, fluorine, chlorine, bromine, and iodine.

By the term "heteroaryl-$C_{1-6}$-alkylene" (including those which are part of other groups) are meant, even though they are already included under "aryl-$C_{1-6}$-alkylene", branched and unbranched alkylene groups with 1 to 6 carbon atoms, which are substituted by a heteroaryl.

A heteroaryl of this kind includes five- or six-membered heterocyclic aromatic groups or 5-10-membered, bicyclic heteroaryl rings which may contain one, two, or three heteroatoms selected from among oxygen, sulfur, and nitrogen, and contain so many conjugated double bonds that an aromatic system is formed. The following are examples of five- or six-membered heterocyclic aromatic groups:

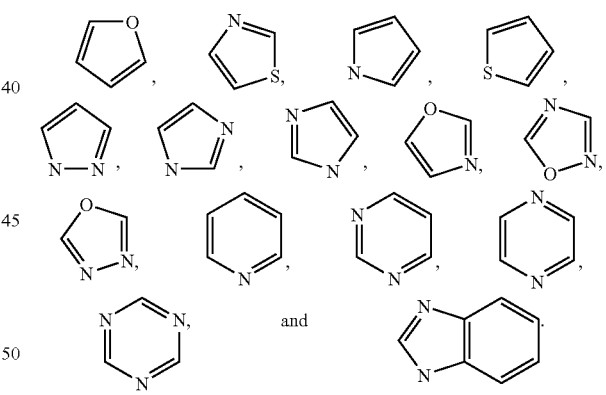

Unless otherwise stated, these heteroaryls may be substituted by one or more groups selected from among methyl, ethyl, isopropyl, tert-butyl, hydroxy, fluorine, chlorine, bromine, and iodine. The following are examples of heteroaryl-$C_{1-6}$-alkylenes:

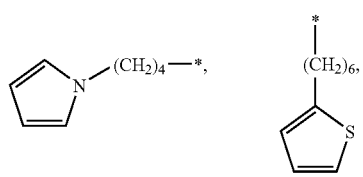

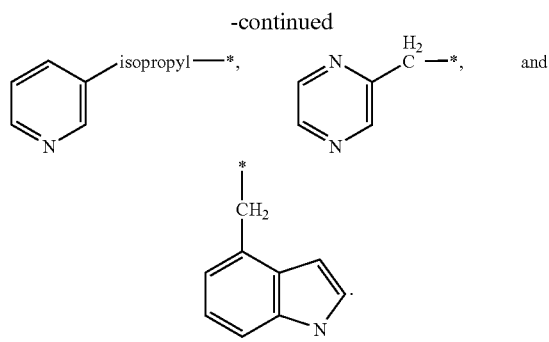

By the term "$C_{1-6}$-haloalkyl" (including those which are part of other groups) are meant branched and unbranched alkyl groups with 1 to 6 carbon atoms, which are substituted by one or more halogen atoms. By the term "$C_{1-4}$-alkyl" are meant branched and unbranched alkyl groups with 1 to 4 carbon atoms, which are substituted by one or more halogen atoms. Alkyl groups with 1 to 4 carbon atoms are preferred. Examples include: $CF_3$, $CHF_2$, $CH_2F$, and $CH_2CF_3$.

By the term "$C_{3-7}$-cycloalkyl" (including those which are part of other groups) are meant cyclic alkyl groups with 3 to 7 carbon atoms. Examples include: cyclopropyl, cyclobutyl, cyclopentyl, cyclohexyl, or cycloheptyl. Unless otherwise stated, the cyclic alkyl groups may be substituted by one or more groups selected from among methyl, ethyl, isopropyl, tert-butyl, hydroxy, fluorine, chlorine, bromine, and iodine.

By the term "heterocyclic rings" or also "heterocycles" are meant five-, six-, or seven-membered, saturated or unsaturated heterocyclic rings which may contain one, two, or three heteroatoms, selected from among oxygen, sulfur, and nitrogen, while the ring may be linked to the molecule through a carbon atom or through a nitrogen atom, if there is one. Although included by the term "heterocyclic rings" or "heterocycles", the term "heterocyclic non-aromatic rings" refers to five-, six-, or seven-membered unsaturated rings. Examples include:

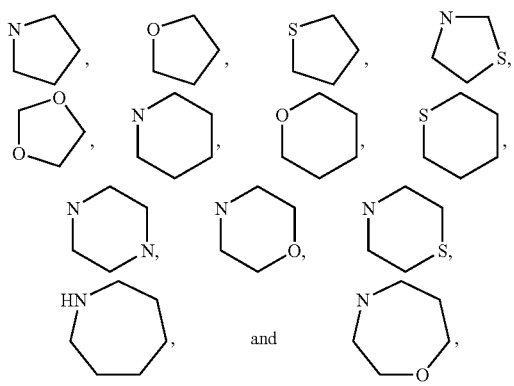

Although included by the term "heterocyclic rings" or "heterocycles", the term "heterocyclic aromatic rings" or "heteroaryl" refers to five- or six-membered heterocyclic aromatic groups or 5-10-membered, bicyclic heteroaryl rings which may contain one, two, or three heteroatoms, selected from among oxygen, sulfur, and nitrogen, and contain so many conjugated double bonds that an aromatic system is formed. Examples of five- or six-membered heterocyclic aromatic groups include:

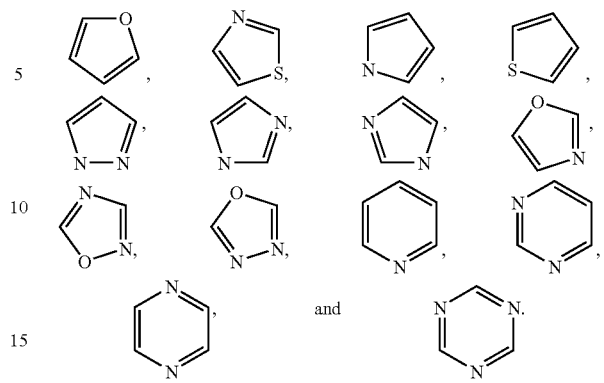

Unless otherwise mentioned, a heterocyclic ring (or "heterocycle") may be provided with a keto group. Examples include:

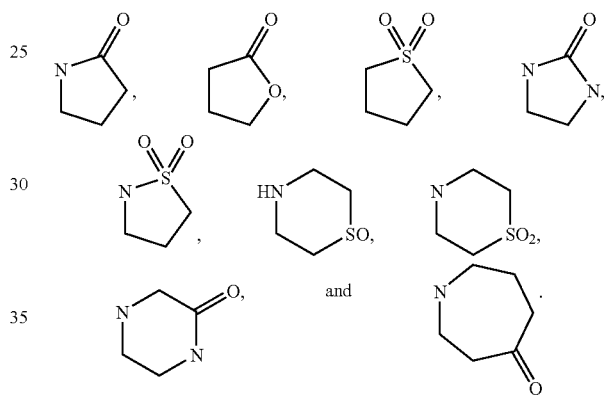

By the term "bicyclic rings" are meant eight-, nine-, or ten-membered bicyclic rings which may optionally contain one or more heteroatoms, selected from among oxygen, sulfur, and nitrogen. The ring may be linked to the molecule through a carbon atom of the ring or through a nitrogen atom of the ring, if there is one. Examples include:

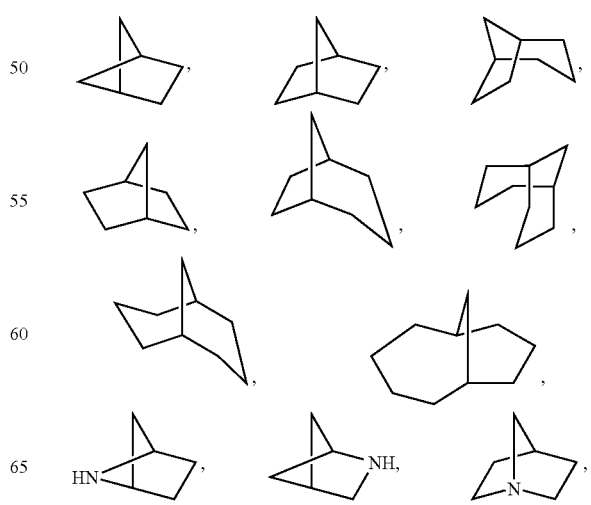

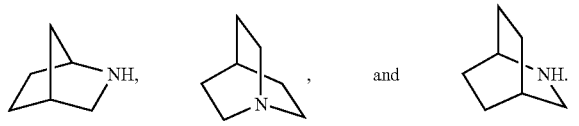

Although included by the term "bicyclic rings", the term "fused bicyclic rings" denotes bicyclic rings wherein the bridge separating the rings denotes a direct single bond. The following are examples of a fused, bicyclic ring:

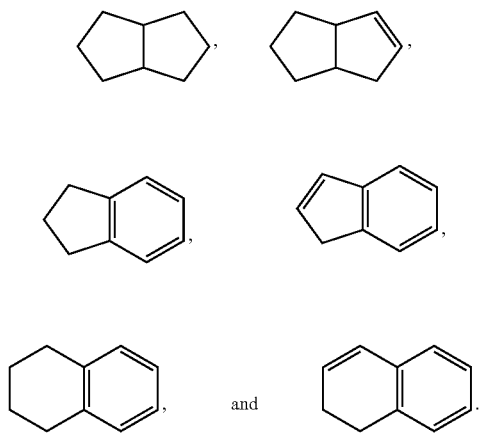

Although included by the term "bicyclic rings", the term "fused bicyclic heterorings" denotes bicyclic 5-10 membered heterorings which contain one, two, or three heteroatoms, selected from among oxygen, sulfur, and nitrogen, and wherein the bridge separating the rings denotes a direct single bond. Examples include pyrrolizine, indole, indolizine, isoindole, indazole, purine, quinoline, isoquinoline, benzimidazole, benzofuran, benzopyran, benzothiazole, benzothiazole, benzoisothiazole, pyridopyrimidine, pteridine, pyrimidopyrimidine,

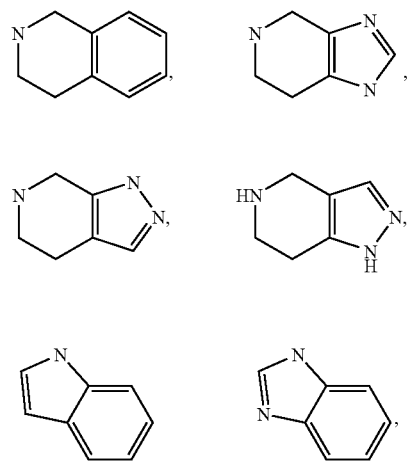

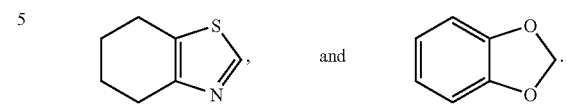

By the term "heterocyclic spirorings" (spiro) are meant 5-10 membered, spirocyclic rings which may optionally contain one, two, or three heteroatoms, selected from among oxygen, sulfur, and nitrogen, while the ring may be linked to the molecule through a carbon atom or through a nitrogen atom, if there is one. Unless otherwise mentioned, a spirocyclic ring may be provided with an oxo, methyl, or ethyl group. Examples include:

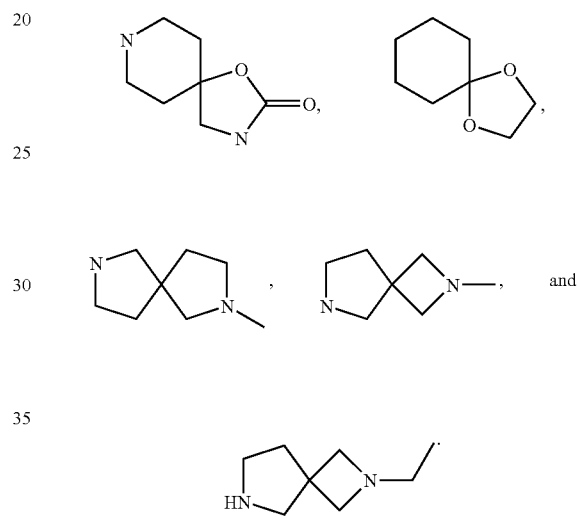

"Halogen" within the scope of the present invention denotes fluorine, chlorine, bromine, or iodine. Unless stated to the contrary, fluorine, chlorine, and bromine are regarded as preferred halogens.

By the term "ambient temperature" is meant normal room temperature.

Compounds of general formula 1 may have acid groups, mainly carboxyl groups, and/or basic groups such as, e.g., amino functions. Compounds of general formula 1 may therefore be present as internal salts, as salts with pharmaceutically useable inorganic acids such as, for example, hydrochloric acid, sulfuric acid, phosphoric acid, sulfonic acid, or organic acids (such as, for example, maleic acid, fumaric acid, citric acid, tartaric acid, or acetic acid) or as salts with pharmaceutically useable bases such as alkali or alkaline earth metal hydroxides or carbonates, zinc, or ammonium hydroxides or organic amines such as e.g., diethylamine, triethylamine, or triethanolamine, inter alia.

As mentioned hereinbefore, the compounds of formula 1 may be converted into the salts thereof, particularly for pharmaceutical use, into the physiologically and pharmacologically acceptable salts thereof. These salts may on the one hand be in the form of the physiologically and pharmacologically acceptable acid addition salts of the compounds of formula 1 with inorganic or organic acids. On the other hand, if R is hydrogen, the compound of formula 1 may also be converted by reaction with inorganic bases into physiologically and pharmacologically acceptable salts with alkali or alkaline earth metal cations as counter ion. The acid addition salts may be prepared, for example, using hydrochloric acid, hydrobromic acid, sulfuric acid, phosphoric acid, methanesulfonic acid, acetic acid, fumaric acid, succinic acid, lactic acid, citric acid, tartaric acid, or maleic acid. It is also possible to use mixtures of the abovementioned acids. The alkali and alkaline earth metal salts of the compound of formula I are preferably prepared using the alkali and alkaline earth metal hydroxides and hydrides thereof, of which the hydroxides and hydrides of the alkaline earth metals, particularly of sodium and potassium, are preferred and sodium and potassium hydroxide are particularly preferred.

If desired, the compounds of general formula (1) may be converted into the salts thereof, particularly, for pharmaceutical use, into the pharmacologically acceptable acid addition salts with an inorganic or organic acid. Suitable acids include, for example, succinic acid, hydrobromic acid, acetic acid, fumaric acid, maleic acid, methanesulfonic acid, lactic acid, phosphoric acid, hydrochloric acid, sulfuric acid, tartaric acid, or citric acid. It is also possible to use mixtures of the abovementioned acids.

The invention relates to the compounds in question, optionally in the form of the individual optical isomers, mixtures of the individual enantiomers or racemates, in the form of the tautomers as well as in the form of the free bases or the corresponding acid addition salts with pharmacologically acceptable acids such as, for example, acid addition salts with hydrohalic acids, for example, hydrochloric or hydrobromic acid or organic acids such as, for example, oxalic, fumaric, diglycolic, or methanesulfonic acid.

The compounds according to the invention may optionally occur as racemates, but they may also be obtained as pure enantiomers, i.e., in the (R) or (S) form. Preferred compounds are those which occur as racemates or as the (S) form.

The invention relates to the compounds in question, optionally in the form of the individual optical isomers, mixtures of the individual enantiomers or racemates, in the form of the tautomers as well as in the form of the free bases or the corresponding acid addition salts with pharmacologically acceptable acids such as, for example, acid addition salts with hydrohalic acids, for example, hydrochloric or hydrobromic acid or organic acids, such as, for example, oxalic, fumaric, diglycolic, or methanesulfonic acid.

METHODS OF SYNTHESIS AND EXAMPLES

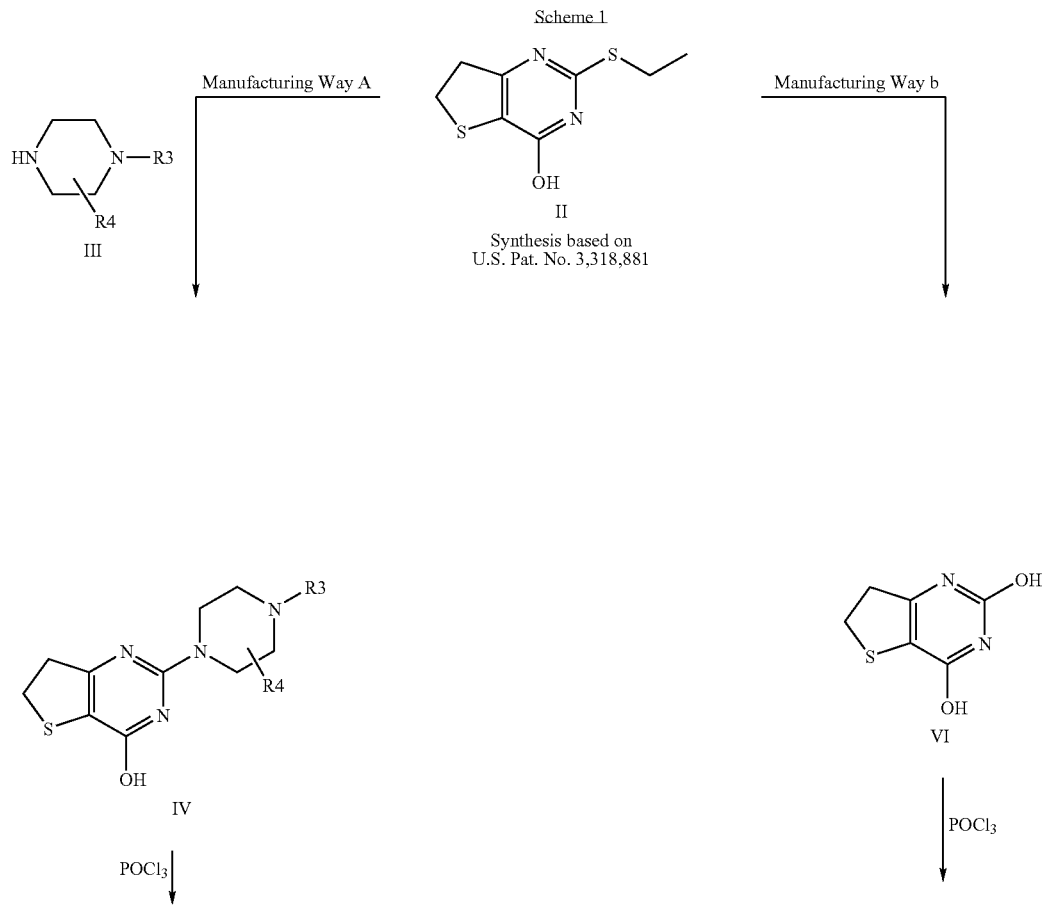

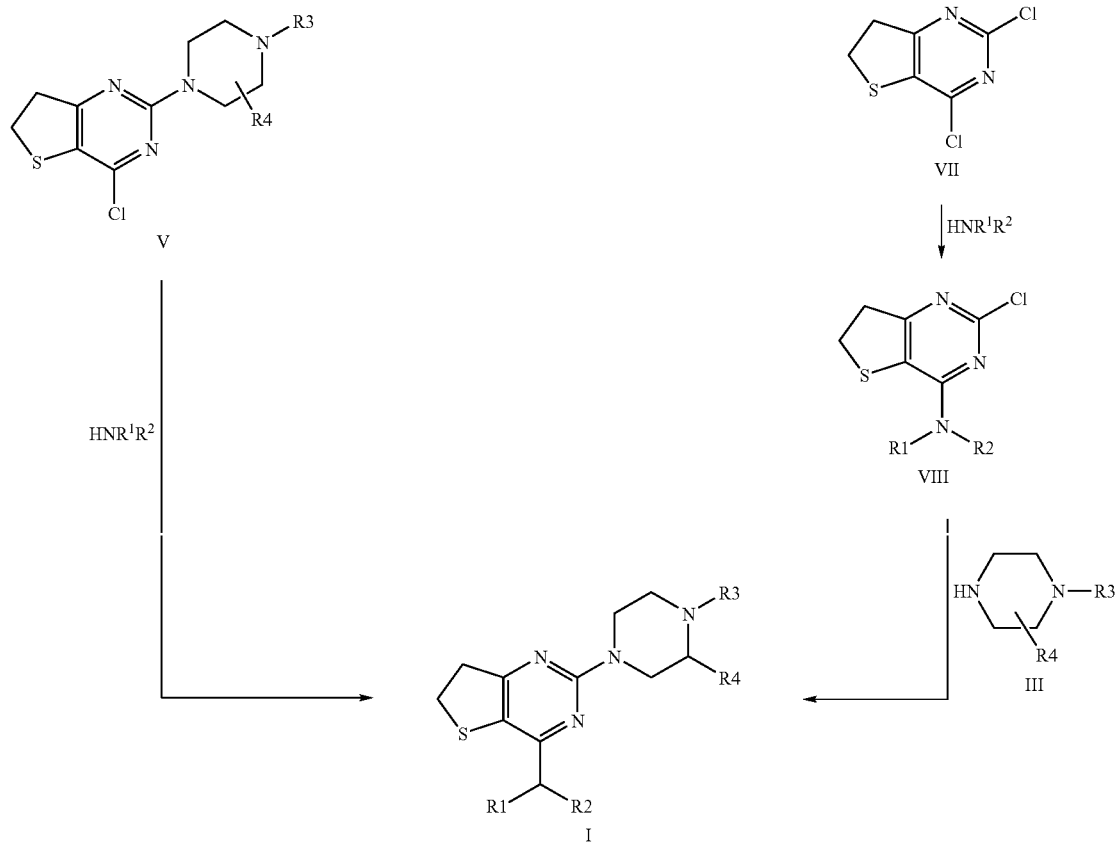

Synthesis of [2-(4-phenylpiperazin-1-yl)-6,7-dihydrothieno[3,2-d]pyrimidine-4-yl]propylamine by Synthesis Method A (1) (Scheme 1)

2-(4-phenylpiperazin-1-yl)-6,7-dihydrothieno[3,2-d]pyrimidin-4-ol (IV): 6.4 g (39 mmol) of N-phenylpiperazine (III) is placed in 2.2 mL of glacial acetic acid, heated to 125° C., then 3.2 g (15 mmol) of 2-ethylsulfanyl-6,7-dihydrothieno[3,2-d]pyrimidin-4-ol (II) is added, and the mixture is heated to 175° C. After 1.5 hours, the resulting solid is stirred with water, suction filtered, washed with ethanol, and dried. 4.3 g product (91%) is obtained as a powder.

4-chloro-2-(4-phenylpiperazin-1-yl)-6,7-dihydrothieno[3,2-d]pyrimidine (V): 4.3 g (13.7 mmol) of 2-(4-phenylpiperazin-1-yl)-6,7-dihydrothieno[3,2-d]pyrimidin-4-ol (IV) and 25 mL of phosphorus oxychloride are combined and stirred for 5 hours at 120° C. Excess phosphorus oxychloride is concentrated by evaporation, the residue is combined with ice water and dichloromethane. The organic phase is separated off and evaporated to dryness. The residue is triturated with water, suction filtered, and dried. 5.6 g of the product (100%) is obtained as a powder.

[2-(4-phenylpiperazin-1-yl)-6,7-dihydrothieno[3,2-d]pyrimidine-4-yl]propylamine (I) (Example 27): 0.83 g (2.5 mmol) of 4-chloro-2-(4-phenylpiperazin-1-yl)-6,7-dihydrothieno[3,2-d]pyrimidine (V) is combined with 8.3 mL of n-propylamine, reacted for 0.2 hours at 130° C. in the microwave. Then the reaction mixture is added to water and extracted with dichloromethane. The organic phase is concentrated by evaporation, the residue is crystallized. The aqueous phase is extracted with ethyl acetate, the organic phase evaporated to dryness. The solids are combined and stirred with methanol. 0.68 g of the product (76%) is obtained as a powder.

Synthesis of [2-(4-phenylpiperazin-1-yl)-6,7-dihydrothieno[3,2-d]pyrimidine-4-yl]propylamine by Synthesis Method B (Scheme 1)

6,7-dihydrothieno[3,2-d]pyrimidine-2,4-diol (VI): 3.5 g (16.33 mmol) of 2-ethylsulfanyl-6,7-dihydrothieno[3,2-d]pyrimidin-4-ol (II) is placed in 70 mL of 1N hydrochloric acid, reacted for 0.75 hours at 150° C. in the microwave (14×0.250 g in 5 mL of hydrochloric acid in each case). Then the reaction mixture is left to stand for 7 hours at ambient temperature. It is suction filtered, washed with water, and dried. 2.6 g of the product VI (95%) is obtained as a powder.

2.4-dichlorothieno[3,2-d]pyrimidine (VII)-2.4 g (14.1 mmol) of 6,7-dihydrothieno[3,2-d]pyrimidine-2,4-diol (VI) is suspended in 14 mL of phosphorus oxychloride, combined with 4.5 mL (28.2 mmol) of diethylaniline and stirred for 22 hours at 80° C. After cooling to ambient temperature, the reaction mixture is added to ice water, the precipitate formed is suction filtered and washed with water. The precipitate is dissolved in dichloromethane, any water present is separated off using a phase separator. The organic phase is evaporated to dryness. 2.5 g of the product VII (85%) is obtained.

(2-chloro-6,7-dihydrothieno[3,2-d]pyrimidin-4-yl)propylamine (VII): 10.4 g (50.2 mmol) of 2,4-dichlorothieno[3,2-d]pyrimidine (VII), 8.2 mL (100 mmol) of N-propylamine, and 17.5 mL (100 mmol) of N-ethyldiisopropylamine are placed in 100 mL of tetrahydrofuran and stirred for 20 hours at ambient temperature. The suspension is filtered, the filtrate is concentrated by evaporation. The residue is combined with 100 mL of water and treated in the ultrasound bath. Solid substance is suction filtered, dried, and stirred with 50 mL of petroleum ether. 10.0 g of the product VIII (86%) is obtained as a powder.

[2-(4-phenylpiperazin-1-yl)-6,7-dihydrothieno[3,2-d]pyrimidin-4-yl]propylamine (Example 27) (1): 9.7 g (42.3 mmol) of 2-chloro-6,7-dihydrothieno[3,2-d]pyrimidin-4-yl) propylamine (VIII) and 25.7 mL (169.2 mmol) of 1-phenylpiperazine (III) are placed in 200 mL of dioxane (carried out in 10 batches), then reacted for 1 hour at 160° C. in the microwave. The reaction mixture is concentrated by evaporation, the residue is combined with 250 mL of water. Then the mixture is suction filtered, washed with water, and dried. The residue is stirred with acetonitrile, then recrystallized from isopropanol. 8.3 g of the product (I) (55%) is obtained as a powder (m.p. 121° C.). $^1$H NMR (400 MHz, DMSO): 7.22 (2H, t); 6.97 (2H, d); 6.79 (1H, t); 6.43 (2H, t); 3.81-3.69 (4H, m); 3.37-3.19 (4H, m); 3.19-3.09 (4H, m); 2.99 (2H, t); 1.62-1.47 (2H, m); 0.87 (3H, t).

The following Examples are prepared by synthesis method A (Scheme 1) as described above (in each case only the last step of the synthesis is described, namely the reaction of V with an amine to form product I).

cyclohexyl-[2-(4-phenylpiperazin-1-yl)-6,7-dihydrothieno[3,2-d]pyrimidin-4-yl]amine (Example 16) (I): 0.300 g (0.90 mmol) of 4-chloro-2-(4-phenylpiperazin-1-yl)-6,7-dihydrothieno[3,2-d]pyrimidine (V) is placed in 4 mL of cyclohexylamine, then reacted for 0.1 hours at 130° C. in the microwave. Then the reaction mixture is concentrated by evaporation, the residue is stirred with water and suction filtered. 0.120 g of product I (34%) is obtained as a powder. $^1$H NMR (400 MHz, DMSO): 7.22 (2H, t); 6.97 (2H, d); 6.79 (1H, t); 6.08 (1H, d); 3.93-3.81 (1H, m); 3.80-3.69 (4H, m); 3.22 (2H, t); 3.18-3.11 (4H, m); 2.98 (2H, t); 1.92-1.79 (2H, m); 1.79-1.66 (2H, m); 1.66-1.55 (1H, m); 1.37-1.21 (4H, m); 1.18-1.04 (1H, m).

(3-chlorophenyl)-[2-(4-phenylpiperazin-1-yl)-6,7-dihydrothieno[3,2-d]pyrimidin-4-yl]amine (Example 10) (1): 0.320 g (0.96 mmol) of 4-chloro-2-(4-phenylpiperazin-1-yl)-6,7-dihydrothieno[3,2-d]pyrimidine (V), 1.0 mL (9.5 mmol) of 3-chlorophenylamine, and 0.33 mL (1.92 mmol) of diisopropylethylamine are combined and the mixture is reacted for 0.5 hours at 130° C. in the microwave. Then the reaction mixture is combined with ethyl acetate and acidically extracted. The organic phase is dried and evaporated to dryness. The residue is combined with acetonitrile, water, and trifluoroacetic acid. The phase containing the product I is purified by chromatography through an RP column by HPLC (column: Microsorb, RP-C18, 300 Å, 10 μm, 21.4*250 mm, eluant: acetonitrile+0.1% formic acid (A), water+0.13% formic acid (B)).

| gradient: minutes | % eluant A | % eluant B |
|---|---|---|
| 0 | 10 | 90 |
| 4.9 | 10 | 90 |

| gradient: minutes | % eluant A | % eluant B |
|---|---|---|
| 27 | 100 | 0 |
| 32 | 100 | 0 |
| 32.5 | 10 | 90 |
| 37.5 | 10 | 90 |

Corresponding fractions are combined and freeze-dried. 0.10.1 g of the product is obtained as a powder. $^1$H NMR (400 MHz, DMSO): 8.63 (1H, s); 7.87 (1H, t); 7.60 (1H, dd); 7.31 (1H, t); 7.26-7.20 (2H, m); 7.05-7.01 (1H, m); 6.99 (2H, d); 7.80 (1H; t); 3.81-3.76 (4H, m); 3.22-3.15 (4H, m); 3.10 (2H, t).

(3-methoxyphenyl)-[2-(4-phenylpiperazin-1-yl)-6,7-dihydrothieno[3,2-d]pyrimidin-4-yl]amine (Example 11) (1): 0.320 g (0.96 mmol) of 4-chloro-2-(4-phenylpiperazin-1-yl)-6,7-dihydrothieno[3,2-d]pyrimidine (V), 1.5 mL (13.1 mmol) of 3-methoxyphenylamine, and 0.33 mL (1.92 mmol) of diisopropylethylamine are combined, and reacted for 0.5 hours at 130° C. in the microwave. Then the reaction mixture is purified by chromatography using HPLC through an RP column (column: Microsorb, RP-C18, 300 Å, 10 μm, 21.4*250 mm, eluant: acetonitrile+0.1% formic acid (A), water+0.13% formic acid (B)).

| gradient: minutes | % eluant A | % eluant B |
|---|---|---|
| 0 | 10 | 90 |
| 4.9 | 10 | 90 |
| 27 | 100 | 0 |
| 32 | 100 | 0 |
| 32.5 | 10 | 90 |
| 37.5 | 10 | 90 |

0.095 g of the product (23%) is obtained as a powder (m.p. 133° C.-135° C.). $^1$H NMR (400 MHz, DMSO): 8.37 (1H, s); 7.36 (1H, t); 7.26-7.14 (4H, m); 6.98 (2H, d); 6.80 (1H, t); 6.57 (1H, dd); 3.82-3.76 (4H, m); 3.75 (3H, s); 3.32-3.24 (2H, m); 3.21-3.15 (4H, m); 3.09 (2H, t).

Phenyl-[2-(4-phenylpiperazin-1-yl)-6,7-dihydrothieno[3,2-d]pyrimidin-4-yl]amine (Example 18) (1): 0.300 g (0.90 mmol) of 4-chloro-2-(4-phenylpiperazin-1-yl)-6,7-dihydrothieno[3,2-d]pyrimidine (V) and 3 mL of phenylamine are combined, then reacted for 0.3 hours at 130° C. in the microwave. Then the reaction mixture is combined with water and extracted with ethyl acetate. The organic phase is dried and evaporated to dryness. The residue is triturated with diethyl ether and suction filtered. 0.18 g of product I (51%) is obtained (m.p. 174° C.-175° C.). $^1$H-NMR (400 MHz, DMSO): 8.59 (1H, s); 7.63 (2H, d); 7.31 (2H, t); 7.22 (2H, t); 7.03 (1H, t); 6.99 (2H, d); 6.80 (1H, t); 3.83-3.73 (4H, m); 3.31 (2H, t); 3.23 (4H, m); 3.12 (2H, t).

The following Examples are prepared by synthesis method B (Scheme 1) as described above (in each case only the last step of the synthesis is described (reaction of VIII with III to obtain produce I).

{2-[4-(4-chlorophenyl)piperazin-1-yl]-6,7-dihydrothieno[3,2-d]pyrimidin-4-yl}propylamine (1) (Example 37): 0.250 g (1.1 mmol) of 2-chloro-6,7-dihydrothieno[3,2-d]pyrimidin-4-yl)propylamine (VIII), 0.700 g (3.6 mmol) of 1-(4-chlorophenyl)piperazine (III), and 0.400 mL (2.3 mmol) of diisopropylethylamine are placed in 4 mL of dioxane, then reacted for 1.5 hours at 160° C. in the microwave. The reaction mixture is combined with water while cooling with ice and treated in the ultrasound bath. The precipitate formed is suction filtered, washed with water and petroleum ether and dried. 0.300 g of product I (72%) is obtained as a powder. $^1$H NMR (400 MHz, DMSO): 7.24 (2H, d); 6.98 (2H, d); 6.42 (1H, t); 3.79-3.70 (4H, m); 3.23 (2H, t); 3.19-3.11 (4H, m); 2.98 (2H, t); 1.61-1.47 (2H, m); 0.87 (4, 3H).

{2-[4-(4-hydroxyphenyl)piperazin-1-yl]-6,7-dihydrothieno[3,2-d]pyrimidin-4-yl}propylamine (1) (Example 39): 0.400 g (1.7 mmol) of 2-chloro-6,7-dihydrothieno[3,2-d]pyrimidin-4-yl)propylamine (VIII), 1.55 g (8.7 mmol) of 1-(4-hydroxyphenyl)piperazine (III), and 0.610 mL (3.5 mmol) of diisopropylethylamine are placed in 4 mL of dimethylformamide, reacted for 2 hours at 160° C. in the microwave. Then the reaction mixture is combined with water and extracted with dichloromethane. The organic phase is dried and evaporated to dryness. The residue is purified by chromatography through a 10 g silica gel cartridge with petroleum ether/ethyl acetate 1:1. 0.370 g of product I (57%) is obtained as a powder. $^1$H NMR (400 MHz, DMSO): 8.80 (1H, s); 6.82 (2H, d); 6.66 (2H, d); 6.39 (1H, t); 3.76-3.69 (4H, m); 3.23 (2H, t); 3.02-2.92 (6H, m); 1.60-1.48 (2H, m); 0.86 (3H, t).

((1R,2R)-2-benzyloxycyclopentyl)-[2-(4-phenylpiperazin-1-yl)-6,7-dihydrothieno[3,2-d]pyrimidin-4-yl]amine (chiral) (Example 112) (1): 0.450 g (1.2 mmol) of ((1R,2R)-2-benzyloxycyclopentyl)(2-chloro-6,7-dihydrothieno[3,2-d]pyrimidin-4-yl)amine (chiral) (VIII) and 0.760 mL (5.0 mmol) of 1-phenylpiperazine (III) are placed in 5 mL of dioxane, then reacted for 1 hour at 160° C. in the microwave. The reaction mixture is concentrated by evaporation, and the residue is combined with water and extracted with dichloromethane. The organic phase is separated off using a phase separator and evaporated to dryness. The crude product I is purified by chromatography through a 100 g silica gel cartridge with a solvent mixture of petroleum ether/ethyl acetate 8/2. 0.540 g of the product (89%) is obtained (m.p. 100° C.-105° C.). $^1$H NMR (400 MHz, DMSO): 7.36-7.18 (7H, m); 6.91 (2H, d); 6.79 (1H, t); 6.39 (1H, d); 4.59-4.40 (3H, m); 3.95-3.89 (1H, m); 3.79-3.69 (4H, m); 3.23 (2H, t); 3.11-3.03 (4H, m); 2.99 (2H, t); 2.11-2.00 (1H, m); 1.93-1.79 (1H, m); 1.77-1.50 (4H, m).

Scheme 2

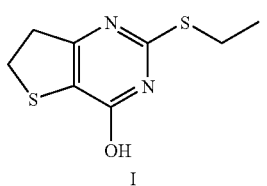

I

Synthesis based on U.S. Pat. No. 3,318,881

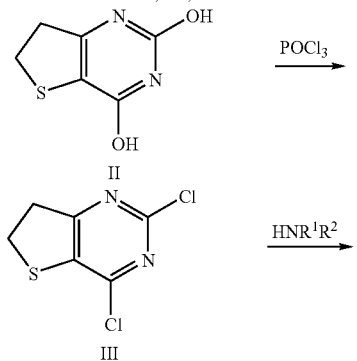

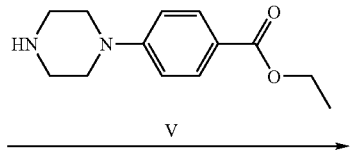

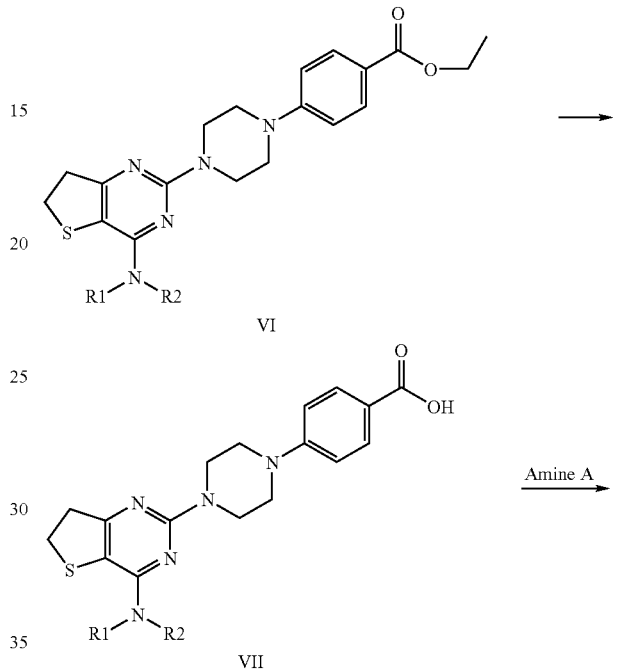

Synthesis of 4-[4-(4-cyclohexylamino-6,7-dihydrothieno[3,2-d]pyrimidin-2-yl)piperazin-1-yl]benzoic acid (According to Scheme 2)

ethyl 4-[4-(4-cyclohexylamino-6,7-dihydrothieno[3,2-d]pyrimidin-2-yl)piperazin-1-yl]benzoate (VI): 2.1 g (7.8 mmol) of (2-chloro-6,7-dihydrothieno[3,2-d]pyrimidin-4-yl) cyclohexylamine (IV), 3.1 g (13.2 mmol) of ethyl 4-piperazin-1-ylbenzoate (V), and 2.9 mL (16.5 mmol) of diisopropylethylamine are placed in 20 mL of dioxane, then the mixture is reacted for 4 hours at 160° C. in the microwave. The precipitated substance is suction filtered, the mother liquor is concentrated by evaporation. The residue is extracted with water and ethyl acetate, the combined organic phases are dried and evaporated to dryness. The crude product is VI is crystallized from petroleum ether/ethyl acetate 9:1. 2.3 g of the product (62%) is obtained.

4-[4-(4-cyclohexylamino-6,7-dihydrothieno[3,2-d]pyrimidin-2-yl)piperazin-1-yl]benzoic acid (VII) (Example 106): 2.3 g (4.8 mmol) of ethyl 4-[4-(4-cyclohexylamino-6,7-dihydrothieno[3,2-d]pyrimidin-2-yl)piperazin-1-yl]benzoate (VI) and 26 mL (26 mmol) of sodium hydroxide is placed in 15 mL of tetrahydrofuran and 15 mL of methanol, and refluxed for 2 hours with stirring. Then the reaction mixture is concentrated by evaporation, the residue is acidified with 2N hydrochloric acid. The precipitate formed is suction filtered, washed with water, and dried. 2.1 g of the product VII (100%) is obtained as a powder.

Standard Method for Synthesizing Amides: A solution of 0.01 mmol of the acid (VII) in 500 μL of dimethylformamide is combined with 1.388 μL (0.01 mmol) of triethylamine and 3.21 mg (0.01 mmol) of O-(1H-benzotriazol-1-yl)-N,N,N',N'-tetramethyluronium tetrafluoroborate (TBTU) and shaken for 15 minutes at ambient temperature. To this reaction mixture is added a solution of 0.01 mmol of the amine (amine A) in 500 μL dimethylformamide and the mixture is shaken for 12 hours at ambient temperature. Then the reaction mixture is evaporated to dryness and purified by preparative HPLC (this yields product VIII).

The following Examples may be prepared analogously to the method of synthesis set out above (according to Scheme 2) (in each case only the reactions of the acids VII with the amines A to yield product VIII are described):

4-[4-(4-propylamino-6,7-dihydrothieno[3,2-d]pyrimidin-2-yl)piperazin-1-yl]-N-(4-pyrrolidin-1-ylmethylbenzyl)benzamide (VIII) (Example 90): 0.350 g (0.9 mmol) of 4-[4-(4-propylamino-6,7-dihydrothieno[3,2-d]pyrimidin-2-yl)piperazin-1-yl]benzoic acid (VII) is placed in 8 mL of dimethylsulfoxide, 0.15 mL (0.9 mmol) of diisopropylethylamine, and 0.340 g (0.9 mmol) of O-(7-azabenzotriazol-1-yl-)-N,N,N',N'-tetramethyluronium hexafluorophosphate (HATU) is added. The mixture is stirred for 0.1 hours at ambient temperature, then 0.170 g (0.9 mmol) of 4-pyrrolidin-1-ylmethylbenzylamine (amine A) is added and a further 0.9 mmol of diisopropylethylamine is added. The reaction mixture is stirred for 3 hours at ambient temperature, then suction filtered through Alox and washed with dimethylsulfoxide. The mother liquor is concentrated by evaporation, the residue is cooled in the ice bath and combined with water. Any precipitate formed is suction filtered and dried. Then it is treated with approx. 50 mL of petroleum ether in the ultrasound bath, and the precipitate is then suction filtered. 0.374 g of product VIII (75%) is obtained (m.p. 157-158° C.). $^1$H NMR (400 MHz, DMSO): 8.71 (1H, t); 7.79 (2H, d); 7.23 (4H, s); 6.99 (2H, d); 6.43 (1H, t); 4.43 (2H, d); 3.79-3.71 (4H, m); 3.52 (2H, s); 3.23 (2H, t); 2.99 (2H, t); 2.44-2.34 (4H, m); 1.72-1.63 (4H, m); 1.61-1.48 (2H, m); 0.87 (3H, t).

N-(1-methylpiperidin-4-yl)-4-[4-(4-propylamino-6,7-dihydrothieno[3,2-d]pyrimidin-2-yl)piperazin-1-yl]benzamide (VIII) (Example 87): 0.500 g (1.3 mmol) of 4-[4-(4-propylamino-6,7-dihydrothieno[3,2-d]pyrimidin-2-yl)piperazin-1-yl]benzoic acid (VII) is placed in 12 mL of dimethylsulfoxide, 0.716 g (1.9 mmol) of O-(7-azabenzotriazol-1-yl-)-N,N,N',N'-tetramethyluronium hexafluorophosphate (HATU) in 6 mL of dimethylsulfoxide is added. The mixture is stirred for 1 hour at ambient temperature. Then 0.143 g (1.3 mmol) of 1-methylpiperidin-4-ylamine (amine A) in 6 mL of dimethylsulfoxide is added, followed by another 2.5 mmol of diisopropylethylamine. The reaction mixture is stirred for 16 hours at ambient temperature, then suction filtered through Alox. The Alox is washed with dimethylsulfoxide. The mother liquor is evaporated to dryness. The residue is stirred with water, suction filtered, and dried. 0.470 g of product VIII (76%) is obtained as a powder (m.p. 229-233° C.). $^1$H NMR (400 MHz, DMSO): 7.90 (1H, d); 7.75 (2H, d); 6.97 (2H, d); 6.43 (1H, d); 3.82-3.66 (5H, m); 3.23 (2H, t); 2.99 (2H, t); 2.80-2.70 (2H, m); 2.15 (3H, s); 1.92 (2H, t); 1.77-1.68 (2H, m); 1.64-1.49 (4H, m); 0.87 (3H, t).

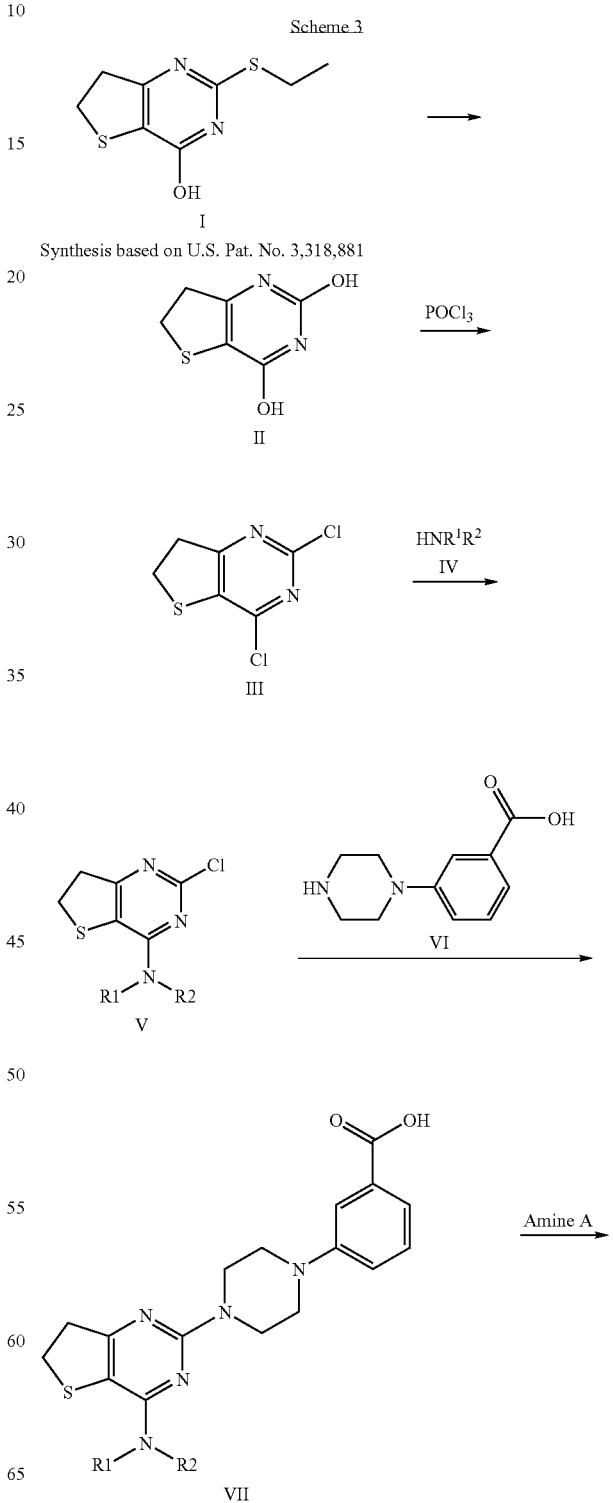

-continued

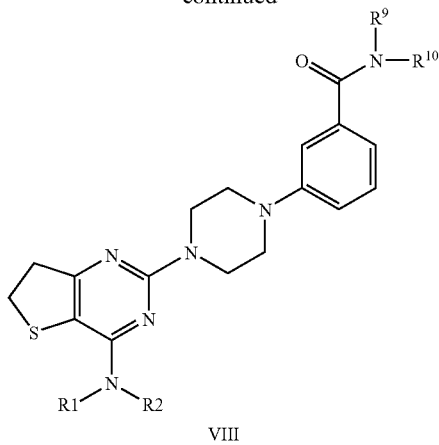

VIII

Synthesis of 3-[4-(4-propylamino-6,7-dihydrothieno[3,2-d]pyrimidin-2-yl)piperazin-1-yl]benzoic acid (Scheme 3) (in each case only the reactions of V with VI and with the amine A to yield the product VIII are described)

3-[4-(4-propylamino-6,7-dihydrothieno[3,2-d]pyrimidin-2-yl)piperazin-1-yl]benzoic acid (VIII) (Example 66) 0.900 g (3.9 mmol) of (2-chloro-6,7-dihydrothieno[3,2-d]pyrimidin-4-yl)propylamine (V) and 1.5 g (4.7 mmol) of 3-piperazin-1-yl]benzoic acid triflate (VI) are placed in 20 mL of dioxane, and 5 mL (36.7 mmol) of diisopropylethylamine (amine A) are added. The suspension is stirred for 24 hours at 180° C. in a pressurised glass container, then concentrated by evaporation. The residue is dissolved in acetonitrile and water, then purified by HPLC through an RP column (column: XTerra, MS-C18, 5 μm, 19*100 mm, eluant: water+0.1% trifluoroacetic acid (A), acetonitrile+0.1% trifluoroacetic acid (B)).

| gradient: minutes | % eluant A | % eluant B |
|---|---|---|
| 0 | 90 | 10 |
| 2 | 90 | 10 |
| 11.5 | 0 | 100 |
| 13 | 0 | 100 |
| 13.5 | 90 | 10 |

Corresponding fractions are combined and freeze-dried. 0.43 g of product VIII (27%) is obtained.

Scheme 4

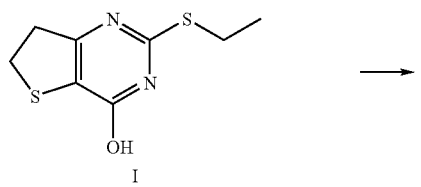

I
Synthesis based on U.S. Pat. No. 3,318,881

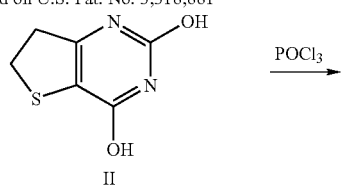

II

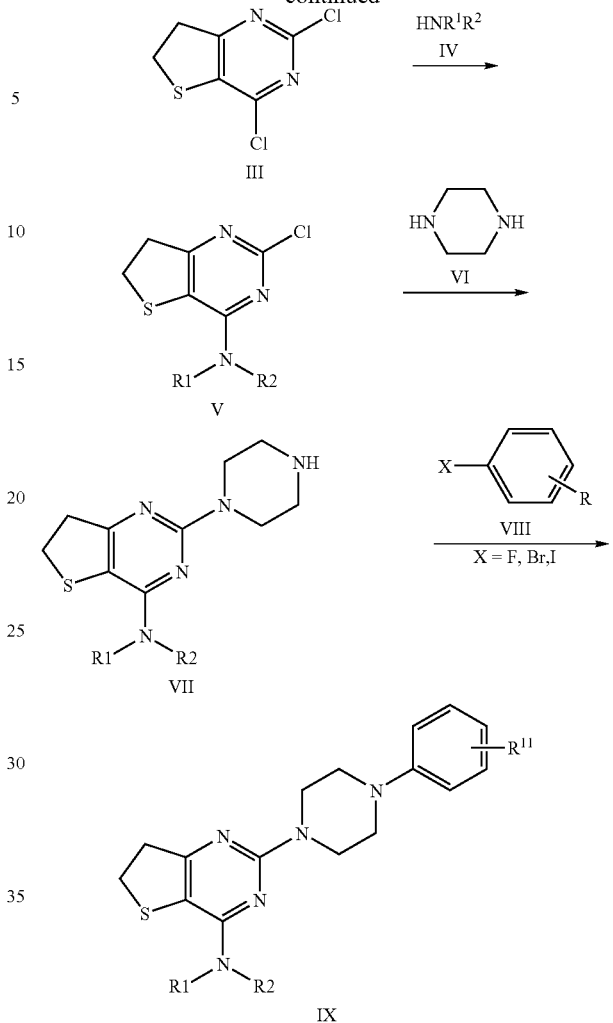

Synthesis of 4-[4-(4-propylamino-6,7-dihydrothieno[3,2-d]pyrimidin-2-yl)piperazin-1-yl]benzonitrile (IX) (Scheme 4) (only the reactions of V with VI to VII and of VII and VIII to IX are described)

(2-piperazin-1-yl-6,7-dihydrothieno[3,2-d]pyrimidin-4-yl)propylamine (VII): 1.0 g (4.4 mmol) of (2-chloro-6,7-dihydrothieno[3,2-d]pyrimidin-4-yl)propylamine (V) and 1.9 g (21.8 mmol) of piperazine (VI) are placed in 10 mL of dioxane, then reacted for 0.7 hours at 150° C. in the microwave. Then the reaction mixture is extracted with water and ethyl acetate, and the organic phase is dried and evaporated to dryness. The residue is triturated with petroleum ether and suction filtered. 0.97 g of product VII (80%) is obtained as a powder.

4-[4-(4-propylamino-6,7-dihydrothieno[3,2-d]pyrimidin-2-yl)piperazin-1-yl]benzonitrile (IX) (Example 76): 0.150 g (0.5 mmol) of (2-piperazin-1-yl-6,7-dihydrothieno[3,2-d]pyrimidin-4-yl)propylamine (VII), 0.082 g (0.45 mmol) of 4-bromobenzonitrile (VIII), 0.011 g (0.05 mmol) of palladium acetate, 0.041 g (0.07 mmol) of Xantphos, and 0.204 g (0.6 mmol) of cesium carbonate are placed in 1 mL of toluene, then stirred for 24 hours at 80° C. Then the reaction mixture is combined with water and extracted with ethyl acetate. The organic phase is washed with water, dried, and evaporated to dryness. The residue is purified by chromatography through an RP column using HPLC (column: Microsorb, RP-C18, 300 Å, 10 μm, 21.4*250 mm, eluant: acetonitrile+0.1% formic acid (A), water+0.13% formic acid (B).

| gradient: minutes | % eluant A | % eluant B |
|---|---|---|
| 0 | 10 | 90 |
| 4.9 | 10 | 90 |
| 27 | 100 | 0 |
| 32 | 100 | 0 |
| 32.5 | 10 | 90 |
| 37.5 | 10 | 90 |

Corresponding fractions are combined and freeze-dried. 0.08 g of product IX (47%) is obtained as a powder. $^1$H NMR (400 MHz, DMSO): 7.59 (2H, d); 7.04 (2H, d); 6.44 (1H, t); 3.78-3.71 (4H, m); 3.43-3.36 (4H, m); 3.23 (2H, t); 2.99 (2H, t); 1.60-1.49 (2H, m); 0.86 (3H, t).

{2-[4-(4-nitrophenyl)piperazin-1-yl]-6,7-dihydrothieno[3,2-d]pyrimidin-4-yl}propylamine (IX) (Example 71): 0.100 g (0.358 mmol) of (2-piperazin-1-yl-6,7-dihydrothieno[3,2-d]pyrimidin-4-yl)propylamine (VII) (cf method explained previously), 0.038 mL (0.358 mmol) of 1-fluoro-4-nitrobenzene (VIII), and 0.148 g (1.07 mmol) of potassium carbonate are placed in 4 mL of tetrahydrofuran, then stirred for 16 hours at ambient temperature and 8 hours at 65° C. and left to stand for a further 16 hours at ambient temperature. Then the solution is combined with water and extracted with ethyl acetate. The organic phase is dried and evaporated to dryness. The residue is combined with water and acetonitrile, whereupon a precipitate forms. This is suction filtered, washed, and dried. 0.023 g of product IX (16%) is obtained as a powder. $^1$H NMR (400 MHz, DMSO): 8.07 (2H, d); 7.04 (2H, d); 6.49-6.43 (1H, m); 3.81-3.73 (4H, m); 3.58-3.50 (4H, m); 3.24 (2H, t); 2.99 (2H, t); 1.61-1.49 (2H, m); 0.87 (3H, t).

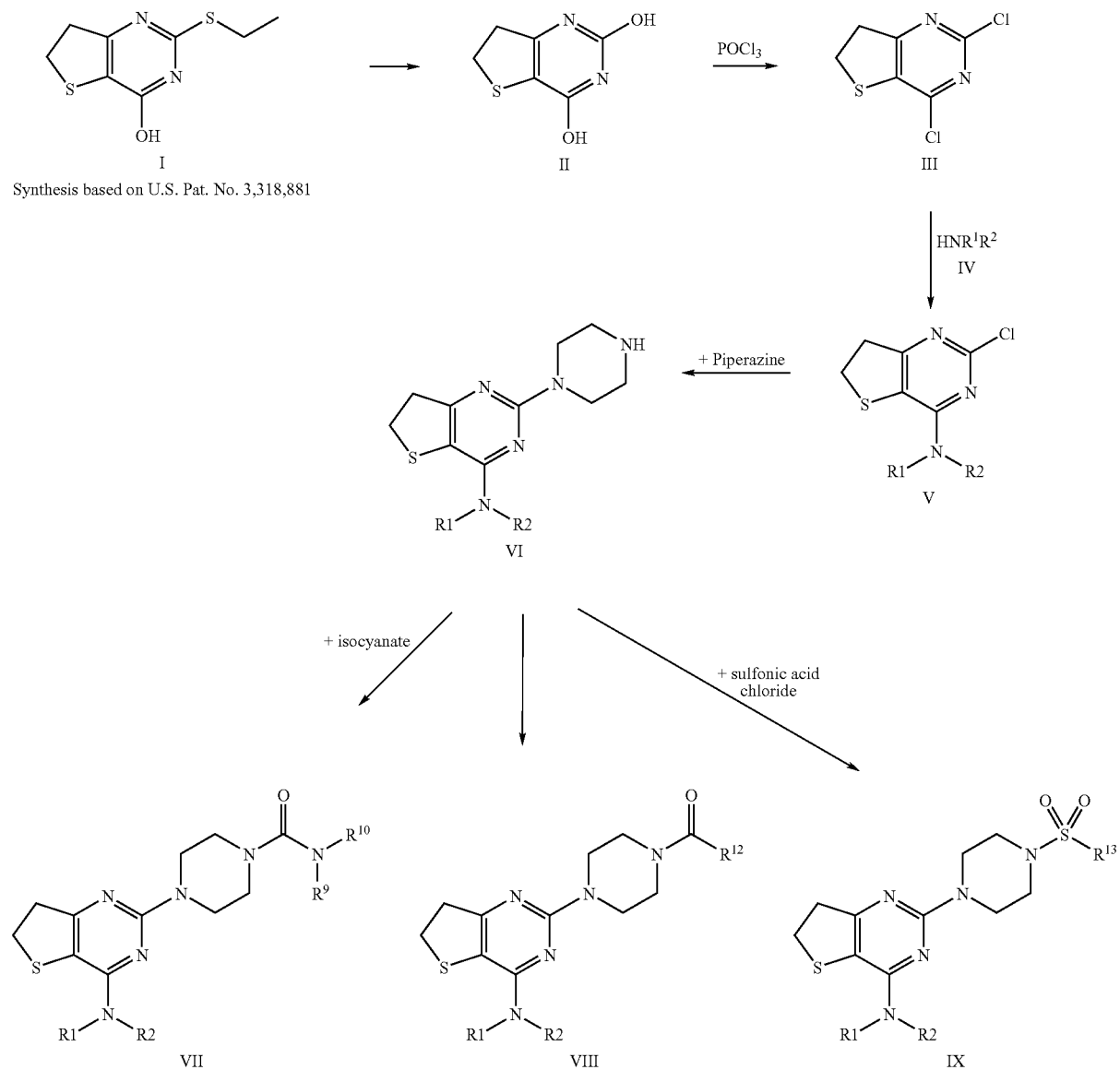

Scheme 5

Synthesis based on U.S. Pat. No. 3,318,881

Standard Methods for the Synthesis of Amides, Ureas, and Sulfonamides from (2-piperazin-1-yl-6,7-dihydrothieno[3,2-d]pyrimidin-4-yl)propylamine (Scheme 5)

Standard Method for the Synthesis of Amides (VIII): see above.

Standard Method for the Synthesis of Sulfonamides (IX): A solution of 0.063 mmol of the amine (VI) in 1 mL of dichloromethane is combined with 30 µL diisopropylamine and 0.065 mmol of sulfonic acid chloride, dissolved in 1 mL of dichloromethane, and stirred for 1 hour at ambient temperature. Then the reaction mixture is evaporated to dryness and purified by preparative HPLC.

Standard Method for the Synthesis of Ureas (VII): A solution of 0.063 mmol of the amine (VI) in 1 mL of tetrahydrofuran is combined with 30 µL of diisopropylamine and 0.065 mmol of isocyanate, dissolved in 1 mL of tetrahydrofuran, and stirred for 1 hour at ambient temperature. Then the reaction mixture is evaporated to dryness and purified by preparative HPLC.

Standard conditions for preparative HPLC purification: column: XTerra, MS-C18, 5 µm, 19*100 mm, eluant: water+ 0.1% trifluoroacetic acid (A), acetonitrile+0.1% trifluoroacetic acid (B).

| gradient: minutes | % eluant A | % eluant B |
| --- | --- | --- |
| 0 | 90 | 10 |
| 2 | 90 | 10 |
| 11.5 | 0 | 100 |
| 13 | 0 | 100 |
| 13.5 | 90 | 10 |

Corresponding fractions are combined and freeze-dried. The following Examples are prepared by the same method of synthesis according to Scheme 5:

4-(4-cyclohexylamino-6,7-dihydrothieno[3,2-d]pyrimidin-2-yl)piperazine-1-carboxylic acid-phenylamide (VII) (Example 102): 0.330 g (1.0 mmol) of cyclohexyl-(2-piperazin-1-yl-6,7-dihydrothieno[3,2-d]pyrimidin-4-yl)amine (VI) and 0.115 mL (1.0 mmol) of phenyl isocyanate are placed in 12.5 mL of tetrahydrofuran, then stirred for 1 hour at ambient temperature. Then the reaction mixture is concentrated by evaporation. The residue is stirred with water, suction filtered, washed with water and petroleum ether, then dried. The crude product is purified by chromatography through a 25 g silica gel cartridge with a solvent mixture of petroleum ether/ethyl acetate 1/1. 0.240 g of product VII (53%) is obtained as a powder (m.p. 207-210° C.). $^1$H NMR (400 MHz, DMSO): 8.51 (1H, s); 7.47 (2H, d); 7.23 (2H, t); 6.92 (1H, t); 6.11 (1H, d); 3.91-3.78 (1H, m); 3.69-3.59 (4H, m); 3.53-3.44 (4H, m); 3.22 (2H, t); 2.98 (2H, t); 1.92-1.78 (2H, m); 1.79-1.67 (2H, m); 1.65-1.56 (1H, m); 1.37-1.21 (4H, m); 1.18-1.04 (1H, m).

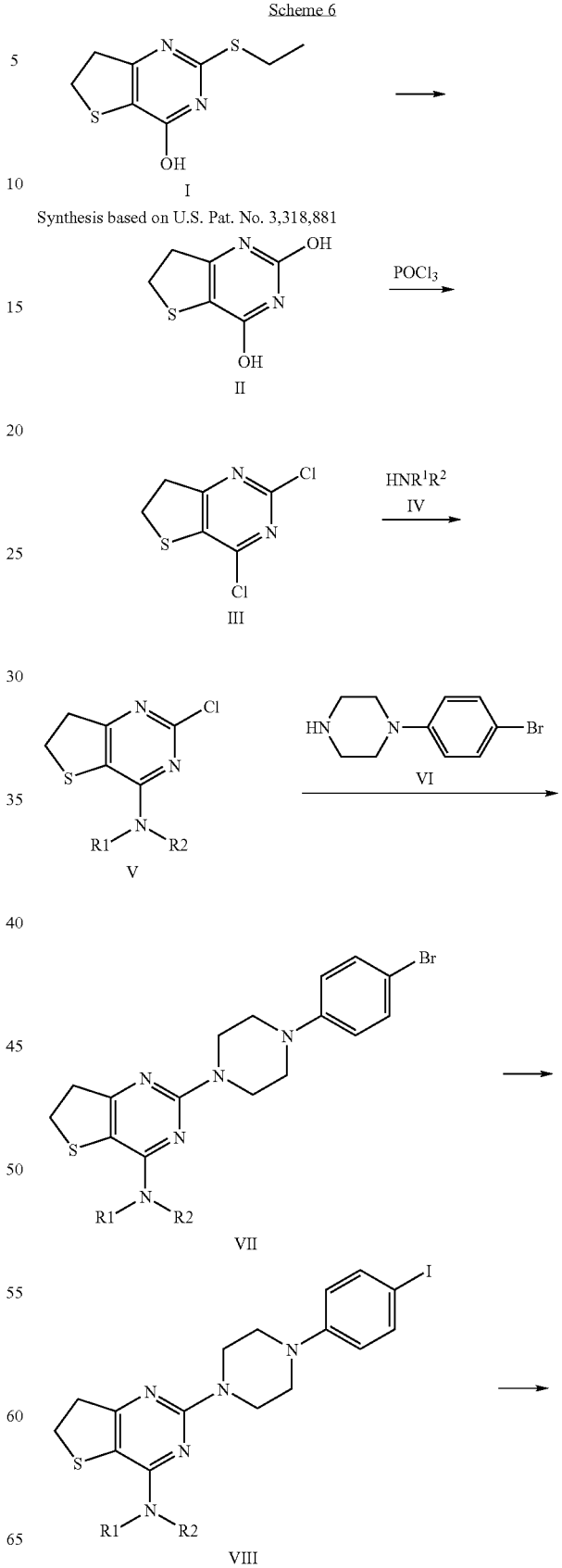

Scheme 6

Synthesis based on U.S. Pat. No. 3,318,881

-continued

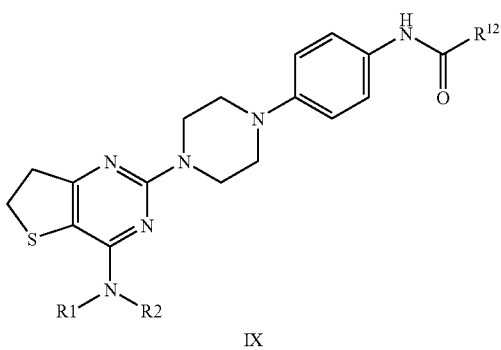

IX

Synthesis of N-{4-[4-(4-propylamino-6,7-dihydrothieno[3,2-d]pyrimidin-2-yl)piperazin-1-yl]phenyl}isonicotinamide (IX) (According to Scheme 6)

{2-[4-(4-bromophenyl)piperazin-1-yl]-6,7-dihydrothieno[3,2-d]pyrimidin-4-yl}propylamine (VII): 1.0 g (4.4 mmol) of (2-chloro-6,7-dihydrothieno[3,2-d]pyrimidin-4-yl)propylamine (V), 4.2 g (17.4 mmol) of 1-(4-bromophenyl)piperazine (VI), and 2.0 mL (11.5 mmol) of diisopropylethylamine are placed in 12 mL of dioxane and reacted for 2.5 hours at 160° C. in the microwave. Then the reaction mixture is combined with water and dichloromethane and extracted. The organic phase is washed with water, dried, and evaporated to dryness. The residue is filtered through silica gel with petroleum ether/ethyl acetate (8/2). Corresponding fractions were concentrated by evaporation. 1.9 g of product VII (100%) is obtained.

{2-[4-(4-iodophenyl)piperazin-1-yl]-6,7-dihydrothieno[3,2-d]pyrimidin-4-yl}propylamine (VIII): 1.55 g (3.6 mmol) of {2-[4-(4-bromophenyl)piperazin-1-yl]-6,7-dihydrothieno[3,2-d]pyrimidin-4-yl}propylamine (VII), 1.1 g (7.2 mmol) of sodium iodide, and 0.036 g (0.19 mmol) of copper iodide are taken, and under an argon atmosphere 0.060 mL (0.38 mmol) of trans-N,N-dimethyl-1,2-cyclohexanediamine and 7 mL of anhydrous/degassed dioxane are added. The reaction mixture is heated for 1.5 hours at 140° C. in the microwave, then diluted with dioxane, and suction filtered through Alox. The dioxane was concentrated by evaporation. 1.70 g of product VIII (81%) is obtained as a powder.

N-{4-[4-(4-propylamino-6,7-dihydrothieno[3,2-d]pyrimidin-2-yl)piperazin-1-yl]phenyl}isonicotinamide (IX) (Example 237): 0.170 g (0.4 mmol) of {2-[4-(4-iodophenyl)piperazin-1-yl]-6,7-dihydrothieno[3,2-d]pyrimidin-4-yl}propylamine (VIII), 0.054 g (0.4 mmol) of isonicotinamide, 0.100 g (0.7 mmol) of potassium carbonate, and 0.004 g (0.02 mmol) of copper iodide are taken, and under an argon atmosphere 1 mL of anhydrous/degassed dioxane and 0.006 mL (0.04 mmol) of trans-N,N-dimethyl-1,2-cyclohexanediamine are added. The reaction mixture is reacted for 2 hours at 140° C. in the microwave, then filtered through silica gel with petroleum ether/ethyl acetate (1/1) and then ethyl acetate/methanol (8/2), and concentrated by evaporation. The residue is purified by chromatography (column: Microsorb, RP-C18, 300 Å, 10 μm, 21.4*250 mm, eluant: acetonitrile+0.1% formic acid (A), water+0.13% formic acid (B)).

| gradient: minutes | % eluant A | % eluant B |
| --- | --- | --- |
| 0 | 10 | 90 |
| 4.9 | 10 | 90 |
| 10.5 | 30 | 70 |
| 20 | 30 | 70 |
| 21 | 100 | 0 |
| 25 | 100 | 0 |
| 26.5 | 10 | 90 |
| 31.5 | 10 | 90 |

0.08 g of product IX (50%) is obtained as a powder. $^1$H NMR (400 MHz, DMSO): 10.29 (1H, s); 8.77 (2H, d); 7.85 (2H, d); 7.64 (2H, d); 7.01 (2H, d); 3.86-3.75 (4H, m); 3.23-3.07 (6H, m); 1.64-1.50 (2H, m); 0.88 (3H, t).

Scheme 7

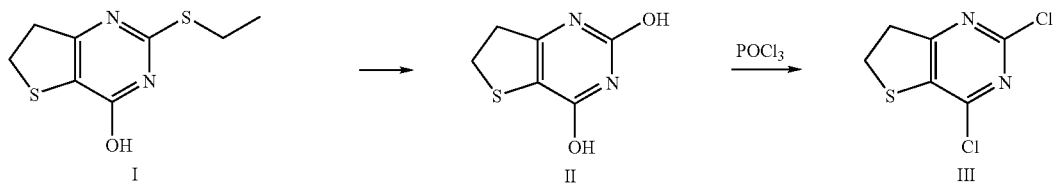

Synthesis based on U.S. Pat. No. 3,318,881

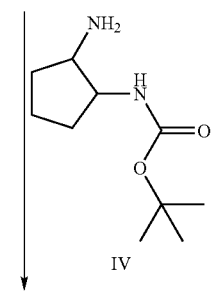

IV

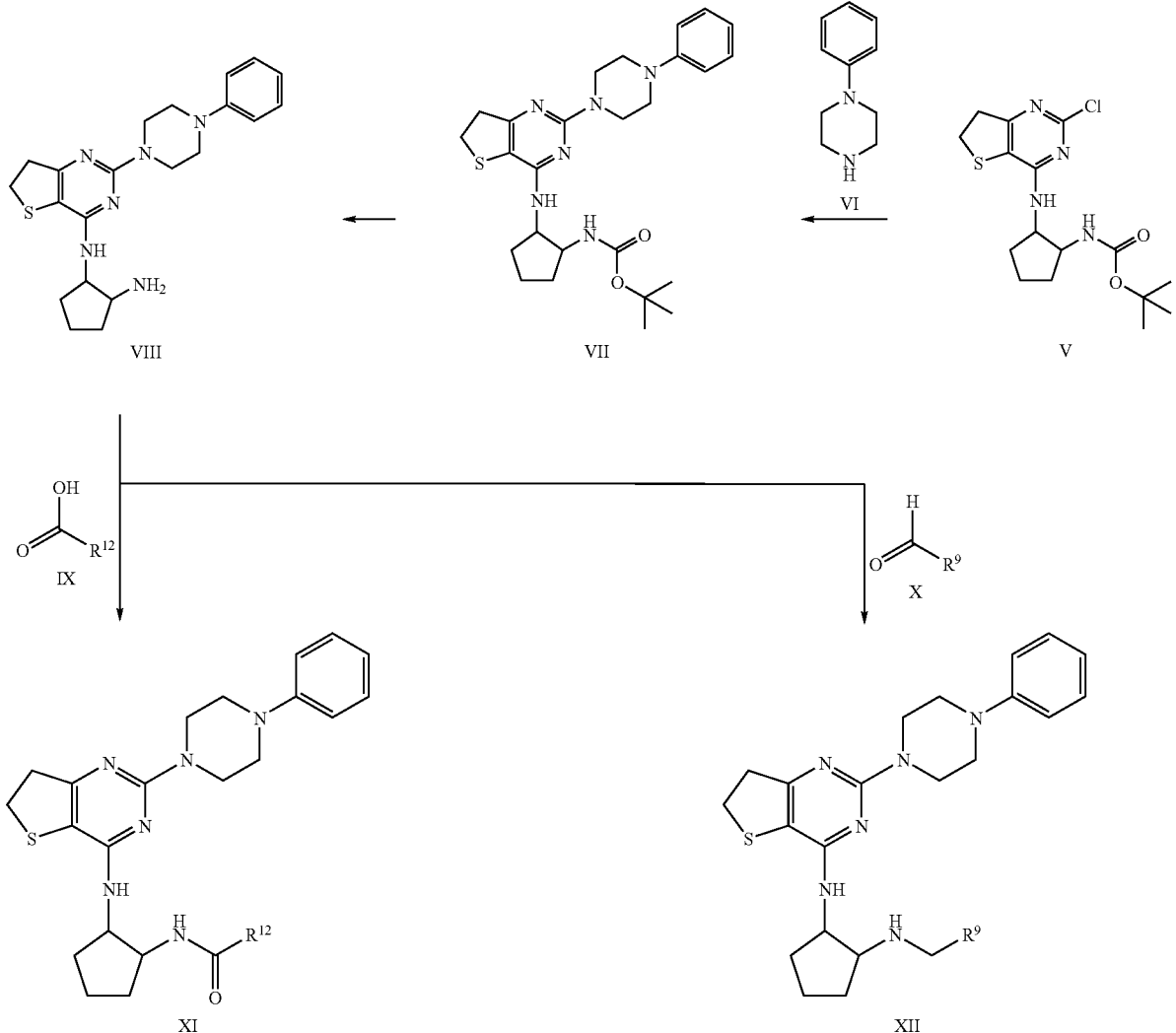

Synthesis of Isoxazole-5-carboxylic acid-{(1S,2S)-2-[2-(4-phenylpiperazin-1-yl)-6,7-dihydrothieno[3,2-d]pyrimidin-4-ylamino]cyclopentyl}amide triflate (XI) (chiral) (According to Scheme 7)

tert-butyl [(1S,2S)-2-(2-chloro-6,7-dihydrothieno[3,2-d]pyrimidin-4-ylamino)cyclopentyl]carbamate (V) (chiral): 0.600 g (2.9 mmol) of 2,4-dichloro-6,7-dihydrothieno[3,2-d]pyrimidine (III), 0.580 g (2.9 mmol) of tert-butyl (2-aminocyclopentyl)carbamate (IV), and 2.5 mL (14.5 mmol) of diisopropylethylamine are placed in 30 mL of tetrahydrofuran, the mixture is stirred for 2 hours at ambient temperature and 72 hours at 80° C. The reaction mixture is concentrated by evaporation and further reacted in the crude state.

tert-butyl {(1S,2S)-2-[2-(4-phenylpiperazin-1-yl)-6,7-dihydrothieno[3,2-d]pyrimidin-4-ylamino]cyclopentyl}carbamate (VII) (chiral): 1.08 g (2.9 mmol) of tert-butyl [(1S,2S)-2-(2-chloro-6,7-dihydrothieno[3,2-d]pyrimidin-4-ylamino)cyclopentyl]carbamate (V) and 9.9 mmol of 1-phenylpiperazine (VI) are placed in 14 mL of dioxane, then heated to 160° C. for 2.3 hours. The reaction mixture is concentrated by evaporation, the residue is then purified by HPLC through an RP column (column: XTerra, MS-C18, 5 µm, 19*100 mm, eluant: water+0.1% trifluoroacetic acid (A), acetonitrile+0.1% trifluoroacetic acid (B)).

| gradient: minutes | % eluant A | % eluant B |
|---|---|---|
| 0 | 90 | 10 |
| 2 | 90 | 10 |
| 11.5 | 0 | 100 |
| 13 | 0 | 100 |
| 13.5 | 90 | 10 |

Corresponding fractions are combined and freeze-dried. 0.97 g of product VII (67%) is obtained.

(1S,2S)-N-[2-(4-phenylpiperazin-1-yl)-6,7-dihydrothieno[3,2-d]pyrimidin-4-yl]cyclopentane-1,2-diamine ditriflate (VIII) (chiral): 0.960 g (1.9 mmol) of tert-butyl {(1S,2S)-2-[2-(4-phenylpiperazin-1-yl)-6,7-dihydrothieno[3,2-d]pyrimidin-4-ylamino]cyclopentyl}carbamate (VII) (chiral) is dissolved in 40 mL of 25% trifluoroacetic acid in dichloromethane and the mixture is stirred for 1 hour at ambient temperature. Then the reaction mixture is concentrated by evaporation, the residue is combined with acetonitrile and water, and freeze-dried. 1.2 g of product VIII (100%) is obtained as a powder.

isoxazole-5-carboxylic acid-{(1S,2S)-2-[2-(4-phenylpiperazin-1-yl)-6,7-dihydrothieno[3,2-d]pyrimidin-4-ylamino]cyclopentyl}amide triflate (chiral) (XI) (Example 277): 0.004 g (0.03 mmol) of isoxazole-5-carboxylic acid (IX), 0.012 g (0.03 mmol) of O-(7-azabenzotriazol-1-yl)-N,N,N',N'-tetramethyluroniumhexafluorophosphate (HATU), and 0.017 mL (0.10 mmol) of diisopropylethylamine are placed in 1 mL of dimethylformamide, stirred for 0.1 hours at ambient temperature. Then 0.020 g (0.03 mmol) of N-[2-(4-phenylpiperazin-1-yl)-6,7-dihydrothieno[3,2-d]pyrimidin-4-yl]cyclopentane-1,2-diamine ditriflate (VIII) (chiral) in 1 mL of dimethylformamide are added. The mixture is shaken for 1 hour at ambient temperature. Then the reaction mixture is purified directly by HPLC through an RP column (column: XTerra, MS-C18, 5 μm, 19*100 mm, eluant: water+0.1% trifluoroacetic acid (A), acetonitrile+0.1% trifluoroacetic acid (B)).

| gradient: minute | % eluant A | % eluant B |
| --- | --- | --- |
| 0 | 90 | 10 |
| 2 | 90 | 10 |
| 11.5 | 0 | 100 |
| 13 | 0 | 100 |
| 13.5 | 90 | 10 |

Corresponding fractions are combined and freeze-dried. 0.003 g of product XI (18%) is obtained.

Synthesis of (1S,2S)-N-(1-methyl-1H-pyrrol-2-ylmethyl)-N'-[2-(4-phenylpiperazin-1-yl)-6,7-dihydrothieno[3,2-d]pyrimidin-4-yl]cyclopentane-1,2-diamine triflate (chiral) (Example 310) (XII) (According to Scheme 7)

0.015 g (0.02 mmol) of N-[2-(4-phenylpiperazin-1-yl)-6,7-dihydrothieno[3,2-d]pyrimidin-4-yl]cyclopentane-1,2-diamine ditriflate (VIII) (chiral), 0.015 mL (0.14 mmol) of 1-methyl-1H-pyrrole-2-carbaldehyde (X), 0.005 mL (0.09 mmol) of glacial acetic acid, and molecular sieve are placed in 2 mL of dimethylformamide, and the mixture is stirred for 0.5 hours at ambient temperature. Then first of all 0.070 g (0.23 mmol) of polyamine resin is added, followed, after another 0.5 hours, by 0.030 g (0.14 mmol) of sodium triacetoxyborohydride. The reaction mixture is shaken for 16 hours at ambient temperature, filtered, and purified through an RP-column by HPLC (column: XTerra, MS-C18, 5 μm, 19*100 mm, eluant: water+0.1% trifluoroacetic acid (A), acetonitrile+ 0.1% trifluoroacetic acid (B)). Corresponding fractions are combined and lyophilized. 0.009 g of product XII (59%) is obtained. ¹H NMR (400 MHz, DMSO): 7.28-7.21 (2H, m); 7.00-6.95 (2H, m); 6.85-6.78 (2H, m); 6.21-6.18 (1H, m); 6.01-5.98 (1H, m); 4.74-4.67 (1H, m); 4.19-4.12 (2H, m); 3.81-3.74 (4H, m); 3.74-3.64 (1H, m); 3.59 (3H, t); 3.20-3.13 (4H, m); 3.11-3.03 (3H, m); 2.19-2.03 (3H, m); 1.78-1.70 (4H, m); 1.67-1.54 (1H, m).

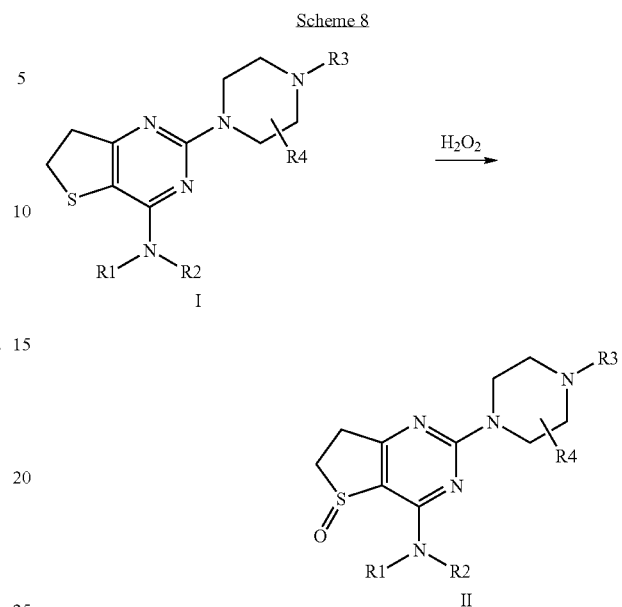

Scheme 8

Synthesis of cyclohexyl-[5-oxo-2-(4-phenylpiperazin-1-yl)-6,7-dihydro-5H-5λ⁴-thieno[3,2-d]pyrimidin-4-yl]amine (Example 297) (II) (According to Scheme 8)

0.120 g (0.3 mmol) of cyclohexyl-[2-(4-phenylpiperazin-1-yl)-6,7-dihydrothieno[3,2-d]pyrimidin-4-yl]amine (I) is dissolved in 4 mL of acetic acid and 0.27 mL of 35% hydrogen peroxide solution is added. The mixture is stirred for 16 hours at ambient temperature, then water is added. The reaction mixture is made basic and extracted with ethyl acetate. The organic phase is dried and evaporated to dryness. The residue is purified by chromatography, the product is triturated with diethyl ether and suction filtered. 0.060 g of product II (48%) is obtained. ¹H NMR (400 MHz, DMSO): 7.40 (1H, d); 7.23 (2H, t); 6.98 (2H, d); 6.80 (1H, t); 4.01-3.86 (5H, m); 3.48-3.37 (1H, m); 3.28-3.13 (5H, m); 3.00-2.82 (2H, m); 1.92-1.81 (2H, m); 1.80-1.69 (2H, m); 1.67-1.57 (1H, m); 1.43-1.21 (4H, m); 1.20-1.05 (1H, m).

The enantiomers were separated by analytical chiral HPLC (column: Chiralpak Diacel AD-H, 5 μM, 250*4.6 mm, flow rate: 1.0 mL/min, eluant: hexane/iPrOH (90/10)): Rt=14.6 min: enantiomer 1 (Example 367) [α$_D^{20}$+183 (CH$_2$Cl$_2$); Rt=16.4 min: enantiomer 2 (Example 368), [α$_D^{20}$−189 (CH$_2$Cl$_2$).

Synthesis of [5-oxo-2-(4-phenylpiperazin-1-yl-6,7-dihydro-5h-5λ⁴-thieno[3,2-d]pyrimidin-4-yl]propylamine (example 298) (II) (According to Scheme 8)

0.240 g (0.68 mmol) of [2-(4-phenylpiperazin-1-yl)-6,7-dihydrothieno[3,2-d]pyrimidin-4-yl]propylamine (I) is dissolved in 5 mL of acetic acid, and 0.60 mL of 35% hydrogen peroxide solution are added while being cooled. The mixture is stirred for 16 hours at ambient temperature, then water is added. The reaction mixture is made basic and extracted with dichloromethane. The organic phase is dried and evaporated to dryness. The residue is purified by chromatography, and the product is triturated with diethyl ether and suction filtered. 0.130 g of product II (52%) is obtained. $^1$H NMR (400 MHz, DMSO): 7.69 (1H, t); 7.23 (2H, t); 6.98 (2H, d); 6.80 (1H, t); 3.95-3.87 (4H, m); 3.49-3.19 (4H, m); 3.22-3.13 (4H, m); 3.01-2.82 (2H, m); 1.64-1.52 (2H, m); 0.88 (3H, t).

Synthesis of [5-oxo-2-(4-phenylpiperazin-1-yl)-6,7-dihydro-5H-5$\lambda^4$-thieno[3,2-d]pyrimidin-4-yl]phenylamine (II) (Example 299) (According to Scheme 8)

0.190 g (0.49 mmol) of phenyl-[2-(4-phenylpiperazin-1-yl)-6,7-dihydrothieno[3,2-d]pyrimidin-4-yl]amine (I) is dissolved in 5 mL of acetic acid, and 0.43 mL of 35% hydrogen peroxide solution is added, with cooling. The mixture is stirred for 16 hours at ambient temperature, then water is added. The reaction mixture is made basic and extracted with dichloromethane. The organic phase is dried and evaporated to dryness. The residue is purified by chromatography, and the product is triturated with diethyl ether and suction filtered. 0.100 g of product II (51%) is obtained. $^1$H NMR (400 MHz, DMSO): 9.54 (1H, s); 7.66 (2H, d); 7.35 (2H, t); 7.23 (2H, t); 7.09 (1H, t); 6.98 (2H, d); 6.80 (1H, t); 3.96-3.85 (4H, m); 3.60-3.47 (1H, m); 3.32-3.15 (4H, m); 3.12-3.02 (1H, m); 3.01-2.92 (1H, m).

The following Examples are prepared as described above according to Scheme 8:
(3-methoxyphenyl)-[5-oxo-2-(4-phenylpiperazin-1-yl)-6,7-dihydro-5h-5$\lambda^4$-thieno[3,2-d]pyrimidin-4-yl]amine (Example 302) (II according to Scheme 8): 0.072 g of product II (17%) is obtained as a powder (m.p. 217° C.-220° C.).
(3-chlorophenyl)-[5-oxo-2-(4-phenylpiperazin-1-yl)-6,7-dihydro-5H-5$\lambda^4$-thieno[3,2-d]pyrimidin-4-yl]amine (Example 300) (II According to Scheme 8): 4.50 g of product II (73%) is obtained as a powder. (m.p. 230° C.-231° C.).

The enantiomers were separated by semipreparative chiral HPLC (column: Chiralpak Diacel IA, 5 μM, 200*25 mm, flow rate: 12 mL/min, eluant: TBME/EtOH (75/25)): Rt=16 min: Enantiomer 1 (Example 370), [α$_D^{20}$+221.3 (c 2.06, CH$_2$Cl$_2$).; Rt=19 min: Enantiomer 2 (Example 371), [α$_D^{20}$−207.9 (c 2.24, CH$_2$Cl$_2$).

Scheme 9

See Scheme 1
Manufacturing Way B

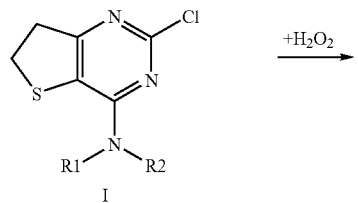

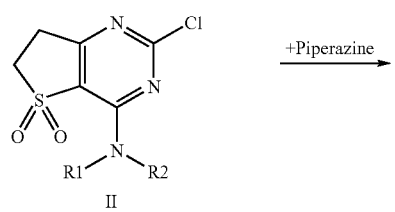

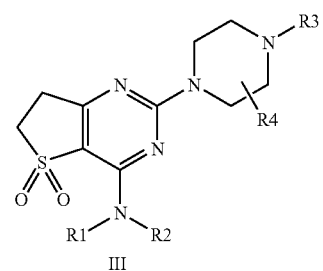

Synthesis of {2-[4-(4-chlorophenyl)piperazin-1-yl]-5,5-dioxo-6,7-dihydro-5h-5$\lambda^6$-thieno[3,2-d]pyrimidin-4-yl}propylamine (Example 377) (III According to Scheme 9)

(2-chloro-5,5-dioxo-6,7-dihydro-5H-5$\lambda^6$-thieno[3,2-d]pyrimidin-4-yl)propylamine (II): 0.805 g (3.50 mmol) of (2-chloro-6,7-dihydrothieno[3,2-d]pyrimidin-4-yl)propylamine (I) (see Scheme 1, preparation method B) is placed at ambient temperature in 14 mL of trifluoroacetic acid, then combined with 0.82 mL (8.40 mmol) of hydrogen peroxide (35% in water). The reaction mixture is stirred for 16 hours at ambient temperature and 2 hours at 45° C. After the addition of 0.5 equiv. hydrogen peroxide, the mixture is stirred for a further 0.5 hours at 45° C., then stirred into ice water and made basic with ammonia solution. Any precipitate formed is suction filtered, washed, and dried. 0.720 g of product II (79%) is obtained as a powder.

{2-[4-(4-chlorophenyl)piperazin-1-yl]-5,5-dioxo-6,7-dihydro-5H-5$\lambda^6$-thieno[3,2-d]pyrimidin-4-yl}propylamine (III): 0.262 g (1.00 mmol) of (2-chloro-5,5-dioxo-6,7-dihydro-5H-5$\lambda^6$-thieno[3,2-d]pyrimidin-4-yl)propylamine (II) and 0.433 g (2.20 mmol) of 1-(4-chlorophenyl)piperazine are placed in 4.50 mL of dioxane, then heated to 150° C. in the microwave for 0.75 hours. Then the reaction mixture is concentrated by evaporation, the residue is treated with water. It is suction filtered, washed with water, and dried. The product which is not yet clean is purified by chromatography (column: 10 g Chromabond SiOH cartridge, solvent: petroleum ether/ether 1:1). Corresponding fractions are combined and concentrated by evaporation. 0.295 g of product III (70%) is obtained as a powder (m.p. 243° C.-245° C.).

The following Examples are prepared as described above according to Scheme 9:
(3-chlorophenyl)-[5,5-dioxo-2-(4-phenylpiperazin-1-yl)-6,7-dihydro-5h-5$\lambda^6$-thieno[3,2-d]pyrimidin-4-yl]amine (Example 375) (III according to Scheme 9): 0.163 g of product III (36%) is obtained as a powder (m.p. 234° C.).
(3-chlorophenyl)-{2-[4-(4-chlorophenyl)piperazin-1-yl]-5,5-dioxo-6,7-dihydro-5h-5$\lambda^6$-thieno[3,2-d]pyrimidin-4-yl}amine (Example 376) (III according to Scheme 9): 0.173 g of product III (35%) is obtained as a powder (m.p. 246° C.).

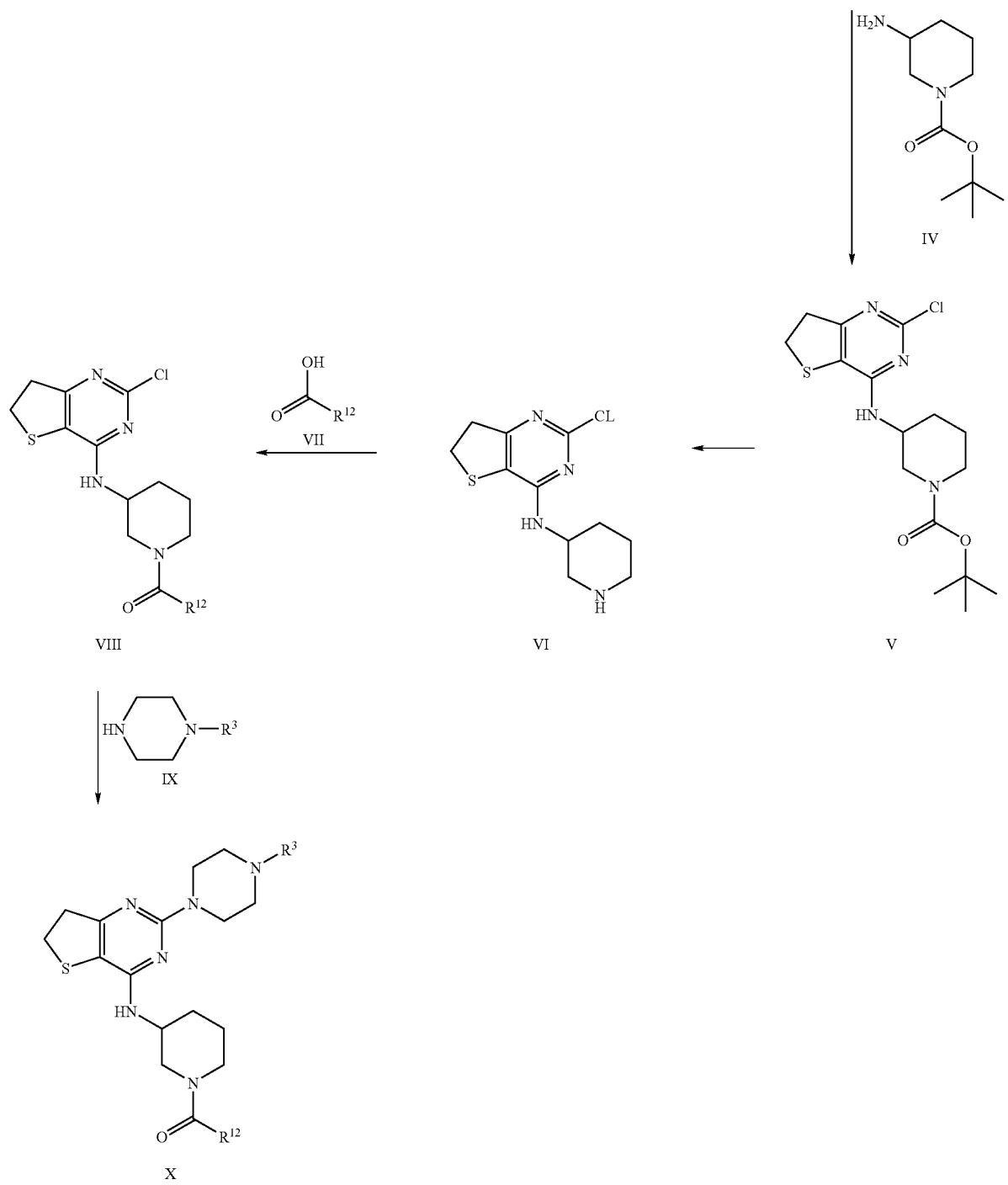

Synthesis of (1-methyl-1H-pyrrol-2-yl)-{3-[2-(4-(4-chlorophenyl)piperazin-1-yl]-6,7-dihydrothieno[3,2-d]pyrimidin-4-ylamino]piperidin-1-yl}methanone (X according to Scheme 10)

tert-butyl 3-(2-chloro-6,7-dihydrothieno[3,2-d]pyrimidin-4-ylamino)piperidine-1-carboxylate (V): 2.07 g (10.0 mmol) of 2,4-dichloro-6,7-dihydrothieno[3,2-d]pyrimidine (III), 2.0 g (10.0 mmol) of tert-butyl 3-aminopiperidin-1-carboxylate (IV), and 3.4 mL (19.3 mmol) of diisopropylethylamine are placed in 40 mL of tetrahydrofuran, then stirred for 40 hours at ambient temperature. Then the reaction mixture is suction filtered and the mother liquor is concentrated by evaporation. The residue is combined with water and extracted with dichloromethane. The organic phase is separated off using a phase separator and evaporated to dryness. The crude product is purified by chromatography through a Biotage silica gel cartridge 40M with petroleum ether/ethyl acetate 9:1. 1.77 g of product V (48%) is obtained.

(2-chloro-6,7-dihydrothieno[3,2-d]pyrimidin-4-yl)piperidin-3-ylamine hydrochloride (VI): 1.77 g (4.8 mmol) of tert-butyl 3-(2-chloro-6,7-dihydrothieno[3,2-d]pyrimidin-4-ylamino)piperidin-1-carboxylate (V) is placed in 21.5 mL of a 4% hydrochloric acid solution in dioxane, and methanol is added. The solution is stirred for 0.5 hours at ambient temperature, whereupon a precipitate is formed. This is suction filtered, washed with diethyl ether, and dried. 1.33 g of product (VI) (91%) is obtained.

(1-methyl-1H-pyrrol-2-yl)-[3-(2-chloro-6,7-dihydrothieno[3,2-d]pyrimidin-4-ylamino)piperidin-1-yl]methanone (VIII): 0.462 g (3.7 mmol) of 1-methyl-1H-pyrrol-2-carboxylic acid (VII), 1.4 g (9.7 mmol) of O-(7-azabenzotriazol-1-yl-)-N,N,N',N'-tetramethyluroniumhexafluorophosphate (HATU), and 0.640 mL (3.7 mmol) of diisopropylethylamine are placed in 10 mL of dimethylsulfoxide, then stirred for 0.1 hours at ambient temperature. 0.814 g (3.0 mmol) of (2-chloro-6,7-dihydrothieno[3,2-d]pyrimidin-4-yl)piperidin-3-ylamine hydrochloride (VI) and 3.7 mmol of diisopropylethylamine are added, then the mixture is stirred for 16 hours at ambient temperature. Then the reaction mixture is suction filtered through Alox, and the mother liquor is concentrated by evaporation. The residue is combined with 1 N sodium hydroxide solution and extracted with dichloromethane. The organic phase is separated off using a phase separator and evaporated to dryness. The crude product is purified by chromatography through a Biotage silica gel cartridge 40 s with petroleum ether/ethyl acetate 1:1. 0.970 g of product VIII (85%) is obtained.

(1-methyl-1H-pyrrol-2-yl)-{3-[2-(4-(4-chlorophenyl)piperazin-1-yl]-6,7-dihydrothieno[3,2-d]pyrimidin-4-ylamino]piperidin-1-yl}methanone (X According to Scheme 10) (Example 230): 0.250 g (0.7 mmol) of (1-methyl-1H-pyrrol-2-yl)-[3-(2-chloro-6,7-dihydrothieno[3,2-d]pyrimidin-4-ylamino)piperidin-1-yl]methanone (VIII), 0.503 g (1.9 mmol) of 1-(4-chlorophenyl)piperazine dihydrochloride (IX), and 0.430 mL (2.5 mmol) of diisopropylethylamine are placed in 3.5 mL of dioxane, then reacted for 2.25 hours at 160° C. in the microwave. Then the reaction mixture is combined with water. Any precipitate formed is suction filtered, washed with water, and dried. 0.167 g of product X (47%) is obtained as a beige powder. $^1$H NMR (400 MHz, DMSO): 7.25 (2H, d); 6.97 (2H, d); 6.84 (1H, t); 6.34-6.31 (1H, m); 5.96 (1H, m); 4.46-4.34 (1H, m); 4.22-4.12 (1H, m); 4.04-4.92 (1H, m); 3.73-3.64 (4H, m); 3.67 (3H, s); 3.24 (2H, t); 3.16-3.09 (4H, m); 3.05-2.84 (4H, m); 1.97-1.88 (1H, m); 1.82-1.65 (2H, m); 1.55-1.43 (1H, m).

Scheme 11

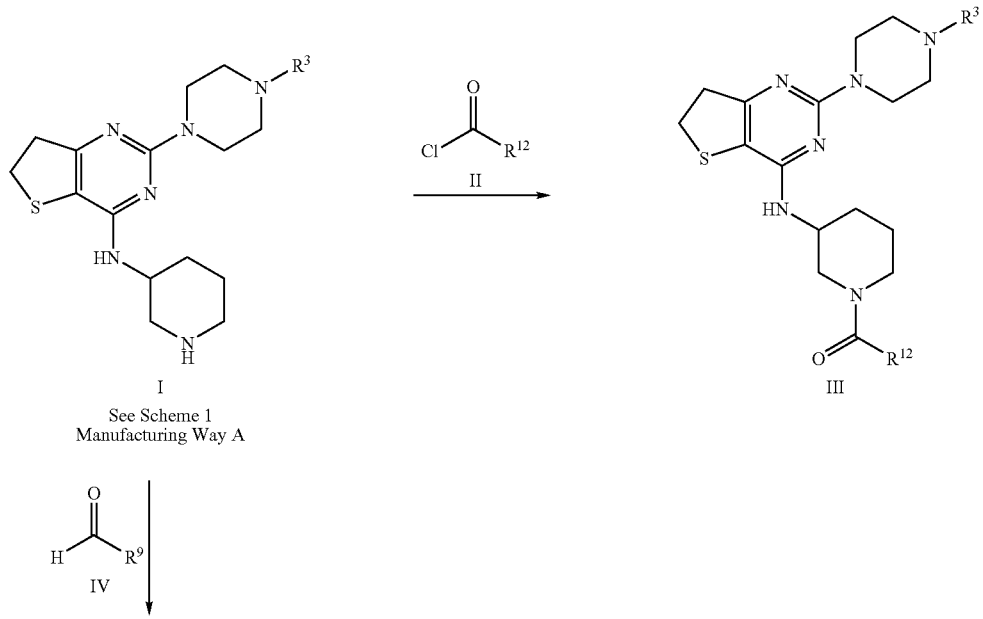

-continued

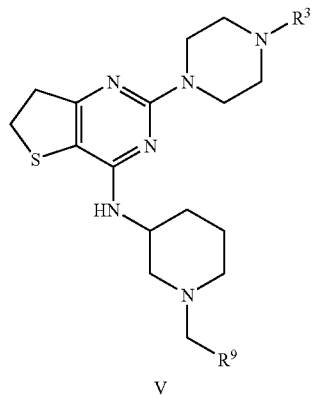

V

Synthesis of (3-{2-[4-(4-chlorophenyl)piperazin-1-yl]-6,7-dihydrothieno[3,2-d]pyrimidin-4-ylamino}piperidin-1-yl)morpholin-4-ylmethanone triflate (Example 357) (III According to Scheme 11)

0.135 g (0.31 mmol) of {2-[4-(4-chlorophenyl)piperazin-1-yl]-6,7-dihydrothieno[3,2-d]pyrimidin-4-yl}piperidin-3-ylamine (I) (see Scheme 1), 0.037 mL (0.31 mmol) of morpholine-4-carbonyl chloride (II), 0.119 g (0.31 mmol) of O-(7-azabenzotriazol-1-yl-)-N,N,N',N'-tetramethyluronium hexafluorophosphate (HATU), and 0.218 mL (1.25 mmol) of diisopropylethylamine are stirred in 6 mL of dimethylformamide for 18 hours at ambient temperature. The reaction mixture is concentrated by evaporation, the residue is purified by chromatography (RP-HPLC). 0.040 g of the product III (19%) is obtained after freeze-drying.

$^1$H NMR (400 MHz, DMSO): 7.26 (2H, d); 7.00 (2H, d); 4.13-3.95 (m); 3.87-3.76 (m); 3.68-3.60 (m); 3.59-3.43 (m); 3.43-3.34 (m); 3.31-3.09 (m); 2.88-2.77 (m); 1.95-1.83 (1H, m); 1.78-1.60 (2H, m); 1.57-1.40 (m).

[2-(4-phenylpiperazin-1-yl)-6,7-dihydrothieno[3,2-d]pyrimidin-4-yl]-(1-pyridin-3-ylmethylpiperidin-3-yl) amine ditriflate (Example 363) (V According to Scheme 11)

0.015 g (0.024 mmol) of {2-[4-(4-chlorophenyl)piperazin-1-yl]-6,7-dihydrothieno[3,2-d]pyrimidin-4-yl}piperidin-3-ylamine (I) (see Scheme 1), 0.015 mL (0.158 mmol) of pyridine-3-aldehyde (IV), and 0.005 mL (0.087 mmol) of glacial acetic acid are stirred into 2 mL of DMF through a molecular sieve for 0.5 hour at ambient temperature. 0.026 mg (0.123 mmol) of sodium triacetoxyborohydride is added and the reaction mixture is stirred for another 12 hours at ambient temperature. The reaction mixture is purified by chromatography (RP-HPLC). 0.009 g of the product V (50%) is obtained after freeze-drying. $^1$H NMR (400 MHz, DMSO): 8.76-8.70 (1H, m); 8.65-8.58 (1H, m); 8.02-7.94 (1H, m); 7.56-7.49 (1H, m); 7.33-7.21 (3H, m); 7.04-6.97 (2H, m); 6.89-6.81 (1H, m); 4.57-3.78 (m); 3.75-3.40 (m); 3.37-3.28 (2H, m); 3.20-3.03 (m); 2.99-2.79 (1H, m); 2.78-2.59 (1H, m); 2.07-1.71 (3H, m); 1.69-1.52 (11H, m).

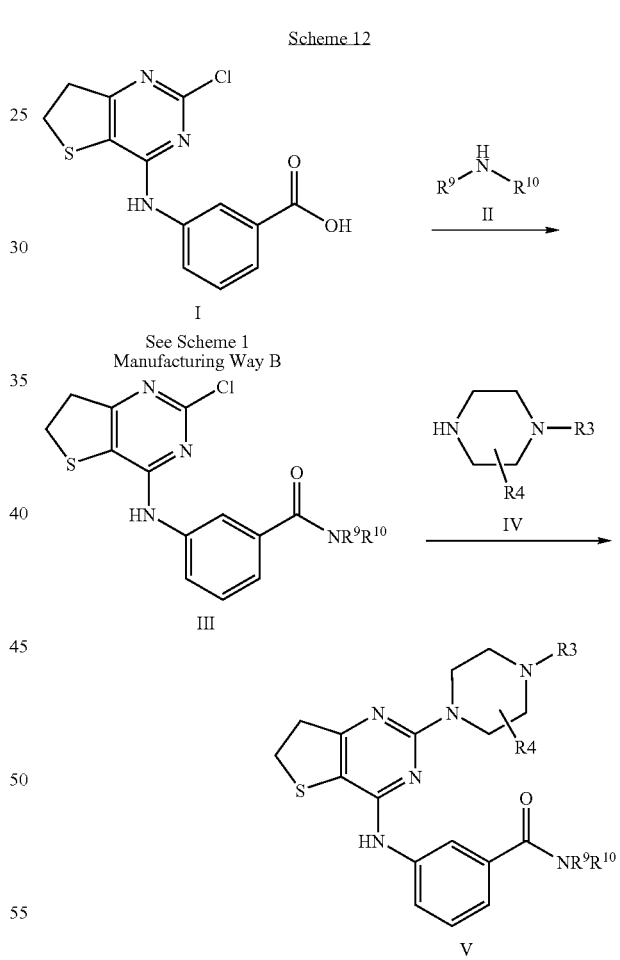

Scheme 12

Synthesis of (4-methylpiperazin-1-yl)-(3-{2-[4-(4-chlorophenyl)piperazin-1-yl]-6,7-dihydrothieno[3,2-d]pyrimidin-4-ylamino}phenyl)methanone (V According to Scheme 12)

3-(2-chloro-6,7-dihydrothieno[3,2-d]pyrimidin-4-ylamino)benzoic acid (1): 0.200 g (0.93 mmol) of 2,4-dichloro-6,7-dihydrothieno[3,2-d]pyrimidine, 0.127 g (0.93 mmol) of 3-aminobenzoic acid, and 0.323 mL (1.85 mmol) of diisopropylethylamine are placed in 4 mL of tetrahydrofuran, stirred for 48 hours at ambient temperature and 48 hours at 70° C. Then the reaction mixture is combined with water and acidified with 1N hydrochloric acid. The precipitate formed is suction filtered and dried. 0.110 g of product I (39%) is obtained.

(4-methylpiperazin-1-yl)-[3-(2-chloro-6,7-dihydrothieno [3,2-d]pyrimidin-4-ylamino)phenyl]methanone (III): 0.600 g (1.95 mmol) of 3-(2-chloro-6,7-dihydrothieno[3,2-d]pyrimidin-4-ylamino)benzoic acid (I), 0.741 g (1.95 mmol) of O-(7-azabenzotriazol-1-yl-)-N,N,N', N'-tetramethyluronium hexafluorophosphate (HATU), and 0.680 mL (3.90 mmol) of diisopropylethylamine are placed in 10 mL of dimethylsulfoxide, then stirred for 0.5 hours at ambient temperature. 0.220 mL (1.95 mmol) of methylpiperazine (II) is added, then the mixture is stirred for 3 hours at ambient temperature. Then the reaction mixture is concentrated by evaporation and the residue is combined with water. Any precipitate formed is suction filtered and dried. The crude product is purified by chromatography through a 50 g silica cartridge with ethyl acetate/methanol 8:2. 0.250 g of product III (33%) is obtained.

(4-methylpiperazin-1-yl)-(3-{2-[4-(4-chlorophenyl)piperazin-1-yl]-6,7-dihydrothieno[3,2-d]pyrimidin-4-ylamino}phenyl)methanone (V) (Example 236): 0.100 g (0.26 mmol) of (4-methylpiperazin-1-yl)-[3-(2-chloro-6,7-dihydrothieno[3,2-d]pyrimidin-4-ylamino)phenyl]methanone (III), 0.207 g (0.77 mmol) of 1-(4-chlorophenyl)piperazine (IV), and 0.180 mL (1.02 mmol) of diisopropylethylamine are placed in 3.5 mL of dioxane, then reacted for a total of 2 hours at 160° C. in the microwave. Then the reaction mixture is combined with water and extracted with ethyl acetate. The organic phase is dried and evaporated to dryness. The residue is purified by chromatography using HPLC through an RP column (column: Microsorb, RP-C18, 300 Å, 10 μm, 21.4*250 mm, eluant: acetonitrile+0.1% formic acid (A), water+0.13% formic acid (B))

| gradient: minutes | % eluant A | % eluant B |
|---|---|---|
| 0 | 10 | 90 |
| 4.9 | 10 | 90 |
| 27 | 100 | 0 |
| 32 | 100 | 0 |
| 32.5 | 10 | 90 |
| 37.5 | 10 | 90 |

Corresponding fractions are combined and freeze-dried. 0.014 g of product V (10%) is obtained. $^1$H NMR (400 MHz, DMSO): 8.60 (1H, s); 7.76-7.70 (2H, m); 7.37 (1H, t); 7.25 (2H, d); 7.03 (1H, d); 6.98 (2H, d); 3.81-3.72 (5H, m); 3.72-3.37 (3H, m); 3.21-3.14 (4H, m); 3.10 (3H, t); 2.97-2.62 (4H, m).

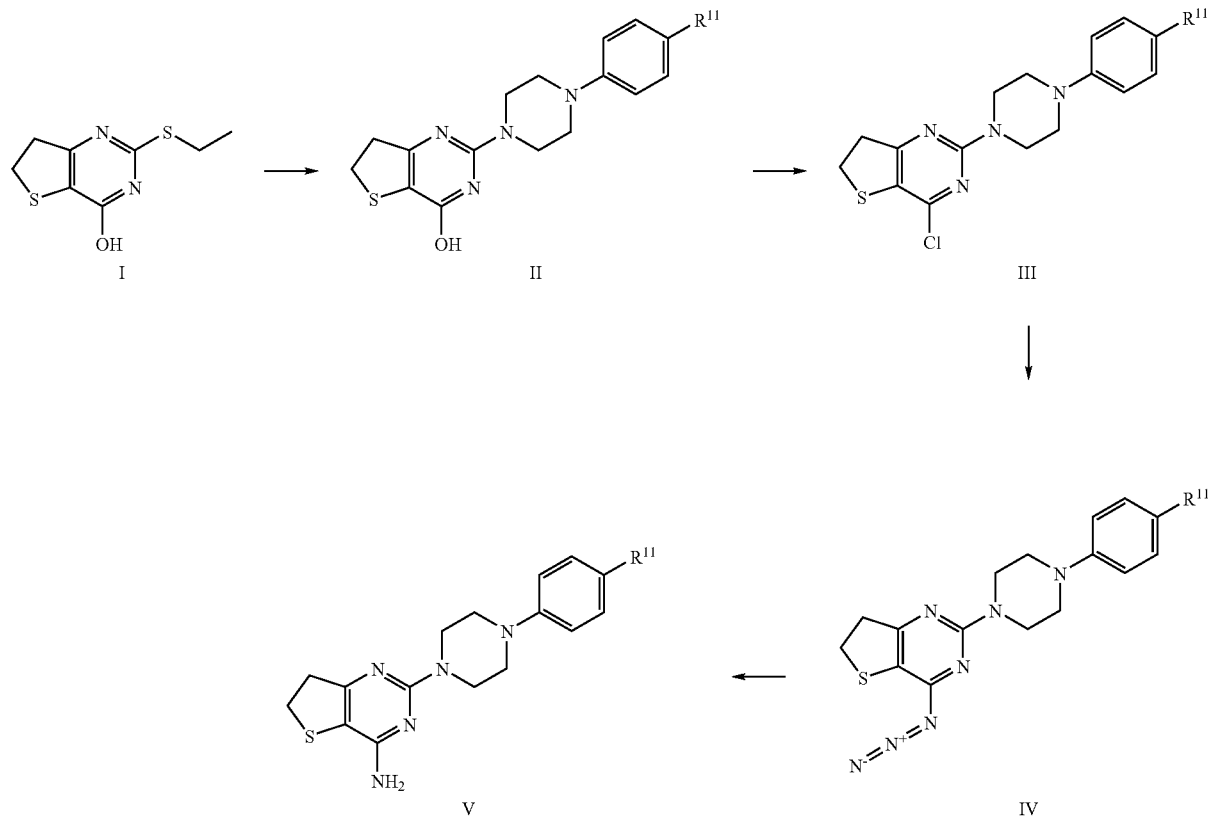

Scheme 13

Synthesis of 4-[4-(4-amino-6,7-dihydrothieno[3,2-d[pyrimidin-2-yl)piperazin-1-yl]phenol (V According to Scheme 13)

2-[4-(4-hydroxyphenyl)piperazin-1-yl]-6,7-dihydrothieno[3,2-d]pyrimidin-4-ol (II): 1.70 g (9.54 mmol) of 4-piperazin-1-ylphenol is placed in 0.55 mL (9.62 mmol) of glacial acetic acid and heated to 180° C. in the heating block. 0.800 g (3.73 mmol) of 2-ethylsulfanyl-6,7-dihydrothieno[3,2-d]pyrimidin-4-ol (I) is added, then the mixture is left to stand for 1.5 hours at 180° C. and 16 hours at ambient temperature. Then the reaction mixture is combined with water and treated in the ultrasound bath. The precipitate is suction filtered, washed, and dried. 1.1 g of product II is obtained as a powder.

4-[4-(4-chloro-6,7-dihydrothieno[3,2-d]pyrimidin-2-yl)piperazin-1-yl]phenol (III): 1.11 g (3.36 mmol) of 2-[4-(4-hydroxyphenyl)piperazin-1-yl]-6,7-dihydrothieno[3,2-d]pyrimidin-4-ol (II) is placed in 5 mL of phosphorus oxychloride, then stirred for 4 hours at 120° C. Excess phosphorus oxychloride is then distilled off and the residue is combined with water. The precipitate formed is suction filtered, washed with plenty of water, and dried. 1.18 g of product III is obtained as a brown powder.

4-[4-(4-azido-6,7-dihydrothieno[3,2-d]pyrimidin-2-yl)piperazin-1-yl]phenol (IV): 1.18 g (2.75 mmol) of 4-[4-(4-chloro-6,7-dihydrothieno[3,2-d]pyrimidin-2-yl)piperazin-1-yl]phenol (III) is placed in 25 mL of dimethylformamide, and 1.20 g (18.46 mmol) of sodium azide is added. The reaction mixture is stirred for 4.5 hours at 100° C. Then it is concentrated by evaporation, and the residue is cooled in the ice bath and combined with water. The precipitate formed is suction filtered, washed, and dried. 0.800 g of product IV is obtained and used further as a crude product.

4-[4-(4-amino-6,7-dihydrothieno[3,2-d]pyrimidin-2-yl)piperazin-1-yl]phenol (V) (Example 218): 0.800 g (1.80 mmol) of 4-[4-(4-azido-6,7-dihydrothieno[3,2-d]pyrimidin-2-yl)piperazin-1-yl]phenol (IV) is placed in 10 mL of tetrahydrofuran and 0.500 g molecular sieve are added. 3.80 mL (3.80 mmol) of lithium aluminum hydride (1M solution in tetrahydrofuran) is slowly added dropwise. The reaction mixture is stirred for 3 hours at ambient temperature. Then 0.55 mL of 1N sodium hydroxide solution and 0.50 mL of water are added, the mixture is boiled for 0.3 hours, then cooled again. It is filtered, and the filtrate is dried and evaporated to dryness. The residue is extracted with ethyl acetate and 1 N hydrochloric acid, the aqueous phase is made basic and extracted with ethyl acetate. The organic phase is washed with water, dried, and evaporated to dryness. 0.280 g of product V is obtained as a light brown foam. $^1$H NMR (400 MHz, DMSO): 8.80 (1H, s); 6.82 (2H, d); 6.66 (2H, d); 6.26 (2H, s); 3.77-3.66 (4H, m); 3.21 (2H, t); 2.98 (2H, t); 2.98-2.90 (4H, m).

Synthesis of 2-[4-(4-chlorophenyl)piperazin-1-yl]-6,7-dihydrothieno[3,2-d]pyrimidin-4-ylamine (V According to Scheme 13)

2-[4-(4-chlorophenyl)piperazin-1-yl]-6,7-dihydrothieno[3,2-d]pyrimidin-4-ol (II): 1.9 g (9.66 mmol) of 1-(4-chlorophenyl)piperazine is placed in 0.55 mL (9.62 mmol) of glacial acetic acid and heated to 180° C. in the heating block. 0.800 g (3.73 mmol) of 2-ethylsulfanyl-6,7-dihydrothieno[3,2-d]pyrimidin-4-ol (I) is added, then the mixture is left to stand for 1.5 hours at 180° C. and 16 hours at ambient temperature. Then the reaction mixture is combined with water and treated in the ultrasound bath. The precipitate is suction filtered, washed, and dried. 1.25 g of product II is obtained and used further in the crude state.

4-chloro-2-[4-(4-chlorophenyl)piperazin-1-yl]-6,7-dihydrothieno[3,2-d]pyrimidine (III): 1.25 g (3.05 mmol) of 2-[4-(4-chlorophenyl)piperazin-1-yl]-6,7-dihydrothieno[3,2-d]pyrimidin-4-ol (II) is placed in 4.50 mL of phosphorus oxychloride, then stirred for 4 hours is at 120° C. Then excess phosphorus oxychloride is distilled off, the residue is combined with water. The precipitate formed is suction filtered, washed with plenty of water, and dried, then stirred with methanol. 0.960 g of product III (85%) is obtained.

4-azido-2-[4-(4-chlorophenyl)piperazin-1-yl]-6,7-dihydrothieno[3,2-d]pyrimidine (IV): 0.950 g (2.59 mmol) of 4-chloro-2-[4-(4-chlorophenyl)piperazin-1-yl]-6,7-dihydrothieno[3,2-d]pyrimidine (III) is placed in 20 mL of dimethylformamide and 0.900 g (13.84 mmol) of sodium azide is added. The reaction mixture is stirred for 4 hours at 100° C. It is then concentrated by evaporation, the residue is cooled in the ice bath and combined with water. The precipitate formed is suction filtered, washed, and dried. 0.920 g of product IV (76%) is obtained and used further in the crude state.

2-[4-(4-chlorophenyl)piperazin-1-yl]-6,7-dihydrothieno[3,2-d]pyrimidin-4-ylamine (Example 219) (V): 0.820 g (1.76 mmol) of 4-azido-2-[4-(4-chlorophenyl)piperazin-1-yl]-6,7-dihydrothieno[3,2-d]pyrimidine (IV) is placed in 10 mL of tetrahydrofuran and 3.80 mL (3.80 mmol) of lithium aluminum hydride (1M solution in tetrahydrofuran) is slowly added dropwise. The reaction mixture is stirred for 4 hours at ambient temperature. Then 0.55 mL of 1N sodium hydroxide solution and 0.50 mL of water are added, the mixture is boiled for 0.3 hours, then cooled again. It is filtered, the filtrate is dried and evaporated to dryness. The residue is extracted with ethyl acetate and 1 N hydrochloric acid. The product precipitates out, is suction filtered, then extracted with ethyl acetate and 1 N sodium hydroxide solution. The organic phase is washed with water, dried, and evaporated to dryness. The residue is stirred with petroleum ether. 0.513 g of product V (84%) is obtained as a solid (m.p. 176-178° C.). $^1$H NMR (400 MHz, DMSO): 7.24 (2H, d); 6.98 (2H, d); 6.30 (2H, s); 3.77-3.68 (4H, m); 3.22 (2H, t); 3.17-3.09 (4H, m); 2.99 (2H, t).

Synthesis of mono-{4-[4-(4-propylamino-6,7-dihydrothieno[3,2-d]pyrimidin-2-yl)piperazin-1-yl]phenyl}sulfate (V According to Scheme 13) (Example 291)

0.100 g (0.269 mmol) of {2-[4-(4-hydroxyphenyl)piperazin-1-yl]-6,7-dihydrothieno[3,2-d]pyrimidin-4-yl}propylamine is dissolved in 3 mL of pyridine at ambient temperature, and 0.009 g (0.0540 mmol) of potassium iodide is added. Then 0.089 mL (1.34 mmol) of chlorosulfonic acid is added dropwise while cooling with ice. After the addition, the reaction mixture is solid and 3 mL of tetrahydrofuran is added. Then it is combined with water and dichloromethane, and the precipitate formed is suction filtered and dried. 0.049 g of the product (33%) is obtained as a powder. $^1$H NMR (400 MHz, DMSO+DCl): 9.01-8.92 (1H, m); 8.21-8.10 (1H, m); 7.90-7.80 (1H, m); 7.79-7.70 (1H, m); 7.40-7.31 (1H, m); 7.02-6.92 (1H, m); 4.49-4.27 (4H, m); 3.82-3.64 (4H, m); 3.57-3.30 (6H, m); 1.65-1.50 (2H, m); 0.96-0.77 (3H, m).

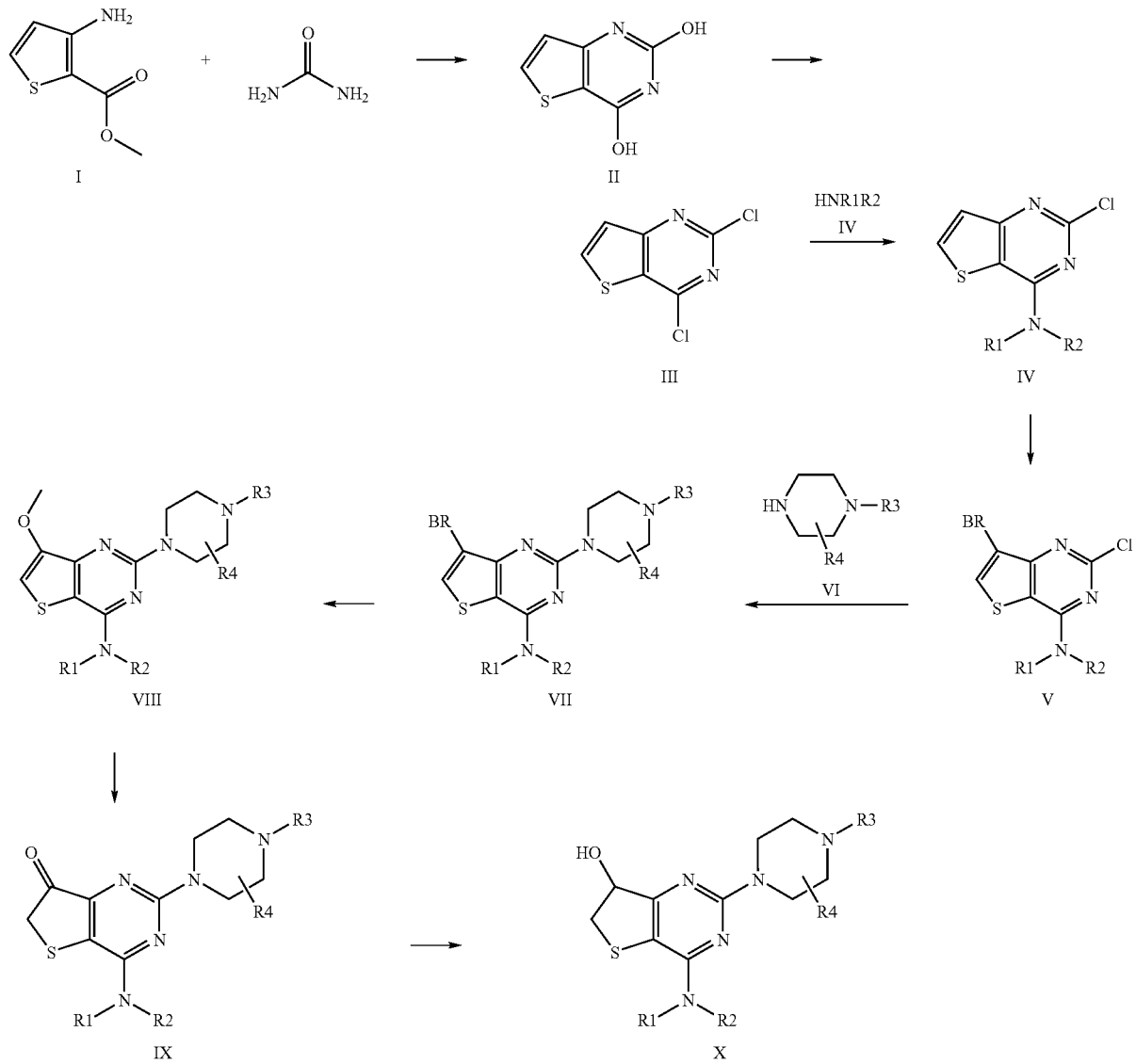

Scheme 14

Synthesis of 2-[4-(4-chlorophenyl)piperazin-1-yl]-4-propylamino-6,7-dihydrothieno[3,2-d]pyrimidin-7-ol triflate (Example 378) (X According to Scheme 14)

thieno[3,2-d]pyrimidine-2,4-diol (II): 10.0 g (64.0 mmol) of methylester 3-aminothiophene-2-carboxylate (I) and 19.0 g (31.60 mmol) of urea are mixed and melted for 2 hours at 200° C. After cooling, the reaction mixture is dissolved in 1 molar sodium hydroxide solution and decolorized with activated charcoal. It is filtered and the filtrate is cooled and acidified with 4M hydrochloric acid. The precipitate formed is suction filtered and dried. 8.03 g of product II (75%) is obtained as a powder.

2,4-dichlorothieno[3,2-d]pyrimidine (III): 7.97 g (47.0 mmol) of thieno[3,2-d]pyrimidine-2,4-diol (II) is placed in 50 mL (54.5 mmol) of phosphorus oxychloride, then refluxed for 14 hours, with stirring. The mixture is then concentrated by evaporation, the residue is combined with ice water. The precipitate formed is suction filtered and dried. 9.00 g of product III (93%) is obtained as a powder.

(2-chlorothieno[3,2-d]pyrimidin-4-yl)propylamine (IV): 3.95 g (19.26 mmol) of 2,4-dichlorothieno[3,2-d]pyrimidine (III), 1.90 mL (23.11 mmol) of propylamine, and 6.71 mL (38.52 mmol) of diisopropylethylamine are stirred for 16 hours in 40 mL of tetrahydrofuran at ambient temperature. Then the reaction mixture is concentrated by evaporation, the residue is combined with water. The precipitate formed is suction filtered and dried. 4.03 g of product IV (92%) is obtained as a powder.

(7-bromo-2-chlorothieno[3,2-d]pyrimidin-4-yl)propylamine (V): 8.34 g (36.63 mmol) of (2-chlorothieno[3,2-d]pyrimidin-4-yl)propylamine (IV) is dissolved in 60 mL of acetonitrile and 7.89 g (44.32 mmol) of N-bromosuccinimide is added. The reaction mixture is stirred for 16 hours at ambient temperature and for 6 hours at 50° C. Then it is concentrated by evaporation and the residue is combined with water.

The precipitate formed is suction filtered, washed, and dried. 7.25 g of product V (61%) is obtained as a powder.

{7-bromo-2-[4-(4-chlorophenyl)piperazin-1-yl]thieno[3,2-d]pyrimidin-4-yl}propylamine (VII): 2.00 g (6.20 mmol) of (7-bromo-2-chlorothieno[3,2-d]pyrimidin-4-yl)propylamine (V), 4.64 g (23.59 mmol) of 1-(4-chlorophenyl)piperazine (VI), and 2.13 mL (12.39 mmol) of diisopropylethylamine are placed in 15 mL of dioxane and heated to 100° C. in the microwave for 0.75 hours. As only 50% reacted, the reaction mixture is heated to 160° C. in the microwave for another 1.5 hours. Then the precipitate formed is suction filtered, washed with water, and stirred with petroleum ether. After suction filtering again, 3.19 g of product VII (100%) is obtained.

{2-[4-(4-chlorophenyl)piperazin-1-yl]-7-methoxythieno[3,2-d]pyrimidin-4-yl}propylamine (VIII): 2.00 g (4.28 mmol) of {7-bromo-2-[4-(4-chlorophenyl)piperazin-1-yl]thieno[3,2-d]pyrimidin-4-yl}propylamine (VII) is placed in 15 mL of methanol and cooled to some extent. First 0.995 g (18.42 mmol) of sodium methoxide, then 0.187 g (2.36 mmol) of copper (II) oxide, and 0.040 g (0.27 mmol) of sodium iodide are added. The reaction mixture is heated to 160° C. in the microwave for 0.75 hours. Then it is suction filtered through silica gel and the mother liquor is concentrated by evaporation. The residue is dissolved and any insoluble matter is removed by suction filtering. Further purification is carried out by preparative HPLC. 0.23 g of product VIII (20%) is obtained.

2-[4-(4-chlorophenyl)piperazin-1-yl]-4-propylaminothieno[3,2-d]pyrimidin-7-ol triflate (IX): 0.430 g (1.03 mmol) of {2-[4-(4-chlorophenyl)piperazin-1-yl]-7-methoxythieno[3,2-d]pyrimidin-4-yl}propylamine (VIII) is dissolved in 4 mL of dichloromethane and cooled somewhat. Under a nitrogen atmosphere, 1.13 mL (1.13 mmol) of boron tribromide solution (1M in heptane) is added dropwise. The reaction mixture is stirred for 48 hours at ambient temperature. After the addition of 0.50 mL of boron tribromide solution, the mixture is stirred for another 24 hours at ambient temperature. Then saturated potassium carbonate solution is added and the mixture is stirred for 0.4 hours. After the addition of dichloromethane, the organic phase is separated off through the phase separator and evaporated to dryness. The residue is purified by chromatography (HPLC), corresponding fractions are lyophilized. 0.150 g of product IX (28%) is obtained.

2-[4-(4-chlorophenyl)piperazin-1-yl]-4-propylamino-6,7-dihydrothieno[3,2-d]pyrimidin-7-ol triflate (X): 0.050 g (0.12 mmol) of 2-[4-(4-chlorophenyl)piperazin-1-yl]-4-propylaminothieno[3,2-d]pyrimidin-7-ol triflate (IX) is dissolved in 1 mL of methanol and 0.020 g (0.53 mmol) of sodium borohydride is added. The reaction mixture is stirred for 16 hours at ambient temperature, then concentrated by evaporation. The residue is purified by chromatography using HPLC through an RP column (column: Microsorb, RP-C18). Corresponding fractions are combined and lyophilized. 0.013 g of product X (20%) is obtained as a powder. $^1$H NMR (400 MHz, DMSO): 7.26 (2H, d); 7.00 (2H, d); 5.15-5.09 (1H, m); 3.86-3.79 (4H, m), 3.63-3.55 (2H, m); 3.42-3.33 (2H, m); 3.28-3.22 (4H, m); 3.18-3.11 (1H, m); 1.63-1.52 (2H, m); 0.88 (3H, t).

The following Examples may be prepared analogously to the methods of synthesis described above illustrated in Schemes 1 to 14 (as indicated). The compounds are suitable as PDE4-inhibitors and have $IC_{50}$ values of less than or equal to 1 µmol.

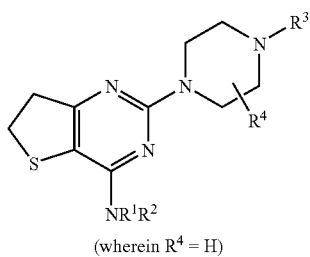

(wherein $R^4$ = H)

| # | $R^1$ | $R^2$ | $R^3$ | Preparation |
|---|---|---|---|---|
| 1. | H | *-cyclohexyl(methyl) | *-phenyl | Scheme 1 |
| 2. | H | *-CH2-phenyl | *-phenyl | Scheme 1 |
| 3. | H | *-CH2-cyclohexyl | *-phenyl | Scheme 1 |

-continued
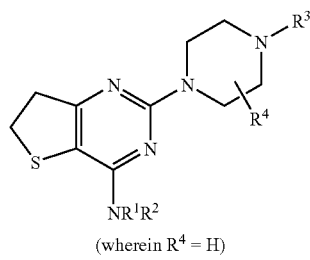
(wherein R⁴ = H)
| # | R¹ | R² | R³ | Preparation |
|---|----|----|----|-------------|
| 4. | H | *–C₆H₄–Cl (para) | *–C₆H₅ | Scheme 1 |
| 5. | H | *–C₆H₄–OCH₃ (para) | *–C₆H₅ | Scheme 1 |
| 6. | H | *–(CH₂)₅–CN | *–C₆H₅ | Scheme 1 |
| 7. | H | *–cyclopropyl | *–C₆H₅ | Scheme 1 |
| 8. | H | *–CH₂CH₂–COOH | *–C₆H₅ | Scheme 1 |
| 9. | H | *–CH(CH₃)–C₆H₅ | *–C₆H₅ | Scheme 1 |
| 10. | H | *–C₆H₄–Cl (meta) | *–C₆H₅ | Scheme 1 |
| 11. | H | *–C₆H₄–OCH₃ (meta) | *–C₆H₅ | Scheme 1 |
| 12. | H | *–(CH₂)₄CH₃ | *–C₆H₅ | Scheme 1 |

-continued
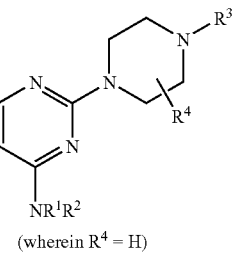
(wherein R⁴ = H)
| #   | R¹ | R²                    | R³     | Preparation |
|-----|----|-----------------------|--------|-------------|
| 13. | H  | *∼∼NMe₂               | *–Ph   | Scheme 1    |
| 14. | H  | *∼∼O–Me               | *–Ph   | Scheme 1    |
| 15. | H  | *–(2-methoxyphenyl)   | *–Ph   | Scheme 1    |
| 16. | H  | *–cyclohexyl          | *–Ph   | Scheme 1    |
| 17. | H  | *–CH₂-(1-methylpyrazol-4-yl) | *–Ph | Scheme 1 |
| 18. | H  | *–Ph                  | *–Ph   | Scheme 1    |
| 19. | H  | *–CH₂CH₂-(imidazolidin-2-one-1-yl) | *–Ph | Scheme 1 |
| 20. | H  | *–CH₂-(pyridin-3-yl)  | *–Ph   | Scheme 1    |
| 21. | H  | *–n-hexyl             | *–Ph   | Scheme 1    |
| 22. | H  | *∼∼OH                 | *–Ph   | Scheme 1    |

-continued
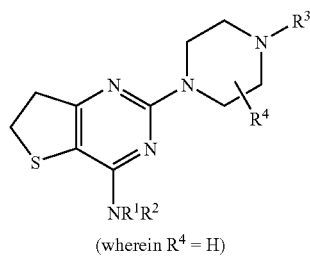
(wherein R⁴ = H)
| # | R¹ | R² | R³ | Preparation |
|---|---|---|---|---|
| 23. | H | *—CF₃ (ethyl with CF₃) | phenyl | Scheme 1 |
| 24. | H | *—CH₂-cyclopropyl | phenyl | Scheme 1 |
| 25. | H | *—cyclopentyl | phenyl | Scheme 1 |
| 26. | H | *—pyrrolidinyl (N-linked) | phenyl | Scheme 1 |
| 27. | H | *—propyl | phenyl | Scheme 1 |
| 28. | H | *—propyl | cyclohexyl | Scheme 1 |
| 29. | H | *—propyl | acetylphenyl | Scheme 1 |
| 30. | H | *—propyl | 4-methoxyphenyl | Scheme 1 |
| 31. | H | *—propyl | 3,4-dimethoxyphenyl | Scheme 1 |
| 32. | H | *—propyl | 2-pyridyl | Scheme 1 |

-continued
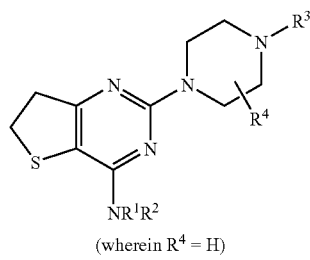
(wherein R⁴ = H)
| # | R¹ | R² | R³ | Preparation |
|---|---|---|---|---|
| 33. | H | *propyl | *pyrimidin-2-yl | Scheme 1 |
| 34. | H | *propyl | *3,4-dichlorophenyl | Scheme 1 |
| 35. | H | *propyl | *pyridin-3-yl | Scheme 1 |
| 36. | H | *propyl | *pyridin-4-yl | Scheme 1 |
| 37. | H | *propyl | *4-chlorophenyl | Scheme 1 |
| 38. | H | *propyl | *4-methylphenyl | Scheme 1 |
| 39. | H | *propyl | *4-hydroxyphenyl | Scheme 1 |
| 40. | H | *propyl | *3-hydroxyphenyl | Scheme 1 |
| 41. | H | *propyl | *4-fluorophenyl | Scheme 1 |
| 42. | H | *1-(hydroxymethyl)cyclopentyl | *phenyl | Scheme 1 |

-continued
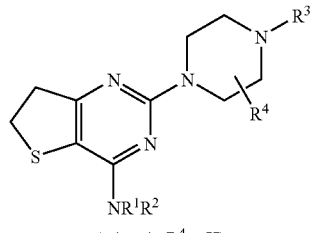

-continued
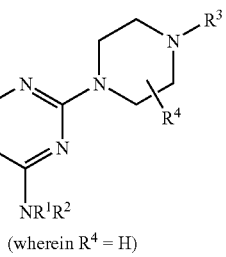
(wherein R⁴ = H)
| # | R¹ | R² | R³ | Preparation |
|---|---|---|---|---|
| 51. | H | 4-piperidinyl substituted with furan-2-carbonyl | phenyl | Scheme 1 |
| 52. | H | 1-benzylpyrrolidin-3-yl | phenyl | Scheme 1 |
| 53. | H | 3-(2-oxoimidazolidin-1-yl)phenyl | phenyl | Scheme 1 |
| 54. | H | 3-fluorophenyl | phenyl | Scheme 1 |
| 55. | H | 3-(3-methyl-2-oxoimidazolidin-1-yl)phenyl | phenyl | Scheme 1 |
| 56. | H | 3,5-dimethoxyphenyl | phenyl | Scheme 1 |

-continued
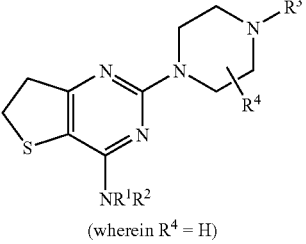

-continued
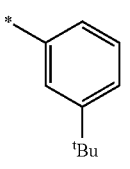
(wherein R⁴ = H)
| # | R¹ | R² | R³ | Preparation |
|---|---|---|---|---|
| 64. | H | 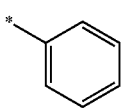 | 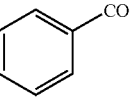 | Scheme 1 |
| 65. | H | 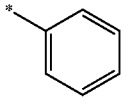 | 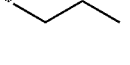 | Scheme 1 |
| 66. | H | 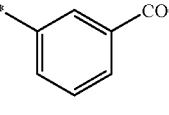 | 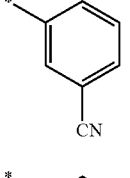 | Scheme 1 |
| 67. | H | 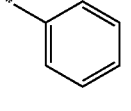 | 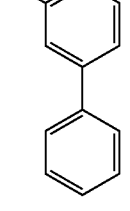 | Scheme 1 |
| 68. | H | 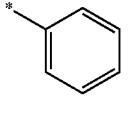 | 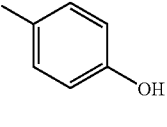 | Scheme 1 |
| 69. | H | 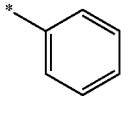 | 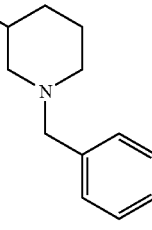 | Scheme 1 |
| 70. | H | 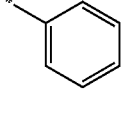 | 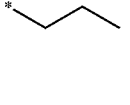 | Scheme 1 |
| 71. | H | * | 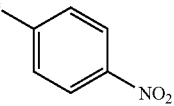 | Scheme 1 |

-continued

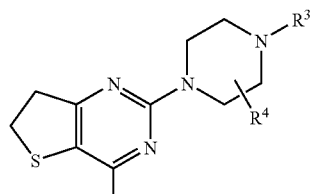

(wherein R⁴ = H)

| # | R¹ | R² | R³ | Preparation |
|---|---|---|---|---|
| 72. | H | *~~~ (n-butyl) | 2,4-difluorophenyl | Scheme 1 |
| 73. | H | *~~~ (n-butyl) | 2-hydroxyphenyl | Scheme 1 |
| 74. | H | *~~~ (n-butyl) | 2-methoxyphenyl | Scheme 1 |
| 75. | H | *~~~ (n-butyl) | 4-bromophenyl | Scheme 1 |
| 76. | H | *~~~ (n-butyl) | 4-cyanophenyl | Scheme 1 |
| 77. | H | *~~~ (n-butyl) | 2-fluorophenyl | Scheme 1 |
| 78. | H | *~~~ (n-butyl) | 2-chlorophenyl | Scheme 1 |
| 79. | H | *~~~ (n-butyl) | 3-chlorophenyl | Scheme 1 |
| 80. | H | *~~~ (n-butyl) | 3-fluorophenyl | Scheme 1 |
| 81. | H | *~~~ (n-butyl) | 2-(acetamidomethyl)phenyl | Scheme 1 |

-continued
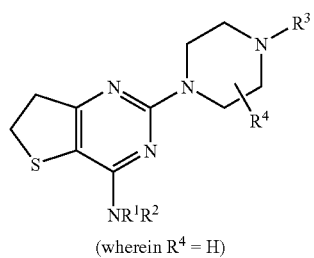
(wherein R⁴ = H)
| # | R¹ | R² | R³ | Preparation |
|---|---|---|---|---|
| 82. | H | *∼∼ | *-C₆H₄-NO₂ (ortho) | Scheme 1 |
| 83. | H | *∼∼ | *-C₆H₄-CN (ortho) | Scheme 1 |
| 84. | H | *-cyclohexyl | 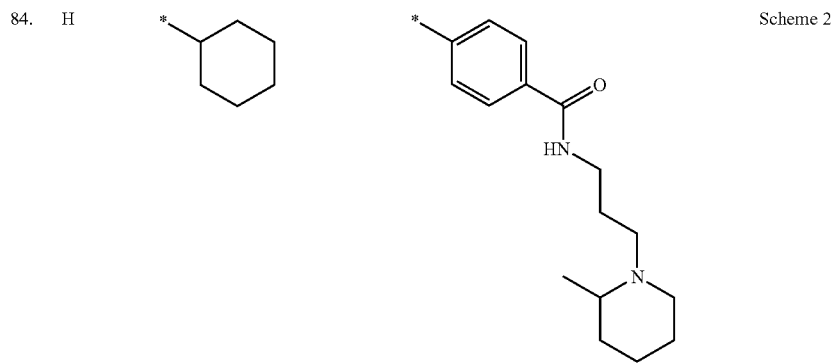 | Scheme 2 |
| 85. | H | *-cyclohexyl | 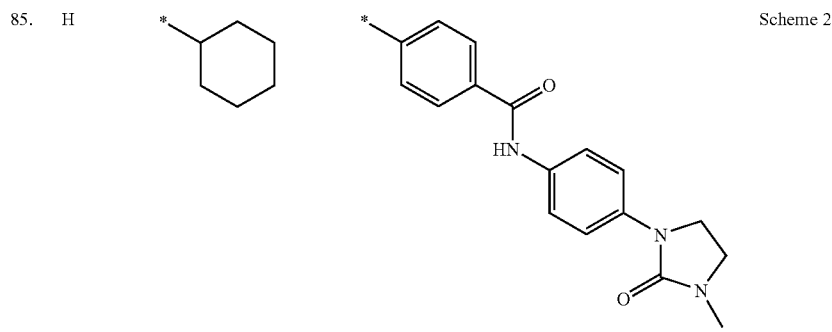 | Scheme 2 |

-continued
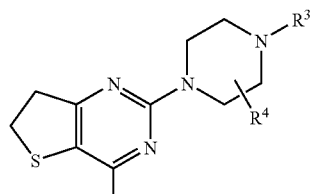
(wherein R⁴ = H)
| # | R¹ | R² | R³ | Preparation |
|---|---|---|---|---|
| 86. | H | *propyl | *4-benzamide-N-(3-(2-methylpiperidin-1-yl)propyl) | Scheme 2 |
| 87. | H | *propyl | *4-benzamide-N-(1-methylpiperidin-4-yl) | Scheme 2 |
| 88. | H | *cyclohexyl | *4-benzamide-N-(4-(pyrrolidin-1-ylmethyl)benzyl) | Scheme 2 |
| 89. | H | *cyclohexyl | *4-benzamide-N-(2-(pyridin-4-yl)ethyl) | Scheme 2 |

-continued
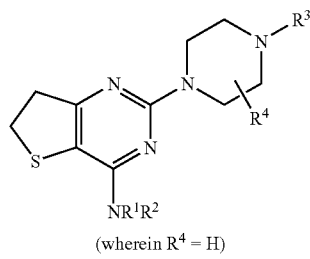
(wherein R⁴ = H)
| # | R¹ | R² | R³ | Preparation |
|---|---|---|---|---|
| 90. | H | *~~~ | *-C₆H₄-C(O)NH-CH₂-C₆H₄-CH₂-N(pyrrolidine) | Scheme 2 |
| 91. | H | *~~~ | *-C₆H₄-C(O)-N(piperazinone-N-Me) | Scheme 2 |
| 92. | H | *~~~ | *-C₆H₄-C(O)NH-CH₂CH₂-(4-pyridyl) | Scheme 2 |
| 93. | H | *~~~ | *-C₆H₄-SO₂NMe₂ (ortho) | Scheme 1 |

-continued
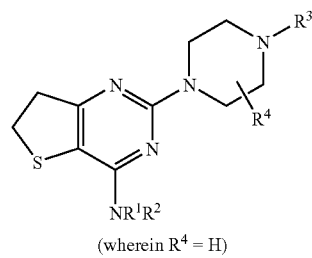
(wherein R⁴ = H)
| # | R¹ | R² | R³ | Preparation |
|---|---|---|---|---|
| 94. | H | 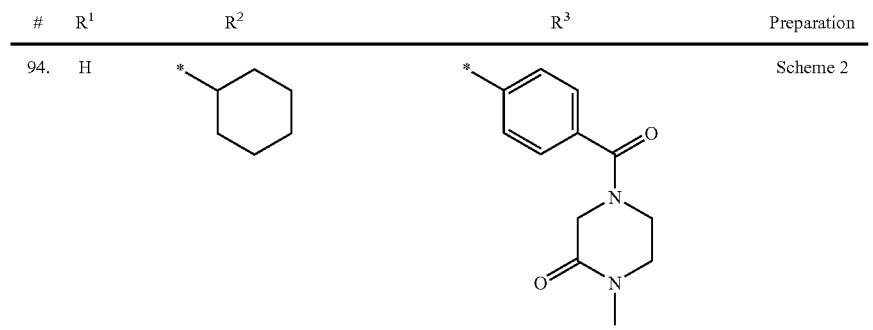 | | Scheme 2 |
| 95. | H | 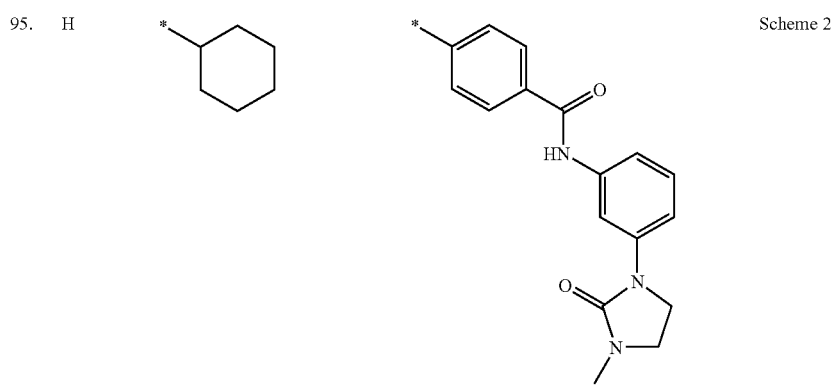 | | Scheme 2 |
| 96. | H | 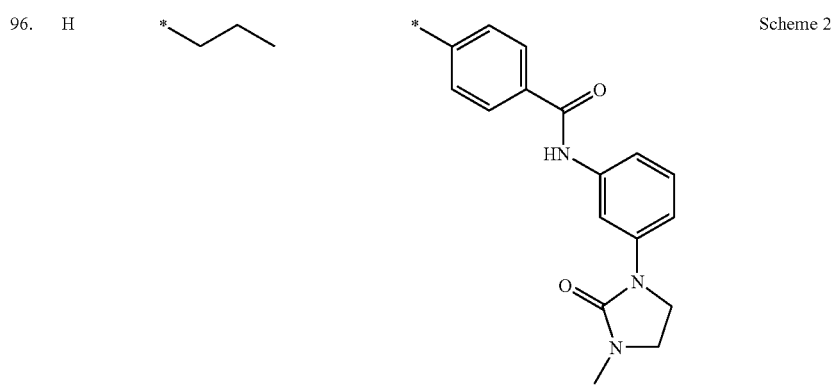 | | Scheme 2 |

-continued
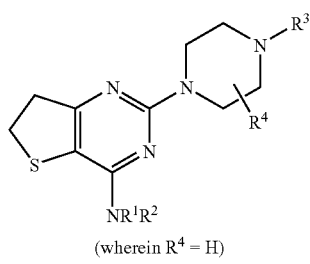
(wherein R⁴ = H)
| # | R¹ | R² | R³ | Preparation |
|---|---|---|---|---|
| 97. | H | *–propyl | *–C₆H₄–NHC(O)–C₆H₄–(N-methylimidazolidinone) | Scheme 2 |
| 98. | H | *–propyl | *–C(O)NH–phenyl | Scheme 5 |
| 99. | H | *–cyclohexyl | *–(4-Cl-phenyl) | Scheme 1 |
| 100. | H | *–propyl | *–(4-CF₃-phenyl) | Scheme 1 |
| 101. | H | *–cyclohexyl | *–C(O)–phenyl | Scheme 5 |
| 102. | H | *–cyclohexyl | *–C(O)NH–phenyl | Scheme 5 |
| 103. | H | *–propyl | *–(3-CN-phenyl) | Scheme 1 |

-continued
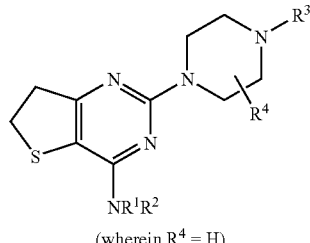
(wherein R⁴ = H)
| # | R¹ | R² | R³ | Preparation |
|---|----|----|----|-------------|
| 104. | H | 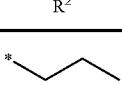 | 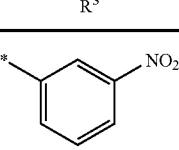 | Scheme 1 |
| 105. | H | 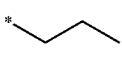 | 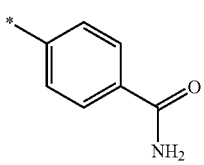 | Scheme 1 |
| 106. | H | 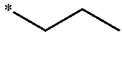 | 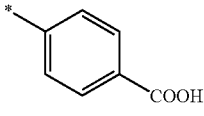 | Scheme 1 |
| 107. | H | 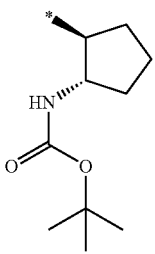 | 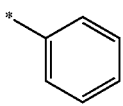 | Scheme 7 |
| 108. | H | 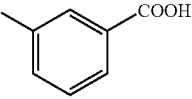 | 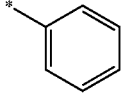 | Scheme 1 |
| 109. | H | 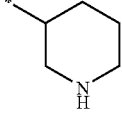 | 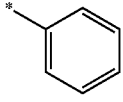 | Scheme 11 |
| 110. | H | 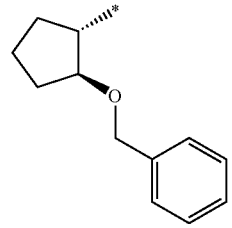 | 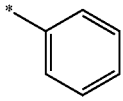 | Scheme 1 |

-continued
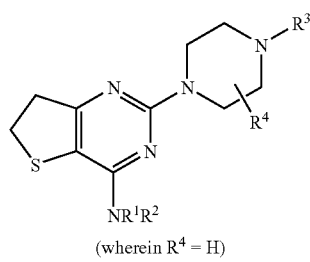
(wherein R⁴ = H)
| # | R¹ | R² | R³ | Preparation |
|---|---|---|---|---|
| 111. | H | 3-(2-oxopyrrolidin-1-yl)propyl | phenyl | Scheme 1 |
| 112. | H | (1,2)-2-(benzyloxy)cyclopentyl | phenyl | Scheme 1 |
| 113. | H | 2-(1H-imidazol-4-yl)ethyl | phenyl | Scheme 1 |
| 114. | H | 3-(methylthio)phenyl | phenyl | Scheme 1 |
| 115. | H | 2-phenylethyl | phenyl | Scheme 1 |
| 116. | H | (1,2)-2-carboxycyclopentyl | phenyl | Scheme 1 |
| 117. | H | (1,2)-2-aminocyclopentyl | phenyl | Scheme 1 |

-continued
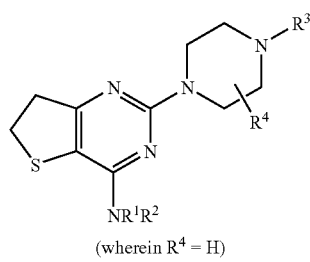
(wherein R⁴ = H)
| # | R¹ | R² | R³ | Preparation |
|---|---|---|---|---|
| 118. | H | *~~CN | *-phenyl | Scheme 1 |
| 119. | H | *-piperidine-N-C(O)-CH₂-OMe | *-phenyl | Scheme 10 |
| 120. | H | *-piperidine-N-C(O)-2-furyl | *-phenyl | Scheme 10 |
| 121. | H | *-piperidine-N-C(O)-3-pyridyl | *-phenyl | Scheme 10 |
| 122. | H | *-piperidine-N-C(O)-(1-methylpyrrol-2-yl) | *-phenyl | Scheme 10 |

-continued
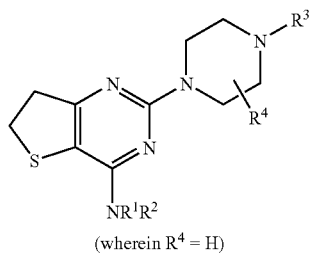
(wherein R⁴ = H)
| # | R¹ | R² | R³ | Preparation |
|---|---|---|---|---|
| 123. | H | 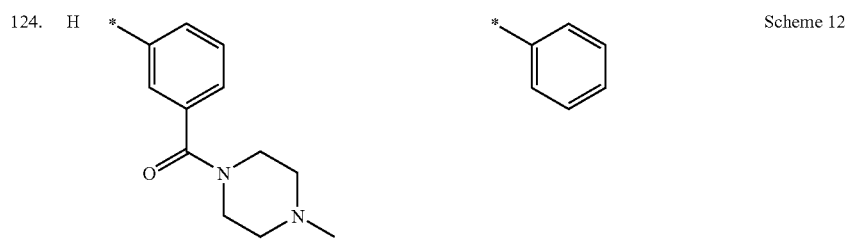 | | Scheme 10 |
| 124. | H | | | Scheme 12 |
| 125. | H | 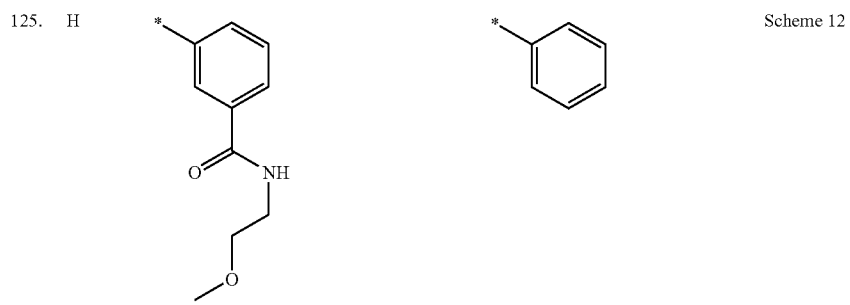 | | Scheme 12 |
| 126. | H | 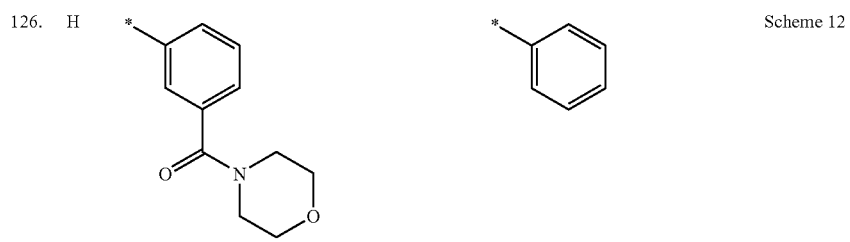 | | Scheme 12 |

-continued
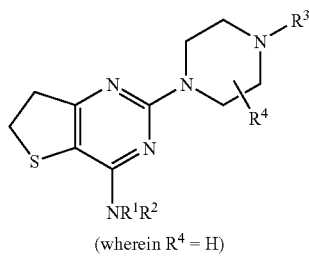
(wherein R⁴ = H)
| # | R¹ | R² | R³ | Preparation |
|---|---|---|---|---|
| 127. | H | *-3-piperidinyl-N-C(O)-C(CH₃)₂-NH₂ | *-phenyl | Scheme 10 |
| 128. | H | *-3-(N-isopropylcarbamoyl)phenyl | *-phenyl | Scheme 12 |
| 129. | H | *-3-(N-cyclopropylcarbamoyl)phenyl | *-phenyl | Scheme 12 |
| 130. | H | *-n-propyl | *-4-[N-methyl-N-(pyridin-4-ylmethyl)carbamoyl]phenyl | Scheme 2 |
| 131. | H | *-n-propyl | *-4-[N-(trans-4-hydroxycyclohexyl)carbamoyl]phenyl | Scheme 2 |

-continued
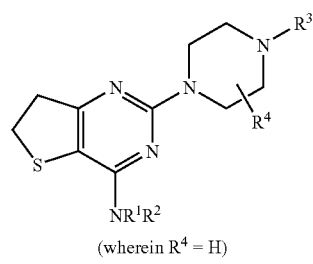
(wherein R⁴ = H)
| # | R¹ | R² | R³ | Preparation |
|---|---|---|---|---|
| 132. | H | *\_\_\_\_\ | *-C₆H₄-C(O)-N(CH₃)-CH₂-(2-pyridyl) | Scheme 2 |
| 133. | H | *\_\_\_\_\ | *-C₆H₄-C(O)-NH-CH₂-(1-methylpiperidin-4-yl) | Scheme 2 |
| 134. | H | *\_\_\_\_\ | *-C₆H₄-C(O)-NH-(1-ethylpiperidin-3-yl) | Scheme 2 |
| 135. | H | *\_\_\_\_\ | *-C₆H₄-C(O)-NH-CH₂-(1-ethylpyrrolidin-2-yl) | Scheme 2 |

-continued
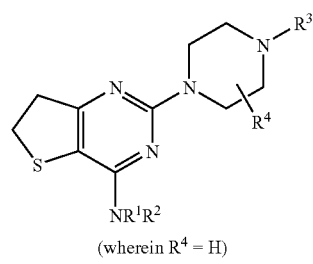
(wherein R⁴ = H)
| # | R¹ | R² | R³ | Preparation |
|---|---|---|---|---|
| 136. | H | *∼∼ (propyl) | *–C₆H₄–C(O)–N(azepan-4-one) | Scheme 2 |
| 137. | H | *∼∼ (propyl) | *–C₆H₄–C(O)–N(CH₃)–(CH₂)₃–N(4-methylpiperazine) | Scheme 2 |
| 138. | H | *∼∼ (propyl) | *–C₆H₄–C(O)–N(3-oxopiperazine) | Scheme 2 |
| 139. | H | *∼∼ (propyl) | *–C₆H₄–C(O)–NH–C(CH₃)₂–CH₂–N(pyrrolidine) | Scheme 2 |

-continued
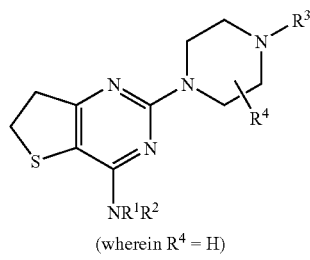
(wherein R⁴ = H)
| # | R¹ | R² | R³ | Preparation |
|---|---|---|---|---|
| 140. | H | 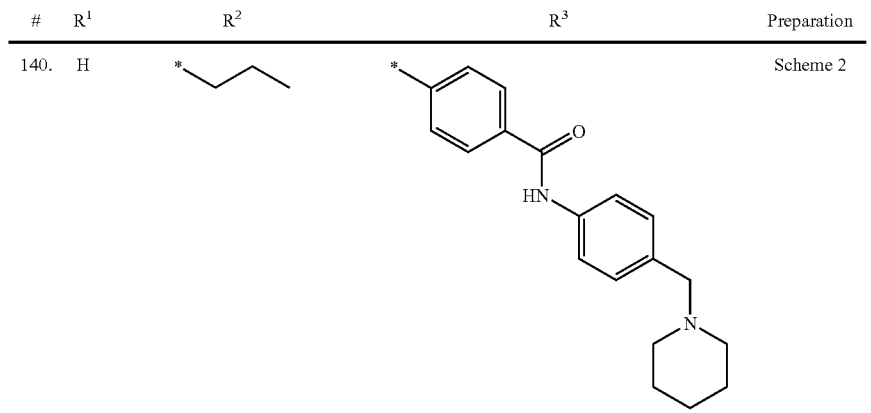 | | Scheme 2 |
| 141. | H | | | Scheme 2 |
| | | 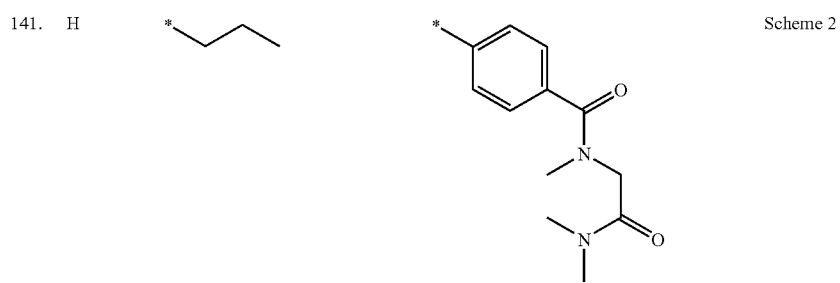 | | |
| 142. | H | | | Scheme 2 |
| | | 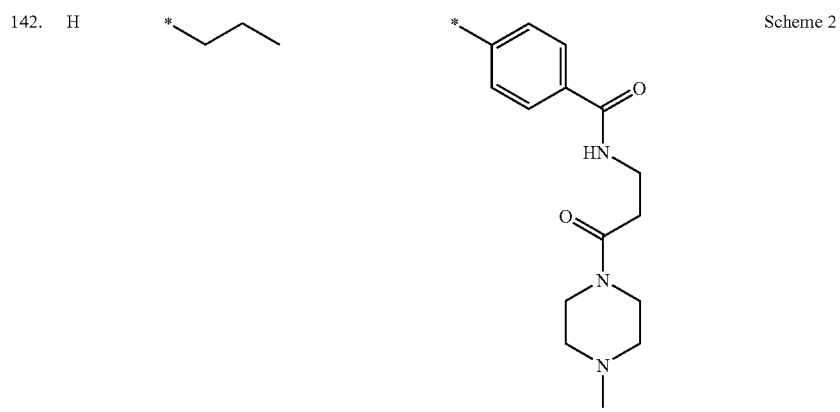 | | |

-continued
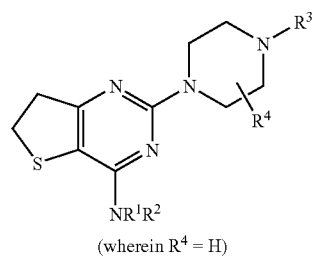
(wherein R⁴ = H)
| # | R¹ | R² | R³ | Preparation |
|---|---|---|---|---|
| 143. | H | *∕∕ | 4-benzamide linked to N-methyl-N-(2-(4-methylpiperazin-1-yl)-2-oxoethyl) | Scheme 2 |
| 144. | H | *∕∕ | 4-benzamide linked to N-(2-(1-phenyl-1H-pyrazol-4-yl)ethyl) | Scheme 2 |
| 145. | H | *∕∕ | 4-benzamide linked to N-methyl-N-((1-methyl-1H-pyrazol-4-yl)methyl) | Scheme 2 |
| 146. | H | *∕∕ | 4-benzamide linked to N-((1-methyl-1H-pyrazol-4-yl)methyl) | Scheme 2 |

-continued
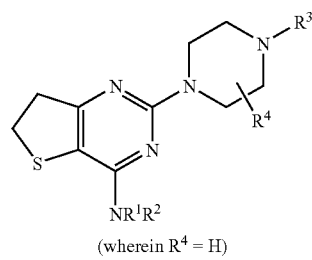
(wherein R⁴ = H)
| # | R¹ | R² | R³ | Preparation |
|---|----|----|----|-------------|
| 147. | H | *∼∼ | 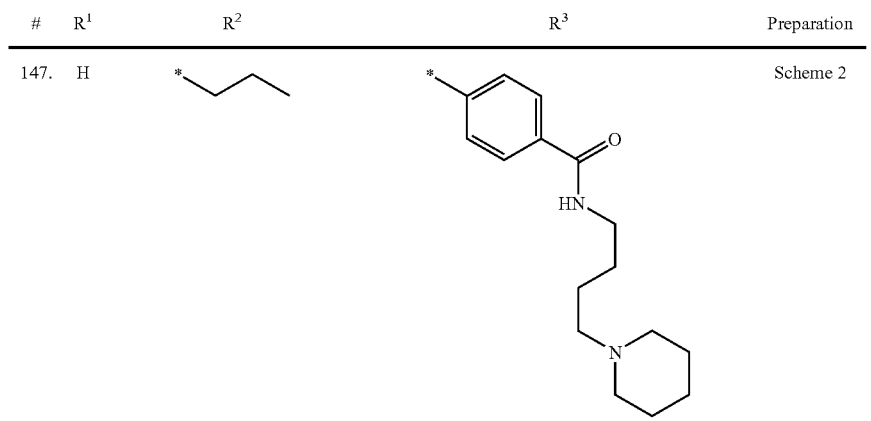 | Scheme 2 |
| 148. | H | *∼∼ | | Scheme 2 |
| 149. | H | *∼∼ | 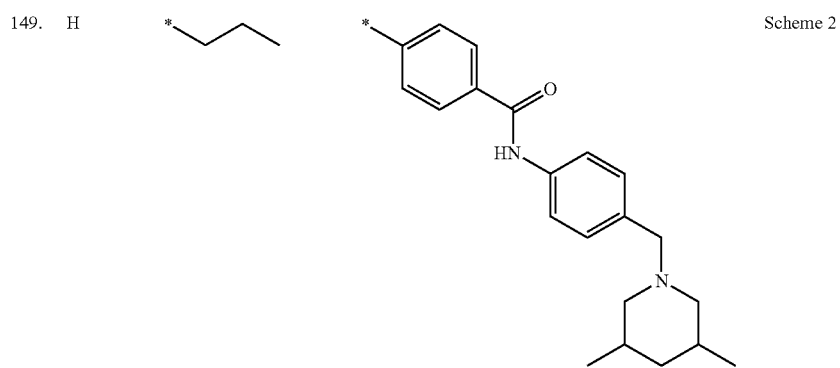 | Scheme 2 |
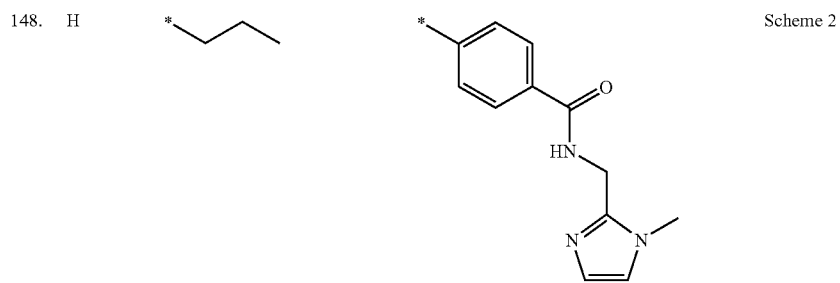

-continued
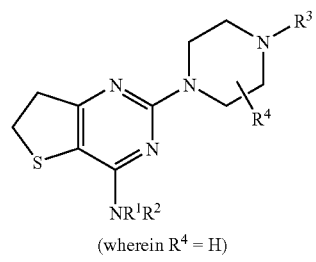
(wherein R⁴ = H)
| # | R¹ | R² | R³ | Preparation |
|---|----|----|----|-------------|
| 150. | H | *∼∼ (n-propyl) | 4-benzamide-CH₂-(4-hydroxy-1-methylpiperidin-4-yl) | Scheme 2 |
| 151. | H | *∼∼ (n-propyl) | 4-benzamide-CH₂CH₂-(1-methyl-1H-pyrazol-4-yl) | Scheme 2 |
| 152. | H | *∼∼ (n-propyl) | 4-benzamide-CH₂CH₂-(3-oxopyrrolidin-1-yl) | Scheme 2 |
| 153. | H | *∼∼ (n-propyl) | 4-benzamide-CH₂CH₂-(1H-imidazol-4-yl) | Scheme 2 |

-continued
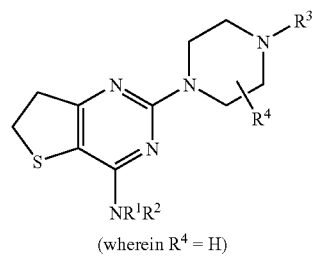
(wherein R⁴ = H)
| # | R¹ | R² | R³ | Preparation |
|---|---|---|---|---|
| 154. | H | *∼∼ (butyl) | *-C₆H₄-C(O)-N(tetrahydroisoquinoline) | Scheme 2 |
| 155. | H | *∼∼ (butyl) | *-C₆H₄-C(O)-NH-CH₂-C₆H₅ | Scheme 2 |
| 156. | H | *∼∼ (butyl) | *-C₆H₄-C(O)-NH-CH₂CH₂-(3-pyridyl) | Scheme 2 |
| 157. | H | *∼∼ (butyl) | *-C₆H₄-C(O)-NH-CH₂CH₂-(4-pyridyl) | Scheme 2 |

-continued
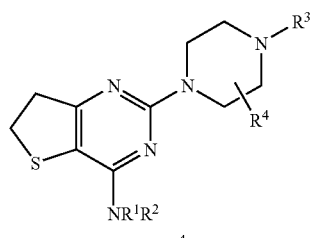
(wherein R⁴ = H)
| # | R¹ | R² | R³ | Preparation |
|---|----|----|----|-------------|
| 158. | H | *∼∼ | 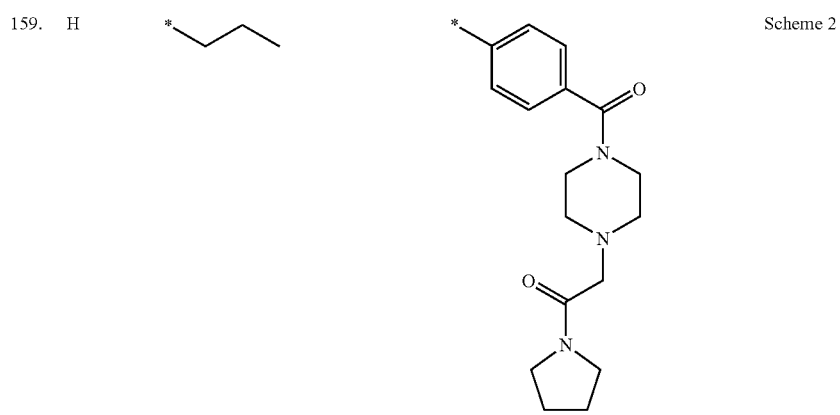 | Scheme 2 |
| 159. | H | *∼∼ | | Scheme 2 |
| 160. | H | *∼∼ | 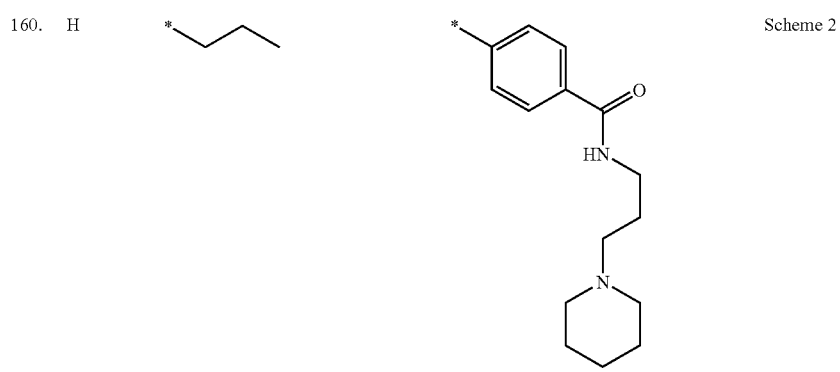 | Scheme 2 |

-continued
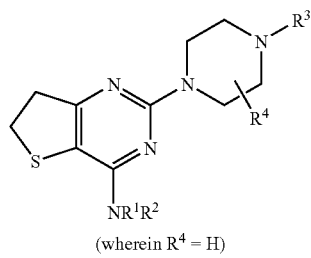
(wherein R⁴ = H)
| # | R¹ | R² | R³ | Preparation |
|---|---|---|---|---|
| 161. | H | *~~~ | *-Ph-C(O)-N(2-ethyl-2,6-diazaspiro[3.4]octane) | Scheme 2 |
| 162. | H | *~~~ | *-Ph-C(O)-NH-CH₂-(3-pyridyl) | Scheme 2 |
| 163. | H | *~~~ | *-Ph-C(O)-N(4-acetylpiperazinyl) | Scheme 2 |
| 164. | H | *~~~ | *-Ph-C(O)-N(1-oxa-3,8-diazaspiro[4.5]decan-2-one-8-yl) | Scheme 2 |

-continued
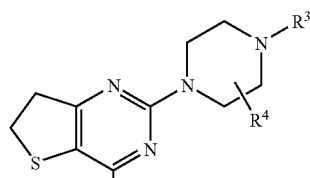
(wherein R⁴ = H)
| # | R¹ | R² | R³ | Preparation |
|---|---|---|---|---|
| 165. | H | *∼∼ (propyl) | | Scheme 2 |
| 166. | H | *∼∼ (propyl) | | Scheme 2 |
| 167. | H | *∼∼ (propyl) | | Scheme 2 |
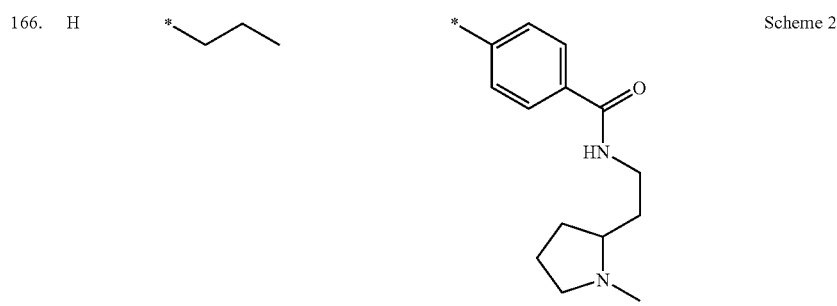
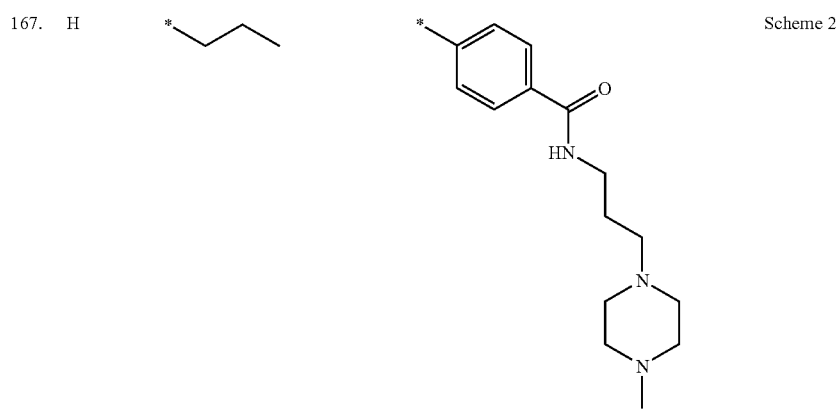

-continued
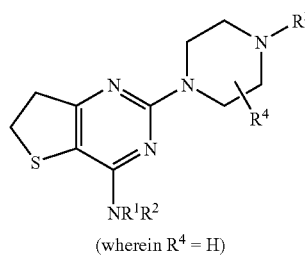
(wherein R⁴ = H)
| # | R¹ | R² | R³ | Preparation |
|---|----|----|----|-------------|
| 168. | H | 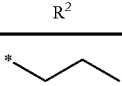 | 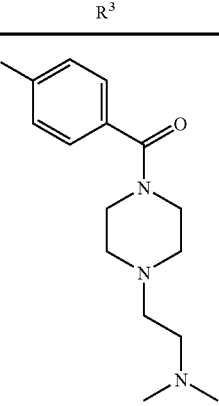 | Scheme 2 |
| 169. | H | 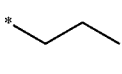 | 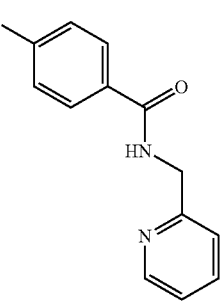 | Scheme 2 |
| 170. | H | 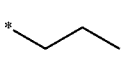 | 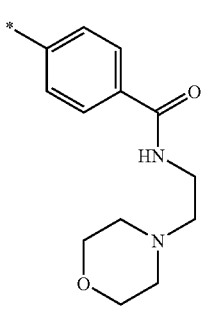 | Scheme 2 |
| 171. | H | 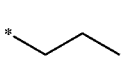 | 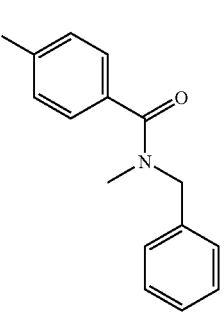 | Scheme 2 |

-continued
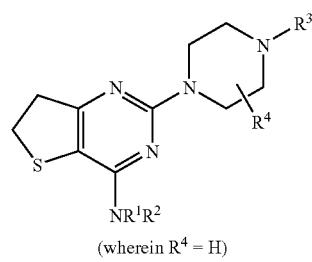
(wherein R⁴ = H)
| # | R¹ | R² | R³ | Preparation |
|---|---|---|---|---|
| 172. | H | *∼∼ (butyl) | *-C₆H₄-C(O)NH-CH₂CH₂CH₂-(N-imidazolyl) | Scheme 2 |
| 173. | H | *∼∼ (butyl) | *-C₆H₄-C(O)NH-CH₂CH₂CH₂-(N-2-oxopyrrolidinyl) | Scheme 2 |
| 174. | H | *∼∼ (butyl) | *-C₆H₄-C(O)-(1-piperidinyl-4-C(O)NH₂) | Scheme 2 |
| 175. | H | *∼∼ (butyl) | *-C₆H₄-C(O)NH-(1-methylpiperidin-4-yl) | Scheme 2 |

-continued
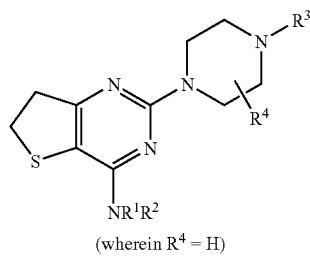
(wherein R⁴ = H)
| # | R¹ | R² | R³ | Preparation |
|---|----|----|----|-------------|
| 176. | H | *\/\ | 4-benzoyl-piperidine-N-(isothiazolidine-1,1-dioxide) | Scheme 2 |
| 177. | H | *\/\ | 4-(2-(imidazol-1-yl)ethylcarbamoyl)phenyl | Scheme 2 |
| 178. | H | *\/\ | 4-((imidazol-2-ylmethyl)carbamoyl)phenyl | Scheme 2 |
| 179. | H | *\/\ | 4-(((1-methylbenzimidazol-2-yl)methyl)carbamoyl)phenyl | Scheme 2 |

-continued
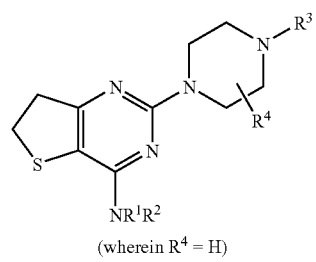
(wherein R⁴ = H)
| # | R¹ | R² | R³ | Preparation |
|---|---|---|---|---|
| 180. | H | *~~\ | *-C₆H₄-C(O)NH-CH₂-(1,3-dimethylpyrazol-4-yl) | Scheme 2 |
| 181. | H | *~~\ | *-C₆H₄-C(O)NH-CH₂CH₂CH₂-(pyrrolidin-1-yl) | Scheme 2 |
| 182. | H | *~~\ | *-C₆H₄-C(O)-(2-((diethylamino)methyl)piperidin-1-yl) | Scheme 2 |
| 183. | H | *~~\ | *-C₆H₄-C(O)NH-(3-phenoxyphenyl) | Scheme 2 |

-continued
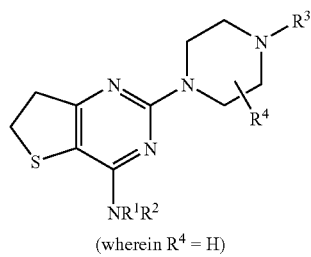
(wherein R⁴ = H)
| # | R¹ | R² | R³ | Preparation |
|---|----|----|----|-------------|
| 184. | H | *~\ | *-C₆H₄-C(O)NH-C₆H₄-NH-C₆H₅ | Scheme 2 |
| 185. | H | *~\ | *-C₆H₄-C(O)NH-(tetrahydrothiophene-3-yl 1,1-dioxide) | Scheme 2 |
| 186. | H | *~\ | *-C₆H₄-C(O)-(thiomorpholine 1,1-dioxide) | Scheme 2 |
| 187. | H | *~\ | *-C₆H₄-C(O)NH-CH₂CH₂-(1H-pyrazol-4-yl) | Scheme 2 |

-continued
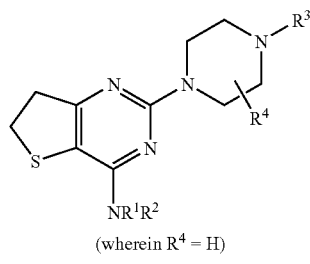
(wherein R⁴ = H)
| # | R¹ | R² | R³ | Preparation |
|---|---|---|---|---|
| 188. | H | *propyl | *4-[(pyrrolidin-1-ylethyl)phenyl]aminocarbonylphenyl | Scheme 2 |
| 189. | H | *propyl | *quinuclidinyl benzamide | Scheme 2 |
| 190. | H | *propyl | *4-[(2,6-dimethylpiperidin-1-yl)methyl]phenylaminocarbonylphenyl | Scheme 2 |
| 191. | H | *propyl | *4-[N-methyl-N-(2-(4-methylpiperazin-1-yl)ethyl)aminocarbonyl]phenyl | Scheme 2 |

-continued
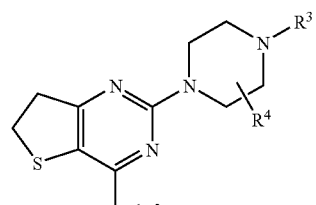
(wherein R⁴ = H)
| # | R¹ | R² | R³ | Preparation |
|---|----|----|----|-------------|
| 192. | H | 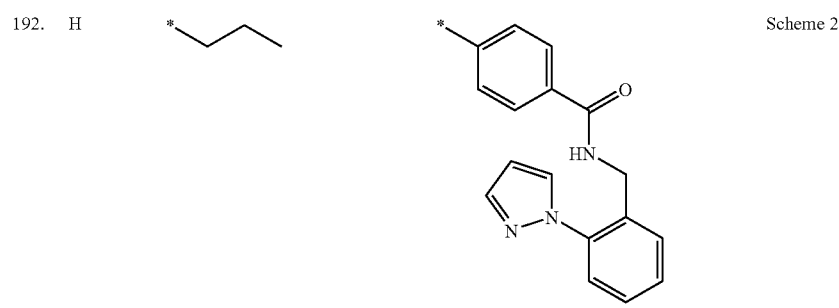 | | Scheme 2 |
| 193. | H | 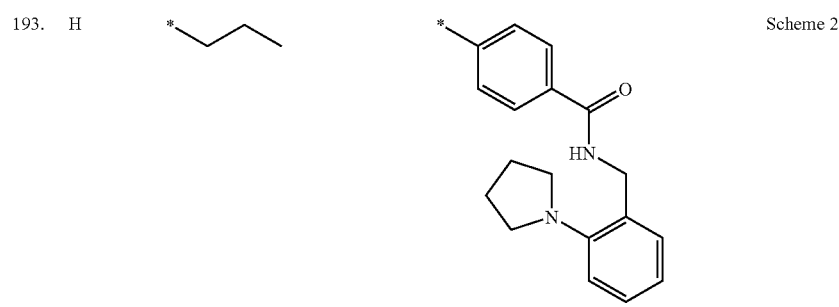 | | Scheme 2 |
| 194. | H | 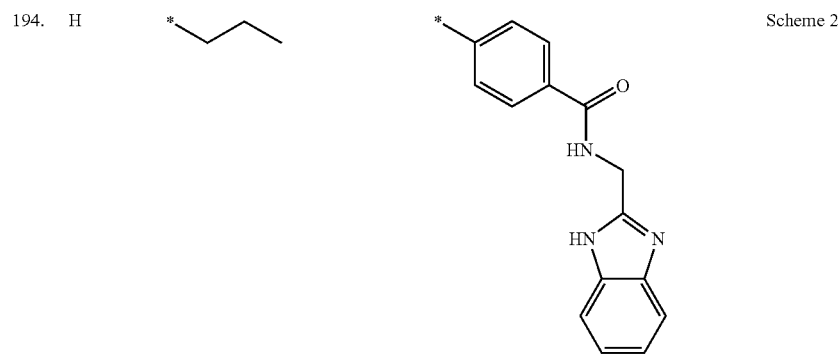 | | Scheme 2 |

-continued
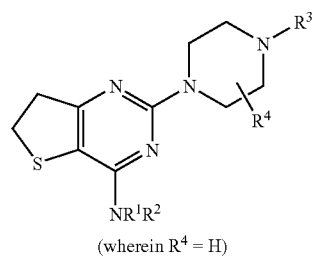
(wherein R⁴ = H)
| # | R¹ | R² | R³ | Preparation |
|---|---|---|---|---|
| 195. | H | *∼∼ (propyl) | *-C₆H₄-C(O)NH-CH₂-C≡C-(3-pyridyl) | Scheme 2 |
| 196. | H | *∼∼ (propyl) | *-C₆H₄-C(O)NH-CH₂CH₂CH₂-(5-methyl-1H-pyrazol-4-yl) | Scheme 2 |
| 197. | H | *∼∼ (propyl) | *-C₆H₄-C(O)NH-CH₂-C≡C-(4-pyridyl) | Scheme 2 |

-continued
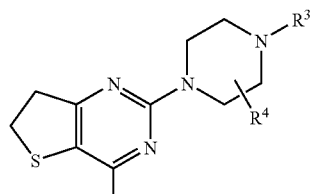
(wherein R⁴ = H)
| # | R¹ | R² | R³ | Preparation |
|---|----|----|----|-------------|
| 198. | H | *∼∼ | *-C₆H₄-C(O)NH-CH₂-C(O)-N(4-methylpiperazinyl) | Scheme 2 |
| 199. | H | *∼∼ | *-C₆H₄-C(O)-N(4,5,6,7-tetrahydropyrazolo[3,4-c]pyridin-5-yl) | Scheme 2 |
| 200. | H | *∼∼ | *-C₆H₄-C(O)NH-CH₂-(2-((1-methylpiperidin-2-yl)methoxy)phenyl) | Scheme 2 |
| 201. | H | *∼∼ | *-C₆H₄-C(O)NH-CH₂-(2-((1-methylpiperidin-3-yl)methoxy)phenyl) | Scheme 2 |

-continued
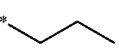
(wherein R⁴ = H)
| # | R¹ | R² | R³ | Preparation |
|---|----|----|----|-------------|
| 202. | H | 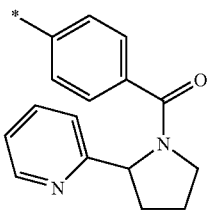 | 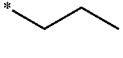 | Scheme 2 |
| 203. | H | 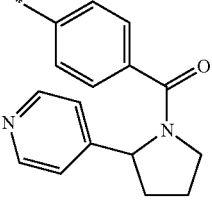 | 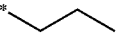 | Scheme 2 |
| 204. | H | 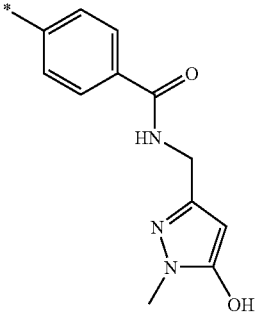 | 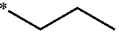 | Scheme 2 |
| 205. | H | 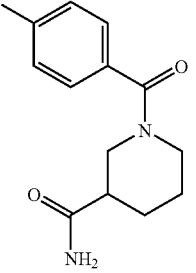 |  | Scheme 2 |

-continued
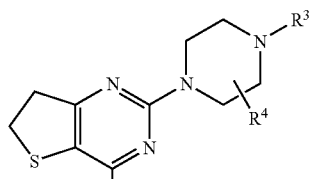
(wherein R⁴ = H)
| # | R¹ | R² | R³ | Preparation |
|---|---|---|---|---|
| 206. | H | *∼∼ (propyl) | *-C₆H₄-C(O)-N(piperazine)-N-(2-pyridyl) | Scheme 2 |
| 207. | H | *∼∼ (propyl) | *-C₆H₄-C(O)-N(piperazine)-N-(4-pyridyl) | Scheme 2 |
| 208. | H | *∼∼ (propyl) | *-C₆H₄-C(O)NH-(CH₂)₃-morpholine | Scheme 2 |
| 209. | H | *∼ (ethyl) | *-phenyl | Scheme 1 |

-continued
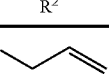
(wherein R⁴ = H)
| # | R¹ | R² | R³ | Preparation |
|---|----|----|----|-------------|
| 210. | H |  |  | Scheme 1 |
| 211. | H |  | 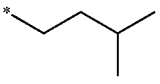 | Scheme 1 |
| 212. | H |  | 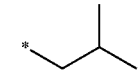 | Scheme 1 |
| 213. | H | 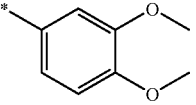 | 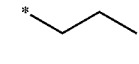 | Scheme 1 |
| 214. | H | 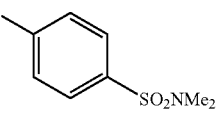 | 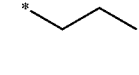 | Scheme 1 |
| 215. | H | 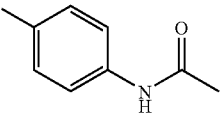 | 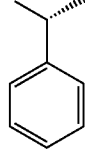 | Scheme 4 |
| 216. | H | 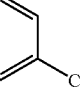 | 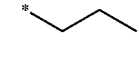 | Scheme 1 |
| 217. | H | 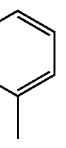 |  | Scheme 1 |
| 218. | H | H | 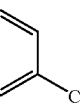 | Scheme 1 |
| 219. | H | H |  | Scheme 1 |

-continued
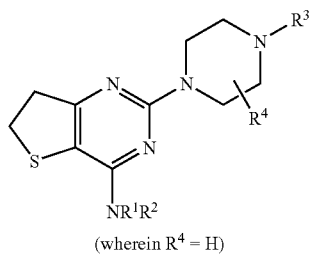
(wherein R⁴ = H)
| # | R¹ | R² | R³ | Preparation |
|---|----|----|----|-------------|
| 220. | H | *-（3-chlorophenyl） | *-（4-chlorophenyl） | Scheme 1 |
| 221. | H | *-propyl | *-（3-methoxyphenyl） | Scheme 1 |
| 222. | H | *-cyclohexyl | *-（4-hydroxyphenyl） | Scheme 1 |
| 223. | H | *-cyclohexyl | *-（3-hydroxyphenyl） | Scheme 1 |
| 224. | H | *-（3-fluorophenyl） | *-（4-chlorophenyl） | Scheme 1 |
| 225. | H | *-（2-benzyloxycyclopentyl） | *-（4-chlorophenyl） | Scheme 1 |
| 226. | H | *-（3-chlorophenyl） | *-C(O)NH-phenyl | Scheme 5 |

-continued
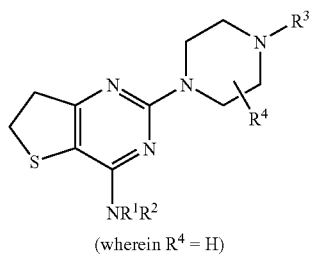
(wherein R⁴ = H)
| # | R¹ | R² | R³ | Preparation |
|---|----|----|----|-------------|
| 227. | H | (S)-1-phenylethyl | *-C(O)-NH-phenyl | Scheme 5 |
| 228. | H | trans-2-benzyloxycyclopentyl | *-C(O)-NH-phenyl | Scheme 5 |
| 229. | H | 3-fluorophenyl | *-C(O)-NH-phenyl | Scheme 5 |
| 230. | H | 1-(1-methylpyrrole-2-carbonyl)piperidin-3-yl | *-4-chlorophenyl | Scheme 10 |
| 231. | H | 1-(1-methylpyrrole-3-carbonyl)piperidin-3-yl | *-C(O)-NH-phenyl | Scheme 5 |
| 232. | H | n-propyl | *-4-(benzoylamino)phenyl | Scheme 5 |

-continued
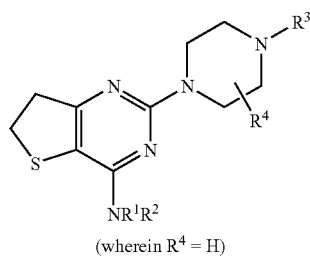
(wherein R⁴ = H)
| # | R¹ | R² | R³ | Preparation |
|---|---|---|---|---|
| 233. | H | *propyl | *-C₆H₄-NHC(O)-pyridinyl-NH₂ | Scheme 5 |
| 234. | H | *propyl | *-C₆H₄-NHC(O)-2-pyridinyl | Scheme 5 |
| 235. | H | *-3-(4-methylpiperazine-1-carbonyl)phenyl | *-C(O)NH-phenyl | Scheme 5 |
| 236. | H | *-3-(4-methylpiperazine-1-carbonyl)phenyl | *-4-chlorophenyl | Scheme 12 |
| 237. | H | *propyl | *-C₆H₄-NHC(O)-4-pyridinyl | Scheme 4 |
| 238. | H | *propyl | *-C₆H₄-NHC(O)-quinuclidinyl | Scheme 4 |

-continued
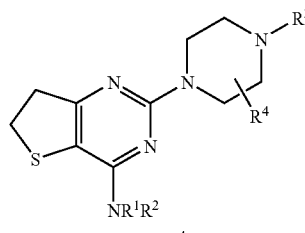

-continued
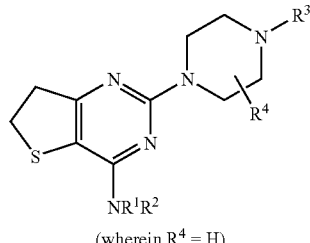
(wherein R⁴ = H)
| # | R¹ | R² | R³ | Preparation |
|---|---|---|---|---|
| 248. | H | 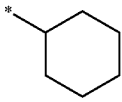 | 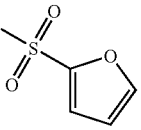 | Scheme 5 |
| 249. | H | 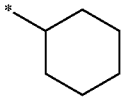 | 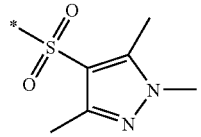 | Scheme 5 |
| 250. | H | 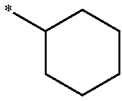 | 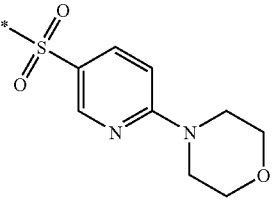 | Scheme 5 |
| 251. | H | 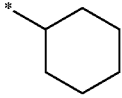 | 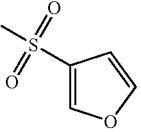 | Scheme 5 |
| 252. | H | 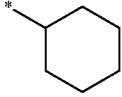 | 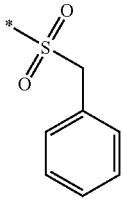 | Scheme 5 |
| 253. | H | 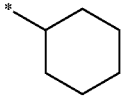 | 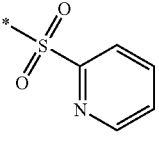 | Scheme 5 |
| 254. | H | 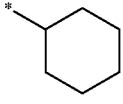 | 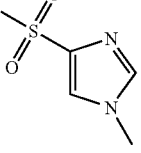 | Scheme 5 |

-continued

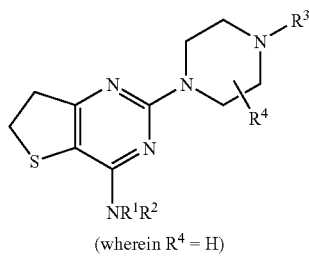

(wherein R⁴ = H)

| # | R¹ | R² | R³ | Preparation |
|---|---|---|---|---|
| 255. | H | *-cyclohexyl | *-S(O)₂-(pyridin-3-yl) | Scheme 5 |
| 256. | H | *-cyclohexyl | *-S(O)₂-(3,5-dimethylisoxazol-4-yl) | Scheme 5 |
| 257. | H | *-cyclohexyl | *-S(O)₂-(5-methyl-3-phenylisoxazol-4-yl) | Scheme 5 |
| 258. | H | *-cyclohexyl | *-C(O)NH-(4-chlorophenyl) | Scheme 5 |
| 259. | H | *-cyclohexyl | *-C(O)NH-cyclohexyl | Scheme 5 |
| 260. | H | *-cyclohexyl | *-C(O)NH-isopropyl | Scheme 5 |
| 261. | H | *-cyclohexyl | *-C(O)NH-benzyl | Scheme 5 |
| 262. | H | *-cyclohexyl | *-C(O)NH-(2-chlorophenyl) | Scheme 5 |

-continued
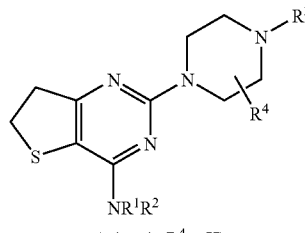
(wherein R⁴ = H)
| # | R¹ | R² | R³ | Preparation |
|---|---|---|---|---|
| 263. | H | 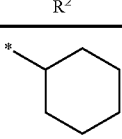 | 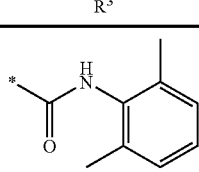 | Scheme 5 |
| 264. | H | 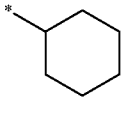 | 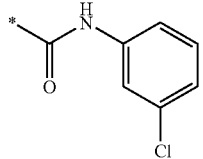 | Scheme 5 |
| 265. | H | 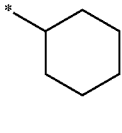 | 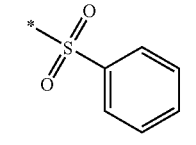 | Scheme 5 |
| 266. | H | 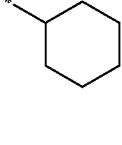 | 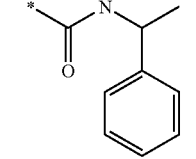 | Scheme 5 |
| 267. | H | 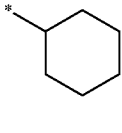 | 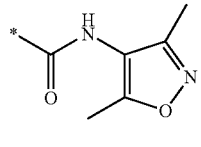 | Scheme 5 |
| 268. | H | 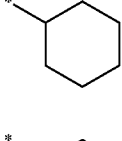 | 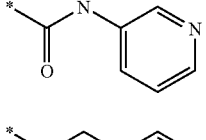 | Scheme 5 |
| 269. | H | 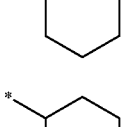 | 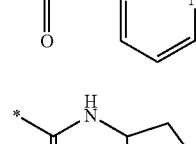 | Scheme 5 |
| 270. | H | 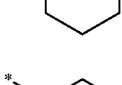 | 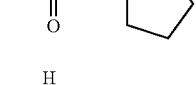 | Scheme 5 |
| 271. | H | 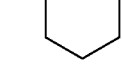 | 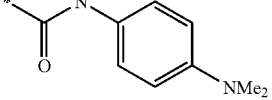 | Scheme 5 |

-continued

| # | R¹ | R² | R³ | Preparation |
|---|----|----|----|-------------|
| 272. | H | *cyclohexyl | *C(=O)CH₂-(1-methylpiperidin-4-yl) | Scheme 5 |
| 273. | H | *cyclohexyl | *C(=O)CH₂NH-(pyridin-3-yl) | Scheme 5 |
| 274. | H | *(1R,2S)-2-(1H-imidazole-4-carboxamido)cyclopentyl | *phenyl | Scheme 7 |
| 275. | H | *(1R,2S)-2-(3-hydroxy-2,2-dimethylpropanamido)cyclopentyl | *phenyl | Scheme 7 |
| 276. | H | *(1R,2S)-2-(cyclopentanecarboxamido)cyclopentyl | *phenyl | Scheme 7 |
| 277. | H | *(1R,2S)-2-(isoxazole-5-carboxamido)cyclopentyl | *phenyl | Scheme 7 |

(wherein R⁴ = H)

-continued
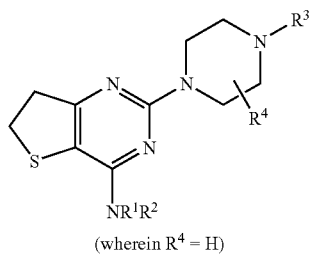
(wherein R⁴ = H)
| # | R¹ | R² | R³ | Preparation |
|---|----|----|----|-------------|
| 278. | H | *cyclopentyl-NH-C(O)-tetrahydrofuran-2-yl | *phenyl | Scheme 7 |
| 279. | H | *cyclopentyl-NH-C(O)-1H-pyrazol-3-yl | *phenyl | Scheme 7 |
| 280. | H | *cyclopentyl-NH-C(O)-CH₂-C(CH₃)₃ | *phenyl | Scheme 7 |
| 281. | H | *cyclopentyl-NH-C(O)-1H-pyrrol-2-yl | *phenyl | Scheme 7 |
| 282. | H | *piperidin-3-yl-N-C(O)-1H-imidazol-4-yl | *phenyl | Scheme 10 |

-continued
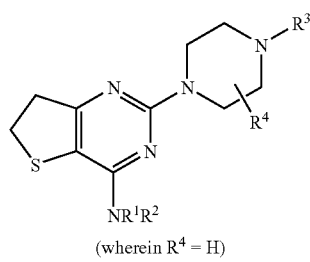
(wherein R⁴ = H)
| # | R¹ | R² | R³ | Preparation |
|---|---|---|---|---|
| 283. | H | *-piperidin-3-yl-N-C(O)-C(CH₃)₂-CH₂OH | *-phenyl | Scheme 10 |
| 284. | H | *-piperidin-3-yl-N-C(O)-(tetrahydrofuran-2-yl) | *-phenyl | Scheme 10 |
| 285. | H | *-piperidin-3-yl-N-C(O)-(1H-pyrazol-3-yl) | *-phenyl | Scheme 10 |
| 286. | H | *-piperidin-3-yl-N-C(O)-CH₂-C(CH₃)₃ | *-phenyl | Scheme 10 |
| 287. | H | *-piperidin-3-yl-N-C(O)-(1-methyl-2-mercapto-1H-imidazol-4-yl) | *-phenyl | Scheme 10 |

-continued
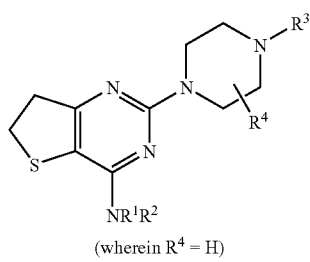
(wherein R⁴ = H)
| # | R¹ | R² | R³ | Preparation |
|---|----|----|----|-------------|
| 288. | H | *-3-(1H-pyrrol-2-ylcarbonyl)piperidin-3-yl | *-phenyl | Scheme 10 |
| 289. | H | *-1-(cyclopentylcarbonyl)piperidin-3-yl | *-phenyl | Scheme 10 |
| 290. | H | *-propyl | *-2-methyl-4-chlorophenyl | Scheme 1 |
| 291. | H | *-propyl | *-4-(sulfooxy)phenyl | Scheme 1 |
| 292. | H | *-propyl | *-2,4-dichlorophenyl | Scheme 1 |
| 293. | H | *-propyl | *-1,3-benzodioxol-5-yl | Scheme 1 |
| 294. | H | *-(2-methyl-2-phenyl)propyl | *-phenyl | Scheme 1 |

-continued
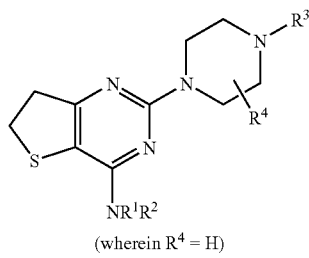
(wherein R⁴ = H)
| # | R¹ | R² | R³ | Preparation |
|---|---|---|---|---|
| 295. | H | *⎯CH(Ph)CH₂OH (S) | *⎯Ph | Scheme 1 |
| 296. | H | *⎯CH(Ph)CH₂OH (R) | *⎯Ph | Scheme 1 |
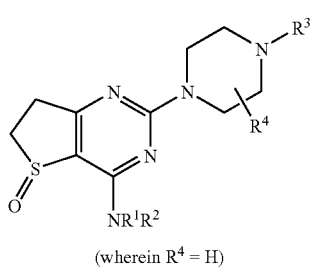
(wherein R⁴ = H)
| # | R¹ | R² | R³ | Preparation |
|---|---|---|---|---|
| 297. | H | *⎯cyclohexyl | *⎯Ph | Scheme 8 |
| 298. | H | *⎯n-Pr | *⎯Ph | Scheme 8 |
| 299. | H | *⎯Ph | *⎯Ph | Scheme 8 |
| 300. | H | *⎯(3-Cl-Ph) | *⎯Ph | Scheme 8 |
-continued
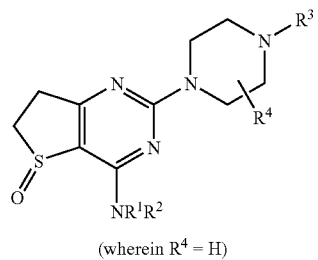
(wherein R⁴ = H)
| # | R¹ | R² | R³ | Preparation |
|---|---|---|---|---|
| 301. | H | *⎯n-Pr | *⎯(4-C(O)NHCH₂-C₆H₄-CH₂-pyrrolidinyl)Ph | Scheme 8 |
| 302. | H | *⎯(3-OMe-Ph) | *⎯Ph | Scheme 8 |

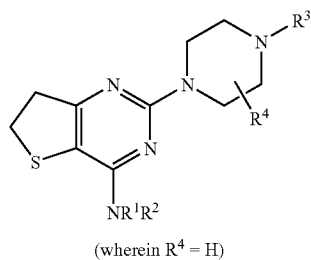
(wherein R⁴ = H)
| # | NR¹R² | R³ | Preparation |
|---|---|---|---|
| 303. |  | | Scheme 1 |
Further Examples include:
| # | Structure | Preparation |
|---|---|---|
| 304. |  | Scheme 1 |
| 305. | | |
| 306. | 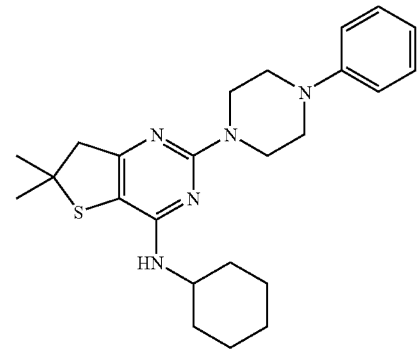 | Scheme 1 |
| 307. | 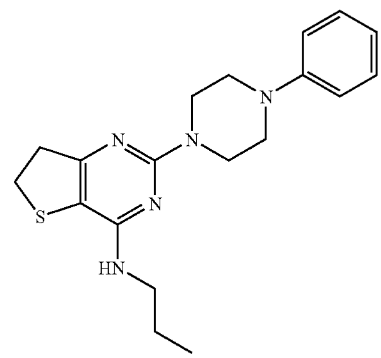 | Scheme 1 |
| 308. | 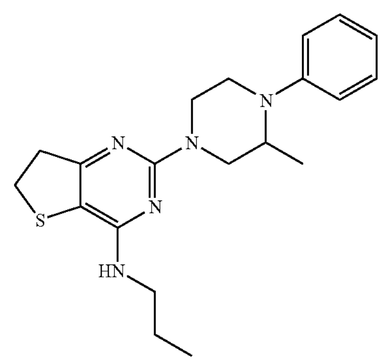 | Scheme 1 |
| 309. | 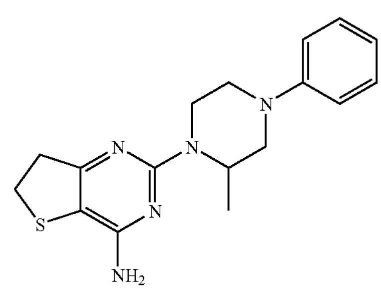 | Scheme 1 |

Examples A1

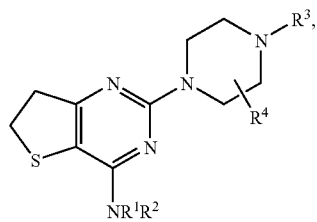

wherein R⁴ = H

| # | R¹ | R² | R³ | Preparation |
|---|---|---|---|---|
| 310. | H | (2-methylcyclopentyl)-N-((1-methyl-1H-pyrrol-2-yl)methyl)amine, chiral | phenyl | Scheme 7 |
| 311. | H | 3-(N-methyl-N-((1-methyl-1H-pyrazol-4-yl)methyl)carbamoyl)phenyl | phenyl | Scheme 12 |
| 312. | H | ethyl 2-phenylacetate, chiral | phenyl | Scheme 1 |
| 313. | H | 3-(pyridin-4-ylmethyl)phenyl | phenyl | Scheme 1 |
| 314. | H | ethyl 2-phenylacetate, chiral | phenyl | Scheme 1 |
| 315. | H | 3-((diethylamino)methyl)phenyl | phenyl | Scheme 1 |

-continued

Examples A1

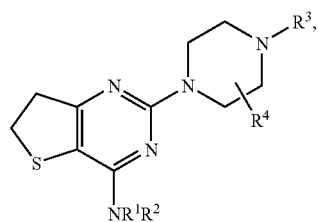

wherein R⁴ = H

| # | R¹ | R² | R³ | Preparation |
|---|----|----|----|-------------|
| 316. | H | *-phenyl-O-CH₂CH₂-N(CH₂CH₃)₂ (3-substituted) | phenyl | Scheme 1 |
| 317. | H | *-CH₂CH₂CH₃ | 2-benzimidazolyl | Scheme 1 |
| 318. | H | *-(3-phenyl)-CH₂CH₂-N(CH₂CH₃)₂ | phenyl | Scheme 1 |
| 319. | H | *-(3-phenyl)-C(O)-N(CH₃)-CH₂-(1-methylpyrazol-4-yl) | phenyl | Scheme 12 |
| 320. | H | *-(3-phenyl)-CH₂CH₂-N(CH₃)(CH₂CH₃) | phenyl | Scheme 1 |
| 321. | H | H₃C-CH₂CH₂-* | 4-(N-(quinuclidin-3-yl)carboxamido)phenyl, chiral | Scheme 2 |
| 322. | H | *-(3-phenyl)-CH₂-morpholin-4-yl | phenyl | Scheme 1 |

-continued
Examples A1
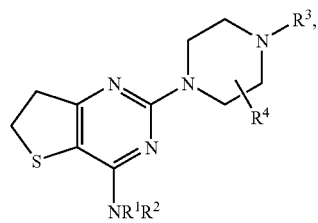
wherein R⁴ = H
| # | R¹ | R² | R³ | Preparation |
|---|----|----|----|-------------|
| 323. | H | *–CH₂CH₂CH₃ (propyl) | 1-methylbenzimidazol-2-yl | Scheme 1 |
| 324. | H | 3-chlorophenyl | benzimidazol-2-yl | Scheme 1 |
| 325. | H | 3-chlorophenyl | 1-methylbenzimidazol-2-yl | Scheme 1 |
| 326. | H | 3-ethynylphenyl | phenyl | Scheme 1 |
| 327. | H | 3-(1H-pyrrol-1-yl)phenyl | phenyl | Scheme 1 |
| 328. | H | 3-(dimethylamino)phenyl | phenyl | Scheme 1 |
| 329. | H | 3-(1H-pyrazol-3-yl)phenyl | phenyl | Scheme 1 |

-continued
Examples A1
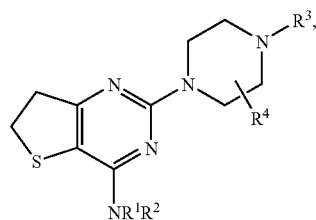
wherein R⁴ = H
| # | R¹ | R² | R³ | Preparation |
|---|---|---|---|---|
| 330. | H | 3-(2-methylpyrimidin-4-yl)phenyl | phenyl | Scheme 1 |
| 331. | H | 2-fluoro-3-chlorophenyl | phenyl | Scheme 1 |
| 332. | H | 3-(1-methyl-1H-pyrazol-3-yl)phenyl | phenyl | Scheme 1 |
| 333. | H | 3-(1-methyl-1H-imidazol-5-yl)phenyl | phenyl | Scheme 1 |
| 334. | H | 3-(1H-tetrazol-5-yl)phenyl | phenyl | Scheme 1 |
| 335. | H | 3-(morpholin-4-ylmethyl)phenyl | 4-chlorophenyl | Scheme 1 |
| 336. | H | 3-chloro-4-fluorophenyl | phenyl | Scheme 1 |

-continued
Examples A1
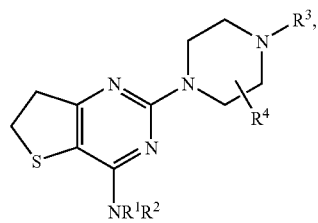
wherein R⁴ = H
| # | R¹ | R² | R³ | Preparation |
|---|---|---|---|---|
| 337. | H | benzo[1,3]dioxol-5-yl | phenyl | Scheme 1 |
| 338. | H | 3,5-difluorophenyl | phenyl | Scheme 1 |
| 339. | H | 3,5-dichlorophenyl | phenyl | Scheme 1 |
| 340. | H | 1H-indazol-5-yl | phenyl | Scheme 1 |
| 341. | H | 3,4-difluorophenyl | phenyl | Scheme 1 |
| 342. | H | 2-fluoro-3-(trifluoromethyl)phenyl | phenyl | Scheme 1 |
| 343. | H | 2-fluoro-5-cyanophenyl | phenyl | Scheme 1 |

-continued

Examples A1

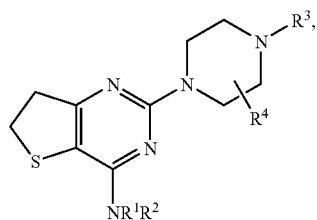

wherein R⁴ = H

| # | R¹ | R² | R³ | Preparation |
|---|---|---|---|---|
| 344. | H | 6-indazolyl | phenyl | Scheme 1 |
| 345. | H | -(CH₂)₃-OH | 4-chlorophenyl | Scheme 1 |
| 346. | H | trans-4-hydroxycyclohexyl | 4-chlorophenyl | Scheme 1 |
| 347. | H | -CH(CH₂OH)₂ | 4-chlorophenyl | Scheme 1 |
| 348. | H | 3,5-dimethylphenyl | phenyl | Scheme 1 |
| 349. | H | 2,3-difluorophenyl | phenyl | Scheme 1 |
| 350. | H | trans-4-hydroxycyclohexyl | 4-chlorophenyl | Scheme 1 |
| 351. | H | (1R,2S)-2-hydroxycyclopentyl (chiral) | 4-chlorophenyl | Scheme 1 |

-continued
Examples A1
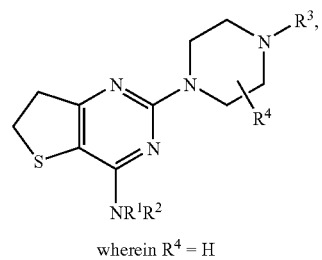
wherein R⁴ = H
| # | R¹ | R² | R³ | Preparation |
|---|---|---|---|---|
| 352. | H | (S)-pyrrolidin-3-ylmethyl, chiral | 4-chlorophenyl | Scheme 1 |
| 353. | H | 3-hydroxyadamantyl | 4-chlorophenyl | Scheme 1 |
| 354. | H | pyrrolidin-3-yl, chiral | 4-chlorophenyl | Scheme 1 |
| 355. | H | pyrrolidin-3-ylmethyl, chiral | 4-chlorophenyl | Scheme 1 |
| 356. | H | pyridin-3-yl | phenyl | Scheme 1 |
| 357. | H | 1-(morpholine-4-carbonyl)piperidin-3-yl | 4-chlorophenyl | Scheme 11 |

-continued
Examples A1
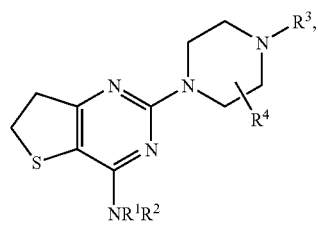
wherein R⁴ = H
| # | R¹ | R² | R³ | Preparation |
|---|----|----|----|-------------|
| 358. | H | 3-piperidinyl with N-C(O)CH₂-morpholine | 3-piperidinyl with N-C(O)CH₂-morpholine | Scheme 11 |
| 359. | H | 3-(hydroxymethyl)pyrrolidin-3-yl | 4-chlorophenyl | Scheme 1 |
| 360. | H | 3-[N-methyl-N-(pyridin-2-ylmethyl)carbamoyl]phenyl | phenyl | Scheme 12 |
| 361. | H | 1-(cyclopentylmethyl)piperidin-3-yl | phenyl | Scheme 11 |
| 362. | H | 1-(pyridin-2-ylmethyl)piperidin-3-yl | phenyl | Scheme 11 |

-continued
Examples A1
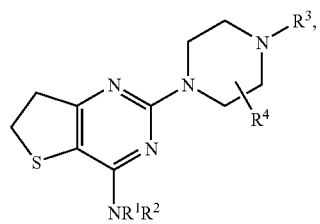
wherein R⁴ = H
| # | R¹ | R² | R³ | Preparation |
|---|---|---|---|---|
| 363. | H | 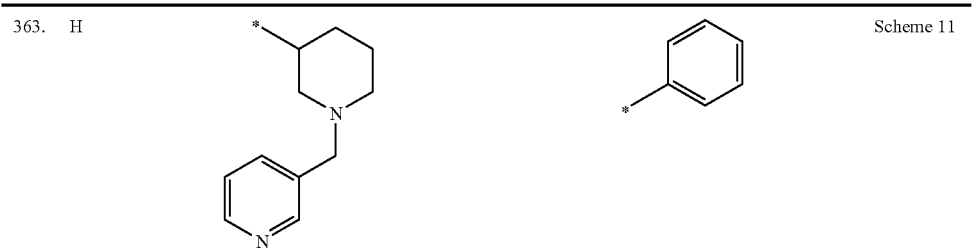 | | Scheme 11 |
| 364. | H |  | | Scheme 11 |
| 365. | H |  | | Scheme 1 |
| 366. | H |  | | Scheme 1 |

Examples B1

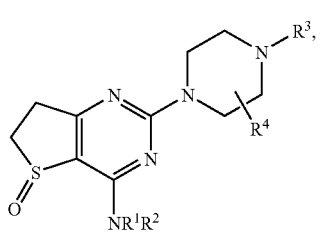

wherein R⁴ = H

| # | R¹ | R² | R³ | Preparation |
|---|---|---|---|---|
| 367. | H | cyclohexyl* | phenyl* | Scheme 1 |
| 368. | H | cyclohexyl* | phenyl* | Scheme 1 Enantiomer 2 of racemate 297 |
| 369. | H | *CH₂CH₂CH₃ | cyclopropyl* | Scheme 1 |
| 370. | H | 3-chlorophenyl* | phenyl* | Scheme 1 Enantiomer 1 of racemate 300 |
| 371. | H | 3-chlorophenyl* | phenyl* | Scheme 1 Enantiomer 2 of racemate 300 |
| 372. | H | 3-chlorophenyl* | cyclopropyl* | Scheme 1 |

Examples C1

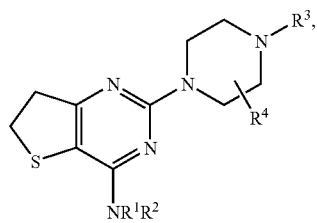

wherein R⁴ = H

| # | NR¹R² | R³ | Preparation |
|---|---|---|---|
| 373. | 4-methylpiperazin-1-yl | phenyl* | Scheme 1 |
| 374. | (2S,4R)-4-hydroxy-2-(hydroxymethyl)-1-methylpyrrolidinyl, chiral | 4-chlorophenyl* | Scheme 1 |

Further Examples include:

Examples D1

| # | Structure | Preparation |
|---|---|---|
| 375. | 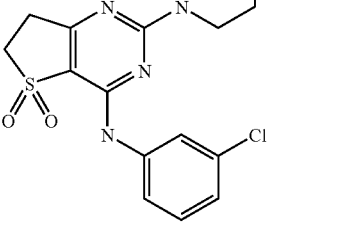 | Scheme 9 |
| 376. | 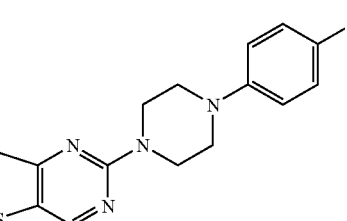 | Scheme 9 |

-continued

Examples D1

| # | Structure | Preparation |
|---|---|---|
| 377. | [structure with Cl, piperazine, thienopyrimidine with S(=O)₂, N-propyl] | Scheme 9 |
| 378. | [structure with Cl, piperazine, thienopyrimidine with HO, N-ethyl-methyl] | Scheme 14 |

Indications

As has been found, the compounds of formula 1 are characterized by their wide range of applications in the therapeutic field. Particular mention should be made of those applications for which the compounds according to the invention of formula 1 are preferably suited on account of their pharmaceutical efficacy as PDE4 inhibitors. Examples include respiratory or gastrointestinal diseases or complaints, inflammatory diseases of the joints, skin, or eyes, cancers, and also diseases of the peripheral or central nervous system.

Particular mention should be made of the prevention and treatment of diseases of the airways and of the lung which are accompanied by increased mucus production, inflammations, and/or obstructive diseases of the airways. Examples include acute, allergic, or chronic bronchitis, chronic obstructive bronchitis (COPD), coughing, pulmonary emphysema, allergic or non-allergic rhinitis or sinusitis, chronic rhinitis or sinusitis, asthma, alveolitis, Farmer's disease, hyperreactive airways, infectious bronchitis or pneumonitis, pediatric asthma, bronchiectases, pulmonary fibrosis, ARDS (acute adult respiratory distress syndrome), bronchial edema, pulmonary edema, bronchitis, pneumonia or interstitial pneumonia triggered by various causes, such as aspiration, inhalation of toxic gases, or bronchitis, pneumonia or interstitial pneumonia as a result of heart failure, irradiation, chemotherapy, cystic fibrosis, or mucoviscidosis, or alpha1-antitrypsin deficiency.

Also deserving special mention is the treatment of inflammatory diseases of the gastrointestinal tract. Examples include acute or chronic inflammatory changes in gall bladder inflammation, Crohn's disease, ulcerative colitis, inflammatory pseudopolyps, juvenile polyps, colitis cystica profunda, pneumatosis cystoides intestinales, diseases of the bile duct, and gall bladder, e.g., gallstones and conglomerates, for the treatment of inflammatory diseases of the joints such as rheumatoid arthritis or inflammatory diseases of the skin and eyes.

Preferential mention should also be made of the treatment of cancers. Examples include all forms of acute and chronic leukemias such as acute lymphatic and acute myeloid leukemia, chronic lymphatic and chronic myeloid leukemia, and bone tumors such as osteosarcoma and all types of glioma such as oligodendroglioma and glioblastoma.

Preferential mention should also be made of the prevention and treatment of diseases of the peripheral or central nervous system. Examples of these include depression, bipolar or manic depression, acute and chronic anxiety states, schizophrenia, Alzheimer's disease, Parkinson's disease, acute and chronic multiple sclerosis, or acute and chronic pain as well as injuries to the brain caused by stroke, hypoxia, or craniocerebral trauma.

Particularly preferably the present invention relates to the use of compounds of formula 1 for preparing a pharmaceutical composition for the treatment of inflammatory or obstructive diseases of the upper and lower respiratory tract including the lungs, such as, for example, allergic rhinitis, chronic rhinitis, bronchiectasis, cystic fibrosis, idiopathic pulmonary fibrosis, fibrosing alveolitis, COPD, chronic bronchitis, chronic sinusitis, asthma, Crohn's disease, ulcerative colitis, particularly COPD, chronic bronchitis, and asthma.

It is most preferable to use the compounds of formula 1 for the treatment of inflammatory and obstructive diseases such as COPD, chronic bronchitis, chronic sinusitis, asthma, Crohn's disease, ulcerative colitis, particularly COPD, chronic bronchitis, and asthma.

It is also preferable to use the compounds of formula 1 for the treatment of diseases of the peripheral or central nervous system such as depression, bipolar or manic depression, acute and chronic anxiety states, schizophrenia, Alzheimer's disease, Parkinson's disease, acute and chronic multiple sclerosis, or acute and chronic pain as well as injuries to the brain caused by stroke, hypoxia, or craniocerebral trauma.

An outstanding aspect of the present invention is the reduced profile of side effects. This means, within the scope of the invention, being able to administer a dose of a pharmaceutical composition without inducing vomiting, preferably nausea and most preferably malaise in the patient. It is particularly preferable to be able to administer a therapeutically effective quantity of substance without inducing emesis or nausea, at every stage of the disease.

Combinations

The compounds of formula 1 may be used on their own or in conjunction with other active substances of formula 1 according to the invention. If desired the compounds of formula 1 may also be used in combination with other pharmacologically active substances. It is preferable to use for this purpose active substances selected, for example, from among betamimetics, anticholinergics, corticosteroids, other PDE4-inhibitors, LTD4-antagonists, EGFR-inhibitors, dopamine agonists, H1-antihistamines, PAF-antagonists, and PI3-kinase inhibitors or double or triple combinations thereof, such as, for example, combinations of betamimetics with corticosteroids, PDE4-inhibitors, EGFR-inhibitors, or LTD4-antagonists, anticholinergics with betamimetics, corticosteroids, PDE4-inhibitors, EGFR-inhibitors, or LTD4-antagonists, corticosteroids with PDE4-inhibitors, EGFR-inhibitors, or LTD4-antagonists PDE4-inhibitors with EGFR-inhibitors, or LTD4-antagonists EGFR-inhibitors with LTD4-antagonists
MRP4-inhibitors.

The invention also encompasses combinations of three active substances, each selected from one of the abovementioned categories of compounds.

Suitable betamimetics used are preferably compounds selected from among albuterol, bambuterol, bitolterol, broxaterol, carbuterol, clenbuterol, fenoterol, formoterol, arformoterol, zinterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmeterol, salmefamol, soterenol, sulfonterol, tiaramide, terbutaline, tolubuterol, is CHF-1035, HOKU-81, KUL-1248, 3-(4-{6-[2-hydroxy-2-(4-hydroxy-3-hydroxymethylphenyl)ethylamino]hexyloxy}butyl)benzylsulfonamide, 5-[2-(5.6-diethylindan-2-ylamino)-1-hydroxyethyl]-8-hydroxy-1H-quinolin-2-one, 4-hydroxy-7-[2-{[2-{[3-(2-phenylethoxy)propyl]sulfonyl}ethyl]amino}ethyl]-2(3H)benzothiazolone, 1-(2-fluoro-4-hydroxyphenyl)-2-[4-(1-benzimidazolyl)-2-methyl-2-butylamino]ethanol, 1-[3-(4-methoxybenzylamino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluoromethylphenyl)-2-tert-butylamino)ethanol, 6-hydroxy-8-{1-hydroxy-2-[2-(4-methoxyphenyl)-1,1-dimethylethylamino]ethyl}-4H-benzo[1,4]oxazin-3-one, 6-hydroxy-8-{1-hydroxy-2-[2-(ethyl 4-phenoxyacetate)-1,1-dimethylethylamino]ethyl}-4H-benzo[1,4]oxazin-3-one, 6-hydroxy-8-{1-hydroxy-2-[2-(4-phenoxyacetic acid)-1,1-dimethylethylamino]ethyl}-4H-benzo[1,4]oxazin-3-one, 8-{2-[1,1-dimethyl-2-(2,4,6-trimethylphenyl)ethylamino]-1-hydroxyethyl}-6-hydroxy-4H-benzo[1,4]oxazin-3-one, 6-hydroxy-8-{1-hydroxy-2-[2-(4-hydroxyphenyl)-1,1-dimethylethylamino]ethyl}-4H-benzo[1,4]oxazin-3-one, 6-hydroxy-8-{1-hydroxy-2-[2-(4-isopropylphenyl)-1,1-dimethylethylamino]ethyl}-4H-benzo[1,4]oxazin-3-one, 8-{2-[2-(4-ethylphenyl)-1,1-dimethylethylamino]-1-hydroxyethyl}-6-hydroxy-4H-benzo[1,4]oxazin-3-one, 8-{2-[2-(4-ethoxyphenyl)-1,1-dimethylethylamino]-1-hydroxyethyl}-6-hydroxy-4H-benzo[1,4]oxazin-3-one, 4-(4-{2-[2-hydroxy-2-(6-hydroxy-3-oxo-3,4-dihydro-2H-benzo[1,4]oxazin-8-yl)ethylamino]-2-methylpropyl}phenoxy)butyric acid, 8-{2-[2-(3,4-difluorophenyl)-1,1-dimethylethylamino]-1-hydroxyethyl}-6-hydroxy-4H-benzo[1,4]oxazin-3-one, and 1-(4-ethoxycarbonylamino-3-cyano-5-fluorophenyl)-2-(tert-butylamino)ethanol, optionally in the form of the racemates, enantiomers, diastereomers, and optionally in the form of the pharmacologically acceptable acid addition salts, solvates, or hydrates thereof.

Preferably the betamimetics are selected from among bambuterol, bitolterol, carbuterol, clenbuterol, fenoterol, formoterol, hexoprenaline, ibuterol, pirbuterol, procaterol, reproterol, salmeterol, sulfonterol, terbutaline, tolubuterol, 3-(4-{6-[2-hydroxy-2-(4-hydroxy-3-hydroxymethylphenyl)ethylamino]hexyloxy}butyl)benzenesulfonamide, 5-[2-(5.6-diethylindan-2-ylamino)-1-hydroxyethyl]-8-hydroxy-1H-quinolin-2-one, 4-hydroxy-7-[2-{[2-{[3-(2-phenylethoxy)propyl]sulfonyl}ethyl]amino}ethyl]-2(3H)benzothiazolone, 1-(2-fluoro-4-hydroxyphenyl)-2-[4-(1-benzimidazolyl)-2-methyl-2-butylamino]ethanol, 1-[3-(4-methoxybenzylamino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 6-hydroxy-8-{1-hydroxy-2-[2-(4-methoxyphenyl)-1,1-dimethylethylamino]ethyl}-4H-benzo[1,4]oxazin-3-one, 6-hydroxy-8-{1-hydroxy-2-[2-(ethyl 4-phenoxyacetate)-1,1-dimethylethylamino]ethyl}-4H-benzo[1,4]oxazin-3-one, 6-hydroxy-8-{1-hydroxy-2-[2-(4-phenoxyacetic acid)-1,1-dimethylethylamino]ethyl}-4H-benzo[1,4]oxazin-3-one, 8-{2-[1,1-dimethyl-2-(2,4,6-trimethylphenyl)ethylamino]-1-hydroxyethyl}-6-hydroxy-4H-benzo[1,4]oxazin-3-one, 6-hydroxy-8-{1-hydroxy-2-[2-(4-hydroxyphenyl)-1,1-dimethylethylamino]ethyl}-4H-benzo[1,4]oxazin-3-one, 6-hydroxy-8-{1-hydroxy-2-[2-(4-isopropylphenyl)-1,1-dimethylethylamino]ethyl}-4H-benzo[1,4]oxazin-3-one, 8-{2-[2-(4-ethylphenyl)-1,1-dimethylethylamino]-1-hydroxyethyl}-

Particularly preferred betamimetics are selected from among fenoterol, formoterol, salmeterol, 3-(4-{6-[2-hydroxy-2-(4-hydroxy-3-hydroxymethylphenyl)ethylamino]hexyloxy}butyl)benzenesulfonamide, 5-[2-(5,6-diethylindan-2-ylamino)-1-hydroxyethyl]-8-hydroxy-1H-quinoline-2-one, 1-[3-(4-methoxybenzylamino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 6-hydroxy-8-{1-hydroxy-2-[2-(4-methoxyphenyl)-1,1-dimethylethylamino]ethyl}-4H-benzo[1,4]oxazin-3-one, 6-hydroxy-8-{1-hydroxy-2-[2-(ethyl 4-phenoxyacetate)-1,1-dimethylethylamino]ethyl}-4H-benzo[1,4]oxazin-3-one, 6-hydroxy-8-{1-hydroxy-2-[2-(4-phenoxyacetic acid)-1,1-dimethylethylamino]ethyl}-4H-benzo[1,4]oxazin-3-one, 8-{2-[1,1-dimethyl-2-(2,4,6-trimethylphenyl)ethylamino]-1-hydroxyethyl}-6-hydroxy-4H-benzo[1,4]oxazin-3-one, 6-hydroxy-8-{1-hydroxy-2-[2-(4-hydroxyphenyl)-1,1-dimethylethylamino]ethyl}-4H-benzo[1,4]oxazin-3-one, 6-hydroxy-8-{1-hydroxy-2-[2-(4-isopropylphenyl)-1,1-dimethylethylamino]ethyl}-4H-benzo[1,4]oxazin-3-one, 8-{2-[2-(4-ethylphenyl)-1,1-dimethylethylamino]-1-hydroxyethyl}-

6-hydroxy-4H-benzo[1,4]oxazin-3-one, 8-{2-[2-(4-ethoxyphenyl)-1,1-dimethylethylamino]-1-hydroxyethyl}-6-hydroxy-4H-benzo[1,4]oxazin-3-one, 4-(4-{2-[2-hydroxy-2-(6-hydroxy-3-oxo-3,4-dihydro-2H-benzo[1,4]oxazin-8-yl)ethylamino]-2-methylpropyl}phenoxy)butyric acid, 8-{2-[2-(3,4-difluorophenyl)-1,1-dimethylethylamino]-1-hydroxyethyl}-6-hydroxy-4H-benzo[1,4]oxazin-3-one, and 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, optionally in the form of the racemates, enantiomers, diastereomers, and optionally in the form of the pharmacologically acceptable acid addition salts, solvates, or hydrates thereof.

Of these betamimetics the particularly preferred ones according to the invention are formoterol, salmeterol, 3-(4-{6-[2-hydroxy-2-(4-hydroxy-3-hydroxymethylphenyl)ethylamino]hexyloxy}butyl)benzenesulfonamide, 6-hydroxy-8-{1-hydroxy-2-[2-(4-methoxyphenyl)-1,1-dimethylethylamino]ethyl}-4H-benzo[1,4]oxazin-3-one, 6-hydroxy-8-{1-hydroxy-2-[2-(ethyl 4-phenoxyacetate)-1,1-dimethylethylamino]ethyl}-4H-benzo[1,4]oxazin-3-one, 6-hydroxy-8-{1-hydroxy-2-[2-(4-phenoxyacetic acid)-1,1-dimethylethylamino]ethyl}-4H-benzo[1,4]oxazin-3-one, 8-{2-[1,1-dimethyl-2-(2,4,6-trimethylphenyl)ethylamino]-1-hydroxyethyl}-6-hydroxy-4H-benzo[1,4]oxazin-3-one, 6-hydroxy-8-{1-hydroxy-2-[2-(4-hydroxyphenyl)-1,1-dimethylethylamino]ethyl}-4H-benzo[1,4]oxazin-3-one, 6-hydroxy-8-{1-hydroxy-2-[2-(4-isopropylphenyl)-1,1-dimethylethylamino]ethyl}-4H-benzo[1,4]oxazin-3-one, 8-{2-[2-(4-ethylphenyl)-1,1-dimethylethylamino]-1-hydroxyethyl}-6-hydroxy-4H-benzo[1,4]oxazin-3-one, 8-{2-[2-(4-ethoxyphenyl)-1,1-dimethylethylamino]-1-hydroxyethyl}-6-hydroxy-4H-benzo[1,4]oxazin-3-one, 4-(4-{2-[2-hydroxy-2-(6-hydroxy-3-oxo-3,4-dihydro-2H-benzo[1,4]oxazin-8-yl)ethylamino]-2-methylpropyl}phenoxy)butyric acid, 8-{2-[2-(3,4-difluorophenyl)-1,1-dimethylethylamino]-1-hydroxyethyl}-6-hydroxy-4H-benzo[1,4]oxazin-3-one, and 5-[2-(5,6-diethylindan-2-ylamino)-1-hydroxyethyl]-8-hydroxy-1H-quinoline-2-one, optionally in the form of the racemates, enantiomers, diastereomers, and optionally in the form of the pharmacologically acceptable acid addition salts, solvates, or hydrates thereof.

According to the invention the acid addition salts of the betamimetics are preferably selected from among the hydrochloride, hydrobromide, hydroiodide, hydrosulfate, hydrophosphate, hydromethanesulfonate, hydronitrate, hydromaleate, hydroacetate, hydrocitrate, hydrofumarate, hydrotartrate, hydrooxalate, hydrosuccinate, hydrobenzoate, and hydro-p-toluenesulfonate, preferably the hydrochloride, hydrobromide, hydrosulfate, hydrophosphate, hydrofumarate, and hydromethanesulfonate. Of the abovementioned acid addition salts the salts of hydrochloric acid, methanesulfonic acid, benzoic acid, and acetic acid are particularly preferred according to the invention.

The anticholinergics used are preferably compounds selected from among the tiotropium salts, oxitropium salts, flutropium salts, ipratropium salts, glycopyrronium salts, trospium salts, tropenol 2,2-diphenylpropionate methobromide, scopine 2,2-diphenylpropionate methobromide, scopine 2-fluoro-2,2-diphenylacetate methobromide, tropenol 2-fluoro-2,2-diphenylacetate methobromide, tropenol 3,3',4,4'-tetrafluorobenzilate methobromide, scopine 3,3',4,4'-tetrafluorobenzilate methobromide, tropenol 4,4'-difluorobenzilate methobromide, scopine 4,4'-difluorobenzilate methobromide, tropenol 3,3'-difluorobenzilate methobromide, -scopine 3,3'-difluorobenzilate methobromide, tropenol 9-hydroxyfluorene-9-carboxylate methobromide, tropenol 9-fluorofluorene-9-carboxylate methobromide, scopine 9-hydroxyfluoren-9-carboxylate methobromide, scopine 9-fluorofluorene-9-carboxylate methobromide, tropenol 9-methylfluorene-9-carboxylate methobromide, scopine 9-methylfluorene-9-carboxylate methobromide, cyclopropyltropine benzilate methobromide, cyclopropyltropine 2,2-diphenylpropionate methobromide, cyclopropyltropine 9-hydroxyxanthene-9-carboxylate methobromide, cyclopropyltropine 9-methylfluorene-9-carboxylate methobromide, cyclopropyltropine 9-methylxanthene-9-carboxylate methobromide, cyclopropyltropine 9-hydroxyfluorene-9-carboxylate methobromide, methyl-cyclopropyltropine 4,4'-difluorobenzilate methobromide, tropenol 9-hydroxyxanthene-9-carboxylate methobromide, scopine 9-hydroxyxanthene-9-carboxylate methobromide, tropenol 9-methylxanthene-9-carboxylate methobromide, scopine 9-methylxanthene-9-carboxylate methobromide, tropenol 9-ethylxanthene-9-carboxylate methobromide, tropenol 9-difluoromethylxanthene-9-carboxylate methobromide, scopine 9-hydroxymethylxanthene-9-carboxylate methobromide, optionally in the form of the solvates, or hydrates thereof.

In the abovementioned salts the cations tiotropium, oxitropium, flutropium, ipratropium, glycopyrronium, and trospium are the pharmacologically active ingredients. As anions, the abovementioned salts may preferably contain chloride, bromide, iodide, sulfate, phosphate, methanesulfonate, nitrate, maleate, acetate, citrate, fumarate, tartrate, oxalate, succinate, benzoate, or p-toluenesulfonate, while chloride, bromide, iodide, sulfate, methanesulfonate, or p-toluenesulfonate are preferred as counter-ions. Of all the salts, the chlorides, bromides, iodides, and methanesulfonate are particularly preferred.

Of particular importance is tiotropium bromide. In the case of tiotropium bromide the pharmaceutical combinations according to the invention preferably contain it in the form of the crystalline tiotropium bromide monohydrate, which is known from WO 02/30928. If the tiotropium bromide is used in anhydrous form in the pharmaceutical combinations according to the invention, it is preferable to use anhydrous crystalline tiotropium bromide, which is known from WO 03/000265.

Corticosteroids used here are preferably compounds selected from among prednisolone, prednisone, butixocortpropionate, flunisolide, beclomethasone, triamcinolone, budesonide, fluticasone, mometasone, ciclesonide, rofleponide, dexamethasone, betamethasone, deflazacort, RPR-106541, NS-126, (S)-fluoromethyl 6,9-difluoro-17-[(2-furanylcarbonyl)oxy]-11-hydroxy-16-methyl-3-oxoandrosta-1,4-diene-17-carbothionate, and (S)-(2-oxotetrahydrofuran-3S-yl) 6,9-difluoro-11-hydroxy-16-methyl-3-oxo-17-propionyloxyandrosta-1,4-diene-17-carbothionate,
optionally in the form of the racemates, enantiomers, or diastereomers thereof, and optionally in the form of the salts and derivatives, solvates, and/or hydrates thereof.

Particularly preferred is the steroid selected from among flunisolide, beclomethasone, triamcinolone, budesonide, fluticasone, mometasone, ciclesonide, rofleponide, dexamethasone, NS-126, (S)-fluoromethyl 6,9-difluoro-17-[(2-furanylcarbonyl)oxy]-11-hydroxy-16-methyl-3-oxoandrosta-1,4-diene-1,7-carbothionate, and (S)-(2-oxotetrahydrofuran-3S-yl) 6,9-difluoro-11-hydroxy-16-methyl-3-oxo-17-propionyloxyandrosta-1,4-diene-17-carbothionate,
optionally in the form of the racemates, enantiomers, or diastereomers thereof, and optionally in the form of the salts and derivatives, solvates, and/or hydrates thereof.

Particularly preferred is the steroid selected from among budesonide, fluticasone, mometasone, ciclesonide, and (S)-fluoromethyl 6,9-difluoro-17-[(2-furanylcarbonyl)oxy]-11-hydroxy-16-methyl-3-oxoandrosta-1,4-diene-17-carbothionate, optionally in the form of the racemates, enantiomers, or diastereomers thereof, and optionally in the form of the salts and derivatives, solvates, and/or hydrates thereof.

Any reference to steroids includes a reference to any salts or derivatives, hydrates, or solvates thereof which may exist. Examples of possible salts and derivatives of the steroids may be: alkali metal salts, such as, for example, sodium or potassium salts, sulfobenzoates, phosphates, isonicotinates, acetates, propionates, dihydrogen phosphates, palmitates, pivalates, or furoates thereof.

Other PDE4 inhibitors which may be used are preferably compounds selected from among enprofyllin, theophyllin, roflumilast, ariflo (cilomilast), tofimilast, pumafentrin, lirimilast, arofyllin, atizoram, D-4396 (Sch-351591), AWD-12-281 (GW-842470), NCS-613, CDP-840, D-4418, PD-168787, T-440, T-2585, V-11294A, CI-1018, CDC-801, CDC-3052, D-22888, YM-58997, Z-15370, N-(3,5-dichloro-1-oxopyridin-4-yl)-4-difluoromethoxy-3-yclopropyl-methoxybenzamide, (−)-p-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide, (R)-(+)-1-(4-bromobenzyl)-4-[(3-cyclopentyloxy)-4-methoxyphenyl]-2-pyrrolidone, 3-(cyclopentyloxy-4-methoxyphenyl)-1-(4-N'-[N-2-cyano-S-methylisothioureido]benzyl)-2-pyrrolidone, cis[4-cyano-4-(3-cyclopentyloxy-4-methoxyphenyl)cyclohexane-1-carboxylic acid], 2-carbomethoxy-4-cyano-4-(3-cyclopropylmethoxy-4-difluoromethoxyphenyl)cyclohexane-1-one, cis[4-cyano-4-(3-cyclopropylmethoxy-4-difluoromethoxyphenyl)cyclohexan-1-ol], (R)-(+)-ethyl[4-(3-cyclopentyloxy-4-methoxyphenyl)pyrrolidin-2-ylidene]acetate, (S)-(−)-ethyl [4-(3-cyclopentyloxy-4-methoxyphenyl)pyrrolidin-2-ylidene]acetate, 9-cyclopentyl-5,6-dihydro-7-ethyl-3-(2-thienyl)-9H-pyrazolo[3,4-c]-1,2,4-triazolo[4,3-a]pyridine, and 9-cyclopentyl-5,6-dihydro-7-ethyl-3-(tert-butyl)-9H-pyrazolo[3,4-c]-1,2,4-triazolo[4,3-a]pyridine, optionally in the form of the racemates, enantiomers, or diastereomers, and optionally in the form of the pharmacologically acceptable acid addition salts, solvates, and/or hydrates thereof.

Particularly preferably the PDE4-inhibitor is selected from among enprofyllin, roflumilast, ariflo (cilomilast), arofyllin, atizoram, AWD-12-281 (GW-842470), T-440, T-2585, PD-168787, V-11294A, Cl-1018, CDC-801, D-22888, YM-58997, Z-15370, N-(3,5-dichloro-1-oxopyridin-4-yl)-4-difluoromethoxy-3-cyclopropylmethoxybenzamide, cis[4-cyano-4-(3-cyclopentyloxy-4-methoxyphenyl)cyclohexane-1-carboxylic acid], 2-carbomethoxy-4-cyano-4-(3-cyclopropylmethoxy-4-difluoromethoxyphenyl)cyclohexan-1-one, cis[4-cyano-4-(3-cyclopropylmethoxy-4-difluoromethoxyphenyl)cyclohexan-1-ol], 9-cyclopentyl-5,6-dihydro-7-ethyl-3-(2-thienyl)-9H-pyrazolo[3,4-c]-1,2,4-triazolo[4,3-a]pyridine, and 9-cyclopentyl-5,6-dihydro-7-ethyl-3-(tert-butyl)-9H-pyrazolo[3,4-c]-1,2,4-triazolo[4,3-a]pyridine, optionally in the form of the racemates, enantiomers, or diastereomers, and optionally in the form of the pharmacologically acceptable acid addition salts, solvates, and/or hydrates thereof.

Particularly preferably the PDE4-inhibitor is selected from among roflumilast, ariflo (cilomilast), arofyllin, AWD-12-281 (GW-842470), 2-carbomethoxy-4-cyano-4-(3-cyclopropylmethoxy-4-difluoromethoxyphenyl)cyclohexan-1-one, cis[4-cyano-4-(3-cyclopropylmethoxy-4-difluoromethoxyphenyl)cyclohexan-1-ol], atizoram, Z-15370, 9-cyclopentyl-5,6-dihydro-7-ethyl-3-(2-thienyl)-9H-pyrazolo[3,4-c]-1,2,4-triazolo[4,3-a]pyridine, and 9-cyclopentyl-5,6-dihydro-7-ethyl-3-(tert-butyl)-9H-pyrazolo[3,4-c]-1,2,4-triazolo[4,3-a]pyridine, optionally in the form of the racemates, enantiomers, or diastereomers, and optionally in the form of the pharmacologically acceptable acid addition salts, solvates, and/or hydrates thereof.

By acid addition salts with pharmacologically acceptable acids which the abovementioned PDE4-inhibitors might be in a position to form are meant, for example, salts selected from among the hydrochloride, hydrobromide, hydroiodide, hydrosulfate, hydrophosphate, hydromethanesulfonate, hydronitrate, hydromaleate, hydroacetate, hydrobenzoate, hydrocitrate, hydrofumarate, hydrotartrate, hydrooxalate, hydrosuccinate, hydrobenzoate, and hydro-p-toluenesulfonate, preferably hydrochloride, hydrobromide, hydrosulfate, hydrophosphate, hydrofumarate, and hydromethanesulfonate.

LTD4-antagonists which may be used are preferably compounds selected from among montelukast, pranlukast, zafirlukast, MCC-847 (ZD-3523), MN-001, MEN-91507 (LM-1507), VUF-5078, VUF-K-8707, L-733321, 1-(((R)-(3-(2-(6,7-difluoro-2-quinolinyl)ethenyl)phenyl)-3-(2-(2-hydroxy-2-propyl)phenyl)thio)methylcyclopropane acetic acid, 1-(((1(R)-3(3-(2-(2,3-dichlorothieno[3,2-b]pyridin-5-yl)-(E)-ethenyl)phenyl)-3-(2-(1-hydroxy-1-methylethyl) phenyl)propyl)thio)methyl)cyclopropane acetic acid, and [2-[[2-(4-tert-butyl-2-thiazolyl)-5-benzofuranyl]oxymethyl] phenyl]acetic acid, optionally in the form of the racemates, enantiomers, or diastereomers, optionally in the form of the pharmacologically acceptable acid addition salts, and optionally in the form of the salts and derivatives, solvates, and/or hydrates thereof.

Preferably the LTD4-antagonist is selected from among montelukast, pranlukast, zafirlukast, MCC-847 (ZD-3523), MN-001, MEN-91507 (LM-1507), VUF-5078, VUF-K-8707, and L-733321, optionally in the form of the racemates, enantiomers, or diastereomers, optionally in the form of the pharmacologically acceptable acid addition salts, and optionally in the form of the salts and derivatives, solvates, and/or hydrates thereof.

Particularly preferably the LTD4-antagonist is selected from among montelukast, pranlukast, zafirlukast, MCC-847 (ZD-3523), MN-001, and MEN-91507 (LM-1507), optionally in the form of the racemates, enantiomers, or diastereomers, optionally in the form of the pharmacologically acceptable acid addition salts, and optionally in the form of the salts and derivatives, solvates, and/or hydrates thereof.

By acid addition salts with pharmacologically acceptable acids which the LTD4-antagonists may be capable of forming are meant, for example, salts selected from among the hydrochloride, hydrobromide, hydroiodide, hydrosulfate, hydrophosphate, hydromethanesulfonate, hydronitrate, hydromaleate, hydroacetate, hydrobenzoate, hydrocitrate, hydrofumarate, hydrotartrate, hydrooxalate, hydrosuccinate, hydrobenzoate, and hydro-p-toluenesulfonate, preferably hydrochloride, hydrobromide, hydrosulfate, hydrophosphate, hydrofumarate, and hydromethanesulfonate. By salts or derivatives which the LTD4-antagonists may be capable of forming are meant, for example: alkali metal salts, such as, for example, sodium or potassium salts, alkaline earth metal salts, sulfobenzoates, phosphates, isonicotinates, acetates, propionates, dihydrogen phosphates, palmitates, pivalates, or furoates.

The EGFR-inhibitors used are preferably compounds selected from among 4-[(3-chloro-4-fluorophenyl)amino]-6-{[4-(morpholin-4-yl)-1-oxo-2-buten-1-yl]amino}-7-cyclopropylmethoxyquinazoline, 4-[(3-chloro-4-fluorophenyl)amino]-6-{4-(N,N-diethylamino)-1-oxo-2-buten-1-yl]amino}-7-cyclopropylmethoxyquinazoline, 4-[(3-chloro-4-fluorophenyl)amino]-6-{[4-(N,N-dimethylamino)-1-oxo-2-buten-1-yl]amino}-7-cyclopropylmethoxyquinazoline, 4-[(R)-(1-phenylethyl)amino]-6-{[4-(morpholin-4-yl)-1-oxo-2-buten-1-yl]amino}-7-cyclopentyloxyquinazoline, 4-[(3-chloro-4-fluorophenyl)amino]-6-{[4-((R)-6-methyl-2-oxomorpholin-4-yl)-1-oxo-2-buten-1-yl]amino}-7-cyclopropylmethoxyquinazoline, 4-[(3-chloro-4-fluorophenyl)amino]-6-{[4-((R)-6-methyl-2-oxomorpholin-4-yl)-1-oxo-2-buten-1-yl]amino}-7-[(S)-(tetrahydrofuran-3-yl)oxy]quinazoline, 4-[(3-chloro-4-fluorophenyl)amino]-6-{[4-((R)-2-methoxymethyl-6-oxomorpholin-4-yl)-1-oxo-2-buten-1-yl]amino}-7-cyclopropylmethokyquinazoline, 4-[(3-chloro-4-fluorophenyl)amino]-6-[2-((S)-6-methyl-2-oxomorpholin-4-yl)ethoxy]-7-methoxyquinazoline, 4-[(3-chloro-4-fluorophenyl)amino]-6-({4-[N-(2-methoxyethyl)-N-methylamino]-1-oxo-2-buten-1-yl}amino)-7-cyclopropylmethoxyquinazoline, 4-[(3-chloro-4-fluorophenyl)amino]-6-{[4-(N,N-dimethylamino)-1-oxo-2-buten-1-yl]amino}-7-cyclopentyloxyquinazoline, 4-[(R)-(1-phenylethyl)amino]-6-{[4-(N,N-bis-(2-methoxyethyl)amino)-1-oxo-2-buten-1-yl]amino}-7-cyclopropylmethoxyquinazoline, 4-[(R)-(1-phenylethyl)amino]-6-({4-[N-(2-methoxyethyl)-N-ethylamino]-1-oxo-2-buten-1-yl}amino)-7-cyclopropylmethoxyquinazoline, 4-[(R)-(1-phenylethyl)amino]-6-({4-[N-(2-methoxyethyl)-N-methylamino]-1-oxo-2-buten-1-yl}amino)-7-cyclopropylmethoxyquinazoline, 4-[(R)-(1-phenylethyl)amino]-6-({4-[N-(tetrahydropyran-4-yl)-N-methylamino]-1-oxo-2-buten-1-yl}amino)-7-cyclopropylmethoxyquinazoline, 4-[(3-chloro-4-fluorophenyl)amino]-6-{[4-(N,N-dimethylamino)-1-oxo-2-buten-1-yl]amino}-7-((R)-tetrahydrofuran-3-yloxy)quinazoline, 4-[(3-chloro-4-fluorophenyl)amino]-6-{[4-(N,N-dimethylamino)-1-oxo-2-buten-1-yl]amino}-7-((S)-tetrahydrofuran-3-yloxy)quinazoline, 4-[(3-chloro-4-fluorophenyl)amino]-6-({4-[N-(2-methoxyethyl)-N-methylamino]-1-oxo-2-buten-1-yl}amino)-7-cyclopentyloxyquinazoline, 4-[(3-chloro-4-fluorophenyl)amino]-6-{[4-(N-cyclopropyl-N-methylamino)-1-oxo-2-buten-1-yl]amino}-7-cyclopentyloxyquinazoline, 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]quinazoline, 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]quinazoline, 4-[(3-ethynylphenyl)amino]-6,7-bis-(2-methoxyethoxy)quinazoline, 4-[(3-chloro-4-fluorophenyl)amino]-7-[3-(morpholin-4-yl)propyloxy]-6-[(vinylcarbonyl)amino]quinazoline, 4-[(R)-(1-phenylethyl)amino]-6-(4-hydroxyphenyl)-7H-pyrrolo[2,3-d]pyrimidine, 3-cyano-4-[(3-chloro-4-fluorophenyl)amino]-6-{[4-(N,N-dimethylamino)-1-oxo-2-buten-1-yl]amino}-7-ethoxyquinoline, 4-{3-chloro-4-(3-fluorobenzyloxy)phenyl]amino)-6-(5-{[(2-methanesulfonylethyl)amino]methyl}furan-2-yl)quinazoline, 4-[(R)-(1-phenylethyl)amino]-6-{[4-((R)-6-methyl-2-oxomorpholin-4-yl)-1-oxo-2-buten-1-yl]amino}-7-methoxyquinazoline, 4-[(3-chloro-4-fluorophenyl)amino]-6-{[4-(morpholin-4-yl)-1-oxo-2-buten-1-yl]amino}-7-[(tetrahydrofuran-2-yl)methoxy]quinazoline, 4-[(3-chloro-4-fluorophenyl)amino]-6-({4-[N,N-bis-(2-methoxyethyl)amino]-1-oxo-2-buten-1-yl}amino)-7-[(tetrahydrofuran-2-yl)methoxy]quinazoline, 4-[(3-ethynylphenyl)amino]-6-{[4-(5,5-dimethyl-2-oxomorpholin-4-yl)-1-oxo-2-buten-1-yl]amino}quinazoline, 4-[(3-chloro-4-fluorophenyl)amino]-6-[2-(2,2-dimethyl-6-oxomorpholin-4-yl)ethoxy]-7-methoxyquinazoline, 4-[(3-chloro-4-fluorophenyl)amino]-6-[2-(2,2-dimethyl-6-oxomorpholin-4-yl)ethoxy]-7-[(R)-(tetrahydrofuran-2-yl)methoxy]quinazoline, 4-[(3-chloro-4-fluorophenyl)amino]-7-[2-(2,2-dimethyl-6-oxomorpholin-4-yl)ethoxy]-6-[(S)-(tetrahydrofuran-2-yl)methoxy]quinazoline, 4-[(3-chloro-4-fluorophenyl)amino]-6-{2-[4-(2-oxomorpholin-4-yl)piperidin-1-yl]ethoxy}-7-methoxyquinazoline, 4-[(3-chloro-4-fluorophenyl)amino]-6-[1-(tert-butyloxycarbonyl)piperidin-4-yloxy]-7-methoxyquinazoline, 4-[(3-chloro-4-fluorophenyl)amino]-6-(trans-4-aminocyclohexan-1-yloxy)-7-methoxyquinazoline, 4-[(3-chloro-4-fluorophenyl)amino]-6-(trans-4-methanesulfonylaminocyclohexan-1-yloxy)-7-methoxyquinazoline, 4-[(3-chloro-4-fluorophenyl)amino]-6-(tetrahydropyran-3-yloxy)-7-methoxyquinazoline, 4-[(3-chloro-4-fluorophenyl)amino]-6-(1-methylpiperidin-4-yloxy)-7-methoxyquinazoline, 4-[(3-chloro-4-fluorophenyl)amino]-6-{1-[(morpholin-4-yl)carbonyl]piperidin-4-yloxy}-7-methoxyquinazoline, 4-[(3-chloro-4-fluorophenyl)amino]-6-{1-[(methoxymethyl)carbonyl]piperidin-4-yloxy}-7-methoxyquinazoline, 4-[(3-chloro-4-fluorophenyl)amino]-6-(piperidin-3-yloxy)-7-methoxyquinazoline, 4-[(3-chloro-4-fluorophenyl)amino]-6-[1-(2-acetylaminoethyl)piperidin-4-yloxy]-7-methoxyquinazoline, 4-[(3-chloro-4-fluorophenyl)amino]-6-(tetrahydropyran-4-yloxy)-7-ethoxyquinazoline, 4-[(3-chloro-4-fluorophenyl)amino]-6-((S)-tetrahydrofuran-3-yloxy)-7-hydroxyquinazoline, 4-[(3-chloro-4-fluorophenyl)amino]-6-(tetrahydropyran-4-yloxy)-7-(2-methoxyethoxy)quinazoline, 4-[(3-chloro-4-fluorophenyl)amino]-6-{trans-4-[(dimethylamino)sulfonylamino]cyclohexan-1-yloxy}-7-methoxyquinazoline, 4-[(3-chloro-4-fluorophenyl)amino]-6-{trans-4-[(morpholin-4-yl)carbonylamino]cyclohexan-1-yloxy}-7-methoxyquinazoline, 4-[(3-chloro-4-fluorophenyl)amino]-6-{trans-4-[(morpholin-4-yl)sulfonylamino]cyclohexan-1-yloxy}-7-methoxyquinazoline, 4-[(3-chloro-4-fluorophenyl)amino]-6-(tetrahydropyran-4-yloxy)-7-(2-acetylaminoethoxy)quinazoline, 4-[(3-chloro-4-fluorophenyl)amino]-6-(tetrahydropyran-4-yloxy)-7-(2-methanesulfonylaminoethoxy)quinazoline, 4-[(3-chloro-4-fluorophenyl)amino]-6-{1-[(piperidin-1-yl)carbonyl]piperidin-4-yloxy}-7-methoxyquinazoline, 4-[(3-chloro-4-fluorophenyl)amino]-6-(1-aminocarbonylmethylpiperidin-4-yloxy)-7-methoxyquinazoline, 4-[(3-chloro-4-fluorophenyl)amino]-6-(cis-4-{N-[(tetrahydropyran-4-yl)carbonyl]-N-methylamino}cyclohexan-1-yloxy)-7-methoxyquinazoline, 4-[(3-chloro-4-fluorophenyl)amino]-6-(cis-4-{N-[(morpholin-4-yl)carbonyl]-N-methylamino}cyclohexan-1-yloxy)-7-methoxyquinazoline, 4-[(3-chloro-4-fluorophenyl)amino]-6-(cis-4-{N-[(morpholin-4-yl)sulfonyl]-N-methylamino}cyclohexan-1-yloxy)-7-methoxy-quinazoline, 4-[(3-chloro-4-fluorophenyl)amino]-6-(trans-4-ethansulfonylaminocyclohexan-1-yloxy)-7-methoxyquinazoline, 4-[(3-chloro-4-fluorophenyl)amino]-6-(1-methanesulfonylpiperidin-4-yloxy)-7-ethoxyquinazoline, 4-[(3-chloro-4-fluorophenyl)amino]-6-(1-methanesulfonylpiperidin-4-yloxy)-7-(2-methoxyethoxy)quinazoline, 4-[(3-chloro-4-fluorophenyl)amino]-6-[1-(2-methoxyacetyl)piperidin-4-yloxy]-7-(2-methoxyethoxy)quinazoline, 4-[(3-chloro-4-fluorophenyl)amino]-6-(cis-4-acetylaminocyclohexan-1-yloxy)-7-methoxyquinazoline, 4-[(3-ethynylphenyl)amino]-6-[1-(tert-butyloxycarbonyl)piperidin-4-yloxy]-7-methoxyquinazoline, 4-[(3-ethynylphenyl)amino]-6-(tetrahydropyran-4-yloxy)-7-methoxyquinazoline, 4-[(3- chloro-4-fluorophenyl)amino]-6-(cis-4-{N-[(piperidin-1-yl)carbonyl]-N-methylamino}cyclohexan-1-yloxy)-7-methoxyquinazoline, 4-[(3-chloro-4-fluorophenyl)amino]-6-(cis-4-{N-[(4-methylpiperazin-1-yl)carbonyl]-N-methylamino}cyclohexan-1-yloxy)-7-methoxyquinazoline, 4-[(3-chloro-4-fluorophenyl)amino]-6-{cis-4-[(morpholin-4-yl)carbonylamino]cyclohexan-1-yloxy}-7-methoxyquinazoline, 4-[(3-chloro-4-fluorophenyl)amino]-6-{1-[2-(2-oxopyrrolidin-1-yl)ethyl]piperidin-4-yloxy}-7-methoxyquinazoline, 4-[(3-chloro-4-fluorophenyl)amino]-6-{1-[(morpholin-4-yl)carbonyl]piperidin-4-yloxy}-7-(2-methoxyethoxy)quinazoline, 4-[(3-ethynylphenyl)amino]-6-(1-acetylpiperidin-4-yloxy)-7-methoxyquinazoline, 4-[(3-ethynylphenyl)amino]-6-(1-methylpiperidin-4-yloxy)-7-methoxyquinazoline, 4-[(3-ethynylphenyl)amino]-6-(1-methanesulfonylpiperidin-4-yloxy)-7-methoxyquinazoline, 4-[(3-chloro-4-fluorophenyl)amino]-6-(1-methylpiperidin-4-yloxy)-7(2-methoxyethoxy)quinazoline, 4-[(3-chloro-4-fluorophenyl)amino]-6-(1-isopropyloxycarbonylpiperidin-4-yloxy)-7-methoxyquinazoline, 4-[(3-chloro-4-fluorophenyl)amino]-6-(cis-4-methylaminocyclohexan-1-yloxy)-7-methoxyquinazoline, 4-[(3-chloro-4-fluorophenyl)amino]-6-{cis-4-[N-(2-methoxyacetyl)-N-methylamino]cyclohexan-1-yloxy}-7-methoxyquinazoline, 4-[(3-ethynylphenyl)amino]-6-(piperidin-4-yloxy)-7-methoxyquinazoline, 4-[(3-ethynylphenyl)amino]-6-[1-(2-methoxyacetyl)piperidin-4-yloxy]-7-methoxyquinazoline, 4-[(3-ethynylphenyl)amino]-6-{1-[(morpholin-4-yl)carbonyl]piperidin-4-yloxy}-7-methoxyquinazoline, 4-[(3-chloro-4-fluorophenyl)amino]-6-{1-[(cis-2,6-dimethylmorpholin-4-yl)carbonyl]piperidin-4-yloxy}-7-methoxyquinazoline, 4-[(3-chloro-4-fluorophenyl)amino]-6-{1-[(2-methylmorpholin-4-yl)carbonyl]piperidin-4-yloxy}-7-methoxyquinazoline, 4-[(3-chloro-4-fluorophenyl)amino]-6-{1-[(S,S)-(2-oxa-5-azabicyclo[2,2,1]hept-5-yl)carbonyl]piperidin-4-yloxy}-7-methoxyquinazoline, 4-[(3-chloro-4-fluorophenyl)amino]-6-{1-[(N-methyl-N-2-methoxyethylamino)carbonyl]piperidin-4-yloxy}-7-methoxyquinazoline, 4-[(3-chloro-4-fluorophenyl)amino]-6-(1-ethylpiperidin-4-yloxy)-7-methoxyquinazoline, 4-[(3-chloro-4-fluorophenyl)amino]-6-{1-[(2-methoxyethyl)carbonyl]piperidin-4-yloxy}-7-methoxyquinazoline, 4-[(3-chloro-4-fluorophenyl)amino]-6-{1-[(3-methoxypropylamino)carbonyl]piperidin-4-yloxy}-7-methoxyquinazoline, 4-[(3-chloro-4-fluorophenyl)amino]-6-[cis-4-(N-methanesulfonyl-N-methylamino)cyclohexan-1-yloxy]-7-methoxyquinazoline, 4-[(3-chloro-4-fluorophenyl)amino]-6-[cis-4-(N-acetyl-N-methylamino)cyclohexan-1-yloxy]-7-methoxyquinazoline, 4-[(3-chloro-4-fluorophenyl)amino]-6-(trans-4-methylaminocyclohexan-1-yloxy)-7-methoxyquinazoline, 4-[(3-chloro-4-fluorophenyl)amino]-6-[trans-4-(N-methanesulfonyl-N-methylamino)cyclohexan-1-yloxy]-7-methoxyquinazoline, 4-[(3-chloro-4-fluorophenyl)amino]-6-(trans-4-dimethylaminocyclohexan-1-yloxy)-7-methoxyquinazoline, 4-[(3-chloro-4-fluorophenyl)amino]-6-(trans-4-{N-[(morpholin-4-yl)carbonyl]-N-methylamino}cyclohexan-1-yloxy)-7-methoxyquinazoline, 4-[(3-chloro-4-fluorophenyl)amino]-6-[2-(2,2-dimethyl-6-oxomorpholin-4-yl)ethoxy]-7-[(S)-(tetrahydrofuran-2-yl)methoxy]quinazoline, 4-[(3-chloro-4-fluorophenyl)amino]-6-(1-methanesulfonylpiperidin-4-yloxy)-7-methoxyquinazoline, 4-[(3-chloro-4-fluorophenyl)amino]-6-(1-cyanopiperidin-4-yloxy)-7-methoxyquinazoline, cetuximab, trastuzumab, ABX-EGF, and Mab ICR-62, optionally in the form of the racemates, enantiomers, or diastereomers thereof, optionally in the form of the pharmacologically acceptable acid addition salts thereof, the solvates, and/or hydrates thereof.

Preferred EGFR-inhibitors are selected from among 4-[(3-chloro-4-fluorophenyl)amino]-6-{[4-(morpholin-4-yl)-1-oxo-2-buten-1-yl]amino}-7-cyclopropylmethoxyquinazoline, 4-[(3-chloro-4-fluorophenyl)amino]-6-{[4-(N,N-diethylamino)-1-oxo-2-buten-1-yl]amino}-7-cyclopropylmethoxyquinazoline, 4-[(3-chloro-4-fluorophenyl)amino]-6-{[4-(N,N-dimethylamino)-1-oxo-2-buten-1-yl]amino}-7-cyclopropylmethoxyquinazoline, 4-[(R)-(1-phenylethyl)amino]-6-{[4-(morpholin-4-yl)-1-oxo-2-buten-1-yl]amino}-7-cyclopentyloxyquinazoline, 4-[(3-chloro-4-fluorophenyl)amino]-6-{[4-((R)-6-methyl-2-oxomorpholin-4-yl)-1-oxo-2-buten-1-yl]amino}-7-cyclopropylmethoxyquinazoline, 4-[(3-chloro-4-fluorophenyl)amino]-6-{[4-((R)-6-methyl-2-oxomorpholin-4-yl)-1-oxo-2-buten-1-yl]amino}-7-[(S)-(tetrahydrofuran-3-yl)oxy]quinazoline, 4-[(3-chloro-4-fluorophenyl)amino]-6-{[4-((R)-2-methoxymethyl-6-oxomorpholin-4-yl)-1-oxo-2-buten-1-yl]amino}-7-cyclopropylmethoxyquinazoline, 4-[(3-chloro-4-fluorophenyl)amino]-6-[2-((S)-6-methyl-2-oxomorpholin-4-yl)ethoxy]-7-methoxyquinazoline, 4-[(3-chloro-4-fluorophenyl)amino]-6-({4-[N-(2-methoxyethyl)-N-methylamino]-1-oxo-2-buten-1-yl}amino)-7-cyclopropylmethoxyquinazoline, 4-[(3-chloro-4-fluorophenyl)amino]-6-{[4-(N,N-dimethylamino)-1-oxo-2-buten-1-yl]amino}-7-cyclopentyloxyquinazoline, 4-[(R)-(1-phenylethyl)amino]-6-{[4-(N,N-bis-(2-methoxyethyl)amino)-1-oxo-2-buten-1-yl]amino}-7-cyclopropylmethoxyquinazoline, 4-[(R)-(1-phenylethyl)amino]-6-({4-[N-(2-methoxyethyl)-N-ethylamino]-1-oxo-2-buten-1-yl}amino)-7-cyclopropylmethoxyquinazoline, 4-[(R)-(1-phenylethyl)amino]-6-({4-[N-(2-methoxyethyl)-N-methylamino]-1-oxo-2-buten-1-yl}amino)-7-cyclopropylmethoxyquinazoline, 4-[(R)-(1-phenylethyl)amino]-6-({4-[N-(tetrahydropyran-4-yl)-N-methylamino]-1-oxo-2-buten-1-yl}amino)-7-cyclopropylmethoxyquinazoline, 4-[(3-chloro-4-fluorophenyl)amino]-6-{[4-(N,N-dimethylamino)-1-oxo-2-buten-1-yl]amino}-7-((R)-tetrahydrofuran-3-yloxy)quinazoline, 4-[(3-chloro-4-fluorophenyl)amino]-6-{[4-(N,N-dimethylamino)-1-oxo-2-buten-1-yl]amino}-7-((S)-tetrahydrofuran-3-yloxy)quinazoline, 4-[(3-chloro-4-fluorophenyl)amino]-6-({4-[N-(2-methoxyethyl)-N-methylamino]-1-oxo-2-buten-1-yl}amino)-7-cyclopentyloxyquinazoline, 4-[(3-chloro-4-fluorophenyl)amino]-6-{[4-(N-cyclopropyl-N-methylamino)-1-oxo-2-buten-1-yl]amino}-7-cyclopentyloxyquinazoline, 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]quinazoline, 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]quinazoline, 4-[(3-ethynylphenyl)amino]-6,7-bis-(2-methoxyethoxy)quinazoline, 4-[(3-chloro-4-fluorophenyl)amino]-7-[3-(morpholin-4-yl)propyloxy]-6-[(vinyl-carbonyl)amino]quinazoline, 4-[(R)-(1-phenylethyl)amino]-6-(4-hydroxyphenyl)-7H-pyrrolo[2,3-d]pyrimidine, 3-cyano-4-[(3-chloro-4-fluorophenyl)amino]-6-{[4-(N,N-dimethylamino)-1-oxo-2-buten-1-yl]amino}-7-ethoxyquinoline, 4-{[3-chloro-4-(3-fluorobenzyloxy)phenyl]amino}-6-(5-{[(2-methanesulfonylethyl)amino]methyl}furan-2-yl)quinazoline, 4-[(R)-(1-phenylethyl)amino]-6-{[4-((R)-6-methyl-2-oxomorpholin-4-yl)-1-oxo-2-buten-1-yl]amino}-7-methoxyquinazoline, 4-[(3-chloro-4-fluorophenyl)amino]-6-{[4-(morpholin-4-yl)-1-oxo-2-buten-1-yl]amino}-7-[(tetrahydrofuran-2-yl)methoxy]quinazoline, 4-[(3-chloro-4-fluorophenyl)amino]-6-({4-[N, N-bis-(2-methoxyethyl)amino]-1-oxo-2-buten-1-yl}amino)-7-[(tetrahydrofuran-2-yl)methoxy]quinazoline, 4-[(3-ethynylphenyl)amino]-6-{[4-(5,5-dimethyl-2-oxomorpholin-4-yl)-1-oxo-2-buten-1-yl]amino}quinazoline, 4-[(3-chloro-4-fluorophenyl)amino]-6-[2-(2,2-dimethyl-6-oxomorpholin-4-yl)ethoxy]-7-methoxyquinazoline, 4-[(3-chloro-4-fluorophenyl)amino]-6-[2-(2,2-dimethyl-6-oxomorpholin-4-yl)ethoxy]-7-[(R)-(tetrahydrofuran-2-yl)methoxy]quinazoline, 4-[(3-chloro-4-fluorophenyl)amino]-7-[2-(2,2-dimethyl-6-oxomorpholin-4-yl)ethoxy]-6-[(S)-(tetrahydrofuran-2-yl)methoxy]quinazoline, 4-[(3-chloro-4-fluorophenyl)amino]-6-{2-[4-(2-oxomorpholin-4-yl)piperidin-1-yl]ethoxy}-7-methoxyquinazoline, 4-[(3-chloro-4-fluorophenyl)amino]-6-[1-(tert-butyloxycarbonyl)piperidin-4-yloxy]-7-methoxyquinazoline, 4-[(3-chloro-4-fluorophenyl)amino]-6-(trans-4-aminocyclohexan-1-yloxy)-7-methoxyquinazoline, 4-[(3-chloro-4-fluorophenyl)amino]-6-(trans-4-methanesulfonylaminocyclohexan-1-yloxy)-7-methoxyquinazoline, 4-[(3-chloro-4-fluorophenyl)amino]-6-(tetrahydropyran-3-yloxy)-7-methoxyquinazoline, 4-[(3-chloro-4-fluorophenyl)amino]-6-(1-methylpiperidin-4-yloxy)-7-methoxyquinazoline, 4-[(3-chloro-4-fluorophenyl)amino]-6-{1-[(morpholin-4-yl)carbonyl]piperidin-4-yloxy}-7-methoxyquinazoline, 4-[(3-chloro-4-fluorophenyl)amino]-6-{1-[(methoxymethyl)carbonyl]piperidin-4-yloxy}-7-methoxyquinazoline, 4-[(3-chloro-4-fluorophenyl)amino]-6-(piperidin-3-yloxy)-7-methoxyquinazoline, 4-[(3-chloro-4-fluorophenyl)amino]-6-[1-(2-acetylaminoethyl)piperidin-4-yloxy]-7-methoxyquinazoline, 4-[(3-chloro-4-fluorophenyl)amino]-6-(tetrahydropyran-4-yloxy)-7-ethoxyquinazoline, 4-[(3-chloro-4-fluorophenyl)amino]-6-((S)-tetrahydrofuran-3-yloxy)-7-hydroxyquinazoline, 4-[(3-chloro-4-fluorophenyl)amino]-6-(tetrahydropyran-4-yloxy)-7-(2-methoxyethoxy)quinazoline, 4-[(3-chloro-4-fluorophenyl)amino]-6-{trans-4-[(dimethylamino)sulfonylamino]cyclohexan-1-yloxy}-7-methoxyquinazoline, 4-[(3-chloro-4-fluorophenyl)amino]-6-{trans-4-[(morpholin-4-yl)carbonylamino]cyclohexan-1-yloxy}-7-methoxyquinazoline, 4-[(3-chloro-4-fluorophenyl)amino]-6-{trans-4-[(morpholin-4-yl)sulfonylamino]cyclohexan-1-yloxy}-7-methoxyquinazoline, 4-[(3-chloro-4-fluorophenyl)amino]-6-(tetrahydropyran-4-yloxy)-7-(2-acetylaminoethoxy)quinazoline, 4-[(3-chloro-4-fluorophenyl)amino]-6-(tetrahydropyran-4-yloxy)-7-(2-methanesulfonylaminoethoxy)quinazoline, 4-[(3-chloro-4-fluorophenyl)amino]-6-{1-[(piperidin-1-yl)carbonyl]piperidin-4-yloxy}-7-methoxyquinazoline, 4-[(3-chloro-4-fluorophenyl)amino]-6-(1-aminocarbonylmethylpiperidin-4-yloxy)-7-methoxyquinazoline, 4-[(3-chloro-4-fluorophenyl)amino]-6-(cis-4-{N-[(tetrahydropyran-4-yl)carbonyl]-N-methylamino}cyclohexan-1-yloxy)-7-methoxyquinazoline, 4-[(3-chloro-4-fluorophenyl)amino]-6-(cis-4-{N-[(morpholin-4-yl)carbonyl]-N-methylamino}cyclohexan-1-yloxy)-7-methoxyquinazoline, 4-[(3-chloro-4-fluorophenyl)amino]-6-(cis-4-{N-[(morpholin-4-yl)sulfonyl]-N-methylamino}cyclohexan-1-yloxy)-7-methoxyquinazoline, 4-[(3-chloro-4-fluorophenyl)amino]-6-(trans-4-ethansulfonylaminocyclohexan-1-yloxy)-7-methoxyquinazoline, 4-[(3-chloro-4-fluorophenyl)amino]-6-(1-methanesulfonylpiperidin-4-yloxy)-7-ethoxyquinazoline, 4-[(3-chloro-4-fluorophenyl)amino]-6-(1-methanesulfonylpiperidin-4-yloxy)-7-(2-methoxyethoxy)quinazoline, 4-[(3-chloro-4-fluorophenyl)amino]-6-[1-(2-methoxyacetyl)piperidin-4-yloxy]-7-(2-methoxyethoxy)quinazoline, 4-[(3-chloro-4-fluorophenyl)amino]-6-(cis-4-acetylaminocyclohexan-1-yloxy)-7-methoxyquinazoline, 4-[(3-ethynylphenyl)amino]-6-[1-(tert-butyloxycarbonyl)piperidin-4-yloxy]-7-methoxyquinazoline, 4-[(3-ethynylphenyl)amino]-6-(tetrahydropyran-4-yloxy)-7-methoxyquinazoline, 4-[(3-chloro-4-fluorophenyl)amino]-6-(cis-4-{N-[(piperidin-1-yl)carbonyl]-N-methylamino}cyclohexan-1-yloxy)-7-methoxyquinazoline, 4-[(3-chloro-4-fluorophenyl)amino]-6-(cis-4-{N-[(4-methylpiperazin-1-yl)carbonyl]-N-methylamino}cyclohexan-1-yloxy)-7-methoxyquinazoline, 4-[(3-chloro-4-fluorophenyl)amino]-6-{cis-4-[(morpholin-4-yl)carbonylamino]cyclohexan-1-yloxy}-7-methoxyquinazoline, 4-[(3-chloro-4-fluorophenyl)amino]-6-{1-[2-(2-oxopyrrolidin-1-yl)ethyl]piperidin-4-yloxy}-7-methoxyquinazoline, 4-[(3-chloro-4-fluorophenyl)amino]-6-{1-[(morpholin-4-yl)carbonyl]piperidin-4-yloxy}-7-(2-methoxyethoxy)quinazoline, 4-[(3-ethynylphenyl)amino]-6-(1-acetylpiperidin-4-yloxy)-7-methoxyquinazoline, 4-[(3-ethynylphenyl)amino]-6-(1-methylpiperidin-4-yloxy)-7-methoxyquinazoline, 4-[(3-ethynylphenyl)amino]-6-(1-methanesulfonylpiperidin-4-yloxy)-7-methoxyquinazoline, 4-[(3-chloro-4-fluorophenyl)amino]-6-(1-methylpiperidin-4-yloxy)-7(2-methoxyethoxy)quinazoline, 4-[(3-chloro-4-fluorophenyl)amino]-6-(1-isopropyloxycarbonylpiperidin-4-yloxy)-7-methoxyquinazoline, 4-[(3-chloro-4-fluorophenyl)amino]-6-(cis-4-methylaminocyclohexan-1-yloxy)-7-methoxyquinazoline, 4-[(3-chloro-4-fluorophenyl)amino]-6-{cis-4-[N-(2-methoxyacetyl)-N-methylamino]cyclohexan-1-yloxy}-7-methoxyquinazoline, 4-[(3-ethynylphenyl)amino]-6-(piperidin-4-yloxy)-7-methoxyquinazoline, 4-[(3-ethynylphenyl)amino]-6-[1-(2-methoxyacetyl)piperidin-4-yloxy]-7-methoxyquinazoline, 4-[(3-ethynylphenyl)amino]-6-{1-[(morpholin-4-yl)carbonyl]piperidin-4-yloxy}-7-methoxyquinazoline, 4-[(3-chloro-4-fluorophenyl)amino]-6-{1-[(cis-2,6-dimethylmorpholin-4-yl)carbonyl]piperidin-4-yloxy}-7-methoxyquinazoline, 4-[(3-chloro-4-fluorophenyl)amino]-6-{1-[(2-methylmorpholin-4-yl)carbonyl]piperidin-4-yloxy}-7-methoxyquinazoline, 4-[(3-chloro-4-fluorophenyl)amino]-6-{1-[(S,S)-(2-oxa-5-azabicyclo[2,2,1]hept-5-yl)carbonyl]piperidin-4-yloxy}-7-methoxyquinazoline, 4-[(3-chloro-4-fluorophenyl)amino]-6-{1-[(N-methyl-N-2-methoxyethylamino)carbonyl]piperidin-4-yloxy}-7-methoxyquinazoline, 4-[(3-chloro-4-fluorophenyl)amino]-6-(1-ethylpiperidin-4-yloxy)-7-methoxyquinazoline, 4-[(3-chloro-4-fluorophenyl)amino]-6-{1-[(2-methoxyethyl)carbonyl]piperidin-4-yloxy}-7-methoxyquinazoline, 4-[(3-chloro-4-fluorophenyl)amino]-6-{1-[(3-methoxypropylamino)carbonyl]piperidin-4-yloxy}-7-methoxyquinazoline, 4-[(3-chloro-4-fluorophenyl)amino]-6-[cis-4-(N-methanesulfonyl-N-methylamino)cyclohexan-1-yloxy]-7-methoxyquinazoline, 4-[(3-chloro-4-fluorophenyl)amino]-6-[cis-4-(N-acetyl-N-methylamino)cyclohexan-1-yloxy]-7-methoxyquinazoline, 4-[(3-chloro-4-fluorophenyl)amino]-6-(trans-4-methylaminocyclohexan-1-yloxy)-7-methoxyquinazoline, 4-[(3-chloro-4-fluorophenyl)amino]-6-[trans-4-(N-methanesulfonyl-N-methylamino)cyclohexan-1-yloxy]-7-methoxyquinazoline, 4-[(3-chloro-4-fluorophenyl)amino]-6-(trans-4-dimethylaminocyclohexan-1-yloxy)-7-methoxyquinazoline, 4-[(3-chloro-4-fluorophenyl)amino]-6-(trans-4-{N-[(morpholin-4-yl)carbonyl]-N-methylamino}cyclohexan-1-yloxy)-7-methoxyquinazoline, 4-[(3-chloro-4-fluorophenyl)amino]-6-[2-(2,2-dimethyl-6-oxomorpholin-4-yl)ethoxy]-7-[(S)-(tetrahydrofuran-2-yl)methoxylquinazoline, 4-[(3-chloro-4-fluorophenyl)amino]-6-(1-methanesulfonylpiperidin-4-yloxy)-7-methoxyquinazoline, 4-[(3-chloro-4-fluorophenyl)

amino]-6-(1-cyanopiperidin-4-yloxy)-7-methoxyquinazoline, and cetuximab, optionally in the form of the racemates, enantiomers, or diastereomers thereof, optionally in the form of the pharmacologically acceptable acid addition salts thereof, the solvates, and/or hydrates thereof.

It is particularly preferable within the scope of the present invention to use those EGFR-inhibitors which are selected from among 4-[(3-chloro-4-fluorophenyl)amino]-6-{[4-(morpholin-4-yl)-1-oxo-2-buten-1-yl]amino}-7-cyclopropylmethoxyquinazoline, 4-[(R)-(1-phenylethyl)amino]-6-{[4-(morpholin-4-yl)-1-oxo-2-buten-1-yl]amino}-7-cyclopentyloxyquinazoline, 4-[(3-chloro-4-fluorophenyl)amino]-6-{[4-((R)-6-methyl-2-oxomorpholin-4-yl)-1-oxo-2-buten-1-yl]amino}-7-[(S)-(tetrahydrofuran-3-yl)oxy]quinazoline, 4-[(3-chloro-4-fluorophenyl)amino]-6-[2-((S)-6-methyl-2-oxomorpholin-4-yl)ethoxy]-7-methoxyquinazoline, 4-[(3-chloro-4-fluorophenyl)amino]-6-({4-[N-(2-methoxyethyl)-N-methylamino]-1-oxo-2-buten-1-yl}amino)-7-cyclopropylmethoxyquinazoline, 4-[(R)-(1-phenylethyl)amino]-6-({4-[N-(tetrahydropyran-4-yl)-N-methylamino]-1-oxo-2-buten-1-yl}amino)-7-cyclopropylmethoxyquinazoline, 4-[(3-chloro-4-fluorophenyl)amino]-6-({4-[N-(2-methoxyethyl)-N-methylamino]-1-oxo-2-buten-1-yl}amino)-7-cyclopentyloxyquinazoline, 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]quinazoline, 4-[(3-ethynylphenyl)amino]-6,7-bis-(2-methoxyethoxy)quinazoline, 4-[(R)-(1-phenylethyl)amino]-6-(4-hydroxyphenyl)-7H-pyrrolo[2,3-d]pyrimidine, 3-cyano-4-[(3-chloro-4-fluorophenyl)amino]-6-{[4-(N,N-dimethylamino)-1-oxo-2-buten-1-yl]amino}-7-ethoxyquinoline, 4-[(R)-(1-phenylethyl)amino]-6-{[4-((R)-6-methyl-2-oxomorpholin-4-yl)-1-oxo-2-buten-1-yl]amino}-7-methoxyquinazoline, 4-[(3-chloro-4-fluorophenyl)amino]-6-{[4-(morpholin-4-yl)-1-oxo-2-buten-1-yl]amino}-7-[(tetrahydrofuran-2-yl)methoxy]quinazoline, 4-[(3-ethynylphenyl)amino]-6-{[4-(5,5-dimethyl-2-oxomorpholin-4-yl)-1-oxo-2-buten-1-yl]amino}quinazoline, 4-[(3-chloro-4-fluorophenyl)amino]-6-{2-[4-(2-oxomorpholin-4-yl)piperidin-1-yl]ethoxy}-7-methoxyquinazoline, 4-[(3-chloro-4-fluorophenyl)amino]-6-(trans-4-aminocyclohexan-1-yloxy)-7-methoxyquinazoline, 4-[(3-chloro-4-fluorophenyl)amino]-6-(trans-4-methanesulfonylaminocyclohexan-1-yloxy)-7-methoxyquinazoline, 4-[(3-chloro-4-fluorophenyl)amino]-6-(tetrahydropyran-3-yloxy)-7-methoxyquinazoline, 4-[(3-chloro-4-fluorophenyl)amino]-6-{1-[(morpholin-4-yl)carbonyl]piperidin-4-yloxy}-7-methoxyquinazoline, 4-[(3-chloro-4-fluorophenyl)amino]-6-(piperidin-3-yloxy)-7-methoxyquinazoline, 4-[(3-chloro-4-fluorophenyl)amino]-6-[1-(2-acetylaminoethyl)piperidin-4-yloxy]-7-methoxyquinazoline, 4-[(3-chloro-4-fluorophenyl)amino]-6-(tetrahydropyran-4-yloxy)-7-ethoxyquinazoline, 4-[(3-chloro-4-fluorophenyl)amino]-6-{trans-4-[(morpholin-4-yl)carbonylamino]cyclohexan-1-yloxy}-7-methoxyquinazoline, 4-[(3-chloro-4-fluorophenyl)amino]-6-{1-[(piperidin-1-yl)carbonyl]piperidin-4-yloxy}-7-methoxyquinazoline, 4-[(3-chloro-4-fluorophenyl)amino]-6-(cis-4-{N-[(morpholin-4-yl)carbonyl]-N-methylamino}cyclohexan-1-yloxy)-7-methoxyquinazoline, 4-[(3-chloro-4-fluorophenyl)amino]-6-(trans-4-ethansulfonylaminocyclohexan-1-yloxy)-7-methoxyquinazoline, 4-[(3-chloro-4-fluorophenyl)amino]-6-(1-methanesulfonylpiperidin-4-yloxy)-7-(2-methoxyethoxy)quinazoline, 4-[(3-chloro-4-fluorophenyl)amino]-6-[1-(2-methoxyacetyl)piperidin-4-yloxy]-7-(2-methoxyethoxy)quinazoline, 4-[(3-ethynylphenyl)amino]-6-(tetrahydropyran-4-yloxy)-7-methoxyquinazoline, 4-[(3-chloro-4-fluorophenyl)amino]-6-(cis-4-{N-[(piperidin-1-yl)carbonyl]-N-methylamino}cyclohexan-1-yloxy)-7-methoxyquinazoline, 4-[(3-chloro-4-fluorophenyl)amino]-6-{cis-4-[(morpholin-4-yl)carbonylamino]cyclohexan-1-yloxy}-7-methoxyquinazoline, 4-[(3-chloro-4-fluorophenyl)amino]-6-{1-[2-(2-oxopyrrolidin-1-yl)ethyl]piperidin-4-yloxy}-7-methoxyquinazoline, 4-[(3-ethynylphenyl)amino]-6-(1-acetylpiperidin-4-yloxy)-7-methoxyquinazoline, 4-[(3-ethynylphenyl)amino]-6-(1-methylpiperidin-4-yloxy)-7-methoxyquinazoline, 4-[(3-ethynylphenyl)amino]-6-(1-methanesulfonylpiperidin-4-yloxy)-7-methoxyquinazoline, 4-[(3-chloro-4-fluorophenyl)amino]-6-(1-methylpiperidin-4-yloxy)-7-(2-methoxyethoxy)quinazoline, 4-[(3-ethynylphenyl)amino]-6-{1-[(morpholin-4-yl)carbonyl]piperidin-4-yloxy}-7-methoxyquinazoline, 4-[(3-chloro-4-fluorophenyl)amino]-6-{1-[(N-methyl-N-2-methoxyethylamino)carbonyl]piperidin-4-yloxy}-7-methoxyquinazoline, 4-[(3-chloro-4-fluorophenyl)amino]-6-(1-ethylpiperidin-4-yloxy)-7-methoxyquinazoline, 4-[(3-chloro-4-fluorophenyl)amino]-6-[cis-4-(N-methanesulfonyl-N-methylamino)cyclohexan-1-yloxy]-7-methoxyquinazoline, 4-[(3-chloro-4-fluorophenyl)amino]-6-[cis-4-(N-acetyl-N-methylamino)cyclohexan-1-yloxy]-7-methoxyquinazoline, 4-[(3-chloro-4-fluorophenyl)amino]-6-(trans-4-methylaminocyclohexan-1-yloxy)-7-methoxyquinazoline, 4-[(3-chloro-4-fluorophenyl)amino]-6-[trans-4-(N-methanesulfonyl-N-methylamino)cyclohexan-1-yloxy]-7-methoxyquinazoline, 4-[(3-chloro-4-fluorophenyl)amino]-6-(trans-4-dimethylaminocyclohexan-1-yloxy)-7-methoxyquinazoline, 4-[(3-chloro-4-fluorophenyl)amino]-6-(trans-4-{N-[(morpholin-4-yl)carbonyl]-N-methylamino}cyclohexan-1-yloxy)-7-methoxyquinazoline, 4-[(3-chloro-4-fluorophenyl)amino]-6-[2-(2,2-dimethyl-6-oxomorpholin-4-yl)ethoxy]-7-[(S)-(tetrahydrofuran-2-yl)methoxy]quinazoline, 4-[(3-chloro-4-fluorophenyl)amino]-6-(1-methanesulfonylpiperidin-4-yloxy)-7-methoxyquinazoline, 4-[(3-chloro-4-fluorophenyl)amino]-6-(1-cyanopiperidin-4-yloxy)-7-methoxyquinazoline, and 4-[(3-chloro-4-fluorophenyl)amino]-6-{1-[(2-methoxyethyl)carbonyl]piperidin-4-yloxy}-7-methoxyquinazoline, optionally in the form of the racemates, enantiomers, or diastereomers thereof, optionally in the form of the pharmacologically acceptable acid addition salts thereof, the solvates, and/or hydrates thereof.

Particularly preferred EGFR-inhibitors according to the invention are the compounds selected from among 4-[(3-chloro-4-fluorophenyl)amino]-6-{[4-(morpholin-4-yl)-1-oxo-2-buten-1-yl]-amino}-7-cyclopropylmethoxyquinazoline, 4-[(3-chloro-4-fluorophenyl)amino]-6-{[4-((R)-6-methyl-2-oxomorpholin-4-yl)-1-oxo-2-buten-1-yl]amino}-7-[(S)-(tetrahydrofuran-3-yl)oxy]quinazoline, 4-[(3-chloro-4-fluorophenyl)amino]-6-[2-((S)-6-methyl-2-oxomorpholin-4-yl)ethoxy]-7-methoxyquinazoline, 4-[(3-chloro-4-fluorophenyl)amino]-6-({4-[N-(2-methoxyethyl)-N-methylamino]-1-oxo-2-buten-1-yl}amino)-7-cyclopropylmethoxyquinazoline, 4-[(3-ethynylphenyl)amino]-6,7-bis-(2-methoxyethoxy)quinazoline, 4-[(3-chloro-4-fluorophenyl)amino]-6-{[4-(morpholin-4-yl)-1-oxo-2-buten-1-yl]amino}-7-[(tetrahydrofuran-2-yl)methoxy]quinazoline, 4-[(3-ethynylphenyl)amino]-6-{[4-(5,5-dimethyl-2-oxomorpholin-4-yl)-1-oxo-2-buten-1-yl]amino}quinazoline, 4-[(3-chloro-4-fluorophenyl)amino]-6-(trans-4-methanesulfonylaminocyclohexan-1-yloxy)-7-methoxyquinazoline, 4-[(3-chloro-4-fluorophenyl)amino]-6-(tetrahydropyran-3-yloxy)-7-methoxyquinazoline, 4-[(3- chloro-4-fluorophenyl)amino]-6-{1-[(morpholin-4-yl) carbonyl]piperidin-4-yloxy}-7-methoxyquinazoline, 4-[(3-chloro-4-fluorophenyl)amino]-6-{1-[2-(2-oxopyrrolidin-1-yl)ethyl]piperidin-4-yloxy}-7-methoxyquinazoline, 4-[(3-ethynylphenyl)amino]-6-(1-acetylpiperidin-4-yloxy)-7-methoxyquinazoline, 4-[(3-ethynylphenyl)amino]-6-(1-methylpiperidin-4-yloxy)-7-methoxyquinazoline, 4-[(3-ethynylphenyl)amino]-6-(1-methanesulfonylpiperidin-4-yloxy)-7-methoxyquinazoline, 4-[(3-ethynylphenyl)amino]-6-{1-[(morpholin-4-yl)carbonyl]piperidin-4-yloxy}-7-methoxyquinazoline, 4-[(3-chloro-4-fluorophenyl)amino]-6-{1-[(2-methoxyethyl)carbonyl]piperidin-4-yloxy}-7-methoxyquinazoline, 4-[(3-chloro-4-fluorophenyl)amino]-6-[cis-4-(N-methanesulfonyl-N-methylamino)cyclohexan-1-yloxy]-7-methoxyquinazoline, 4-[(3-chloro-4-fluorophenyl)amino]-6-[cis-4-(N-acetyl-N-methylamino) cyclohexan-1-yloxy]-7-methoxyquinazoline, 4-[(3-chloro-4-fluorophenyl)amino]-6-(trans-4-methylaminocyclohexan-1-yloxy)-7-methoxyquinazoline, 4-[(3-chloro-4-fluorophenyl)amino]-6-[trans-4-(N-methanesulfonyl-N-methylamino)cyclohexan-1-yloxy]-7-methoxyquinazoline, 4-[(3-chloro-4-fluorophenyl)amino]-6-(trans-4-dimethylaminocyclohexan-1-yloxy)-7-methoxyquinazoline, 4-[(3-chloro-4-fluorophenyl)amino]-6-(trans-4-{N-[(morpholin-4-yl)carbonyl]-N-methylamino}cyclohexan-1-yloxy)-7-methoxyquinazoline, 4-[(3-chloro-4-fluorophenyl)amino]-6-[2-(2,2-dimethyl-6-oxomorpholin-4-yl)ethoxy]-7-[(S)-(tetrahydrofuran-2-yl)methoxyl]quinazoline, 4-[(3-chloro-4-fluorophenyl)amino]-6-(1-methanesulfonylpiperidin-4-yloxy)-7-methoxyquinazoline, and 4-[(3-chloro-4-fluorophenyl)amino]-6-(1-cyanopiperidin-4-yloxy)-7-methoxyquinazoline, optionally in the form of the racemates, enantiomers, or diastereomers thereof, optionally in the form of the pharmacologically acceptable acid addition salts thereof, the solvates, and/or hydrates thereof.

By acid addition salts with pharmacologically acceptable acids which the EGFR-inhibitors may be capable of forming are meant, for example, salts selected from among the hydrochloride, hydrobromide, hydroiodide, hydrosulfate, hydrophosphate, hydromethanesulfonate, hydronitrate, hydromaleate, hydroacetate, hydrobenzoate, hydrocitrate, hydrofumarate, hydrotartrate, hydrooxalate, hydrosuccinate, hydrobenzoate, and hydro-p-toluenesulfonate, preferably hydrochloride, hydrobromide, hydrosulfate, hydrophosphate, hydrofumarate, and hydromethanesulfonate.

Examples of dopamine agonists which may be used preferably include compounds selected from among bromocriptine, cabergoline, alpha-dihydroergocryptine, lisuride, pergolide, pramipexole, roxindole, ropinirole, talipexole, terguride, and viozan. Any reference to the abovementioned dopamine agonists within the scope of the present invention includes a reference to any pharmacologically acceptable acid addition salts and optionally hydrates thereof which may exist. By the physiologically acceptable acid addition salts which may be formed by the abovementioned dopamine agonists are meant, for example, pharmaceutically acceptable salts which are selected from the salts of hydrochloric acid, hydrobromic acid, sulfuric acid, phosphoric acid, methanesulfonic acid, acetic acid, fumaric acid, succinic acid, lactic acid, citric acid, tartaric acid, and maleic acid.

Examples of H1-antihistamines preferably include compounds selected from among epinastine, cetirizine, azelastine, fexofenadine, levocabastine, loratadine, mizolastine, ketotifen, emedastine, dimethindene, clemastine, bamipine, dexchlorpheniramine, pheniramine, doxylamine, chlorphenoxamine, dimenhydrinate, diphenhydramine, promethazine, ebastine, desloratidine, and meclizine. Any reference to the abovementioned H1-antihistamines within the scope of the present invention includes a reference to any pharmacologically acceptable acid addition salts which may exist.

Examples of PAF-antagonists preferably include compounds selected from 4-(2-chlorophenyl)-9-methyl-2-[3 (4-morpholinyl)-3-propanon-1-yl]-6H-thieno-[3,2-f]-[1,2,4]triazolo[4,3-a][1,4]diazepines, and 6-(2-chlorophenyl)-8,9-dihydro-1-methyl-8-[(4-morpholinyl)carbonyl]-4H,7H-cyclopenta-[4,5]thieno-[3,2-f][1,2,4]triazolo[4,3-a][1,4] diazepines.

MRP4-inhibitors used are preferably compounds selected from among N-acetyldinitrophenylcysteine, cGMP, cholate, diclofenac, dehydroepiandrosterone 3-glucuronide, dehydroepiandrosterone 3-sulfate, dilazep, dinitrophenyl-S-glutathione, estradiol 17-β-glucuronide, estradiol 3,17-disulfate, estradiol 3-glucuronide, estradiol 3-sulfate, estrone 3-sulfate, flurbiprofen, folate, $N^5$-formyltetrahydrofolate, glycocholate, clycolithocholic acid sulfate, ibuprofen, indomethacin, indoprofen, ketoprofen, lithocholic acid sulfate, methotrexate, MK571 ((E)-3-[[[3-[2-(7-chloro-2-quinolinyl)ethenyl] phenyl]-[[3-dimethylamino)-3-oxopropyl]thio]methyl]thio] propanoic acid), α-naphthyl-β-D-glucuronide, nitrobenzyl mercaptopurine riboside, probenecid, PSC833, sildenafil, sulfinpyrazone, taurochenodeoxycholate, taurocholate, taurodeoxycholate, taurolithocholate, taurolithocholic acid sulfate, topotecan, trequinsin, and zaprinast, dipyridamole, optionally in the form of the racemates, enantiomers, diastereomers, and the pharmacologically acceptable acid addition salts and hydrates thereof.

Preferably the invention relates to the use of MRP4-inhibitors for preparing a pharmaceutical composition for the treatment of respiratory complaints, containing the PDE4B-inhibitors and MRP4-inhibitors, the MRP4-inhibitors preferably being selected from among N-acetyldinitrophenylcysteine, dehydroepiandrosterone 3-sulfate, dilazep, dinitrophenyl-S-glutathione, estradiol 3,17-disulfate, flurbiprofen, glycocholate, glycolithocholic acid sulfate, ibuprofen, indomethacin, indoprofen, lithocholic acid sulfate, MK571, PSC833, sildenafil, taurochenodeoxycholate, taurocholate, taurolithocholate, taurolithocholic acid sulfate, trequinsin, and zaprinast, dipyridamole, optionally in the form of the racemates, enantiomers, diastereomers, and the pharmacologically acceptable acid addition salts and hydrates thereof.

The invention relates more preferably to the use of MRP4-inhibitors for preparing a pharmaceutical composition for treating respiratory complaints, containing the PDE4B-inhibitors and MRP4-inhibitors according to the invention, the MRP4-inhibitors preferably being selected from among dehydroepiandrosterone 3-sulfate, estradiol 3,17-disulfate, flurbiprofen, indomethacin, indoprofen, MK571, taurocholate, optionally in the form of the racemates, enantiomers, diastereomers, and the pharmacologically acceptable acid addition salts and hydrates thereof. The separation of enantiomers from the racemates can be carried out using methods known from the art (e.g., chromatography on chiral phases, etc.).

By acid addition salts with pharmacologically acceptable acids are meant, for example, salts selected from among the hydrochlorides, hydrobromides, hydroiodides, hydrosulfates, hydrophosphates, hydromethanesulfonates, hydronitrates, hydromaleates, hydroacetates, hydrobenzoates, hydrocitrates, hydrofumarates, hydrotartrates, hydrooxalates, hydrosuccinates, hydrobenzoates, and hydro-p-toluenesulfonates, preferably the hydrochlorides, hydrobromides, hydrosulfates, hydrophosphates, hydrofumarates, and hydromethanesulfonates.

The invention further relates to pharmaceutical preparations which contain a triple combination of the PDE4B-inhibitors, MRP4-inhibitors, and another active substance according to the invention, such as, for example, an anticholinergic, a steroid, an LTD4-antagonist, or a betamimetic, and the preparation thereof, and the use thereof for treating respiratory complaints.

Formulations

Suitable forms for administration are, for example, tablets, capsules, solutions, syrups, emulsions, or inhalable powders or aerosols. The content of the pharmaceutically effective compound(s) in each case should be in the range from 0.1 to 90 wt. %, preferably 0.5 to 50 wt. % of the total composition, i.e., in amounts which are sufficient to achieve the dosage range specified hereinafter.

The preparations may be administered orally in the form of a tablet, as a powder, as a powder in a capsule (e.g., a hard gelatine capsule), as a solution or suspension. When administered by inhalation the active substance combination may be given as a powder, as an aqueous or aqueous-ethanolic solution or using a propellant gas formulation.

Preferably, therefore, pharmaceutical formulations are characterized by the content of one or more compounds of formula 1 according to the preferred embodiments above.

It is particularly preferable if the compounds of formula 1 are administered orally, and it is also particularly preferable if they are administered once or twice a day. Suitable tablets may be obtained, for example, by mixing the active substance(s) with known excipients, for example, inert diluents such as calcium carbonate, calcium phosphate, or lactose, disintegrants such as corn starch or alginic acid, binders such as starch or gelatine, lubricants such as magnesium stearate or talc, and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example, collidone or shellac, gum arabic, talc, titanium dioxide, or sugar. To achieve delayed release or prevent incompatibilities the core may also consist of a number of layers. Similarly the tablet coating may consist of a number of layers to achieve delayed release, possibly using the excipients mentioned above for the tablets.

Syrups containing the active substances or combinations thereof according to the invention may additionally contain a sweetener such as saccharine, cyclamate, glycerol, or sugar, and a flavor enhancer, e.g., a flavoring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Capsules containing one or more active substances or combinations of active substances may, for example, be prepared by mixing the active substances with inert carriers such as lactose or sorbitol and packing them into gelatine capsules.

Suitable suppositories may be made, for example, by mixing with carriers provided for this purpose, such as neutral fats or polyethyleneglycol or the derivatives thereof.

Excipients which may be used include, for example, water, pharmaceutically acceptable organic solvents such as paraffins (e.g., petroleum fractions), vegetable oils (e.g., groundnut or sesame oil), mono- or polyfunctional alcohols (e.g., ethanol or glycerol), carriers such as, e.g., natural mineral powders (e.g., kaolins, clays, talc, chalk), synthetic mineral powders (e.g., highly dispersed silicic acid and silicates), sugars (e.g., cane sugar, lactose, and glucose), emulsifiers (e.g., lignin, spent sulfite liquors, methylcellulose, starch, and polyvinylpyrrolidone), and lubricants (e.g., magnesium stearate, talc, stearic acid, and sodium lauryl sulfate).

For oral administration the tablets may, of course, contain, apart from the abovementioned carriers, additives such as sodium citrate, calcium carbonate, and dicalcium phosphate together with various additives such as starch, preferably potato starch, gelatine, and the like. Moreover, lubricants such as magnesium stearate, sodium lauryl sulfate, and talc may be used at the same time for the tabletting process. In the case of aqueous suspensions the active substances may be combined with various flavor enhancers or colorings in addition to the excipients mentioned above.

It is also preferred if the compounds of formula 1 are administered by inhalation, particularly preferably if they are administered once or twice a day. For this purpose, the compounds of formula 1 have to be made available in forms suitable for inhalation. Inhalable preparations include inhalable powders, propellant-containing metered-dose aerosols or propellant-free inhalable solutions, which are optionally present in admixture with conventional physiologically acceptable excipients.

Within the scope of the present invention, the term propellant-free inhalable solutions also includes concentrates or sterile ready-to-use inhalable solutions. The preparations which may be used according to the invention are described in more detail in the next part of the specification.

Inhalable Powders

If the active substances of formula 1 are present in admixture with physiologically acceptable excipients, the following physiologically acceptable excipients may be used to prepare the inhalable powders according to the invention: monosaccharides (e.g., glucose or arabinose), disaccharides (e.g., lactose, saccharose, maltose), oligo- and polysaccharides (e.g., dextran), polyalcohols (e.g., sorbitol, mannitol, xylitol), salts (e.g., sodium chloride, calcium carbonate) or mixtures of these excipients with one another. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred. Methods of preparing the inhalable powders according to the invention by grinding and micronizing and by finally mixing the components together are known from the prior art.

Propellant-containing Inhalable Aerosols

The propellant-containing inhalable aerosols which may be used according to the invention may contain 1 dissolved in the propellant gas or in dispersed form. The propellant gases which may be used to prepare the inhalation aerosols according to the invention are known from the prior art. Suitable propellant gases are selected from among hydrocarbons such as n-propane, n-butane, or isobutane, and halohydrocarbons such as preferably fluorinated derivatives of methane, ethane, propane, butane, cyclopropane, or cyclobutane. The propellant gases mentioned above may be used on their own or in mixtures thereof. Particularly preferred propellant gases are fluorinated alkane derivatives selected from TG134a (1,1,1,2-tetrafluoroethane), TG227 (1,1,1,2,3,3,3-heptafluoropropane), and mixtures thereof. The propellant-driven inhalation aerosols used within the scope of the use according to the invention may also contain other ingredients such as co-solvents, stabilizers, surfactants, antioxidants, lubricants, and pH adjusters. All these ingredients are known in the art.

Propellant-free Inhalable Solutions

The compounds of formula 1 according to the invention are preferably used to prepare propellant-free inhalable solutions and inhalable suspensions. Solvents used for this purpose include aqueous or alcoholic, preferably ethanolic solutions. The solvent may be water on its own or a mixture of water and ethanol. The solutions or suspensions are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulfuric acid, and/or phosphoric acid. Examples of particularly suitable organic acids include ascorbic acid, citric acid, malic acid, tartaric acid, maleic acid, succinic acid, fumaric acid, acetic acid, formic acid, and/or propionic acid, etc. Preferred inorganic acids are hydrochloric and sulfuric acids. It is also possible to use the acids which have already formed an acid addition salt with one of the active substances. Of the organic acids, ascorbic acid, fumaric acid, and citric acid are preferred. If desired, mixtures of the above acids may also be used, particularly in the case of acids which have other properties in addition to their acidifying qualities, e.g., as flavorings, antioxidants, or complexing agents, such as citric acid or ascorbic acid, for example. According to the invention, it is particularly preferred to use hydrochloric acid to adjust the pH.

Co-solvents and/or other excipients may be added to the propellant-free inhalable solutions used for the purpose according to the invention. Preferred co-solvents are those which contain hydroxyl groups or other polar groups, e.g., alcohols—particularly isopropyl alcohol, glycols—particularly propyleneglycol, polyethyleneglycol, polypropylene glycol, glycol ether, glycerol, polyoxyethylene alcohols, and polyoxyethylene fatty acid esters. The terms excipients and additives in this context denote any pharmacologically acceptable substance which is not an active substance but which can be formulated with the active substance or substances in the pharmacologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilizers, complexing agents, antioxidants, and/or preservatives which guarantee or prolong the shelf life of the finished pharmaceutical formulation, flavorings, vitamins, and/or other additives known in the art. The additives also include pharmacologically acceptable salts such as sodium chloride as isotonic agents. The preferred excipients include antioxidants such as ascorbic acid, for example, provided that it has not already been used to adjust the pH, vitamin A, vitamin E, tocopherols, and similar vitamins or provitamins occurring in the human body. Preservatives may be used to protect the formulation from contamination with pathogens. Suitable preservatives are those which are known in the art, particularly cetyl pyridinium chloride, benzalkonium chloride, or benzoic acid or benzoates such as sodium benzoate in the concentration known from the prior art.

For the treatment forms described above, ready-to-use packs of a medicament for the treatment of respiratory complaints are provided, containing an enclosed description including, for example, the words respiratory disease, COPD, or asthma, a pteridine and one or more combination partners selected from those described above.

We claim:

1. A compound of formula 1

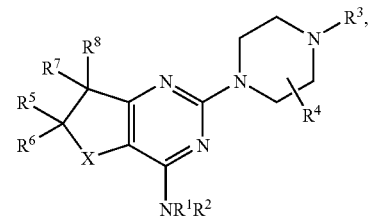

wherein:
X is O, S, SO, or $SO_2$;

$R^1$ is H, $C_{1-6}$-alkyl, $C_{2-6}$-alkenyl, $C_{2-6}$-alkynyl, $C_{6-10}$-aryl, $C_{6-10}$-aryl-$C_{1-6}$-alkylene, or $C_{5-10}$-heteroaryl-$C_{1-6}$-alkylene, $R^2$ is H or $C_{1-6}$-alkyl optionally substituted by one or more groups selected from $C_{1-6}$-haloalkyl, CN, $OR^{2.1}$, $NR^{2.1}R^{2.2}$, $COOR^{2.1}$, $CONR^{2.1}R^{2.2}$, $C_{3-7}$-cycloalkyl optionally substituted by $C_{1-4}$-alkyl or oxo, an aromatic or non-aromatic heterocycle optionally substituted by $C_{1-4}$-alkyl, oxo, OH, or halogen, $C_{6-10}$-aryl optionally substituted by $C_{1-4}$-alkyl or oxo, and $C_{6-10}$-aryl fused to a $C_{5-6}$ heterocycle, wherein this fused ring system is optionally substituted by $C_{1-4}$-alkyl or oxo, wherein:

$R^{2.1}$ is H or $C_{1-6}$-alkyl optionally substituted by a $C_{3-7}$-cycloalkyl, $C_{3-10}$ heterocycle, or $C_{6-10}$-aryl, each optionally substituted as defined above and $R^{2.2}$ is H or $C_{1-6}$-alkyl; or $R^2$ is an optionally mono- or poly-bridged $C_{3-10}$-cycloalkyl or a $C_{3-10}$-cycloalkyl, each optionally fused to a $C_{6-10}$-aryl ring optionally substituted by one or more groups selected from $C_{1-6}$-alkyl, OH, $CH_2OR^{2.3}$, $COOR^{2.3}$, $COR^{2.3}$, $CONR^{2.3}R^{2.4}$, O—$C_{1-6}$-alkyl, O—$C_{7-11}$-aralkyl, $NR^{2.3}R^{2.4}$, and $NHCOR^{2.5}$, wherein:

$R^{2.3}$ is H or a heterocycle or a $C_{1-6}$-alkyl, optionally substituted by a group selected from $C_{3-7}$-cycloalkyl, $C_{3-10}$ heterocycle, and $C_{6-10}$-aryl, wherein this group is optionally substituted by one or more groups selected from $C_{1-6}$-alkyl, halogen, OH, and O—$C_{1-6}$-alkyl, $R^{2.4}$ is H or $C_{1-6}$-alkyl, $R^{2.5}$ is selected from the group consisting of $C_{3-7}$-cycloalkyl, a $C_{3-10}$ heterocycle, and $C_{1-6}$-alkyl optionally substituted by OH; or $R^2$ is a group of formula 1a

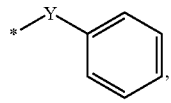, wherein:

Y is $C_{1-6}$-alkylene optionally substituted by one or two $R^{2.7}$, wherein $R^{2.7}$ are independently $C_{1-6}$-alkyl, COOH, $CONH_2OR^{2.1}$, or $COOR^{2.1}$, or $R^{2.7}$ together with one or two carbon atoms of Y forms a carbocyclic ring with 3 carbon atoms, or $R^2$ is $C_{6-10}$-aryl optionally independently substituted by one or more groups selected from $C_{1-6}$-alkyl, $C_{1-6}$-haloalkyl, $C_{2-6}$-alkenyl, $C_{2-6}$-alkynyl, CN, halogen, $OR^{2.8}$, $COOR^{2.8}$, $COR^{2.10}$, NHCOMe, $CONR^{2.3}R^{2.4}$, a $C_{1-4}$ alkylene group substituted by $NR^{2.1}R^{2.2}$, or $NR^{2.1}R^{2.2}$, or $R^2$ is $C_{6-10}$-aryl optionally independently substituted by one or more groups selected from $C_{6-10}$-aryl-$C_{1-6}$-alkylene, $C_{5-10}$-heteroaryl-$C_{1-6}$-alkylene, $C_{3-7}$-cycloalkyl, a $C_{3-7}$-cycloalkyl-$C_{1-4}$-alkylene, $C_{6-10}$-aryl, and a $C_{3-10}$ heterocycle, wherein these groups are each optionally substituted by one or more groups selected from $C_{1-6}$-alkyl, $C_{1-6}$-haloalkyl, $COOR^{2.8}$, CN, halogen, $OR^{2.8}$, $NHCOR^{2.8}$, oxo, a $C_{3-10}$ heterocycle, a $C_{3-7}$-cycloalkyl-$C_{1-4}$ alkylene, a $C_{5-10}$ heterocycle-$C_{1-4}$-alkylene, and a $NR^{2.1}R^{2.2}$—$C_{1-4}$ alkylene, wherein:

$R^{2.8}$ is H, $C_{1-6}$-alkyl, $C_{6-10}$-aryl, or a $NR^{2.1}R^{2.2}$—$C_{1-4}$ alkylene group, and $R^{2.10}$ is $NHR^{2.10.1}$ or a $C_{3-10}$ heterocycle optionally substituted by $C_{1-4}$-alkyl, wherein $R^{2.10.1}$ is H, $C_{3-7}$-cycloalkyl, $C_{2-6}$-alkenyl, $C_{2-6}$-alkynyl, $C_{1-6}$-alkyl, or $C_{1-6}$-alkyl-O—$C_{1-4}$-alkyl, or $R^2$ is $C_{6-10}$-aryl to which an aromatic or non-aromatic $C_{3-10}$ heterocycle is fused, or $R^2$ is an aromatic or non-aromatic $C_{3-10}$ heterocycle optionally substituted by one or more groups selected from halogen, OH, oxo, CN, $C_{1-6}$-alkyl, $C_{1-6}$-alkanol, $C_{6-10}$-aryl-$C_{1-6}$-alkylene, $C_{5-10}$-heteroaryl-$C_{1-6}$-alkylene, $COR^{2.11}$, $C_{3-7}$-cycloalkyl-$C_{1-4}$-alkylene, and $C_{3-10}$ heterocycle-$C_{1-4}$-alkylene, wherein $R^{2.11}$ is a group selected from $C_{3-10}$ heterocycle-$C_{1-4}$-alkylene, $C_{3-7}$-cycloalkyl, and a $C_{3-10}$ heterocycle, optionally substituted by $C_{1-6}$-alkyl optionally substituted by OH, $CH_2OH$, OMe, $NH_2$, a $C_{3-10}$ heterocycle, or $NHCOO$-$^tBu$, or $R^2$ is $C_{2-6}$-alkenyl or a bicyclic ring, each optionally substituted by methyl, or $NR^1R^2$ together is a heterocycle optionally substituted by one or more groups selected from $C_{1-4}$-alkyl, $C_{2-6}$-alkenyl, $C_{2-6}$-alkynyl, OH, straight-chain or branched $C_{1-6}$-alkanol, and oxo;

$R^3$ is a group selected from a $C_{3-10}$ heterocycle, a $C_{3-7}$-cycloalkyl, a bicyclic, fused aromatic or non-aromatic ring system, which optionally contains 1 to 4 heteroatoms selected from S, N, O, or it is $C_{6-10}$-aryl-$C_{1-6}$-alkylene, $C_{5-10}$-heteroaryl-$C_{1-6}$-alkylene, and $CH_2$-benzo[1,3]dioxolyl, optionally substituted by one or more groups selected from OH, halogen, $C_{1-6}$-alkyl, O—$C_{1-6}$-alkyl, $C_{1-6}$-haloalkyl, and CO—$R^{3.1}$, or $R^3$ is phenyl optionally substituted by one or more groups selected from $C_{1-6}$-alkyl, $C_{2-6}$-alkenyl, $C_{2-6}$-alkynyl, $C_{1-4}$-haloalkyl, $C_{1-6}$-alkylene-$NR^{3.1}R^{3.2}$, CN, $COOR^{3.1}$, $CONR^{3.1}R^{3.2}$, $NR^{3.1}R^{3.2}$, $NHCOR^{3.1}$, $CF_3$, $OR^{3.1}$, halogen, $NHCOR^{3.1}$, $NO_2$, $SO_2NR^{3.1}R^{3.2}$, and $C_{1-6}$-alkylene-$NHCOR^{3.1}$, wherein:

$R^{3.1}$ is H, $C_{1-6}$-alkyl; $C_{2-6}$-alkenyl, or $C_{2-6}$-alkynyl, optionally bridged, mono- or bicyclic $C_{3-10}$ heterocycle, or $C_{3-10}$ heterocycle-$C_{1-4}$-alkylene group, and $R^{3.2}$ is H, $C_{1-6}$-alkyl, $C_{2-6}$-alkenyl, or $C_{2-6}$-alkynyl, or $R^3$ is a group of formula 1b

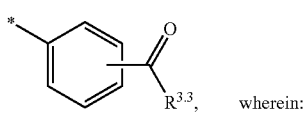

wherein:

$R^{3.3}$ is a $C_{3-10}$ heterocycle optionally substituted by one or more groups selected from $C_{1-6}$-alkyl, oxo, $COR^{3.3.1}$, $COR^{3.3.2}$, $C_{1-6}$-alkylene-$R^{3.3.2}$, $CH_2CO$-pyrrolidine, and a $C_{3-10}$ heterocycle, wherein a sulfur atom optionally contained in the heterocycle ring is optionally in the form of the oxide or dioxide, wherein: $R^{3.3.1}$ is $C_{1-6}$-alkyl, and $R^{3.3.2}$ is $NH_2$, $NH(C_{1-6}$-alkyl), or $N(C_{1-6}$-alkyl)$_2$, or $R^{3.3}$ is a bicyclic ring or heterocycle spiro ring, or $R^3$ is a group of formula 1c

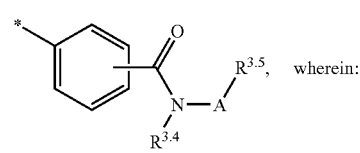

wherein:

A is a bond or $C_{1-6}$-alkyl optionally substituted by oxo or $NMe_2$;

$R^{3.4}$ is H or $C_{1-6}$-alkyl;

$R^{3.5}$ is $C_{1-6}$-alkyl optionally substituted by one or more groups selected from $C_{3-7}$-cycloalkyl, $C_{6-10}$-aryl, and a $C_{3-10}$ heterocycle, while this group is optionally substituted in each case by a group selected from OH, oxo, $C_{1-6}$-alkyl, O—$C_{1-6}$-alkyl, and $C_{1-6}$-haloalkyl, or a group selected from a $C_{3-10}$ heterocycle and a bicyclic ring, optionally substituted by one or more groups selected independently of one another from oxo, $C_{1-6}$-alkyl, OH, $C_{6-10}$-aryl, a $C_{3-10}$ heterocycle, $C_{1-6}$-alkylene-$R^{3.5.1}$, O—$C_{1-6}$-alkylene-$R^{3.5.1}$, and NH—$C_{1-6}$-alkylene-$R^{3.5.1}$, wherein $R^{3.5.1}$ is a group selected from $C_{6-10}$-aryl and a $C_{3-10}$ heterocycle optionally substituted by $C_{1-6}$-alkyl; or $R^3$ is a group of formula 1d

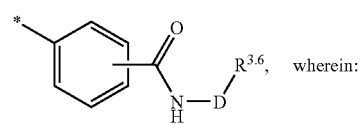

wherein:

D is $C_{2-4}$-alkynyl or an optionally bridged, bicyclic $C_{3-10}$-cycloalkyl group, each optionally substituted by one or more groups selected from $C_{1-6}$-alkyl, halogen, OH, $C_{1-6}$-haloalkyl, and O—$C_{1-6}$-alkyl, $R^{3.6}$ is pyridinyl, or $R^3$ is $COR^{3.7}$, $COCH_2R^{3.8}$, $CONHR^{3.8}$, $SO_2R^{3.8}$, or a heterocycle fused to a $C_{6-10}$-aryl group, each optionally substituted by methyl, or $R^3$ is a group of formula 1e

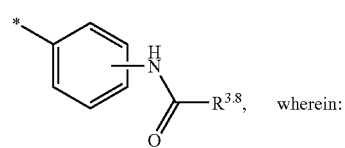

wherein:

$R^{3.7}$ is H, $C_{1-6}$-alkyl, $C_{2-6}$-alkenyl, $C_{2-6}$-alkynyl, or $C_{6-10}$-aryl;

$R^{3.8}$ is $C_{1-6}$-alkyl, $C_{2-6}$-alkenyl, $C_{2-6}$-alkynyl, $C_{3-7}$-cycloalkyl, or a group selected from $C_{6-10}$-aryl, a $C_{3-10}$ heterocycle, and a bicyclic ring optionally substituted by one or more groups selected from $C_{1-6}$-alkyl, $C_{2-6}$- alkenyl, $C_{2-6}$-alkynyl, halogen, $NR^{3.8.1}R^{3.8.2}$, $C_{6-10}$-aryl, and a $C_{3-10}$ heterocycle, wherein:
$R^{3.8.1}$ is H, $C_{1-6}$-alkyl, $C_{2-6}$-alkenyl, or $C_{2-6}$-alkynyl, and
$R^{3.8.2}$ is H, $C_{1-6}$-alkyl, $C_{2-6}$-alkenyl, or $C_{2-6}$-alkynyl;
$R^4$ is H, $C_{1-4}$-alkyl, $C_{2-4}$-alkenyl, $C_{2-4}$-alkynyl, or oxo;
$R^5$ is H, $C_{1-4}$-alkyl, $C_{2-4}$-alkenyl, or $C_{2-4}$-alkynyl;
$R^6$ is H, $C_{1-4}$-alkyl, $C_{2-4}$-alkenyl, or $C_{2-4}$-alkynyl;
$R^7$ is H, $C_{1-4}$-alkyl, $C_{2-4}$-alkenyl, $C_{2-4}$-alkynyl, $C_{6-10}$-aryl, or OH; and
$R^8$ is H, $C_{1-4}$-alkyl, $C_{2-4}$-alkenyl, $C_{2-4}$-alkynyl, $C_{6-10}$-aryl, or OH; or
$R^7$ and $R^8$ together form oxo;
wherein the terms heteroaryl and $C_{5-10}$-heteroaryl both either refer to a five- or six-membered heterocyclic aromatic group or a 5-10-membered, bicyclic heteroaryl ring which each contains one, two, or three heteroatoms, selected from among oxygen, sulfur, and nitrogen, and which each contains conjugated double bonds such that an aromatic system is formed,
wherein the term heterocyclic refers to a five-, six-, or seven-membered, saturated or unsaturated heterocyclic rings which contain one, two, or three heteroatoms, selected from among oxygen, sulfur, and nitrogen, while the ring may be linked to the molecule through a carbon atom or through a nitrogen atom, if there is one,
wherein the term $C_{3-10}$ heterocycle or heterocycle refers to a three-, four-, five-, six-, seven-, eight-, nine- or ten-membered mono- or bicyclic, saturated or unsaturated heterocyclic ring system which contains one, two, or three heteroatoms, selected from among oxygen, sulfur, and nitrogen,
wherein the term $C_{5-6}$ heterocycle refers to a five-, or six-membered mono-cyclic, saturated or unsaturated heterocyclic ring system which contains one, two, or three heteroatoms, selected from among oxygen, sulfur, and nitrogen, and
wherein the term $C_{5-6}$ heterocyclic spiro ring refers to a 5-10 membered spirocyclic ring system which contains one, two, or three heteroatoms, selected from among oxygen, sulfur, and nitrogen,
or a pharmacologically acceptable salt, enantiomer, or hydrate, thereof.

2. The compound of formula 1 according to claim 1, wherein:
X is O, S, SO, or $SO_2$;
$R^1$ is H, $C_{1-6}$-alkyl, $C_{6-10}$-aryl, $C_{6-10}$-aryl-$C_{1-6}$-alkylene, or $C_{5-10}$-heteroaryl-$C_{1-6}$-alkylene,
$R^2$ is H or $C_{1-6}$-alkyl optionally substituted by one or more groups selected from $C_{1-6}$-haloalkyl, CN, $OR^{2.1}$, $NR^{2.1}R^{2.2}$, $COOR^{2.1}$, $CONR^{2.1}R^{2.2}$, $C_{3-7}$-cycloalkyl optionally substituted by $C_{1-4}$-alkyl or oxo, an aromatic or non-aromatic heterocycle optionally substituted by $C_{1-4}$-alkyl oxo, OH, or halogen, $C_{6-10}$-aryl optionally substituted by $C_{1-4}$-alkyl or oxo, and $C_{6-10}$-aryl fused to a $C_{5-6}$ heterocycle, wherein this fused ring system is optionally substituted by $C_{1-4}$-alkyl or oxo, wherein:
$R^{2.1}$ is H or $C_{1-6}$-alkyl optionally substituted by a $C_{3-7}$-cycloalkyl, $C_{3-10}$ heterocycle, or $C_{6-10}$-aryl, each optionally substituted as defined above, and
$R^{2.2}$ is H or $C_{1-6}$-alkyl; or
$R^2$ is an optionally mono- or poly-bridged $C_{3-10}$-cycloalkyl or a $C_{3-10}$-cycloalkyl, each optionally fused to a $C_{6-10}$-aryl ring optionally substituted by one or more groups selected from $C_{1-6}$-alkyl, OH, $CH_2OR^{2.3}$, $COOR^{2.3}$, $COR^{2.3}$, $CONR^{2.3}R^{2.4}$, O—$C_{1-6}$-alkyl, O—$C_{7-11}$-aralkyl, $NR^{2.3}R^{2.4}$, and $NHCOR^{2.5}$, wherein:
$R^{2.3}$ is H or a heterocycle or a $C_{1-6}$-alkyl, optionally substituted by a group selected from $C_{3-7}$-cycloalkyl, $C_{3-10}$ heterocycle, and $C_{6-10}$-aryl, wherein this group is optionally substituted by one or more groups selected from $C_{1-6}$-alkyl, halogen, OH, and O—$C_{1-6}$-alkyl,
$R^{2.4}$ is H or $C_{1-6}$-alkyl;
$R^{2.5}$ is selected from the group consisting of $C_{3-7}$-cycloalkyl, a $C_{3-10}$ heterocycle, and $C_{1-6}$-alkyl optionally substituted by OH; or
$R^2$ is a group of formula 1a

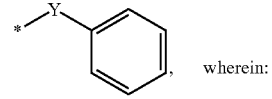, wherein:

Y is $C_{1-6}$-alkylene optionally substituted by one or two $R^{2.7}$, wherein $R^{2.7}$ are independently $C_{1-6}$-alkyl, COOH, $CONH_2$, $OR^{2.1}$, or $COOR^{2.1}$, or $R^{2.7}$ together with one or two carbon atoms of Y forms a carbocyclic ring with 3 carbon atoms, or
$R^2$ is $C_{6-10}$-aryl optionally independently substituted by one or more groups selected from $C_{1-6}$-alkyl, $C_{1-6}$-haloalkyl, $C_{2-6}$-alkenyl, $C_{2-6}$-alkynyl, CN, halogen, $OR^{2.8}$, $COOR^{2.8}$, $COR^{2.10}$, NHCOMe, $CONR^{2.3}R^{2.4}$, a $C_{1-4}$ alkylene group substituted by $NR^{2.1}R^{2.2}$, or $NR^{2.1}R^{2.2}$ or
$R^2$ is $C_{6-10}$-aryl optionally independently substituted by one or more groups selected from $C_{6-10}$-aryl-$C_{1-6}$-alkylene, $C_{5-10}$-heteroaryl-$C_{1-6}$-alkylene, $C_{3-7}$-cycloalkyl, a $C_{3-7}$-cycloalkyl-$C_{1-4}$-alkylene, $C_{6-10}$-aryl, and a $C_{3-10}$ heterocycle, wherein these groups are each optionally substituted by one or more groups selected from $C_{1-6}$-alkyl, $C_{1-6}$-haloalkyl, $COOR^{2.8}$, CN, halogen, $OR^{2.8}$, $NHCOR^{2.8}$, oxo, a $C_{3-10}$ heterocycle, a $C_{3-7}$-cycloalkyl-$C_{1-4}$ alkylene, a $C_{5-10}$ heterocycle -$C_{1-4}$-alkylene, and a $NR^{2.1}R^{2.2}$—$C_{1-4}$ alkylene, wherein:
$R^{2.8}$ is H, $C_{1-6}$-alkyl, $C_{6-10}$-aryl, or a $NR^{2.1}R^{2.2}$—$C_{1-4}$ alkylene group, and
$R^{2.10}$ is $NHR^{2.10.1}$ or a $C_{3-10}$ heterocycle optionally substituted by $C_{1-4}$-alkyl, wherein $R^{2.10.1}$ is H, $C_{3-7}$-cycloalkyl, $C_{2-6}$-alkenyl, $C_{2-6}$-alkynyl, $C_{1-6}$-alkyl, or $C_{1-6}$-alkyl-O—$C_{1-4}$-alkyl, or
$R^2$ is $C_{6-10}$-aryl to which an aromatic or non-aromatic $C_{3-10}$ heterocycle is fused, or $R^2$ is an aromatic or non-aromatic $C_{3-10}$ heterocycle optionally substituted by one or more groups selected from halogen, OH, oxo, CN, $C_{1-6}$-alkyl, $C_{1-6}$-alkanol, $C_{6-10}$-aryl-$C_{1-6}$-alkylene, $C_{5-10}$-heteroaryl-$C_{1-6}$-alkylene, $COR^{2.11}$, $C_{3-7}$-cycloalkyl-$C_{1-4}$-alkylene, and $C_{3-10}$ heterocycle-$C_{1-4}$-alkylene, wherein $R^{2.11}$ is a group selected from $C_{3-10}$ heterocycle-$C_{1-4}$-alkylene, $C_{3-7}$-cycloalkyl, and a $C_{3-10}$ heterocycle, optionally substituted by $C_{1-6}$-alkyl optionally substituted by OH, $CH_2OH$, OMe, $NH_2$, a $C_{3-10}$ heterocycle, or NHCOO-$^tBu$, or
$R^2$ is $C_{2-6}$-alkenyl or a bicyclic ring, each optionally substituted by methyl, or
$NR^1R^2$ is a heterocycle optionally substituted by one or more groups selected from $C_{1-4}$-alkyl, OH, and $C_{1-4}$-alkanol;
$R^3$ is a group selected from a $C_{3-10}$ heterocycle, a $C_{3-7}$-cycloalkyl, a bicyclic, fused aromatic or non-aromatic ring system, which optionally contains 1 to 4 heteroatoms selected from S, N, O, or it is $C_{6-10}$-aryl-$C_{1-6}$-alkylene, $C_{5-10}$-heteroaryl-$C_{1-6}$-alkylene, and $CH_2$-benzo[1,3]dioxolyl, optionally substituted by one or more groups selected from OH, halogen, $C_{1-6}$-alkyl, O—$C_{1-6}$-alkyl, $C_{1-6}$-haloalkyl, and CO—$R^{3.1}$, or $R^3$ is phenyl optionally substituted by one or more groups selected from $C_{1-6}$-alkyl, $C_{2-6}$-alkenyl, $C_{2-6}$-alkynyl, $C_{1-4}$-haloalkyl, $C_{1-6}$-alkylene-$NR^{3.1}R^{3.2}$, CN, $COOR^{3.1}$, $CONR^{3.1}R^{3.2}$, $NR^{3.1}R^{3.2}$, $NHCOR^{3.1}$, $CF_3$, $OR^{3.1}$, halogen, $NHCOR^{3.1}$, $NO_2$, $SO_2NR^{3.1}R^{3.2}$, and $C_{1-6}$-alkylene-$NHCOR^{3.1}$, wherein:

$R^{3.1}$ is H, $C_{1-6}$-alkyl; $C_{2-6}$-alkenyl, or $C_{2-6}$-alkynyl, optionally bridged, mono- or bicyclic $C_{3-10}$ heterocycle, or $C_{3-10}$ heterocycle-$C_{1-4}$-alkylene group, and $R^{3.2}$ is H, $C_{1-6}$-alkyl, $C_{2-6}$-alkenyl, or $C_{2-6}$-alkynyl, or $R^3$ is a group of formula 1b

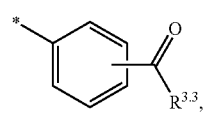

1b wherein:

$R^{3.3}$ is a $C_{3-10}$ heterocycle optionally substituted by one or more groups selected from $C_{1-6}$-alkyl, oxo, $COR^{3.3.1}$, $COR^{3.3.2}$, $C_{1-6}$-alkylene-$R^{3.3.2}$, $CH_2CO$-pyrrolidine, and a $C_{3-10}$ heterocycle, wherein a sulfur atom optionally contained in the heterocyclic ring is optionally in the form of the oxide or dioxide, wherein: $R^{3.3.1}$ is $C_{1-6}$-alkyl, and $R^{3.3.2}$ is $NH_2$, $NH(C_{1-6}$-alkyl), or $N(C_{1-6}$-alkyl)$_2$, or $R^{3.3}$ is a bicyclic ring or heterocycle spiro ring, or $R^3$ is a group of formula 1c

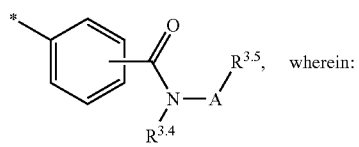

1c wherein:

A is a bond or $C_{1-6}$-alkyl optionally substituted by oxo or $NMe_2$;

$R^{3.4}$ is H or $C_{1-6}$-alkyl;

$R^{3.5}$ is $C_{1-6}$-alkyl optionally substituted by one or more groups selected from $C_{3-7}$-cycloalkyl, $C_{6-10}$-aryl, and a $C_{3-10}$ heterocycle, while this group is optionally substituted in each case by a group selected from OH, oxo, $C_{1-6}$-alkyl, O—$C_{1-6}$-alkyl, and $C_{1-6}$-haloalkyl, or a group selected from a $C_{3-10}$ heterocycle and a bicyclic ring, optionally substituted by one or more groups selected independently of one another from oxo, $C_{1-6}$-alkyl, OH, $C_{6-10}$-aryl, a $C_{3-10}$ heterocycle, $C_{1-6}$-alkylene-$R^{3.5.1}$, O—$C_{1-6}$-alkylene-$R^{3.5.1}$, and NH—$C_{1-6}$-alkylene-$R^{3.5.1}$, wherein $R^{3.5.1}$ is a group selected from $C_{6-10}$-aryl and a $C_{3-10}$ heterocycle optionally substituted by $C_{1-6}$-alkyl; or $R^3$ is a group of formula 1d

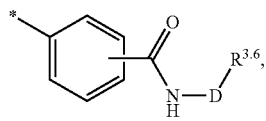

1d wherein:

D is $C_{2-4}$-alkynyl or an optionally bridged, bicyclic $C_{3-10}$-cycloalkyl group, each optionally substituted by one or more groups selected from $C_{1-6}$-alkyl, halogen, OH, $C_{1-6}$-haloalkyl, and O—$C_{1-6}$-alkyl, $R^{3.6}$ is pyridinyl, or $R^3$ is $COR^{3.7}$, $COCH_2R^{3.8}$, $CONHR^{3.8}$, $SO_2R^{3.8}$, or a heterocycle fused to a $C_{6-10}$-aryl group, each optionally substituted by methyl, or $R^3$ is a group of formula 1e

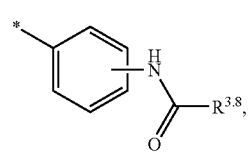

1e wherein:

$R^{3.7}$ is H, $C_{1-6}$-alkyl, or $C_{6-10}$-aryl;

$R^{3.8}$ is a group selected from $C_{1-6}$-alkyl, $C_{3-7}$-cycloalkyl, or a group selected from $C_{6-10}$-aryl, a $C_{3-10}$ heterocycle, and a bicyclic ring, optionally substituted by one or more groups selected from $C_{1-6}$-alkyl, halogen, $NR^{3.8.1}R^{3.8.2}$, $C_{6-10}$-aryl, and a $C_{3-10}$ heterocycle, wherein: $R^{3.8.1}$ is H or $C_{1-6}$-alkyl, and $R^{3.8.2}$ is H or $C_{1-6}$-alkyl;

$R^4$ is H, $C_{1-4}$-alkyl, or oxo;

$R^5$ is H or $C_{1-4}$-alkyl;

$R^6$ is H or $C_{1-4}$-alkyl;

$R^7$ is H, $C_{1-4}$-alkyl, $C_{6-10}$-aryl, or OH;

$R^8$ is H, $C_{1-4}$-alkyl, $C_{6-10}$-aryl, or OH; or $R^7$ and $R^8$ together form oxo; or a pharmacologically acceptable salt, enantiomer, or hydrate, thereof.

3. The compound of formula 1 according to claim 1, wherein:

X is O, S, SO, or $SO_2$;

$R^1$ is H, methyl, ethyl, or propyl;

$R^2$ is H or $C_{1-6}$-alkyl optionally substituted by one or more groups selected from $CF_3$, CN, OH, $NMe_2$, OMe, COOH, and $CONMe_2$, or $R^2$ is $C_{1-6}$-alkyl optionally substituted by one or more groups selected from cyclopropyl, cyclopentyl, cyclohexyl, phenyl, pyrrolidinyl, imidazolidinyl, pyrazolyl, imidazolyl, and pyridinyl, each optionally substituted by methyl or oxo; or $R^2$ is $C_{3-7}$-cycloalkyl optionally substituted by a group selected from methyl, $OR^{2.3}$, $CH_2OR^{2.3}$, COOH, CONR$^{2.3}$R$^{2.4}$, CONH-$^t$Bu, O-benzyl, NR$^{2.3}$R$^{2.4}$, and NHCOR$^{2.5}$, wherein:

R$^{2.3}$ is H, methyl, or

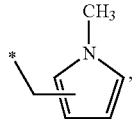

R$^{2.4}$ is H or methyl, and

R$^{2.5}$ is CH$_2$C(CH$_3$)$_3$, CH$_2$C(CH$_3$)$_2$(CH$_2$OH), cyclopentyl, tetrahydrofuranyl, pyrrolyl, pyrazolyl, imidazolyl, or isoxazolyl; or R$^2$ is a group of formula 1a

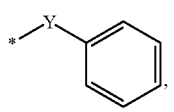

wherein:

Y is C$_{1-4}$-alkylene optionally substituted by one or two R$^{2.7}$, and

R$^{2.7}$ are each independently C$_{1-4}$-alkyl, COOH, or CONH$_2$, or R$^{2.7}$ together with one or two carbon atoms of Y forms a carbocyclic ring with 3 carbon atoms; or R$^2$ is C$_{6-10}$-aryl optionally substituted by one or more groups independently selected from methyl, tert-butyl, CN, F, Cl, Br, OH, OMe, OEt, O-phenyl, COOH, COOMe, COR$^{2.10}$, NHCOMe, and morpholine-substituted C$_{1-4}$-alkylene, wherein R$^{2.10}$ is NH$_2$, NHMe, NH-$^i$Pr, NH-cyclopropyl, NHCH$_2$CH$_2$OMe, or a C$_{3-10}$ heterocycle, containing one, two, or three heteroatoms selected from oxygen and nitrogen; or R$^2$ is C$_{6-10}$-aryl optionally substituted by phenyl or a C$_{3-10}$ heterocycle, each optionally substituted by one or more groups selected from methyl, tert-butyl, COOH, COOMe, CN, F, Cl, Br, OH, OMe, OEt, and NHCOMe, and oxo; or R$^2$ is a C$_{3-10}$ heterocycle optionally substituted by benzyl or COR$^{2.11}$, wherein R$^{2.11}$ is a group selected from cyclopentyl, tetrahydrofuranyl, furan, pyridyl, pyrrolyl, pyrazolyl, or imidazolyl, each optionally substituted by one or two methyl groups or by one or more groups selected from CH$_2$C(CH$_3$)$_3$, C(CH$_3$)$_2$(CH$_2$OH), CH$_2$OMe, C(CH$_3$)$_2$NH$_2$, and C(CH$_3$)$_2$NHCOO-$^t$Bu; or R$^2$ is C$_{2-6}$-alkenyl, indanyl, 1,2,3,4-tetrahydronaphthalyl, or 8-methyl-8-azabicyclo[3.2.1]octane; or NR$^1$R$^2$ is pyrrolidinyl, piperidinyl, piperazinyl, or morpholinyl, each optionally substituted by methyl;

R$^3$ is pyridinyl, pyrimidine, benzyl, or CH$_2$-benzo[1,3]dioxolyl; or

R$^3$ is phenyl optionally substituted by one, two, or three groups selected from methyl, CH$_2$NH$_2$, CN, COOH, CONH$_2$, CF$_3$, OH, F, Cl, Br, OMe, NHCOMe, NR$^{3.1}$COR$^{3.2}$, CONR$^{3.1}$R$^{3.2}$, NO$_2$, SONMe$_2$, and CH$_2$NHCOMe, wherein:

R$^{3.1}$ is H, C$_{1-6}$-alkyl, or an optionally bridged, mono- or bicyclic C$_{3-10}$ heterocycle, and R$^{3.2}$ is H or C$_{1-6}$-alkyl; or R$^3$ is a group of formula 1b

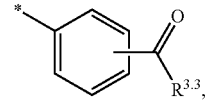

wherein:

R$^{3.3}$ is piperidinyl, piperazinyl, or azepanyl, each optionally independently substituted by one or more groups selected from methyl, oxo, COCH$_3$, CONH$_2$, CH$_2$NEt$_2$, CH$_2$CH$_2$NMe$_2$, CH$_2$COpyrrolidine, pyridinyl, isothiazolidinyl-1,1-dioxide, and thiazolidinyl-1,1-dioxide, or R$^{3.3}$ is a group of formula

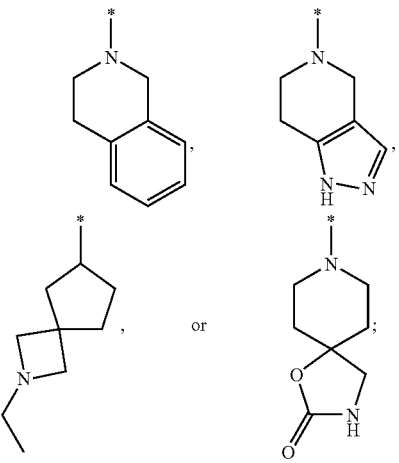

R$^3$ is a group of formula 1c

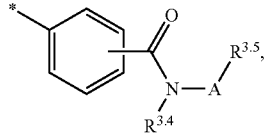

wherein:

A is a bond or C$_{1-4}$-alkyl optionally substituted by oxo or NMe$_2$,

R$^{3.4}$ is H or methyl, and

R$^{3.5}$ is pyrrolidinyl, piperidinyl, piperazinyl, morpholinyl, cyclohexyl, imidazolyl, pyrazolyl, phenyl, pyridinyl, benzimidazolyl, imidazolidin-2-one, pyrrolidin-2-one, pyrrolidin-3-one, tetrahydrothiophene-1,1-dioxide, or 1-azabicyclo[2.2.2]octane, each optionally independently substituted by one or more groups selected from methyl, ethyl, OH, phenyl, pyridinyl, pyrazolyl, pyrrolidinyl, (CH$_2$)$_o$—R$^{3.5.1}$, O—(CH$_2$)$_o$—R$^{3.5.1}$, and NH—(CH$_2$)$_o$—R$^{3.5.1}$, wherein: o is 0, 1, or 2, and R$^{3.5.1}$ is phenyl, pyrrolidinyl, piperidinyl, or imidazolidin-2-one, each optionally substituted by methyl; or $R^3$ is a group of formula 1d

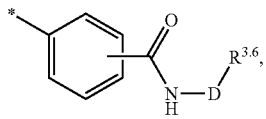

wherein:

D is $C_{2-4}$-alkynyl;
$R^{3.6}$ is pyridinyl; or
$R^3$ is $COR^{3.7}$, $COCH_2R^{3.8}$, $CONHR^{3.8}$, $SO_2R^{3.8}$, or a group of formula 1e

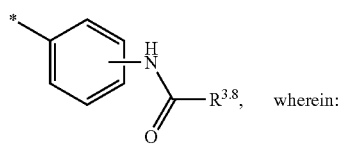

$R^{3.7}$ is H, methyl, or phenyl, and
$R^{3.8}$ is isopropyl, cyclopropyl, cyclopentyl, cyclohexyl, pyrrolidinyl, pyrrolidin-2-one, furanyl, azabicyclo[2.2.2]octanyl, or a group selected from piperidinyl, pyrazolyl, imidazolyl, isoxazolyl, pyridinyl, phenyl, or benzyl, each optionally independently substituted by one or more groups selected from methyl, chlorine, $NH_2$, $NMe_2$, phenyl, and morpholinyl;
$R^4$ is H, methyl, or oxo;
$R^5$ is H or methyl;
$R^6$ is H or methyl;
$R^7$ is H, methyl, or OH;
$R^8$ is H, methyl, or OH;
or $R^7$ and $R^8$ together form oxo;
or a pharmacologically acceptable salt, enantiomer, hydrate, or solvate thereof.

4. The compound of formula 1 according to one of claims 1 to 3, wherein $R^1$ is H,
or a pharmacologically acceptable salt, enantiomer, or hydrate, thereof.

5. The compound of formula 1 according to one of claims 1 to 3, wherein X is SO,
or a pharmacologically acceptable salt, enantiomer, or hydrate, thereof.

6. The compound of formula 1 according to one of claims 1 to 3, wherein $R^5$, $R^6$, $R^7$, and $R^8$ are each H,
or a pharmacologically acceptable salt, enantiomer, or hydrate, thereof.

7. The compound of formula 1 according to claim 1 to 3, wherein $R^4$ is H,
or a pharmacologically acceptable salt, enantiomer, or hydrate, thereof.

8. The compound of formula 1 according to claim 1, wherein:
$R^2$ is $C_{6-10}$-aryl optionally independently substituted by one or more groups selected from $C_{1-6}$-alkyl, $C_{1-4}$-haloalkyl, $C_{2-6}$-alkenyl, $C_{2-6}$-alkynyl, CN, halogen, $OR^{2.8}$, $COOR^{2.8}$, $COR^{2.10}$, $NR^{2.8}R^{2.9}$, $NHCOR^{2.8}$, $SR^{2.8}$, $SOR^{2.8}$, $SO_2R^{2.8}$ and $SO_2NR^{2.8}R^{2.9}$; or
$R^2$ is $C_{6-10}$-aryl optionally independently substituted by one or more groups selected from $C_{6-10}$-aryl-$C_{1-6}$-alkylene, $C_{5-10}$-heteroaryl-$C_{1-6}$-alkylene, $C_{6-10}$-aryl, and a $C_{3-10}$ heterocycle, each optionally substituted by a group selected from $C_{1-6}$-alkyl, $C_{1-6}$-haloalkyl, $COOR^{2.8}$, CN, halogen, $OR^{2.8}$, $NHCOR^{2.8}$, oxo, a $C_{3-7}$-cycloalkyl-$C_{1-4}$ alkylene, a heterocycle-$C_{1-4}$ alkylene, and a $NR^{2.1}R^{2.2}$—$C_{1-4}$-alkylene, wherein:
$R^{2.8}$ is H, $C_{1-6}$-alkyl, $C_{2-6}$-alkenyl, $C_{2-6}$-alkynyl, a $NR^{2.1}R^{2.2}$—$C_{1-4}$-alkylene, or $C_{6-10}$-aryl, $R^{2.9}$ is H, $C_{1-6}$-alkyl, $C_{2-6}$-alkenyl, or $C_{2-6}$-alkynyl, and
$R^{2.10}$ is $NHR^{2.10.1}$, $C_{1-6}$-alkylene-O—$C_{1-4}$-alkyl, or a $C_{3-10}$ heterocycle optionally substituted by $C_{1-4}$-alkyl, wherein $R^{2.10.1}$ is H, $C_{1-6}$-alkyl, $C_{2-6}$-alkenyl, $C_{2-6}$-alkynyl, or $C_{3-7}$-cycloalkyl; or
$R^2$ is $C_{6-10}$-aryl to which an aromatic or non-aromatic $C_{3-10}$ heterocycle is fused; or
$R^2$ is $C_{6-10}$-aryl optionally substituted by a group selected from $C_{6-10}$-aryl and a $C_{3-10}$ heterocycle, each optionally substituted by one or more groups selected from $C_{1-6}$-alkyl, $C_{2-6}$-alkenyl, $C_{2-6}$-alkynyl, $C_{1-4}$-haloalkyl, CN, halogen, $OR^{2.8}$, $COOR^{2.8}$, $COR^{2.10}$ $NR^{2.8}R^{2.9}$, $NHCOR^{2.8}$, $SR^{2.8}$, $SOR^{2.8}$, $SO_2R^{2.8}$, $SO_2NR^{2.8}R^{2.9}$, and oxo;
or a pharmacologically acceptable salt, enantiomer or hydrate, thereof.

9. The compound of formula 1 according to claim 1, wherein:
$R^2$ is $C_{6-10}$-aryl optionally substituted by one or more groups selected from $C_{1-4}$-alkyl, CN, halogen, $OR^{2.8}$, $COOR^{2.8}$, $COR^{2.10}$, and NHCOMe, wherein:
$R^{2.8}$ is $C_{1-4}$-alkyl or $C_{6-10}$-aryl;
$R^{2.10}$ is $NHR^{2.10.1}$ morpholinyl, or methylpiperazinyl; and
$R^{2.10.1}$ is H, cyclopropyl, or $C_{1-4}$-alkyl optionally substituted by one or more groups selected from O—$C_{1-4}$-alkyl, OH, or $C_{6-10}$-aryl; or
$R^2$ is $C_{6-10}$-aryl optionally substituted by a group selected from phenyl and a $C_{3-10}$ heterocycle, each optionally substituted by $C_{1-4}$-alkyl, $COOR^{2.8}$, CN, halogen, $OR^{2.8}$, NHCOMe, or oxo;
or a pharmacologically acceptable salt, enantiomer or hydrate, thereof.

10. The compound of formula 1 according to claim 1, wherein:
$R^2$ is $C_{1-6}$-alkyl, $C_{2-6}$-alkenyl, or $C_{2-6}$-alkynyl, each optionally substituted by $C_{1-6}$-haloalkyl, CN, $OR^{2.1}$, $NR^{2.1}R^{2.2}$, $NHCOR^{2.1}$, $SR^{2.1}$, $SOR^{2.1}$, $SO_2R^{2.1}$, $SO_2NR^{2.1}R^{2.2}$, $COOR^{2.1}$, or $CONR^{2.1}R^{2.2}$, each optionally substituted by $C_{3-7}$-cycloalkyl, $C_{6-10}$-aryl, or a $C_{3-10}$ heterocycle, each optionally substituted by one or more groups selected from $C_{1-6}$-alkyl, $C_{2-6}$-alkenyl, $C_{2-6}$-alkynyl, and oxo, wherein:
$R^{2.1}$ is H, $C_{1-6}$-alkyl, $C_{2-6}$-alkenyl, or $C_{2-6}$-alkynyl, and
$R^{2.2}$ is H, $C_{1-6}$-alkyl, $C_{2-6}$-alkenyl, or $C_{2-6}$-alkynyl,
or a pharmacologically acceptable salt, enantiomer or hydrate, thereof.

11. The compound of formula 1 according to claim 1, wherein:
$R^2$ is $C_{1-6}$-alkyl optionally substituted by $C_{1-4}$-haloalkyl, CN, $OR^{2.1}$, $NR^{2.1}R^{2.2}$, $COOR^{2.1}$, or $CONR^{2.1}R^{2.2}$, or optionally substituted by $C_{3-7}$-cycloalkyl, $C_{6-10}$-aryl, or an aromatic $C_{3-10}$ heterocycle, each optionally substituted by methyl or oxo, wherein:
$R^{2.1}$ is H or $C_{1-4}$-alkyl; and
$R^{2.2}$ is H or $C_{1-4}$-alkyl,
or a pharmacologically acceptable salt, enantiomer or hydrate, thereof.

12. The compound of formula 1 according to claim 1, wherein:
$R^2$ is $C_{6-10}$-aryl optionally independently substituted in the meta position by one or more groups selected from $C_{1-4}$-alkyl, CN, halogen, $OR^{2.8}$, $COOR^{2.8}$, $COR^{2.10}$, and NHCOMe, wherein:
$R^{2.8}$ is $C_{1-4}$-alkyl or $C_{6-10}$-aryl,
$R^{2.10}$ is $NHR^{2.10.1}$, morpholinyl, or methylpiperazinyl, and
$R^{2.10.1}$ is H, cyclopropyl, or $C_{1-4}$-alkyl, wherein the $C_{1-4}$-alkyl is optionally independently substituted by one or more groups selected from $O-C_{1-4}$-alkyl, OH, and $C_{6-10}$-aryl; or
$R^2$ is $NH(R^{2.10.1})$ or cyclohexyl; or
$NR^1R^2$ is pyrrolidine and piperazine, each optionally substituted by one or more groups selected from $C_{1-4}$-alkyl, OH, and $C_{1-4}$-alkanol
or a pharmacologically acceptable salt, enantiomer or hydrate, thereof.

13. The compound of formula 1 according to claim 1, wherein:
$R^3$ is phenyl optionally substituted by one or more groups selected from $C_{1-6}$-alkyl, $C_{2-6}$-alkenyl, $C_{2-6}$-alkynyl, $C_{1-4}$-haloalkyl, $C_{1-6}$-alkylene-$N^{3.1}R^{3.2}$, CN, halogen, $OR^{3.1}$, $COOR^{3.1}$, $CONR^{3.1}R^{3.2}$, $NR^{3.1}R^{3.2}$, $NHCOR^{3.1}$, $NO_2$, $SR^{3.1}$, $SOR^{3.1}$, $SO_2R^{3.1}$, $SO_2NR^{3.1}R^{3.2}$, and $C_{1-6}$-alkylene-$NHCOR^{3.1}$, wherein:
$R^{3.1}$ is H, $C_{1-6}$-alkyl, $C_{2-6}$-alkenyl, or $C_{2-6}$-alkynyl, and
$R^{3.2}$ is H, $C_{1-6}$-alkyl, $C_{2-6}$-alkenyl, or $C_{2-6}$-alkynyl;
or a pharmacologically acceptable salt, enantiomer, or hydrate, thereof.

14. The compound of formula 1 according to claim 1, wherein:
$R^3$ is phenyl optionally substituted in the para position by $C_{1-6}$-alkyl, $C_{2-6}$-alkenyl, $C_{2-6}$-alkynyl, $C_{1-4}$-haloalkyl, $C_{1-6}$-alkylene-$NR^{3.1}R^{3.2}$, CN, halogen, $OR^{3.1}$, $COOR^{3.1}$, $CONR^{3.1}R^{3.2}$, $NR^{3.1}R^{3.2}$, $NHCOR^{3.1}$, $NO_2$, $SR^{3.1}$, $SOR^{3.1}$, $SO_2R^{3.1}$, $SO_2NR^{3.1}R^{3.2}$, or $C_{1-6}$-alkylene-$NHCOR^{3.1}$, wherein:
$R^{3.1}$ is H, $C_{1-6}$-alkyl, $C_{2-6}$-alkenyl, or $C_{2-6}$-alkynyl, and
$R^{3.2}$ is H, $C_{1-6}$-alkyl, $C_{2-6}$-alkenyl, or $C_{2-6}$-alkynyl;
or a pharmacologically acceptable salt, enantiomer or hydrate, thereof.

15. The compound of formula 1 according to claim 1, wherein:
$R^3$ is a group of formula 1b

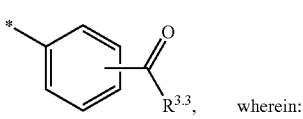

wherein:

$R^{3.3}$ is a $C_{3-10}$ heterocycle optionally independently substituted by one or more groups selected from $C_{1-6}$-alkyl, oxo, $COR^{3.3.1}$, $COR^{3.3.2}$, $C_{1-6}$-alkylene-$R^{3.3.2}$ $CH_2COpyrrolidine$, and a $C_{3-10}$ heterocycle, wherein a sulfur atom optionally contained in the $C_{3-10}$ heterocycle is optionally present as the oxide or dioxide, wherein: $R^{3.3.1}$ is $C_{1-6}$-alkyl, and $R^{3.3.2}$ is $NH_2$, $NH(C_{1-6}$-alkyl), or $N(C_{1-6}$-alkyl)$_2$; or
$R^{3.3}$ is a bicyclic ring or a heterocycle spiro ring;
or a pharmacologically acceptable salt, enantiomer or hydrate, thereof.

16. The compound of formula 1 according to claim 1, wherein:
$R^3$ is a group of formula 1c

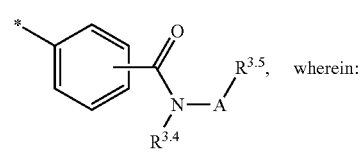

A is a bond or $C_{1-6}$-alkyl optionally substituted by oxo or $NMe_2$;
$R^{3.4}$ is H or $C_{1-6}$-alkyl;
$R^{3.5}$ is $C_{1-6}$-alkyl optionally substituted by a group selected from $C_{3-7}$-cycloalkyl, $C_{6-10}$-aryl, and a $C_{5-10}$ heterocycle, each optionally substituted by one or more groups selected from halogen, OH, oxo, $C_{1-6}$-alkyl, $O-C_{1-6}$-alkyl, $C_{1-6}$-haloalkyl, a $C_{3-10}$ heterocycle, and a bicyclic ring, wherein each of these groups is optionally independently substituted by one or more groups selected from oxo, $C_{1-6}$-alkyl, OH, $C_{6-10}$-aryl, a heterocycle, $C_{1-6}$-alkylene-$R^{3.5.1}$, $O-C_{1-6}$-alkylene-$R^{3.5.1}$, and $NH-C_{1-6}$-alkylene-$R^{3.5.1}$, wherein $R^{3.5.1}$ is $C_{6-10}$-aryl or a $C_{3-10}$ heterocycle, each optionally substituted by $C_{1-6}$-alkyl,
or a pharmacologically acceptable salt, enantiomer or hydrate, thereof.

17. The compound of formula 1 according to claim 1, wherein:
$R^3$ is a group of formula 1d

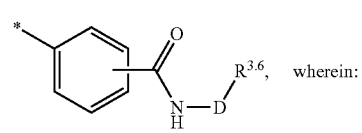

D is $C_{2-4}$-alkynyl; and
$R^{3.6}$ is pyridinyl,
or a pharmacologically acceptable salt, enantiomer or hydrate, thereof.

18. The compound of formula 1 according to claim 1, wherein:
$R^3$ is a group of formula 1e

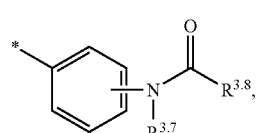

wherein:

$R^{3.7}$ is H, halogen, $C_{1-6}$-alkyl, $C_{2-6}$-alkenyl, $C_{2-6}$-alkynyl, or $C_{1-6}$-haloalkyl;
$R^{3.8}$ is H, OH, halogen or a group selected from $C_{1-6}$-alkyl, $C_{2-6}$-alkenyl, $C_{2-6}$-alkynyl, $C_{1-6}$-haloalkyl, $O-C_{1-6}$-alkyl, $C_{6-10}$-aryl, a $C_{3-10}$ heterocycle, and a bicyclic ring, each optionally independently substituted by one or more groups selected from halogen, $C_{1-6}$-alkyl, OH, $C_{1-6}$-haloalkyl, and O—$C_{1-6}$-alkyl, or a pharmacologically acceptable salt, enantiomer or hydrate, thereof.

19. A pharmaceutical formulation comprising a compound of formula 1 according to one of claims 1 to 18 and a pharmaceutically acceptable excipient.

* * * * *